US009011871B2

(12) United States Patent
Levine et al.

(10) Patent No.: US 9,011,871 B2
(45) Date of Patent: Apr. 21, 2015

(54) **BROAD SPECTRUM VACCINE AGAINST TYPHOIDAL AND NON-TYPHOIDAL *SALMONELLA* DISEASE**

(71) Applicant: University of Maryland, Baltimore, Baltimore, MD (US)

(72) Inventors: Myron M. Levine, Columbia, MD (US); James E. Galen, Eldersburg, MD (US); Sharon M. Tennant, Baltimore, MD (US); Raphael Simon, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 13/670,153

(22) Filed: Nov. 6, 2012

(65) Prior Publication Data

US 2013/0129776 A1 May 23, 2013

Related U.S. Application Data

(60) Provisional application No. 61/556,330, filed on Nov. 7, 2011.

(51) Int. Cl.
| | |
|---|---|
| *A61K 39/385* | (2006.01) |
| *A61K 39/112* | (2006.01) |
| *A61K 39/00* | (2006.01) |
| *A61K 45/00* | (2006.01) |
| *A61K 39/38* | (2006.01) |

(52) U.S. Cl.
CPC ........... *A61K 39/385* (2013.01); *A61K 39/0275* (2013.01); *A61K 2039/522* (2013.01); *A61K 2039/55544* (2013.01); *A61K 2039/6068* (2013.01)

(58) Field of Classification Search
CPC ........... A61K 2039/70; A61K 2039/60; A61K 2039/6012; A61K 2039/00; A61K 39/00; A61K 39/0275
See application file for complete search history.

(56) References Cited

U.S. PATENT DOCUMENTS

| | | | |
|---|---|---|---|
| 6,130,082 | A | 10/2000 | Majarian |
| 8,137,930 | B2 | 3/2012 | Vindurampulle et al. |
| 2011/0274714 | A1 | 11/2011 | Levine et al. |

FOREIGN PATENT DOCUMENTS

| | | | |
|---|---|---|---|
| WO | 2007/053489 | A2 | 5/2007 |
| WO | 2007/106956 | A1 | 9/2007 |
| WO | WO 2010/083477 | A2 * | 7/2010 |
| WO | 2010/101750 | A2 | 9/2010 |

OTHER PUBLICATIONS

McGregor et al., Current Opinion Infectious diseases, 2013; 26(3): 254-262.*
Matsui et al., Oral Immunization with ATP-Dependent Protease-Deficient Mutants Protects Mice against Subsequent Oral Challenge with Virulent *Salmonella enterica* Serovar Typhimurium, Infection and Immunity, 71: 30-39 (2003).
Watson et al., Protection of Mice against *Salmonella typhimunium* with an O-Specific Polysaccharide-Protein Conjugate Vaccine, Infection and Immunity, 60: 4679-4686 (1992).
McDermott et al., High-Affinity Interaction between Gram-Negative Flagellin and a Cell Surface Polypeptide Results in Human Monocyte Activation, Infection and Immunity, 68: 5525-5529 (2000).
Brett et al., Structural and Immunological Characterization of *Burkholderia pseudomallei* O-Polysaccharide-Flagellin Protein Conjugates, Infection and Immunity, 64: 2824-2828 (1996).
Svenson et al., Artificial *Salmonella* Vaccines: *Salmonella typhimurium* O-Antigen-Specific Oligosaccharide-Protein Conjugates Elicit Protective Antibodies in Rabbits and Mice, Infection and Immunity, 32: 490-496 (1981).
Das Gracas Luna et al., Salmonella flagellin fused with a linear epitope of colonization factor antigen I (CFA/I) can prime antibody responses against homologous and heterologous fimbriae of enterotoxigenic *Escherichia coli*, Research in Microbiology, 151: 575-582 (2000).
Simon et al., *Salmonella enterica* Serovar Enteritidis Core O Polysaccharide Conjugated to H:g,m Flagellin as a Candidate Vaccine for Protection against Invasive Infection with *S. enteritidis*, Infection and Immunity, 79: 4240-4249 (Oct. 2011).
English translation of Alekseeva et al.,Experimental Study of Synthetic Vaccines Against Salmonellosis Infection, Immunologiya, 1:32-36 (1986).
Wang et al., Construction, Genotypic, and Phenotypic Characterization, and Immunogenicity of Attenuated guaBA *Salmonella enterica* Serovar Typhi Strain CVD 915, Infection and Immunity, 69(8):4734-41 (2001).
Zuniga et al., *Salmonella enterica* Serovar Typhi O:1, 9, 12, Polysaccharide-Protein Conjugate as a Diagnostic Tool for Typhoid Fever, Journal of Clinical Microbiology, 43(9):4545-4550 (2005).
Alekseeva et al.,Experimental Study of Synthetic Vaccines Against Salmonellosis Infection, Immunologiya, 1:32-36 (Abstract Only) (1986).
Office Action from pending U.S. Appl. No. 13/144,336, mailed Sep. 16, 2014.
Office Action from pending U.S. Appl. No. 13/144,336, mailed Dec. 31, 2013.

* cited by examiner

*Primary Examiner* — Gary Nickol
*Assistant Examiner* — Lakia Tongue
(74) *Attorney, Agent, or Firm* — Nevrivy Patent Law Group P.L.L.C.

(57) ABSTRACT

The present invention is drawn to multivalent *Salmonella enterica* serovar conjugate vaccines comprising conjugates of *S. Typhimurium*, *S. Enteritidis*, *S. Choleraesuis*, *S. Typhi*, *S. Paratyphi* A and optionally *S. Paratyphi* B, wherein the conjugates comprise a hapten antigen and a carrier antigen, wherein at least one of the hapten antigens or carrier antigens is characteristic of the *Salmonella enterica* serovar. The present invention also provides *Salmonella enterica* serovar reagent strains to produce the multivalent conjugate vaccines and attenuated *Salmonella enterica* serovars for use as vaccines.

13 Claims, 37 Drawing Sheets

US 9,011,871 B2

BROAD SPECTRUM VACCINE AGAINST TYPHOIDAL AND NON-TYPHOIDAL *SALMONELLA* DISEASE

CROSS-REFERENCE TO RELATED APPLICATIONS

This application claims the benefit of U.S. Provisional Appl. No. 61/556,330, filed Nov. 7, 2011. The content of the aforementioned application is relied upon and is incorporated by reference in its entirety.

STATEMENT OF FEDERALLY SPONSORED RESEARCH AND DEVELOPMENT

This invention was made with government support under Grant No. AI057168 awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable sequence listing submitted concurrently herewith and identified as follows: One 94,935 Byte ASCII (Text) file named "seq_listing_ST25.txt," created on Oct. 25, 2012.

FIELD OF THE INVENTION

The field of the invention relates to vaccines directed to *Salmonella*.

BACKGROUND OF THE INVENTION

Bacteriology of the Complex Genus *Salmonella*. Only two species are currently recognized within the genus *Salmonella*, *Salmonella enterica* and *Salmonella bongori*, and only the former is important with respect to human disease. There are six subspecies of *Salmonella enterica*, of which subspecies I, *S. enterica* subspecies *enterica*, contains all the important pathogens that cause human disease. *S. enterica* subspecies *enterica* is further sub-divided into more than 2500 serovars (i.e., distinct serotypes) based on the presence of specific somatic O antigens, capsular polysaccharide surface Vi antigen and flagellar H antigens expressed by the organism. The antigenic serotyping scheme (previously called the Kauffman-White scheme and more recently the White-Kauffmann-Le Minor scheme) defines a serovar (i.e., serotype) by its O polysaccharide antigens (and also whether capsular polysaccharide Vi is expressed) and its H flagella antigens. The serogroup of a *Salmonella* is defined by its O antigens, while the serovar is defined by the full antigenic structure that includes all the flagellar antigens and whether Vi polysaccharide is expressed. O antigens are part of the lipopolysaccharide (LPS) surface structure that is part of the outer membrane of the bacteria. The lipid A (endotoxin) portion of the LPS, is a glucosamine-based phospholipid that makes up the outer monolayer of the outer membrane of the bacteria. Attached to the lipid A is a core polysaccharide that is essentially identical in all the important *Salmonella* serovars that cause human disease, particularly invasive disease. The more internal portion of the core polysaccharide is the "inner core", while the more external portion is the "outer core" (FIG. 1). Finally, the most external surface component that is attached to the outer core polysaccharide is a terminal O polysaccharide that consists of terminal O repeat units linked one to another; this is what is exposed to the environment. The terminal O polysaccharide varies in structure depending on the sugars comprising the core unit and their linkages one to another. Many of the most important *Salmonella* serovars associated with human disease fall into serogroup B and serogroup D. The O repeat units of *Salmonella* serogroups B and D share a common trisaccharide backbone that consists of repeats of mannose-rhamnose and galactose (Wyk P and Reeves P. *J. Bacteriol.* 1989; 171:5687-5693). This backbone is the structure for the common *Salmonella* epitope 12 that is found in serogroup A, B and Group D Attached to the backbone is another dideoxyhexose sugar that is alpha 1,3-linked to the mannose residue. If that dideoxyhexose sugar is abequose, the resultant structure constitutes the immunodominant antigen "4" that defines O serogroup B. If the dideoxyhexose sugar that is alpha 1,3-linked to mannose is tyvelose, the resultant structure creates immunodominant antigen "9" that defines O serogroup D.

Some *Salmonella* can express two different antigenic forms of flagella, called Phase 1 and Phase 2. *Salmonella Typhimurium* has the antigenic scheme 1,4,(5),12:i:1,2. This indicates that it falls within O serogroup B (defined by antigen 4), expresses minor O antigens 1 and 12 and sometimes antigen 5 and expresses Phase 1 flagella which manifest antigen H:i and Phase 2 flagella which manifest antigen H:1,2.

Treatment of *Salmonella* infection continues to be a major public health burden and represents a very significant cost in many countries, particularly countries without adequate access to effective antibiotics or medical care. Millions of human cases are reported worldwide every year and the disease results in thousands of deaths.

In recent years problems related to *Salmonella* infection have increased in terms of incidence and severity. Of particular concern is the emergence of *Salmonella* strains that are resistant to a range of antibiotics.

Thus, there remains a need for a broad spectrum *Salmonella enterica* vaccine that is effective against typhoidal and non-typhoidal *Salmonella*. The present invention provides multivalent conjugate vaccines directed against various *Salmonella enterica* serovars as well as engineered attenuated *Salmonella enterica* serovars for use in vaccines and as reagent strains to produce the multivalent conjugate vaccines of the invention.

SUMMARY OF THE INVENTION

According to non-limiting example embodiments, in one aspect, the invention is directed to a multivalent *Salmonella enterica* serovar conjugate vaccine comprising conjugates from *S. Typhimurium*, *S. Enteritidis*, *S. Choleraesuis*, *S. Typhi* and *S. Paratyphi* A, wherein the conjugates comprise a hapten antigen and a carrier antigen, wherein at least one of the hapten antigens or carrier antigens is characteristic of the *Salmonella enterica* serovar.

In some embodiments, in one or more of the conjugates, the hapten is a polysaccharide antigen from the *Salmonella enterica* serovar and the carrier protein is a phase 1 flagella protein (FliC) or an antigenic fragment or derivative thereof. In some embodiments, the carrier protein is a mutant FliC, namely, $FliC^{I411 4}$. In some embodiments, the polysaccharide is a core-O polysaccharide (COPS) from the *Salmonella enterica* serovar.

In some embodiments, the *Salmonella enterica* vaccine further comprises a *S. Paratyphi* B conjugate comprising core-O polysaccharide (OPS) linked to FliC or $FliC^{I411 4}$.

In some embodiments, one or more of the conjugates are produced from *Salmonella enterica* serovar reagent strains that have one or more mutations. In some embodiments, the one or more mutations are selected from the group consisting of an inactivating mutation in the guaBA locus, an inactivating mutation in the clpP locus, an inactivating mutation in the clpX locus, an inactivating mutation in the IUD locus, an inactivating mutation in the fljB locus, and a I411A substitution mutation in the fliC locus (fliC$^{I411A}$).

In another aspect, the present invention is directed to a method of inducing an immune response, comprising administering to a subject in need thereof an immunologically-effective amount of a multivalent conjugate *Salmonella enterica* vaccine, comprising conjugates from *Salmonella enterica* serovars *S. Typhimurium, S. Enteritidis, S. Choleraesuis, S. Typhi* and *S. Paratyphi* A, wherein the conjugates comprise a hapten antigen and a carrier antigen, wherein at least one of the hapten antigens or carrier antigens is characteristic of the *Salmonella enterica* serovar.

In another aspect, the invention provides an isolated *Salmonella enterica* serovar *S. Typhimurium* for use as a reagent strain, wherein said *S. Typhimurium* comprises the following mutations: an inactivating guaBA mutation; an inactivating mutation in clpP or clpX; an inactivating mutation in fliD; an inactivating mutation in fljB; and optionally fliC$^{I411A}$.

In another aspect, the invention provides an isolated *Salmonella enterica* serovar *S. Enteritidis* for use as a reagent strain, wherein said *S. Enteritidis* comprises the following mutations: an inactivating guaBA mutation; an inactivating mutation in clpP or clpX; an inactivating mutation in fliD; and optionally fliC$^{I411A}$.

In another aspect, the invention provides an isolated *Salmonella enterica* serovar *S. Typhi* for use as a reagent strain, wherein said *S. Typhi* comprises the following mutations: an inactivating guaBA mutation; an inactivating mutation in clpP or clpX; an inactivating mutation in fliD; and optionally fliC$^{I411A}$.

In another aspect, the invention provides an isolated *Salmonella enterica* serovar *S. Paratyphi* A for use as a reagent strain, wherein said *S. Paratyphi* A comprises the following mutations: an inactivating guaBA mutation; an inactivating mutation in clpP or clpX; an inactivating mutation in fliD; and optionally fliC$^{I411A}$.

In another aspect, the invention provides an isolated *Salmonella enterica* serovar *S. Paratyphi* B for use as a reagent strain, wherein said *S. Paratyphi* B comprises the following mutations: an inactivating guaBA mutation; an inactivating mutation in clpP or clpX; an inactivating mutation in fliD; and optionally fliC$^{I411A}$.

In another aspect, the invention provides an isolated *Salmonella enterica* serovar *S. Choleraesuis* for use as a reagent strain, wherein said *S. Choleraesuis* comprises the following mutations: an inactivating guaBA mutation; an inactivating mutation in clpP or clpX; an inactivating mutation in fliD; an inactivating mutation in fljB; and optionally fliC$^{I411A}$.

In another aspect, the invention provides an isolated *Salmonella enterica* serovar *S. Typhimurium* for use as a live vaccine, wherein said *S. Typhimurium* comprises the following mutations: an inactivating guaBA mutation; an inactivating mutation in clpP or clpX; and optionally fliC$^{I411A}$.

In another aspect, the invention provides an attenuated *Salmonella enterica* serovar *S. Enteritidis* for use as a live vaccine, wherein said *S. Enteritidis* comprises the following mutations: an inactivating guaBA mutation; an inactivating mutation in clpP or clpX; and optionally fliC$^{I411A}$.

In another aspect, the invention provides an attenuated *Salmonella enterica* serovar *S. Paratyphi* A for use as a live vaccine, comprising the following mutations: an inactivating guaBA mutation; an inactivating mutation in clpP or clpX; and optionally fliC$^{I411A}$.

In another aspect, the invention provides an attenuated *Salmonella enterica* serovar *S. Paratyphi* B for use as a live vaccine comprising the following mutations: an inactivating guaBA mutation; an inactivating mutation in clpP or clpX; and optionally fliC$^{I411A}$.

In another aspect, the invention provides an attenuated *Salmonella enterica* serovar S. Choleraesuis for use as a live vaccine comprising the following mutations: an inactivating guaBA mutation; an inactivating mutation in clpP or clpX; and optionally fliC$^{I411A}$.

In another aspect, the invention provides a multivalent *Salmonella enterica* vaccine comprising live attenuated *Salmonella enterica* serovars of the invention and further comprising an attenuated *S. Typhi* comprising the following mutations: an inactivating aroC mutation; an inactivating aroD mutation; and an inactivating htrA mutation. In some embodiments, the multivalent vaccine further comprises an attenuated *S. Paratyphi* B of the invention.

BRIEF DESCRIPTION OF THE FIGURES

The skilled artisan will understand that the drawings, described below, are for illustration purposes only. The drawings are not intended to limit the scope of the present teachings in any way.

DETAILED DESCRIPTION OF THE INVENTION

Figure 1:
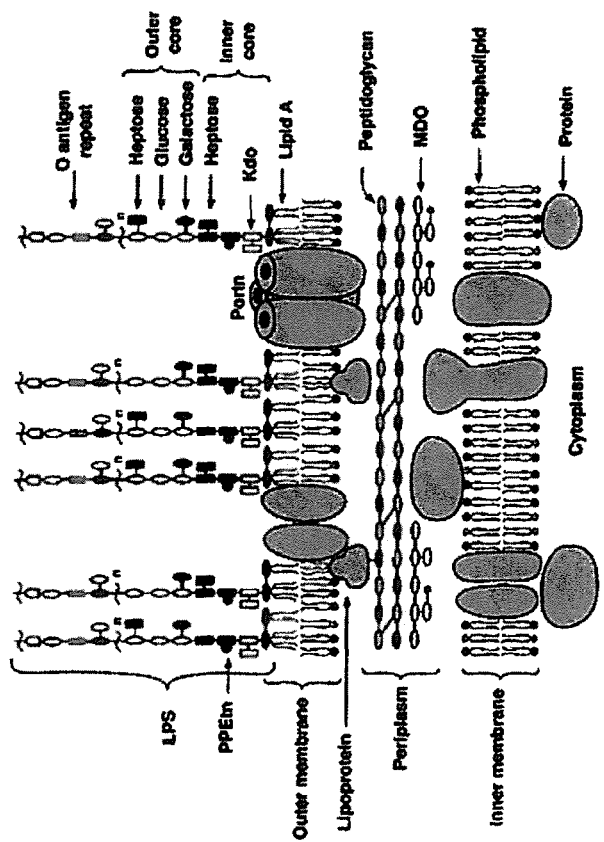
FIG. 1. Structure of the cell wall from a typical Gram-negative bacterium.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar technical references.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

Multivalent Conjugate Vaccine

In one aspect, the present invention provides a multivalent *Salmonella enterica* serovar vaccine capable of inducing an immune response comprising conjugates from S. Typhimurium (serogroup B), S. Enteritidis (serogroup D), S. Choleraesuis (serogroup C), S. Typhi (serogroup D) and S. Paratyphi A (serogroup A), wherein the conjugates comprise a hapten antigen and a carrier antigen, wherein at least one of the hapten antigens or carrier antigens is from the *Salmonella enterica* serovar. In some embodiments, the multivalent vaccine further comprises a conjugate from *Salmonella enterica* serovar *S. Paratyphi* B (serogroup B).

In some embodiments, the multivalent vaccine is a pentavalent *Salmonella enterica* serovar vaccine directed to *S. Typhimurium, S. Enteritidis, S. Choleraesuis, S. Typhi* and *S. Paratyphi* A.

In some embodiments, the multivalent vaccine is a hexavalent *Salmonella enterica* serovar vaccine directed to *S. Typhimurium, S. Enteritidis, S. Choleraesuis, S. Typhi, S. Paratyphi* A and *S. Paratyphi* B.

In some embodiments, the hapten of the serovar conjugate comprises one or more polysaccharides that are characteristic or isolated from the *Salmonella enterica* serovar. In some embodiments, the hapten for one or more of the conjugates of the multivalent vaccine comprises core-O-polysaccharide (COPS). As used herein, "core-O-polysaccharide" or "COPS," is a polysaccharide in which the lipid A moiety from lipopolysaccharide (LPS) has been removed.

In some embodiments, the *S. Typhi* conjugate comprises Vi capsular polysaccharide as the hapten. The Vi capsular polysaccharide of *S. Typhi* is a linear homopolymer of poly-alpha(1-4)GalNAcp variably O acetylated at the C-3 position. See, e.g., Tacket et al., *J. Infect. Diseases*, 190:565-70 (2004); Szu et al., *Infect Immun.* 59(12): 4555-4561 (1991).

The antigenic carrier of the serovar conjugate is non-limiting and can comprise, for example, an antigen that is characteristic or isolated from the same *Salmonella enterica* serovar from which the hapten is derived. In some embodiments, the carrier is a phase 1 flagella protein (FliC) that is characteristic of the *Salmonella enterica* serovar. As used herein, the term "phase 1 flagella" and FliC protein are used interchangeably. "Phase 1 flagella" encompasses: 1] phase 1 flagella expressed from biphasic serovars such as *S. Typhimurium*, where both a phase 1 (FliC) and an additional phase 2 flagella (FljB) are expressed, 2] flagella expressed by monophasic *Salmonella* serovars such as *S. Enteritidis*, which express only one type of flagella (FliC) and 3] fragments or derivatives of FliC. In some embodiments, the carrier is a mutant of FliC with diminished or no capability to activate host inflammatory responses through its interaction with Toll-like receptor 5 (TLR5). In some embodiments, the carrier is the mutant FliC$^{I411A}$, or antigenic fragments thereof which retain the diminished capability to activate host inflammatory responses through TLR5.

In some embodiments, the carrier of the conjugate vaccine is not from a *Salmonella enterica* serovar, and includes antigenic carriers typically used in conjugate vaccines. Non-limiting examples of a carrier for one or more conjugates include tetanus toxin/toxoid, NTHi high molecular weight protein, diphtheria toxin/toxoid, detoxified *Pseudomonas aeruginosa* toxin A, cholera toxin/toxoid, pertussis toxin/toxoid, *Clostridium perfringens* exotoxins/toxoid, hepatitis B surface antigen, hepatitis B core antigen, rotavirus VP 7 protein, respiratory syncytial virus F and G protein, detoxified ETEC LT and genetically engineered mutant derivatives, detoxified *Shigella* Stx1/2 and genetically engineered mutants thereof.

Examples of fragments or derivatives of the Phase 1 flagella protein can include fragments of the natural protein, including internal sequence fragments of the protein that retain their ability to elicit protective antibodies against the *Salmonella* from which it is derived. The derivatives are also intended to include variants of the natural protein such as proteins having changes in amino acid sequence but that retain the ability to elicit an immunogenic, biological, or antigenic property as exhibited by the natural molecule.

By derivative is further meant an amino acid sequence that is not identical to the wild type amino acid sequence, but rather contains at least one or more amino acid changes (deletion, substitutions, inversion, insertions, etc.) that do not essentially affect the immunogenicity or protective antibody responses induced by the modified protein as compared to a similar activity of the wild type amino acid sequence, when used for the desired purpose. In some embodiments, a derivative amino acid sequence contains at least 85-99% homology at the amino acid level to the specific amino acid sequence. In further embodiments, the derivative has at least 90% homology at the amino acid level, while in other embodiments, the derivative has at least 95% homology.

The Phase 1 flagella protein that is conjugated to the polysaccharide in the vaccine of the invention may be a peptide encoding the native amino acid sequence or it may be a derivative or fragment of the native amino acid sequence.

In some embodiments, Phase 1 flagella protein from other serovars of *Salmonella* may also be prepared and used in a similar manner as a slight variability in the sequence of the protein might not alter the biological properties and their functional ability to elicit protective antibodies against other serovars. In some embodiments, a conjugate vaccine comprising a Phase 1 flagella protein from a particular group B serovar can provide protection against other group B serovars, for example, in addition to protection against the group B serovar from which it was derived.

The carriers used in the invention, whether encoding a native protein or a derivative thereof, are conjugated to a hapten, such as COPS by any means that retains the ability of the carrier and/or hapten to induce protective antibodies against *Salmonella*.

As used herein, a polysaccharide or protein is "characteristic" of the *Salmonella enterica* serovar if it is substantially similar or identical in structure or sequence to a molecule naturally associated with the bacteria. The term is intended to include both molecules which are specific to the organism, as well as molecules which, though present on other organisms, are involved in the virulence or antigenicity of the *Salmonella enterica* serovar in a human or animal host.

In some embodiments, the multivalent vaccine comprises one or more conjugates wherein the hapten from one *Salmonella* serovar is conjugated to a carrier from the same *Salmonella* serovar. In some embodiments, the multivalent vaccine comprises one or more conjugates wherein the hapten from one *Salmonella* serovar is conjugated to a carrier from a different *Salmonella* serovar. In some embodiments, the multivalent vaccine comprises one or more conjugates wherein the hapten from one *Salmonella* serovar is conjugated to a carrier that is not from a *Salmonella* serovar.

In some embodiments, one or more of the conjugates of the multivalent vaccine comprises a core-O-polysaccharide (COPS) from a *Salmonella* serovar (selected from *S. Typhimurium, S. Enteritidis,* S. *Choleraesuis, S. Typhi, S. Paratyphi* A, *S. Paratyphi* B and combinations thereof) as the hapten conjugated to a phase 1 flagella (FliC) protein or an antigenic fragment or derivative thereof (including FliC$^{I411A}$) from a *Salmonella* serovar (selected from *S. Typhimurium, S. Enteritidis, S. Choleraesuis, S. Typhi, S. Paratyphi* A, *S. Paratyphi* B and combinations thereof) as the carrier. In some embodiments, COPS from a specific *Salmonella* serovar is conjugated to FliC from the same serovar. In some embodiments, the carrier is a mutant FliC, such as FliC$^{I411A}$.

In some embodiments, the multivalent vaccine comprises conjugates comprising FliC or FliC$^{T411A}$ as the carrier and COPS from a *Salmonella* serovar as the hapten, all of which are from the *Salmonella enterica* serovars *S. Typhimurium, S. Enteritidis, S. Choleraesuis, S. Typhi* and *S. Paratyphi* A.

In some embodiments, the multivalent vaccine comprises *Salmonella enterica* serovar conjugates wherein the *S. Typhimurium* conjugate comprises COPS from *S. Typhimurium* and FliC or FliC$^{T411A}$ from *S. Typhimurium*.

In some embodiments, the multivalent vaccine comprises *Salmonella enterica* serovar conjugates wherein the *S. Enteritidis* conjugate comprises COPS from *S. Enteritidis* and FliC or FliC$^{T411A}$ from *S. Enteritidis*.

In some embodiments, the multivalent vaccine comprises *Salmonella enterica* serovar conjugates wherein the *S. Typhi* conjugate comprises a conjugate selected from the group consisting of: a conjugate comprising Vi from *S. Typhi* as the hapten and FliC or FliC$^{T411A}$ from *S. Typhi* as the carrier; a conjugate comprising Vi from *S. Typhi* as the hapten and tetanus toxoid as the carrier, a conjugate comprising COPS from *S. Typhi* as the hapten and FliC or FliC$^{T411A}$ from *S. Typhi* as the carrier, and a conjugate comprising COPS from *S. Typhi* as the hapten and tetanus toxoid as the carrier.

In some embodiments, the multivalent vaccine comprises *Salmonella enterica* serovar conjugates wherein the *S. Paratyphi* A conjugate comprises COPS from *S. Paratyphi* A and FliC or FliC$^{T411A}$ from *S. Paratyphi* A.

In some embodiments, the multivalent vaccine comprises *Salmonella enterica* serovar conjugates wherein the *S. Paratyphi* B conjugate comprises COPS from *S. Paratyphi* B as the hapten and FliC or FliC$^{T411A}$ from *S. Paratyphi* B as the carrier.

In some embodiments, the multivalent vaccine comprises *Salmonella enterica* serovar conjugates wherein the S. Choleraesuis conjugate comprises COPS from S. Choleraesuis and FliC or FliC$^{T411A}$ from *S. Choleraesuis*.

In some embodiments, the multivalent vaccine comprises *Salmonella enterica* serovar conjugates wherein the *S. Typhimurium* conjugate comprises COPS from *S. Typhimurium* and FliC or FliC$^{T411A}$ from *S. Typhimurium*; the *S. Enteritidis* conjugate comprises COPS from *S. Enteritidis* and FliC or FliC$^{T411A}$ from *S. Enteritidis*; the *S. Paratyphi* A conjugate comprises COPS from *S. Paratyphi* A and FliC or FliC$^{T411A}$ from *S. Paratyphi* A; the *S. Choleraesuis* conjugate comprises COPS from *S. Choleraesuis* and FliC or FliC$^{T411A}$ from *S. Choleraesuis*; and the *S. Typhi* conjugate comprises one or more conjugates selected from the group consisting of: a conjugate comprising Vi from *S. Typhi* as the hapten and FliC or FliC$^{T411A}$ from *S. Typhi* as the carrier; a conjugate comprising Vi from *S. Typhi* as the hapten and tetanus toxoid as the carrier, a conjugate comprising COPS from *S. Typhi* as the hapten and FliC or FliC$^{T411A}$ from *S. Typhi* as the carrier, and a conjugate comprising COPS from *S. Typhi* as the hapten and tetanus toxoid as the carrier. In some embodiments, the multivalent vaccine further comprises a *S. Paratyphi* B conjugate comprising COPS from *S. Paratyphi* B as the hapten and FliC or FliC$^{T411A}$ from *S. Paratyphi* B as the carrier.

In some embodiments, the COPS and/or phase 1 flagella protein of the conjugated vaccine is identical to a molecule which is characteristic of a *Salmonella* serovar, or it can be a derivative or antigenic fragment of such a molecule.

In another embodiment, the invention provides a multivalent conjugate vaccine capable of preventing or attenuating an infection caused by *S. Typhimurium, S. Enteritidis, S. Typhi, S. Paratyphi* A, and *S. Choleraesuis*. In some embodiments, the multivalent conjugate vaccine is also capable of preventing or attenuating an infection caused by *S. Paratyphi* B. In some embodiments, the multivalent conjugate vaccine capable of preventing or attenuating an infection against other serogroup A, B, C or D *Salmonella enterica* strains.

Attenuated *Salmonella enterica* Strains for use as Vaccines and Reagent *Salmonella enterica* Strains to Produce the Multivalent Conjugate Vaccines Vaccine Strains The present invention further provides attenuated *Salmonella enterica* serovars for use as vaccines. The attenuated strains include *Salmonella enterica* serovars *S. Typhimurium, S. Enteritidis, S. Typhi S. Paratyphi* A, *S. Paratyphi* B, and *S. Choleraesuis*.

In some embodiments, the *Salmonella enterica* serovars used as the reagent strains to produce the haptens or carriers of the multivalent conjugate vaccine can also be used as a live or killed *Salmonella enterica* vaccine.

As used herein, attenuated strains are those that have a reduced, decreased, or suppressed ability to cause disease in a subject, or those completely lacking in the ability to cause disease in a subject. Attenuated strains may exhibit reduced or no expression of one or more genes, may express one or more proteins with reduced or no activity, may exhibit a reduced ability to grow and divide, or a combination of two or more of these characteristics. The attenuated strains of the present invention can be living or dead. In some embodiments, the attenuated serovars are administered as a live *Salmonella* vaccine. In some embodiments, the attenuated serovars are administered substantially together as a multivalent vaccine. In some embodiments, the following attenuated serovars are administered: *S. Typhimurium, S. Enteritidis, S. Typhi S. Paratyphi* A, and *S. Choleraesuis*. In some embodiments, an attenuated *S. Paratyphi* B is also administered.

In some embodiments, the attenuated strains are administered independently of the multivalent conjugate vaccine of the invention and induce an immune response in the subject. In some embodiments, a protective immune response is achieved. In other embodiments, the attenuated *Salmonella* strains are administered to a subject as either a priming or boosting composition, along with the multivalent conjugate vaccine of the invention as part of a prime/boost immunization strategy.

In some embodiments, the attenuated strains of the present invention for use as live vaccines have a mutation in one or more of the guaBA locus, the guaB gene, the guaA gene, the clpP gene, the clpX gene and the clpPX locus. For example, the attenuated strains can have a mutation (i) in the guaB gene and the clpP gene, (ii) in the guaA gene and the clpP gene, (iii) in the guaBA locus, and the clpP gene, (iv) in the guaB gene and the clpX gene, (v) in the guaA gene and the clpX gene, (vi) in the guaBA locus, and the clpX gene, (vii) in the guaB gene and the clpPX locus, (viii) in the guaA gene and the clpPX locus, or (ix) in both the guaBA locus and the clpPX locus.

In some embodiments, attenuated *S. Typhimurium, S. Enteritidis, S. Typhi S. Paratyphi* A, *S. Paratyphi* A, and S. Choleraesuis strains are prepared having inactivating mutations (such as chromosomal deletions) in both the guaBA locus (encoding enzymes involved in guanine nucleotide biosynthesis) and the clpPX locus (encoding an important metabolic ATPase) genes. In some embodiments, one or more of the attenuated strains also harbor a fliC$^{T411A}$ mutation.

The mutations of the loci and genes described herein can be any mutation, such as one or more nucleic acid deletions, insertions or substitutions. The mutations can be any deletion, insertion or substitution of the loci or genes that results in a reduction or absence of expression from the loci or genes, or a reduction or absence of activity of a polypeptide encoded by the loci or genes. The mutations may be in the coding or non-coding regions of the loci or genes.

In some embodiments, the chromosomal genome of the Salmonella serovars is modified by removing or otherwise modifying the guaBA locus, and thus blocking the de novo biosynthesis of guanine nucleotides. In some embodiments, a mutation in the guaBA locus inactivates the purine metabolic pathway enzymes IMP dehydrogenase (encoded by guaB) and GMP synthetase (encoded by guaA). In some embodiments, the strains are unable to de novo synthesize GMP, and consequently GDP and GTP nucleotides, which severely limits bacterial growth in mammalian tissues. The ΔguaBA mutants of the present invention are unable to grow in minimal medium unless supplemented with guanine.

In some embodiments, the guaA gene of S. Enteritidis, which encodes GMP synthetase, is 1578 bp in size (GenBank Accession Number NC_011294.1 (2623838-2625415) (SEQ ID NO:1). In some embodiments, the guaA gene of S. Typhimurium, is 1578 bp in size (GenBank Accession Number NC_003197.1 (2622805 . . . 2624382, complement) (SEQ ID NO:2). In some embodiments, the guaA gene of S. Typhi, is 1578 bp in size (GenBank Accession Number NC_004631.1 (415601 . . . 417178) (SEQ ID NO:72). In some embodiments, the guaA gene of S. Paratyphi A, is 1578 bp in size (GenBank Accession Number NC_006511.1 (421828 . . . 423405) (SEQ ID NO:73). In some embodiments, the guaA gene of S. Paratyphi B is 1578 bp in size (GenBank Accession Number NC_010102.1 (418694 . . . 420271) (SEQ ID NO:74). In some embodiments, the guaA gene of S. Choleraesuis is 1578 bp in size (GenBank Accession Number NC_006905.1 (2643546 . . . 2645123, complement) (SEQ ID NO:75). Deletion mutants can be produced by eliminating portions of the coding region of the guaA gene so that proper folding or activity of GuaA is prevented. For example, about 25 to about 1500 bp, about 75 to about 1400 bp, about 100 to about 1300 bp, or all of the coding region can be deleted. Alternatively, the deletion mutants can be produced by eliminating, for example, a 1 to 100 bp fragment of the guaA gene so that the proper reading frame of the gene is shifted. In the latter instance, a nonsense polypeptide may be produced or polypeptide synthesis may be aborted due to a frame-shift-induced stop codon. The preferred size of the deletion removes both guaB and guaA, from the ATG start codon of guaB to the stop codon of guaA.

In some embodiments, the guaB gene of S. Enteritidis which encodes IMP dehydrogenase, is 1467 bp in size (GenBank Accession Number NC_011294.1 (2625485-2626951, complement) (SEQ ID NO:3). In some embodiments, the guaB gene of S. Typhimurium is 1467 bp in size (GenBank Accession Number NC_003197.1 (2624452 . . . 2625918, complement) (SEQ ID NO:4). In some embodiments, the guaB gene of S. Typhi, is 1473 bp in size (GenBank Accession Number NC_004631.1 (414059 . . . 415531)) (SEQ ID NO:76). In some embodiments, the guaB gene of S. Paratyphi A is 1467 bp in size (GenBank Accession Number NC_006511.1 (420292 . . . 421758) (SEQ ID NO:77). In some embodiments, the guaB gene of S. Paratyphi B, is 1551 bp in size (GenBank Accession Number NC_010102.1 (417074 . . . 418624) (SEQ ID NO:78). In some embodiments, the guaB gene of S. Choleraesuis is 1467 bp in size (SEQ ID NO:104) (the genome sequence of S. Choleraesuis strain SC-B67 can be found in GenBank Accession Number NC_006905.1). Deletion mutants can be produced by eliminating portions of the coding region of the guaB gene so that proper folding or activity of GuaB is prevented. For example, about 25 to about 1400 bp, about 75 to about 1300 bp, about 100 to about 1200 bp, or all of the coding region can be deleted. Alternatively, the deletion mutants can be produced by eliminating, for example, a 1 to 100 bp fragment of the guaB gene so that the proper reading frame of the gene is shifted. In the latter instance, a nonsense polypeptide may be produced or polypeptide synthesis may be aborted due to a frame-shift-induced stop codon. The preferred size of the deletion removes both guaB and guaA, from the ATG start codon of guaB to the stop codon of guaA.

In some embodiments, the clpP gene of S. Enteritidis, which encodes a serine-protease, is 624 bp in size (GenBank Accession Number NC_011294.1 (482580-483203) (SEQ ID NO:5). In some embodiments, the clpP gene of S. Typhimurium is 624 bp in size (GenBank Accession Number NC_003197.1 (503210 . . . 503833) (SEQ ID NO:6). In some embodiments, the clpP gene of S. Typhi is 624 bp in size (GenBank Accession Number NC_004631.1 (2485120 . . . 2485743, complement)) (SEQ ID NO:79). In some embodiments, the clpP gene of S. Paratyphi A is 624 bp in size (GenBank Accession Number NC_006511.1 (2369275 . . . 2369898, complement) (SEQ ID NO:80). In some embodiments, the clpP gene of S. Paratyphi B, is 732 bp in size (GenBank Accession Number NC_010102.1 (2614575 . . . 2615306, complement) (SEQ ID NO:81). In some embodiments, the clpP gene of S. Choleraesuis is 624 bp in size (GenBank Accession Number NC_006905.1 (547568 . . . 548191) (SEQ ID NO:82). Deletion mutants can be produced by eliminating portions of the coding region of the clpP gene so that proper folding or activity of ClpP is prevented. For example, about 25 to about 600 bp, about 75 to about 500 bp, about 100 to about 400 bp, or all of the coding region can be deleted. Alternatively, the deletion mutants can be produced by eliminating, for example, a 1 to 100 bp fragment of the clpP gene so that the proper reading frame of the gene is shifted. In the latter instance, a nonsense polypeptide may be produced or polypeptide synthesis may be aborted due to a frame-shift-induced stop codon. clpP forms an operon with clpX; the preferred size of the deletion encompasses only the downstream clpX gene and extends from the ATG start codon to the stop codon, inclusive.

In some embodiments, the clpX gene of S. Enteritidis, which encodes a chaperone ATPase, is 1272 bp in size (GenBank Accession Number NC_011294.1 (483455-484726) (SEQ ID NO:7). In some embodiments, the clpX gene of S. Typhimurium is 1272 bp in size (GenBank Accession Number NC_003197.1 (504085 . . . 505356) (SEQ ID NO:8). In some embodiments, the clpX gene of S. Typhi, is 1272 bp in size (GenBank Accession Number NC_004631.1 (2483597 . . . 2484868, complement)) (SEQ ID NO:83). In some embodiments, the clpX gene of S. Paratyphi A is 1272 bp in size (GenBank Accession Number NC_006511.1 (2367752 . . . 2369023, complement) (SEQ ID NO:84). In some embodiments, the clpX gene of S. Paratyphi B is 1272 bp in size (GenBank Accession Number NC_010102.1 (2613052 . . . 2614323, complement) (SEQ ID NO:85). In some embodiments, the clpX gene of S. Choleraesuis is 1272 bp in size (GenBank Accession Number NC_006905.1 (548443 . . . 549714) (SEQ ID NO:86). Deletion mutants can be produced by eliminating portions of the coding region of the clpX gene so that proper folding or activity of ClpX is prevented. For example, about 25 to about 1200 bp, about 75 to about 1100 bp, about 100 to about 1000 bp, or all of the coding region can be deleted. Alternatively, the deletion mutants can be produced by eliminating, for example, a 1 to 100 bp fragment of the clpX gene so that the proper reading frame of the gene is shifted. In the latter instance, a nonsense polypeptide may be produced or polypeptide synthesis may be aborted due to a frame-shift-induced stop codon. clpP forms an operon with clpX; the preferred size of the deletion encompasses only the downstream clpX gene and extends from the ATG start codon to the stop codon, inclusive.

In some embodiments, the attenuated S. Typhi stain carries inactivating mutations in the aroC, aroD, and htrA genes. In some embodiments, the aroC gene of S. Typhi is 1086 bp in size (GenBank Accession Number NC_004631.1 (554066 ... 555151) (SEQ ID NO:87). In some embodiments, the aroD gene of S. Typhi is 759 bp in size (GenBank Accession NC_004631.1 (1298692 ... 1299450, complement) (SEQ ID NO:88). In some embodiments, the htrA gene of S. Typhi is 1428 bp in size (GenBank Accession Number NC_004631.1 (241491 ... 242918)) (SEQ ID NO:89).

The fliC gene can be mutated to fliC$^{I411A}$ using conventional techniques known in the art. The fliC gene encodes a flagellin protein. In some embodiments, the fliC gene from S. Enteritidis is 1518 bp in size (GenBank Accession Number NC_011294.1 (1146600 ... 1148117) (SEQ ID NO:90). In some embodiments, the fliC gene of S. Typhimurium is 1488 bp in size (GenBank Accession Number NC_003197.1 (2047658 ... 2049145, complement) (SEQ ID NO:91). In some embodiments, the fliC gene of S. Typhi is 1521 bp in size (GenBank Accession Number NC_004631.1 (1013788 ... 1015308) (SEQ ID NO:92). In some embodiments, the fliC gene of S. Paratyphi A, is 1488 bp in size (GenBank Accession Number NC_006511.1 (989787 ... 991274) (SEQ ID NO:93). In some embodiments, the fliC gene of S. Paratyphi B, is 1488 bp in size (GenBank Accession Number NC_010102.1 (1060540 ... 1062027) (SEQ ID NO:94). In some embodiments, the fliC gene of S. Choleraesuis is 1506 bp in size (GenBank Accession Number NC_006905.1 (2069412 ... 2070917, complement) (SEQ ID NO:95). Given that the size of FliC varies with serovar, we stipulate here that the engineering of the desired mutation fliC$^{I411A}$ for a given serovar, hereafter referred to as fliC$^{I411A}$ regardless of serovar, is understood to apply to all FliC proteins such that the codon encoding residue 411 (directly corresponding to isoleucine for S. Typhimurium), or the corresponding residue of a larger FliC protein, will be re-engineered to encode the new residue alanine.

In some embodiments, the live attenuated Salmonella enterica serovars have the following genotypes:

| Serovar | O group | H type (Phase 1; Phase 2) | Name | Live attenuated vaccine Genotype |
|---|---|---|---|---|
| Typhimurium | B | i; 1, 2 | CVD 1931 | ΔguaBA ΔclpX<br>ΔguaBA ΔclpX fliC$^{I411A}$ |
| Enteritidis | D | g, m | CVD 1944 | ΔguaBA ΔclpX<br>ΔguaBA ΔclpX fliC$^{I411A}$ |
| Typhi | D | d | CVD 908 htrA | ΔaroC ΔaroD ΔhtrA<br>(CVD 908 htrA)<br>or |
| | | | CVD 909 | ΔaroC ΔaroD ΔhtrA P$_{tac}$-tviABCDE |
| Paratyphi A | A | a | CVD 1902 | ΔguaBA ΔclpX<br>ΔguaBA ΔclpX fliC$^{I411A}$ |
| Paratyphi B | B | b | | ΔguaBA ΔclpX<br>ΔguaBA ΔclpX fliC$^{I411A}$ |
| Choleraesuis | C | c; 1, 5 | | ΔguaBA ΔclpX<br>ΔguaBA ΔclpX fliC$^{I411A}$ |

In some embodiments, S. Enteritidis strain R11 is used as the starting material strain in constructing the live attenuated S. Enteritidis vaccine. In some embodiments, S. Typhimurium strain 177 is used as starting material strain to construct the S. Typhimurium attenuated strain.

In some embodiments, deletions can be made in any of the loci or genes included herein by using convenient restriction sites located within the loci or genes, or by site-directed mutagenesis with oligonucleotides (Sambrook et al., *Molecular Cloning, A Laboratory Manual*, Eds., Cold Spring Harbor Publications (1989)).

In some embodiments, inactivation of the loci or genes can also be carried out by an insertion of foreign DNA using any convenient restriction site, or by site-directed mutagenesis with oligonucleotides (Sambrook et al., supra) so as to interrupt the correct transcription of the loci or genes. The typical size of an insertion that can inactivate the loci or genes is from 1 base pair to 100 kbp, although insertions smaller than 100 kbp are preferable. In some embodiments, the insertion can be made anywhere inside the loci or gene coding regions or between the coding regions and the promoters. In some embodiments, the bacterial loci and genes are mutated using Lambda Red-mediated mutagenesis (see, e.g., Datsenko and Wanner, *PNAS USA* 97:6640-6645 (2000)).

The attenuated live strains of the present invention can be administered to a subject to induce an immune response. In some embodiments, the immune response confers protective immunity on the subject upon subsequent challenge with any of S. Typhimurium, S. Enteritidis, S. Typhi S. Paratyphi A, S. Paratyphi B or S. Choleraesuis. In some embodiments, live attenuated serovars are administered as a multivalent vaccine in a pharmaceutical composition with one or more pharmaceutically acceptable excipients.

In general, the amount of an immunizing composition administered to a subject is an amount sufficient to induce an immune response in the subject to a S. Typhimurium, S. Enteritidis, S. Typhi S. Paratyphi A, S. Paratyphi B or S. Choleraesuis strain or to the selected antigen being expressed by the serovar (an immunologically-effective amount).

In some embodiments, the attenuated strains are administered live and mucosally. In some embodiments, the dosage employed for mucosal delivery will contain about $10^5$ cfu to $10^{10}$ cfu of each serovar, in some embodiments, about $10^5$ cfu to $10^7$ cfu, or about $10^6$ cfu to $10^9$ cfu.

The immunizing compositions comprising the live attenuated *Salmonella* serovars may be administered in a single dose, or in multiple doses over prolonged periods of time. In particular, the immunizing compositions may be administered over a period of one week, two weeks, three weeks, one month, six weeks, two months, ten weeks, three months, four months, six months, one year, or for extended periods longer than one year.

The immunizing compositions comprising the live attenuated *Salmonella* serovars may be provided in dosage units for uniform dosage and ease of administration. Each dosage unit form contains a predetermined quantity of the strains of the present invention calculated to produce a desired immune response, in association with a pharmaceutically acceptable carrier, excipient, or other ingredient.

In some embodiments, the compositions of the attenuated *Salmonella* serovars are administered as live vaccines. In other embodiments, the attenuated *Salmonella* serovars are killed formulations, e.g., by heat, prior to administration.

Reagent Strains

In some embodiments, the haptens and/or carriers of the multivalent conjugate vaccines of the invention can be isolated from wild-type, modified or attenuated *Salmonella enterica* strains (selected from S. Typhimurium, S. Enteritidis, S. Choleraesuis, S. Typhi, S. Paratyphi A and S. Paratyphi B). In some embodiments, the COPS and Phase 1 flagella protein are isolated from attenuated *Salmonella* enteric serovars having one or more mutations. In some embodiments, the one or more mutations are selected from the group consisting of an inactivating mutation in the guaBA locus, an inactivating mutation in the clpP locus, an inactivating mutation in the clpX locus, an inactivating mutation in the IUD locus, an inactivating mutation in the fljB locus, and an I411A substitution mutation in the fliC locus (fliC$^{I411A}$). Combinations of attenuating mutations are further contemplated in accordance with the invention. In some embodiments, one or more of the conjugates are produced from *Salmonella enterica* serovar reagent strains described herein.

In accordance with the invention, the invention further provides *Salmonella enterica* serovar reagent strains for use in isolating haptens and/or carriers of the multivalent conjugate vaccine of the invention, as well as methods of isolating and purifying the haptens and carriers from the reagent strains. In some embodiments, the strains have been attenuated and optimized to improve yields and harvesting of carrier protein for production of the conjugates.

In some embodiments, clpP or clpX is inactivated. *Salmonella* serovars harboring a mutation in either the clpP or clpX genes are hyper-flagellated yet do not exhibit diminished bacterial cell growth at 30° or 37° C.

In some embodiments, the guaBA locus, the guaB gene, or the guaA gene (encoding enzymes involved in guanine nucleotide biosynthesis) can be mutated resulting in an attenuating mutation.

In some embodiments, a mutation in the fliD gene, flgL gene, or flgK gene causes export of flagellin monomers into the supernatant. Therefore, in some embodiments, an attenuated *Salmonella enterica* strain of the invention can be further engineered to contain an additional mutation in either the fliD gene, flgL gene, or flgK gene to export FliC monomers into the extracellular medium. In a preferred embodiment, FliD will be mutated. In some embodiments, the fliD gene from *S. Enteritidis* is 1407 bp in size (GenBank Accession Number NC_011294.1 (1144938 . . . 1146344, complement) (SEQ ID NO:96). In some embodiments, the fliD gene of *S. Typhimurium* is 1404 bp in size (GenBank Accession Number NC_003197.1 (2049402 . . . 2050805) (SEQ ID NO:97). In some embodiments, the fliD gene of *S. Typhi* is 1404 bp in size (GenBank Accession Number NC_004631.1 (1012128 . . . 1013531, complement) (SEQ ID NO:98). In some embodiments, the IUD gene of *S. Paratyphi* A, is 1404 bp in size (GenBank Accession Number NC_006511.1 (988127 . . . 989530, complement) (SEQ ID NO:99). In some embodiments, the fliD gene of *S. Paratyphi* B, is 1404 bp in size (GenBank Accession Number NC_010102.1 (1058880 . . . 1060283, complement) (SEQ ID NO:100). In some embodiments, the fliD gene of *S. Choleraesuis* is 1404 bp in size (GenBank Accession Number NC_006905.1 (2071174 . . . 2072577) (SEQ ID NO:101).

In some embodiments, the fljB gene of *S. Typhimurium* and *S. Choleraesuis* is also deleted, which encodes an alternate phase 2 flagellin (FljB). In some embodiments, the fljB gene of *S. Typhimurium* is 1521 bp in size (GenBank Accession Number NC_003197.1 (2913230 . . . 2914750, complement) (SEQ ID NO:102). The fljB gene of S. Choleraesuis may not have to be deleted, depending on the parent strain to be used in constructing attenuations. For the sequenced strain SC-B67, fljB is a pseudogene, apparently inactivated by a Tn10-like insertion. In some embodiments, this pseudogene is 2859 bp in size (GenBank Accession Number NC_006905.1 (2866574 . . . 2869432, complement) (SEQ ID NO:103).

In some embodiments, the *Salmonella* serovar reagent strains are engineered to overexpress FliC Phase 1 flagella monomers. In some embodiments, the reagent strains harbor the mutation fliC$^{I411A}$, the gene product of which in some embodiments is used as the carrier antigen. In some embodiments, the Phase 1 flagella protein is recombinantly produced, for example, in *E. coli*.

In some embodiments, the following reagent strains as shown below can theoretically be used to produce haptens and/or carriers for the conjugate vaccines:

| Serovar | O Group | H type (Phase 1; Phase 2) | Reagent Strain Name | Genotype | Conjugate vaccine Hapten | Carrier |
|---|---|---|---|---|---|---|
| *Typhimurium* | B | i; 1, 2 | CVD 1925 | ΔguaBA ΔclpP ΔfliD ΔfljB | COPS | FliC |
| | | | CVD 1928 | ΔguaBA ΔclpP (ΔfliD) ΔfljB fliC$^{I411A}$ | COPS | FliC $^{I411A}$ |
| *Enteritidis* | D | g, m | CVD 1943 | ΔguaBA ΔclpP ΔfliD | COPS | FliC |
| | | | CVD 1948 | ΔguaBA ΔclpP (ΔfliD) fliC$^{I411A}$ | COPS | FliC $^{I411A}$ |
| *Typhi* | D | d | | ΔguaBA ΔclpP or clpX ΔfliD | Vi | Tetanus toxoid |
| | | | | ΔguaBA ΔclpP or clpX ΔfliD | Vi | FliC |
| | | | | ΔguaBA ΔclpP or clpX (ΔfliD) fliC$^{I411A}$ | Vi | FliC $^{I411A}$ |
| *Paratyphi* A | A | a | | ΔguaBA ΔclpP or clpX ΔfliD | COPS | FliC |
| | | | | ΔguaBA ΔclpP or clpX (ΔfliD) fliC$^{I411A}$ | COPS | FliC $^{I411A}$ |
| *Paratyphi* B | B | b | | ΔguaBA ΔclpP or clpX ΔfliD | COPS | FliC |
| | | | | ΔguaBA ΔclpP or clpX (ΔfliD) fliC$^{I411A}$ | COPS | FliC $^{I411A}$ |
| *Choleraesuis* | C | c; 1, 5 | | ΔguaBA ΔclpP or clpX ΔfliD ΔfljB | COPS | FliC |
| | | | | ΔguaBA ΔclpP or clpX (ΔfliD) ΔfljB fliC$^{I411A}$ | COPS | FliC $^{I411A}$ |

In some embodiments, the invention provides an isolated *Salmonella enterica* serovar *S. Typhimurium* for use as a reagent strain, wherein said *S. Typhimurium* comprises the following mutations: an inactivating guaBA mutation; an inactivating mutation in clpP or clpX; an inactivating mutation in fliD; an inactivating mutation in fljB; and optionally fliC$^{J411.4}$.

In some embodiments, the invention provides an isolated *Salmonella enterica* serovar *S. Enteritidis* for use as a reagent strain, wherein said *S. Enteritidis* comprises the following mutations: an inactivating guaBA mutation; an inactivating mutation in clpP or clpX; an inactivating mutation in fliD; and optionally fliC$^{I411A}$.

In some embodiments, the invention provides an isolated *Salmonella enterica* serovar *S. Typhi* for use as a reagent strain, wherein said *S. Typhi* comprises the following mutations: an inactivating guaBA mutation; an inactivating mutation in clpP or clpX; an inactivating mutation in fliD; and optionally fliC$^{I411A}$. In some embodiments, Vi for use in the *S. Typhi* conjugate can be purified from other strains, such as other attenuated *S. Typhi*, wild-type *S. Typhi* or Vi+ *Citrobacter* strains.

In some embodiments, the invention provides an isolated *Salmonella enterica* serovar *S. Paratyphi* A for use as a reagent strain, wherein said *S. Paratyphi* A comprises the following mutations: an inactivating guaBA mutation; an inactivating mutation in clpP or clpX; an inactivating mutation in fliD; and optionally fliC$^{I411A}$.

In some embodiments, the invention provides an isolated *Salmonella enterica* serovar *S. Paratyphi* B for use as a reagent strain, wherein said *S. Paratyphi* B comprises the following mutations: an inactivating guaBA mutation; an inactivating mutation in clpP or clpX; an inactivating mutation in fliD; and optionally fliC$^{I411A}$.

In some embodiments, the invention provides an isolated *Salmonella enterica* serovar S. Choleraesuis for use as a reagent strain, wherein said S. Choleraesuis comprises the following mutations: an inactivating guaBA mutation; an inactivating mutation in clpP or clpX; an inactivating mutation in fliD; an inactivating mutation in fljB if functionally present in the parent strain; and optionally fliC$^{I411A}$.

Methods of Inducing an Immune Response

The present invention also includes methods of inducing an immune response in a subject. In some embodiments, the immune response can be to one or more of the attenuated *S. Salmonella* serovars of the invention, one or more of the conjugates of the multivalent conjugate vaccine of the invention, or to some combination thereof.

In one embodiment, the method of inducing an immune response comprises administering one or more (or all) of the attenuated *Salmonella enterica* serovars of the present invention to a subject in an amount sufficient to induce an immune response in the subject. All serovars do not have to be administered within the same inoculum, but may be divided into separate doses administered on sequential days to achieve complete coverage.

In a further embodiment, the method of inducing an immune response comprises administering a multivalent conjugate vaccine of the present invention to a subject in an amount sufficient to induce an immune response in the subject.

As used herein, an "immune response" is the physiological response of the subject's immune system to an immunizing composition. An immune response may include an innate immune response, an adaptive immune response, or both. In some embodiments of the present invention, the immune response is a protective immune response. A protective immune response confers immunological cellular memory upon the subject, with the effect that a secondary exposure to the same or a similar antigen is characterized by one or more of the following characteristics: shorter lag phase than the lag phase resulting from exposure to the selected antigen in the absence of prior exposure to the immunizing composition; production of antibody which continues for a longer period than production of antibody resulting from exposure to the selected antigen in the absence of prior exposure to the immunizing composition; a change in the type and quality of antibody produced in comparison to the type and quality of antibody produced upon exposure to the selected antigen in the absence of prior exposure to the immunizing composition; a shift in class response, with IgG antibodies appearing in higher concentrations and with greater persistence than IgM, than occurs in response to exposure to the selected antigen in the absence of prior exposure to the immunizing composition; an increased average affinity (binding constant) of the antibodies for the antigen in comparison with the average affinity of antibodies for the antigen resulting from exposure to the selected antigen in the absence of prior exposure to the immunizing composition; and/or other characteristics known in the art to characterize a secondary immune response.

In some embodiments, the invention is directed to methods of inducing an immune response, comprising administering to a subject in need thereof an immunologically-effective amount of a multivalent conjugate *Salmonella enterica* vaccine, comprising conjugates from *Salmonella enterica* serovars *S. Typhimurium, S. Enteritidis, S. Choleraesuis, S. Typhi* and *S. Paratyphi* A, wherein the conjugates comprise a hapten antigen and a carrier antigen, wherein at least one of the hapten antigens or carrier antigens is from the *Salmonella enterica* serovar. In some embodiments, the hapten antigen is a core-O polysaccharide (COPS) from the *Salmonella enterica* serovar and the carrier is a phase 1 flagella protein (FliC) or an antigenic fragment or derivative thereof from the *Salmonella enterica* serovar. In some embodiments, the carrier is FliC$^{I411A}$. In some embodiments, the multivalent vaccine further comprises a conjugate comprising COPS and FliC or FliC$^{I411A}$ from *S. Paratyphi* B.

In some embodiments, the invention is directed to methods of inducing an immune response, comprising administering to a subject in need thereof a vaccine comprising an immunologically-effective amount of genetically modified attenuated *Salmonella* serovar as described herein selected from the group consisting of *S. Typhimurium, S. Enteritidis, S. Choleraesuis, S. Typhi, S. Paratyphi* A, and *S. Paratyphi* B and combinations thereof.

In some embodiments, the immunogenicity of the conjugates of the invention is greater than the immunogenicity of at least one of the carriers alone. Methods of measuring immunogenicity are well known to those in the art and primarily include measurement of serum antibody including measurement of amount, avidity, and isotype distribution at various times after injection of the conjugate vaccine. Greater immunogenicity may be reflected by a higher titer and/or increased life span of the antibodies. Immunogenicity may also be measured by the ability to induce protection to challenge with noxious substances or virulent organisms. Immunogenicity may also be measured by the ability to immunize neonatal and/or immune deficient mice. Immunogenicity may be measured in the patient population to be treated or in a population that mimics the immune response of the patient population.

In some embodiments, the immune response that is generated by the multivalent conjugate vaccine or attenuated *Salmonella* serovars is a protective immune response against infection by one or more *Salmonella enterica* serovars, including those serovars described herein.

In some embodiments, the multivalent conjugate vaccine is administered alone in a single dose or administered in sequential doses. In other aspects of the invention, the multivalent conjugate vaccine is administered as a component of a homologous or heterologous prime/boost regimen in conjunction with one or more vaccines, such as a subunit vaccine or one or more attenuated *Salmonella enterica* servovars as described herein. In some embodiments of the invention, a single boost is used. In some embodiments of the invention, multiple boost immunizations are performed. In particular aspects of the invention drawn to a heterologous prime/boost, a mucosal bacterial prime/parenteral conjugate boost immunization strategy is used. For example, one or more (or all) of the live (or killed) attenuated *Salmonella enterica* serovars as taught herein can be administered orally to a subject and the subject can be subsequently boosted parentally with a multivalent conjugate vaccine as described herein.

In another aspect, the invention is directed to methods of inducing an immune response, comprising administering to a subject in need thereof a first multivalent vaccine comprising an immunologically-effective amount of genetically modified attenuated *Salmonella* serovars as described herein and a second multivalent vaccine comprising immunologically-effective amounts of conjugates comprising the homologous COPS and FliC or FliC$^{T411A}$ protein or a fragment or a derivative thereof. In one embodiment, a subject is orally administered attenuated live strains of *S. Typhimurium, S. Enteritidis, S. Choleraesuis, S. Typhi S. Paratyphi* A, and optionally *S. Paratyphi* B of the invention, followed by a boost immunization administered parenterally, comprising a multivalent conjugate vaccine of the invention, which in some embodiments, comprises COPS covalently linked to FliC or FliC$^{T411A}$ (for conjugates from *S. Typhimurium, S. Enteritidis*, S. Choleraesuis, S. Paratyphi A, and optionally *S. Paratyphi* B) and Vi covalently linked to tetanus toxoid, FliC or FliC$^{T411A}$ (for the *S. Typhi* conjugate).

The present invention is not limited to the order in which attenuated *Salmonella* serovars and the multivalent conjugate vaccine is administered. In some embodiments, the time interval between the first and second vaccinations is one week, two weeks, three weeks, 1 month, 2 months, 3 months, 4 months, 5 months, 6 months, 7 months, 8 months, 9 months, 10 months, 11 months, one year, 1.5 years and two years. Immunization schedules have been scheduled and administered at 1 month intervals, with a priming immunization followed by two sequential booster immunizations.

In practicing immunization protocols for treatment and/or prevention, an immunologically-effective amount of conjugate is administered to a subject. As used herein, the term "immunologically-effective amount" means the total amount of therapeutic agent (e.g., conjugate) or other active component that is sufficient to show an enhanced immune response in the subject. When "immunologically-effective amount" is applied to an individual therapeutic agent administered alone, the term refers to that therapeutic agent alone. When applied to a combination, the term refers to combined amounts of the ingredients that result in the therapeutic effect, whether administered in combination, serially or simultaneously, and regardless of order of administration.

The particular dosage depends upon the age, weight, sex and medical condition of the subject to be treated, as well as on the method of administration. Suitable doses can be readily determined by those of skill in the art.

The multivalent conjugate vaccine of the invention can be administered by either single or multiple dosages of an effective amount. In some embodiments, an effective amount of the compositions of the invention can vary from 0.01-5,000 µg/ml per dose. In other embodiments, an effective amount of the composition of the invention can vary from 0.1-500 µg/ml per dose, and in other embodiments, it can vary from 10-300 µg/ml per dose. In one embodiment, the dosage of the conjugate administered will range from about 10 µg to about 1000 µg. In another embodiment, the amount administered will be between about 20 µg and about 500 µg. In some embodiments, the amount administered will be between about 75 µg and 250 µg. Greater doses may be administered on the basis of body weight. The exact dosage can be determined by routine dose/response protocols known to one of ordinary skill in the art.

In some embodiments, the amount of conjugate that provides an immunologically-effective amount for vaccination against bacterial infection is from about 1 µg or less to about 100 µg or more. In some embodiments, it is from about 2, 3, 4, 5, 6, 7, 8, 9, 10, 15, 20, 25, 30, 35, 40, 45 or 50 µg to about 55, 60, 65, 70, 75, 80, 85, 90, or 95 µg per kg body weight. In some embodiments, the immunologically-effective amount for vaccination against bacterial infection is from 0.01 µg to 10 µg.

The term "subject" as used herein, refers to animals, such as mammals. For example, mammals contemplated include humans, primates, dogs, cats, sheep, cattle, goats, pigs, horses, chickens, mice, rats, rabbits, guinea pigs, and the like. The terms "subject", "patient", and "host" are used interchangeably.

The multivalent conjugate vaccine of the present invention may confer resistance to *Salmonella enterica* infections by either passive immunization or active immunization. In one embodiment of passive immunization, the vaccine is provided to a subject (i.e. a human or mammal), and the elicited antisera is recovered and directly provided to a recipient suspected of having an infection caused by a *Salmonella enterica* serovar as described herein.

In some embodiments, the present invention provides a means for preventing or attenuating infection by *S. Typhimurium, S. Enteritidis, S. Typhi, S. Paratyphi* A, *S. Paratyphi* B, or S. Choleraesuis or by organisms which have antigens that can be recognized and bound by antisera to the polysaccharide and/or protein of either the multivalent conjugate vaccine or the attenuated bacterial vaccine strains.

The administration of the vaccine (or the antisera which it elicits) may be for either a "prophylactic" or "therapeutic" purpose. When provided prophylactically, the vaccine is provided in advance of any symptom of *Salmonella* infection. The prophylactic administration of the vaccine serves to prevent or attenuate any subsequent infection. When provided therapeutically, the vaccine is provided upon the detection of a symptom of actual infection. The therapeutic administration of the vaccine serves to attenuate any actual infection.

Either the multivalent conjugate vaccine (or antisera which it elicits) or the attenuated bacterial vaccine strains of the present invention may, thus, be provided either prior to the onset of infection (so as to prevent or attenuate an anticipated infection) or after the initiation of an actual infection.

The multivalent conjugate vaccine of the invention may be administered to warm-blooded mammals of any age. The multivalent conjugate vaccines can be administered as a single dose or in a series including one or more boosters. In some embodiments, the immunization schedule would involve a primary series of three immunizations with a spacing of 1-2 months between the doses. In some settings a booster dose could be administered ~6-12 months later. For example, an infant can receive three doses at 6, 10 and 14 weeks of age (schedule for infants in sub-Saharan Africa) or at 2, 4, and 6 months of life (schedule for U.S. infants). In some embodiments, U.S. infants might receive a booster at 12-18 months of age. Another target population would be U.S. elderly who would likely receive 2-3 doses spaced 1-2 months apart.

Preparing the Conjugates for the Multivalent Vaccine

The carrier antigen can be purified and isolated using conventional techniques and methods. Such methods can include mechanical shearing, removal at low pH, heating or purification from bacterial supernatants. Methods of purification of a flagellin protein from whole flagella are known in the art or can be readily modified by one of ordinary skill in the art using methods know in the art. For example, by modifying the method of Ibrahim et al., purification of flagella is achieved; below pH 3.0, flagella dissociate into flagellin subunits (Ibrahim et al. *J. Clin. Microbiol.* 1985; 22:1040-4). Further methods for purification include adaptation of the mechanical shearing, and sequential centrifugation steps for purification of flagellin in flagella from bacterial cells. In other aspects of the invention, export of a flagellin protein monomer from an attenuated *Salmonella enterica* reagent strain as discussed herein is used to derive a flagellin protein used to construct a conjugate vaccine of the invention. In some embodiments, the carrier protein, such as FliC or FliC$^{T411A}$ is purified from the bacterial supernatant of the *Salmonella enterica* serovar reagent strains described herein by chromotagraphic methods. In some embodiments, the carrier protein, such as FliC or FliC$^{T411A}$ is purified by mechanical shearing.

In some embodiments, purification and isolation of the hapten can be accomplished using conventional techniques and methods. In some embodiments, COPS can be isolated by methods including, but not limited to mild acid hydrolysis removal of lipid A from LPS. Other embodiments may include use of hydrazine as an agent for COPS preparation. Preparation of LPS can be accomplished by known methods in the art. In some embodiments, LPS is prepared according to methods of Darveau et al. *J. Bacteriol.*, 155(2):831-838 (1983), or Westphal et al. *Methods in Carbohydrate Chemistry.* 5:83-91 (1965) which are incorporated by reference herein.

Figure 8:
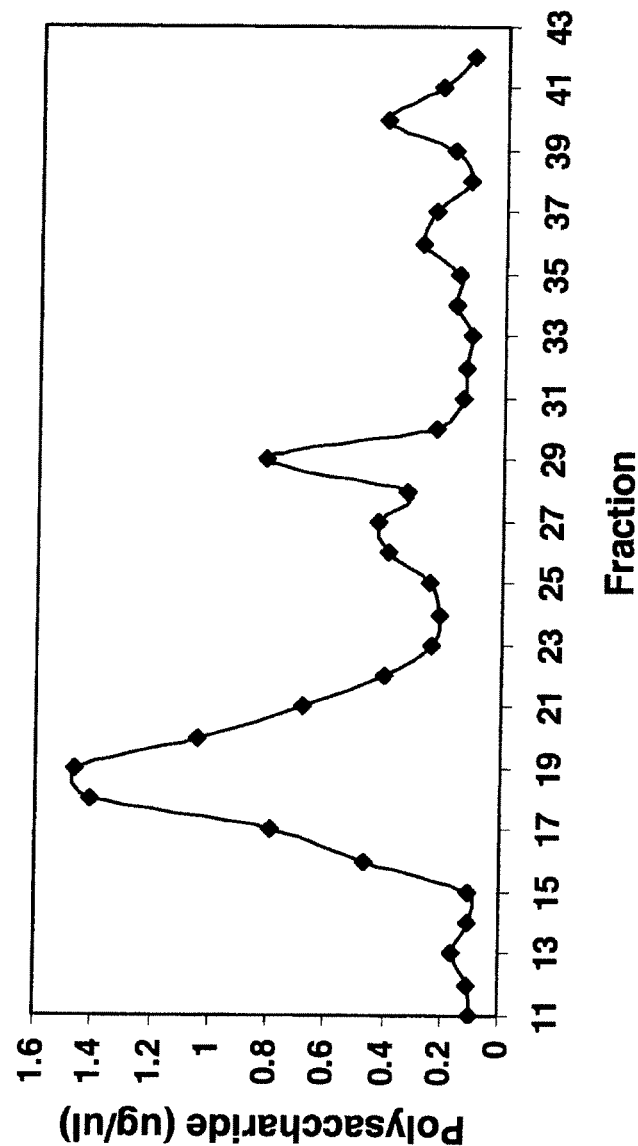
FIG. 8. Purification of *Salmonella* Lipopolysaccharide. (A) Emerald Green stained SDS-PAGE pattern of *S. Enteritidis* LPS. Lane: 1, 37.5 ug; 2, 70 ug. (B) Size exclusion gel filtration profile of *S. Enteritidis* OPS through a Superdex 70 sepharose column in PBS. High molecular weight OPS fractions are designated 16-22. Polysaccharide concentrations were assessed by resorcinol assay, using the homologous LPS as a standard.
Figure 8:
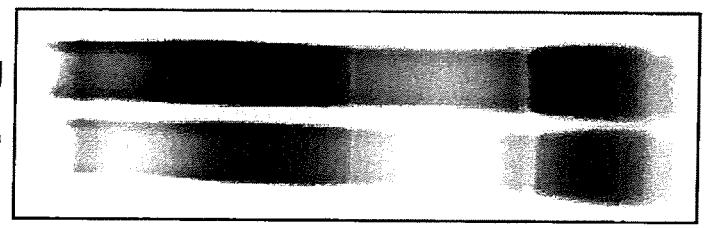
Figure 9:
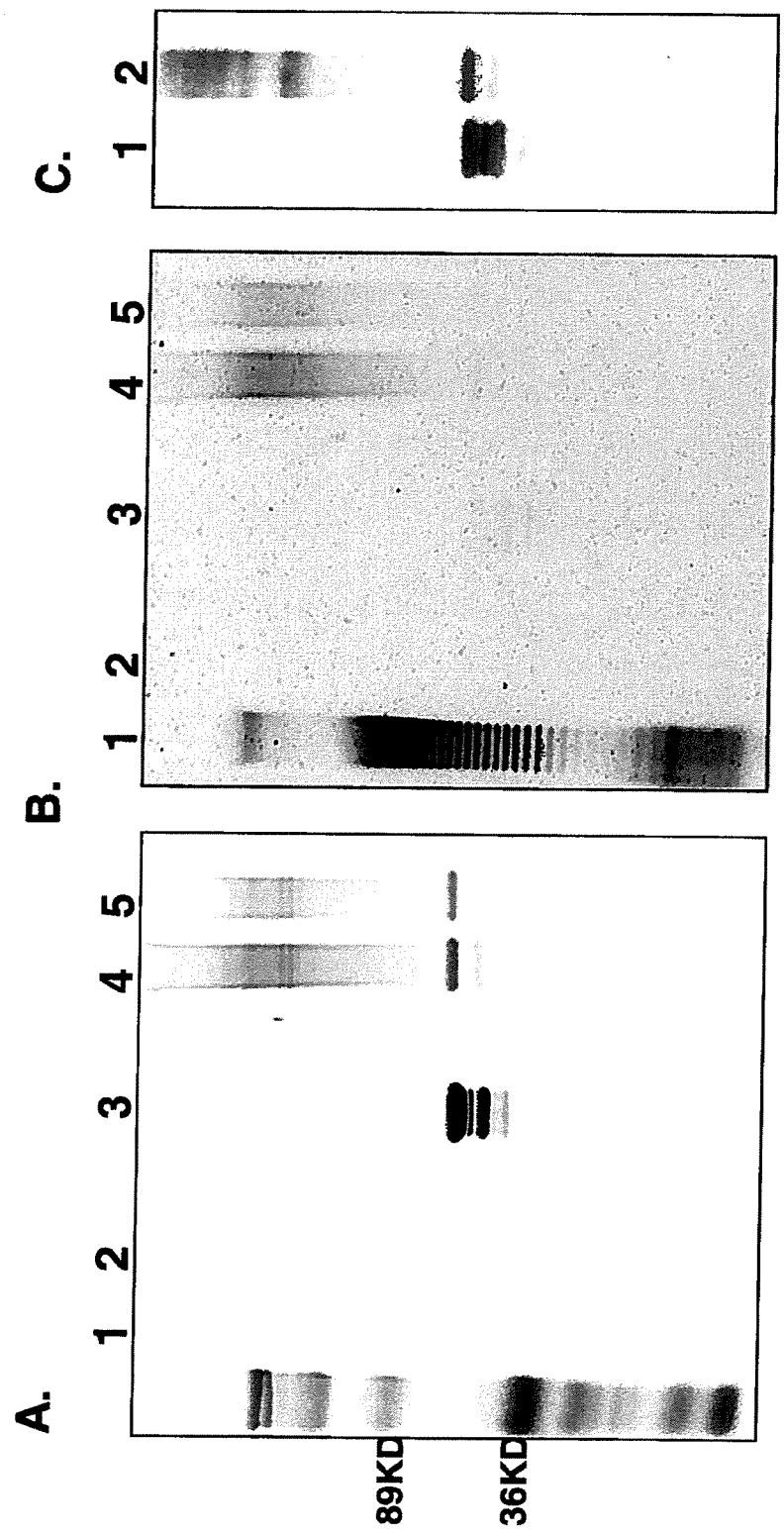
FIG. 9. Conjugation of *Salmonella* Outer Membrane Polysaccharide to Flagellin monomers. 4-20% SDS-Gel followed by Coomassie (A) or Emerald Green (B) staining Lane: 1, 10 ug LPS; 2, 6 ug HMW-OPS; 3, 6 ug de-polymerized flagella; 4, 6 ug protein as conjugate to HMW-OPS; 5, 3 ug protein as conjugate to HMW-OPS. (C) Western Blot analysis for flagellin. Lane: 1, 0.4 ug depolymerized flagella; 2, 0.4 ug protein as conjugate to HMW-OPS.

In some embodiments (as shown in FIGS. 8 and 9), the LPS is purified by a modification of the methods of Darveau et al., supra, followed by mild acid hydrolysis to remove lipid A and liberate free Core/KDO linked OPS.

The hapten and carrier can be conjugated using known techniques and methods. For example, techniques to conjugate COPS and the Phase 1 flagella protein can include, in part, coupling through available functional groups (such as amino, carboxyl, thio and aldehyde groups). See, e.g., Hermanson, Bioconjugate Techniques (Academic Press; 1992); Aslam and Dent, eds. Bioconjugation: Protein coupling Techniques for the Biomedical Sciences (MacMillan: 1998); S. S. Wong, *Chemistry of Protein Conjugate and Crosslinking CRC Press* (1991), and Brenkeley et al., Brief Survey of Methods for Preparing Protein Conjugates With Dyes, Haptens and Cross-Linking Agents, *Bioconjugate Chemistry* 3 #1 (January 1992).

In some embodiments of the present invention, the hapten and carrier, such as COPS and the Phase 1 flagella protein (FliC) or fragments or derivatives thereof, can include functional groups or, alternatively, can be chemically manipulated to bear functional groups. In some embodiments, the presence of functional groups can facilitate covalent conjugation. Such functional groups can include amino groups, carboxyl groups, aldehydes, hydrazides, epoxides, and thiols, for example.

For example, functional amino and sulfhydryl groups can be incorporated therein by conventional chemistry. Primary amino groups can be incorporated by reaction with ethylenediamine in the presence of sodium cyanoborohydride and sulfhydryls may be introduced by reaction of cysteamine dihydrochloride followed by reduction with a standard disulfide reducing agent.

The carrier, such as FliC protein, may contain amino acid side chains such as amino, carbonyl, hydroxyl, or sulfhydryl groups or aromatic rings that can serve as sites for conjugation. Residues that have such functional groups can be added to either the hapten (e.g., COPS) or to the carrier (e.g., FliC) protein. Such residues may be incorporated by solid phase synthesis techniques or recombinant techniques, for example.

The hapten and carrier of the conjugate can be chemically conjugated using conventional crosslinking agents such as carbodiimides. Examples of carbodiimides are 1-cyclohexyl-3-(2-morpholinyl-(4-ethyl) carbodiimide (CMC), 1-ethyl-3-(3-dimethyaminopropyl) carbodiimide (EDC), and 1-ethyl-3-(4-azonia-44-dimethylpentyl) carbodiimide.

Examples of other crosslinking agents are cyanogen bromide, glutaraldehyde and succinic anhydride. In general, any of a number of homobifunctional agents including a homobifunctional aldehyde, a homobifunctional epoxide, a homobifunctional imidoester, a homobifunctional N-hydroxysuccinimide ester, a homobifunctional maleimide, a homobifunctional alkyl halide, a homobifunctional pyridyl disulfide, a homobifunctional aryl halide, a homobifunctional hydrazide, a homobifunctional diazonium derivative or a homobifunctional photoreactive compound can be used. Also included are heterobifunctional compounds, for example, compounds having an amine-reactive and a sulfhydryl-reactive group, compounds with an amine-reactive and a photoreactive group, and compounds with a carbonyl-reactive and a sulfhydryl-reactive group.

Specific examples of homobifunctional crosslinking agents include the bifunctional N-hydroxysuccinimide esters dithiobis (succinimidylpropionate), disuccinimidyl suberate, and disuccinimidyl tartarate; the bifunctional imidoesters dimethyl adipimidate, dimethyl pimelimidate, and dimethyl suberimidate; the bifunctional sulfhydryl-reactive crosslinkers 1,4-di-[3'-(2'-pyridyldithio) propion-amido]butane, bis-maleimidohexane, and bis-N-maleimido-1,8-octane; the bifunctional aryl halides 1,5-difluoro-2,4-dinitrobenzene and 4,4'-difluoro-3,3'-dinitrophenylsulfone; bifunctional photoreactive agents such as bis-[b-(4-azidosalicylamide)ethyl] disulfide; the bifunctional aldehydes formaldehyde, malondialdehyde, succinaldehyde, glutaraldehyde, and adiphaldehyde; a bifunctional epoxied such as 1,4-butaneodiol diglycidyl ether; the bifunctional hydrazides adipic acid dihydrazide, carbohydrazide, and succinic acid dihydrazide; the bifunctional diazoniums o-tolidine, diazotized and bis-diazotized benzidine; the bifunctional alkylhalides N1N'-ethylene-bis(iodoacetamide), N1N'-hexamethylene-bis(iodoacetamide), N1N'-undec amethylene-bis(iodoacetamide), as well as benzylhalides and halomustards, such as ala'-diiodo-p-xylene sulfonic acid and tri(2-chloroethyl)amine, respectively.

Examples of other common heterobifunctional crosslinking agents that may be used include, but are not limited to, SMCC (succinimidyl-4-(N-maleimidomethyl)cyclohexane-1-carboxylate), MBS (m-maleimidobenzoyl-N-hydroxysuccinimide ester), SIAB (N-succinimidyl(4-iodacteyl)aminobenzoate), SMPB (succinimidyl-4-(p-maleimidophenyl) butyrate), GMBS (N-(-maleimidobutyryloxy)succinimide ester), MPHB (4-(4-N-maleimidopohenyl) butyric acid hydrazide), M2C2H (4-(N-maleimidomethyl)cyclohexane-1-carboxyl-hydrazide), SMPT (succinimidyloxycarbonyl-a-methyl-a-(2-pyridyldithio)toluene), and SPDP(N-succinimidyl 3-(2-pyridyldithio) propionate). For example, crosslinking may be accomplished by coupling a carbonyl group to an amine group or to a hydrazide group by reductive amination.

In another aspect of the invention, the hapten and the carrier can be conjugated through polymers, such as PEG, poly-D-lysine, polyvinyl alcohol, polyvinylpyrollidone, immunoglobulins, and copolymers of D-lysine and D-glutamic acid. Conjugation of the hapten and carrier may be achieved in any number of ways, including involving one or more crosslinking agents and functional groups on the hapten and/or the carrier protein. The polymer can be derivatized to contain functional groups if it does not already possess appropriate functional groups.

In a preferred embodiment, 1-cyano-4-dimethylaminopyridinium tetrafluoroborate (CDAP) conjugation chemistry is used to achieve efficient synthesis of the hapten-carrier conjugates. In some embodiments, 1-cyano-4-dimethylaminopyridinium tetrafluoroborate (CDAP) is used to conjugate COPS—FliC conjugates, COPS-FliC$^{T411A}$, Vi-FliC conjugates, Vi-FliC$^{T411A}$, and Vi-tetanus toxoid conjugates (see e.g. Lees A. et al. 1996. *Vaccine*. 14(3):190-198, and Shafer D E et al. *Vaccine*. 2000. 18(13):1273-81 which is incorporated by reference herein). As shown in FIG. 9, activation and derivitization of COPS with CDAP chemistry, followed by direct coupling to flagellin protein has been demonstrated to be effective as a method of chemical conjugation.

In some embodiments, the hapten or carrier is conjugated to a linker prior to conjugation. In some embodiments, the linker is adipic acid dihydrazide (ADH). The present invention contemplates the use of any linker capable of conjugating the hapten (such as COPS or Vi) to a carrier (such as FliC or FliC$^{T411A}$). In some embodiments, the presence of a linker promotes optimum immunogenicity of the conjugate and more efficient coupling. In some embodiments, the linkers separate the two antigenic components by chains whose length and flexibility can be adjusted as desired. Between the bifunctional sites, the chains can contain a variety of structural features, including heteroatoms and cleavage sites. In some embodiments, linkers also permit corresponding increases in translational and rotational characteristics of the antigens, increasing access of the binding sites to soluble antibodies. Besides ADH, suitable linkers include, for example, heterodifunctional linkers such as ε-aminohexanoic acid, chlorohexanol dimethyl acetal, D-glucuronolactone and p-nitrophenyl amine. Coupling reagents contemplated for use in the present invention include hydroxysuccinimides and carbodiimides. Many other linkers and coupling reagents known to those of ordinary skill in the art are also suitable for use in the invention. Such compounds are discussed in detail by Dick et al., *Conjugate Vaccines*, J. M. Cruse and R. E. Lewis, Jr., eds., Karger, New York, pp. 48-114, hereby incorporated by reference.

In some embodiments, ADH is used as the linker. In some embodiments, the molar ratio of ADH to hapten such as COPS in the reaction mixture is typically between about 10:1 and about 250:1. In some embodiments, a molar excess of ADH is used to ensure more efficient coupling and to limit COPS-COPS coupling. In some embodiments, the molar ratio is between about 50:1 and about 150:1. In other embodiments, the molar ratio is about 100:1. Similar ratios of AH-COPS to the Phase I flagella protein in the reaction mixture are also contemplated. In some embodiments, one ADH per COPS is present in the AH-COPS conjugate.

Other linkers are available and can be used to link two aldehyde moieties, two carboxylic acid moieties, or mixtures thereof. Such linkers include ($C_1$-$C_6$) alkylene dihydrazides, ($C_1$-$C_6$) alkylene or arylene diamines, -aminoalkanoic acids, alkylene diols or oxyalkene diols or dithiols, cyclic amides and anhydrides and the like. For examples, see U.S. Pat. No. 5,739,313.

In some embodiments, conjugation is conducted at a temperature of from about 0° C. to about 5° C. for about 36 to about 48 hours. In one embodiment, conjugation is conducted at about 4° C. for about 36 hours, followed by about an additional 18 to 24 hours at a temperature of from about 20° C. to about 25° C. In another embodiment, conjugation is conducted for about 18 hours at about 20 to 24° C., such that the residual cyanate groups react with water and decompose. Longer or shorter conjugation times and/or higher or lower conjugation temperatures can be employed, as desired. In some embodiments, it is desirable, however, to conduct the conjugation reaction, at least initially, at low temperatures, for example, from about 0° C. to about 5° C., such as about 4° C., so as to reduce the degree of precipitation of the conjugate.

In some embodiments of the invention, conjugation of the hapten (such as COPS) to the carrier (such as FliC) protein is on the terminal amino group of lysine residues. In some embodiments of the invention, conjugation is to cysteine groups. In some embodiments of the invention, conjugation of the hapten is to N-terminal serine groups. In some embodiments of the invention, conjugation of the hapten to the carrier is directed towards the C-terminal carboxylic acid group. In some embodiments of the invention, conjugation is to naturally occurring amino acid groups. In other embodiments of the invention, conjugation is to engineered amino acid sequences and residues within the carrier protein.

In some embodiments of the invention, conjugation of the carrier (such as FliC) to the hapten (such as COPS) is on random free hydroxyl groups on the OPS polysaccharide chain. In some embodiments of the invention, conjugation of carrier to hapten is at the terminal end of the polysaccharide chain.

In some embodiments of the invention, the hapten and carrier protein reactants contain multiple reactive groups per molecule. In some embodiments, an activated hapten molecule can react with and form more than one linkage to more than one carrier protein molecule. Likewise, an activated carrier protein molecule can react with and form more than one linkage to more than one activated hapten molecule. Therefore, in some embodiments, the conjugate product is a mixture of various cross-linked matrix-type lattice structures. For example, a single linkage can be present, or 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more linkages can be present. The average number of linkages between an hapten and a carrier protein can be adjusted, as desired. In some embodiments, the average number of linkages can depend upon the type of COPS polysaccharide, the type of Phase I flagella protein, the conjugation method, the reaction conditions, and the like.

In some embodiments, purification processes such as column chromatography and/or ammonium sulfate precipitation of the conjugate from unconjugated polysaccharide may not be necessary. However, in certain embodiments it can be desirable to conduct one or more purification steps. In some embodiments, after conjugation, the conjugate can be purified by any suitable method. Purification can be employed to remove unreacted polysaccharide, protein, or small molecule reaction byproducts. Purification methods include ultrafiltration, size exclusion chromatography, density gradient centrifugation, hydrophobic interaction chromatography, ammonium sulfate fractionation, ion exchange chromatography, ligand exchange chromatography, immuno-affinity chromatography, polymyxin-b chromatography, and the like, as are known in the art. In some embodiments, the conjugation reactions proceed with higher yield, and generate fewer undesirable small molecule reaction byproducts. Accordingly, in some embodiments no purification may be necessary, or only a minor degree of purification can be desirable.

Figure 10:
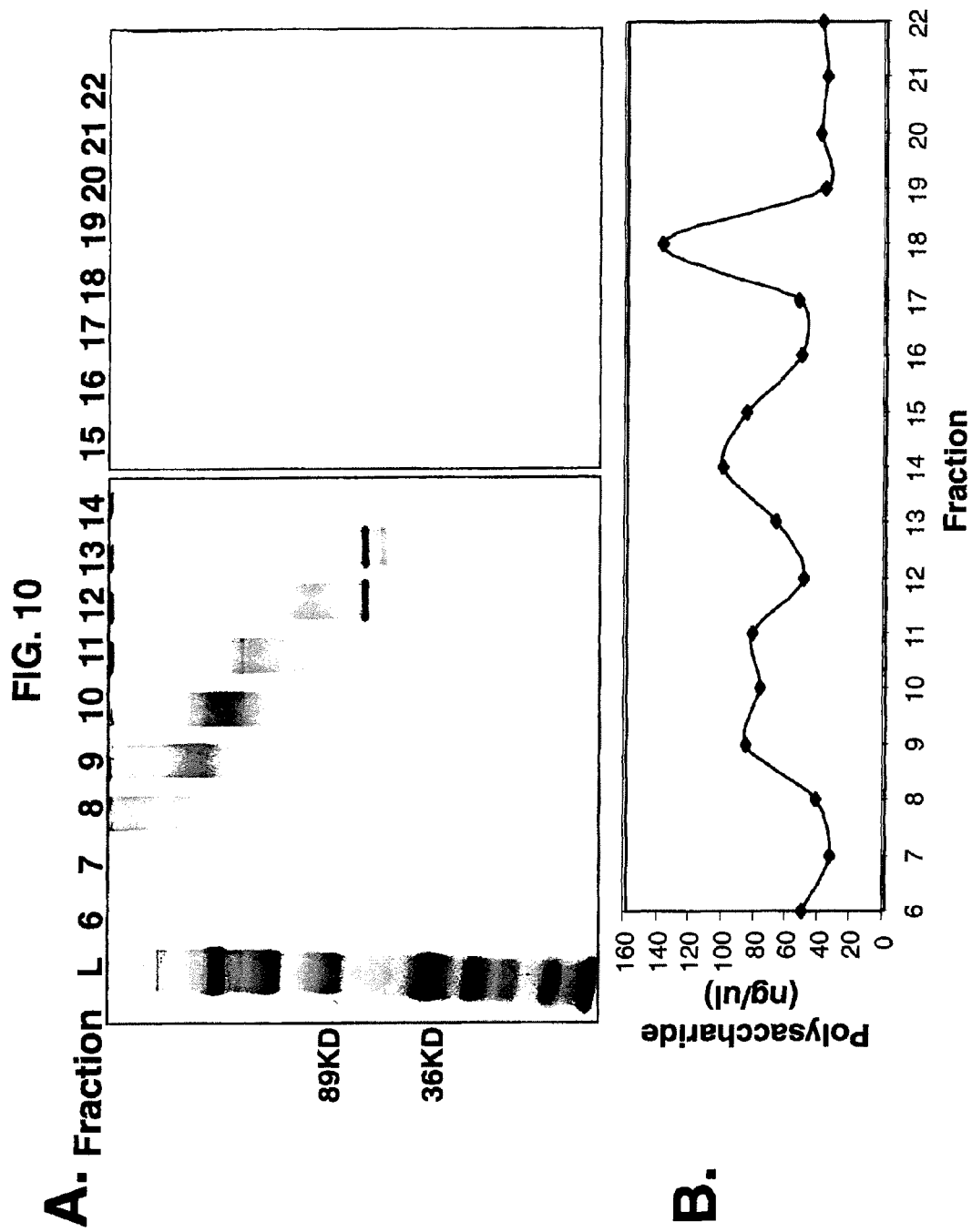
FIG. 10. Purification of Flagellin-OPS Conjugates. Gel filtration pattern of Flagella-HMW-OPS conjugates through a Superdex 700 size exclusion column. (A) Fractions were analyzed by SDS-PAGE with staining with Coomassie dye for protein. (B) Polysaccharide content in each fraction.

The conjugate can be concentrated or diluted, or processed into any suitable form for use in pharmaceutical compositions, as desired. Purification of COPS-flagellin conjugates is shown with the use of size exclusion chromatography (see FIG. 10).

Pharmaceutical Compositions

In some embodiments, the multivalent conjugate vaccine or the attenuated *Salmonella enterica* serovars of the present invention are administered to a subject as a pharmaceutical composition, which may contain salts, buffers, adjuvants, or other substances which are desirable for improving the efficacy of the composition. Adjuvants are substances that can be used to specifically augment a specific immune response. Normally, the adjuvant and the composition are mixed prior to presentation to the immune system, or presented separately, but into the same site of the animal being immunized. Adjuvants can be loosely divided into several groups based upon their composition. These groups include oil adjuvants (for example, Freund's complete and incomplete), mineral salts (for example, $AlK(SO_4)_2$, $AlNa(SO_4)_2$, $AlNH_4(SO_4)$, silica, kaolin, and carbon), polynucleotides (for example, poly IC and poly AU acids), and certain natural substances (for example, wax D from *Mycobacterium tuberculosis*, as well as substances found in *Corynebacterium parvum*, or *Bordetella pertussis*, and members of the genus *Brucella*. Adjuvants are described by Warren et al. (*Ann. Rev. Biochem.*, 4:369-388, 1986), the entire disclosure of which is hereby incorporated by reference.

In some embodiments of the invention the use of a phase I flagellin protein (FliC) as a carrier for a conjugate provides an inherent adjuvant boost, and stimulates a robust immune response without the addition of further adjuvant. Thus, in some embodiments, the flagellin protein acts an adjuvant which stimulates innate immunity through TLR5 to improve the immunogenicity of hapten (e.g., COPS) within the conjugate vaccine. In some embodiments, the carrier is a mutant FliC (such as $FliC^{T411A}$) which has a diminished capability to stimulate innate immunity through TLR5. In some embodiments, an adjuvant is added to the multivalent vaccine compositions comprising $FliC^{T411A}$ as the carrier, while in other embodiments, no adjuvant is added.

In some embodiments, conventional adjuvants can be administered. Among those substances that can be included are the saponins such as, for example, Quil A. (Superfos A/S, Denmark). In some embodiments, immunogenicity of the conjugates in both mice and rabbits is enhanced by the use of monophosphoryl lipid A plus trehalose dimycolate (Ribi-700; Ribi Immunochemical Research, Hamilton, Mont.) as an adjuvant. Examples of materials suitable for use in vaccine compositions are provided in *Remington's Pharmaceutical Sciences* (Osol, A, Ed, Mack Publishing Co, Easton, Pa., pp. 1324-1341 (1980), which disclosure is incorporated herein by reference).

The multivalent conjugate vaccine can be formulated into liquid preparations for, e.g., nasal, rectal, buccal, vaginal, peroral, intragastric, mucosal, perlinqual, alveolar, gingival, olfactory, or respiratory mucosa administration. Suitable forms for such administration include solutions, suspensions, emulsions, syrups, and elixirs. The conjugate vaccines can also be formulated for parenteral, subcutaneous, intradermal, intramuscular, intraperitoneal or intravenous administration, injectable administration, sustained release from implants, or administration by eye drops. Suitable forms for such administration include sterile suspensions and emulsions. Such conjugate vaccines can be in admixture with a suitable carrier, diluent, or excipient such as sterile water, physiological saline, glucose, and the like. The conjugate vaccines can also be lyophilized. The conjugate vaccines can contain auxiliary substances such as wetting or emulsifying agents, pH buffering agents, gelling or viscosity enhancing additives, preservatives, flavoring agents, colors, and the like, depending upon the route of administration and the preparation desired. Texts, such as *Remington: The Science and Practice of Pharmacy*, Lippincott Williams & Wilkins; 20th edition (Jun. 1, 2003) and Remington's Pharmaceutical Sciences, Mack Pub. Co.; $18^{th}$ and $19^{th}$ editions (December 1985, and June 1990, respectively), incorporated herein by reference in their entirety, can be consulted to prepare suitable preparations. Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components can influence the physical state, solubility, stability, rate of in vivo release, and rate of in vivo clearance, and are thus chosen according to the intended application, such that the characteristics of the carrier are tailored to the selected route of administration.

In some embodiments, the multivalent conjugate vaccine of the invention is administered parenterally. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. In some embodiments, the OPS-Phase 1 flagella protein conjugates for parenteral administration may be in the form of a sterile injectable preparation, such as a sterile injectable aqueous or nonaqueous solutions, suspensions, and emulsions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Suspensions may be formulated according to methods well known in the art using suitable dispersing or wetting agents and suspending agents. The sterile injectable preparation may also be a sterile injectable solution or suspension in a parenterally acceptable diluent or solvent, such as a solution in 1,3-butanediol. Suitable diluents include, for example, water, Ringer's solution and isotonic sodium chloride solution. In addition, sterile fixed oils may be employed conventionally as a solvent or suspending medium. For this purpose, any bland fixed oil may be employed including synthetic mono- or diglycerides. In addition, fatty acids such as oleic acid may likewise be used in the preparation of injectable preparations.

Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

In some embodiments, the multivalent conjugate vaccine is provided as a liquid suspension or as a freeze-dried product. Suitable liquid preparations include, e.g., isotonic aqueous solutions, suspensions, emulsions, or viscous compositions that are buffered to a selected pH. Transdermal preparations include lotions, gels, sprays, ointments or other suitable techniques. If nasal or respiratory (mucosal) administration is desired (e.g., aerosol inhalation or insufflation), compositions can be in a form and dispensed by a squeeze spray dispenser, pump dispenser or aerosol dispenser. Aerosols are usually under pressure by means of a hydrocarbon. Pump dispensers can preferably dispense a metered dose or a dose having a particular particle size, as discussed below.

When in the form of solutions, suspensions and gels, in some embodiments, the formulations of the conjugates contain a major amount of water (preferably purified water) in addition to the active ingredient. Minor amounts of other ingredients such as pH adjusters, emulsifiers, dispersing agents, buffering agents, preservatives, wetting agents, jelling agents, colors, and the like can also be present.

In some embodiments, the compositions are preferably isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. In some embodiments of the invention, phosphate buffered saline is used for suspension.

In some embodiments, the viscosity of the compositions can be maintained at the selected level using a pharmaceutically acceptable thickening agent. In some embodiments, methylcellulose is used because it is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. In some embodiments, viscous compositions are prepared from solutions by the addition of such thickening agents.

In some embodiments, a pharmaceutically acceptable preservative can be employed to increase the shelf life of the compositions. Benzyl alcohol can be suitable, although a variety of preservatives including, for example, parabens, thimerosal, chlorobutanol, or benzalkonium chloride can also be employed. A suitable concentration of the preservative can be from 0.02% to 2% based on the total weight although there can be appreciable variation depending upon the agent selected.

In some embodiments, pulmonary delivery of the conjugates can also be employed. In some embodiments, the conjugate is delivered to the lungs of a mammal while inhaling and traverses across the lung epithelial lining to the blood stream. A wide range of mechanical devices designed for pulmonary delivery of therapeutic products can be employed, including but not limited to nebulizers, metered dose inhalers, and powder inhalers, all of which are familiar to those skilled in the art. These devices employ formulations suitable for the dispensing of the conjugate. Typically, each formulation is specific to the type of device employed and can involve the use of an appropriate propellant material, in addition to diluents, adjuvants and/or carriers useful in therapy.

In embodiments where the conjugates are prepared for pulmonary delivery in particulate form, it has an average particle size of from 0.1 µm or less to 10 µm or more. In some embodiments, it has an average particle size of from about 0.2, 0.3, 0.4, 0.5, 0.6, 0.7, 0.8, or 0.9 µm to about 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5 µm for pulmonary delivery. Pharmaceutically acceptable carriers for pulmonary delivery of the conjugates include carbohydrates such as trehalose, mannitol, xylitol, sucrose, lactose, and sorbitol. Other ingredients for use in formulations can include DPPC, DOPE, DSPC and DOPC. Natural or synthetic surfactants can be used, including polyethylene glycol and dextrans, such as cyclodextran and other related enhancers, as well as cellulose and cellulose derivatives, and amino acids can also be used. Liposomes, microcapsules, microspheres, inclusion complexes, and other types of carriers can also be employed.

Formulations suitable for use with a nebulizer, either jet or ultrasonic, typically comprise the conjugate dissolved or suspended in water at a concentration of about 0.01 or less to 100 mg or more of conjugate per mL of solution, preferably from about 0.1, 1, 2, 3, 4, 5, 6, 7, 8, 9, or 10 mg to about 15, 20, 25, 30, 35, 40, 45, 50, 55, 60, 65, 70, 75, 80, 85, or 90 mg of conjugate per mL of solution. The formulation can also include a buffer and a simple sugar (e.g., for protein stabilization and regulation of osmotic pressure). The nebulizer formulation can also contain a surfactant, to reduce or prevent surface induced aggregation of the conjugate caused by atomization of the solution in forming the aerosol.

Formulations for use with a metered-dose inhaler device generally comprise a finely divided powder containing the inventive compound suspended in a propellant with the aid of a surfactant. The propellant can include conventional propellants, such chlorofluorocarbon, a hydrochlorofluorocarbon, hydrofluorocarbons, and hydrocarbons, such as trichlorofluoromethane, dichlorodifluoromethane, dichlorotetrafluoroethanol, and 1,1,1,2-tetrafluoroethane, and combinations thereof. Suitable surfactants include sorbitan trioleate, soya lecithin, and oleic acid.

Formulations for dispensing from a powder inhaler device typically comprise a finely divided dry powder containing the conjugate, optionally including a bulking agent, such as lactose, sorbitol, sucrose, mannitol, trehalose, or xylitol in an amount that facilitates dispersal of the powder from the device, typically from about 1 wt. % or less to 99 wt. % or more of the formulation, preferably from about 5, 10, 15, 20, 25, 30, 35, 40, 45, or 50 wt. % to about 55, 60, 65, 70, 75, 80, 85, or 90 wt. % of the formulation.

Kits

In some embodiments, the invention is directed to kits comprising one or more vaccines of the invention. Such kits can be provided to an administering physician or other health care professional.

In some embodiments, the kit is a package which houses one or more containers which comprises one or more multivalent conjugate vaccine compositions and instructions for administering the multivalent conjugate vaccine composition to a subject. In some embodiments, the kit can also comprise one or more other therapeutic agents. The kit can optionally contain one or more diagnostic tools and instructions for use.

In some embodiments, the kit comprises an immunization schedule. In some embodiments, a vaccine cocktail containing two or more vaccines can be included, or separate pharmaceutical compositions containing different vaccines or therapeutic agents. The kit can also contain separate doses of the multivalent conjugate vaccine for serial or sequential administration. The kit can also comprise one or more compositions comprising one or more attenuated *Salmonella enterica* strains as described herein for use as a vaccine, or for use as a vaccine as a prime or boost in conjunction with a multivalent conjugate vaccine described herein.

In some embodiments, the kit further comprises suitable delivery devices, e.g., syringes, inhalation devices, and the like, along with instructions for administrating the therapeutic agents. The kit can optionally contain instructions for storage, reconstitution (if applicable), and administration of any or all therapeutic agents included. The kits can include a plurality of containers reflecting the number of administrations to be given to a subject. If the kit contains a first and second container, then a plurality of these can be present.

While the invention has been described with reference to certain particular examples and embodiments herein, those skilled in the art will appreciate that various examples and embodiments can be combined for the purpose of complying with all relevant patent laws (e.g., methods described in specific examples can be used to describe particular aspects of the invention and its operation even though such are not explicitly set forth in reference thereto).

EXAMPLE 1

Construction of Safe *S. Enteritidis* and *S. Typhimurium* Strains

One aspect of the invention is the construction of clinically well tolerated attenuated strains of *S. Enteritidis* and *S. Typhimurium* for use as live oral vaccines; for safer, more economical manufacture of purified COPS and flagellin subunit protein to prepare conjugate vaccines for parenteral administration, as well as using these strains in a heterologous mucosal prime/parenteral boost immunization strategy to broaden both the immunogenicity and protective capacity of the conjugate vaccines. We therefore deleted both the guaBA and clpP genes from both *S. Enteritidis* strain R11 and *S. Typhimurium* strain 177, using a highly efficient site-directed lambda ☐Red-mediated mutagenesis technique. Deletion regions in the chromosomes of each of the resulting attenuated strains were sequenced to confirm that only the intended genes and DNA sequences had been removed. Having created these basic attenuated candidate vaccine strains, we then sequentially introduced further mutations into fliD to secrete FliC monomers, as well as deleting the fljBA locus encoding phase 2 flagellin FljB and the FliC repressor protein FljA from *S. Typhimurium* (*S. Enteritidis* encodes only phase 1 flagella). A list of the attenuated strains now available for purification of COPS and FliC conjugate components is shown in Table 1.

TABLE 1

Attenuated NTS strains and expected levels of flagellin production*

| Strain | Chromosomal deletions | Expected phenotype |
|---|---|---|
| *S. Typhimurium* | | |
| CVD 1920 | guaBA | Wildtype FliC and FljB flagella |
| CVD 1921 | guaBA clpP | Hyper-expression of FliC and FljB flagella |
| CVD 1922 | guaBA fliD | Expression of FliC and FljB monomers |
| CVD 1923 | guaBA clpP fliD | Hyper-expression of FliC and FljB monomers |
| CVD 1924 | guaBA clpP fljBA | Hyper-expression of FliC flagella |
| CVD 1925 | guaBA clpP fliD fljBA | Hyper-expression of FliC monomers |
| *S. Enteritidis* | | |
| CVD 1940 | guaBA | Wildtype FliC expression |
| CVD 1941 | guaBA clpP | Hyper-expression of FliC flagella |
| CVD 1942 | guaBA fliD | Expression of FliC monomers |
| CVD 1943 | guaBA clpP fliD | Hyper-expression of FliC monomers |

*All strains containing the guaBA deletion are dependent on guanine supplementation for growth A detailed discussion of the engineering of attenuated *S. Typhimurium* strain CVD 1925 is included here. Since the homologous chromosomal regions for both *S. Typhimurium* and *S. Enteritidis* are nearly identical for guaBA, clpPX, and fliD, primers used for lambda Red-mediated mutagenesis were identical, so mutagenesis of *S. Typhimurium* illustrates the engineering steps taken for generation of mutants for both serovars (with the exception of fljBA which is not encoded by *S. Enteritidis*). All primers used for this work are listed in Table 2).

TABLE 2

| Name | Sequence | SEQ ID NO: |
|---|---|---|
| P1 | GTGTAGGCTGGAGCTGCTTC | 9 |
| P4 | ATTCCGGGGATCCGTCGACC | 10 |
| guaBAF | TGTTTATGCTGCTGATCGAAC | 11 |
| guamutR2 | GAAGCAGCTCCAGCCTACACGGGC AATATCTCACCTGG | 12 |
| guamutF3 | GGTCGACGGATCCCCGGATGCCGA TAATCCTTCCTGTG | 13 |
| guaBAR2 | ATAACCTGGACACTTCTGAG | 14 |
| guaBAF2 | TTCGAAGTGATCACCCCAAC | 15 |
| guaBAR3 | TATTTGGGCTGAATCGCCAC | 16 |
| clpPXF | TAAGCGTCGTGTAGTTGTCG | 17 |
| clpmutR | GAAGCAGCTCCAGCCTACACATTA CATTTCCGTCTCCTGG | 18 |
| clpmutF3 | GGTCGACGGATCCCCGGAATTGAT GCCCTGGACGCAAGTG | 19 |
| clpPR | TAACGTAATCGTCCAGGTGG | 20 |
| clpPXF2 | AGAAACAGGCTCTGGAGCTG | 21 |
| CVOL88 | ACGGCGTGTTTACAGGAAAAACGAA AGGGG | 22 |
| fljBAF2 | TATGACACTTGATCATGTGATG | 23 |
| fljBAmutR3 | GAAGCAGCTCCAGCCTACACCCAA TAAATCGTGTGGCTG | 24 |
| fljBAmutF3 | GGTCGACGGATCCCCGGAATCGCC TACGGTAATAAAAAATTC | 25 |
| fljBAR | TGAGAACTTCAGCAAATCGAC | 26 |
| fljBAF3 | ACGTCATAAATCGAACAAGTCG | 27 |
| fljBAR2 | AGCTTCAGCATTGCATCAGC | 28 |
| g998 | GAATTCTCACGCACACGCTGCAGG | 29 |
| g999 | GCTAGCACCTAATGATGAAATTGAA GCCATGC | 30 |
| g1000 | GAATTCGCTAGCGCTGGAGCTGCTT CGAAGTTC | 31 |
| g986 | CTCGAGTTCCGGGGATCCGTCGACC TGCAGTTC | 32 |
| g987 | GGATCCGCTATGAACAAGTCCTGAT AACAGAGGT | 33 |
| g988 | CTCGAGTTAACGAGACTCCTGGAAA GATGCTTTCGGTGAAATCTGC | 34 |

TABLE 2 -continued

| Name | Sequence | SEQ ID NO: |
|---|---|---|
| g1020 | GATTGACTGAGCAGCGCAATACGCTG | 35 |
| g1028 | GGTGATTTCAGCCTGGATGGAGTCGA | 36 |

* Bold indicates DNA complementary to primers P1 and P4

Figure 2:
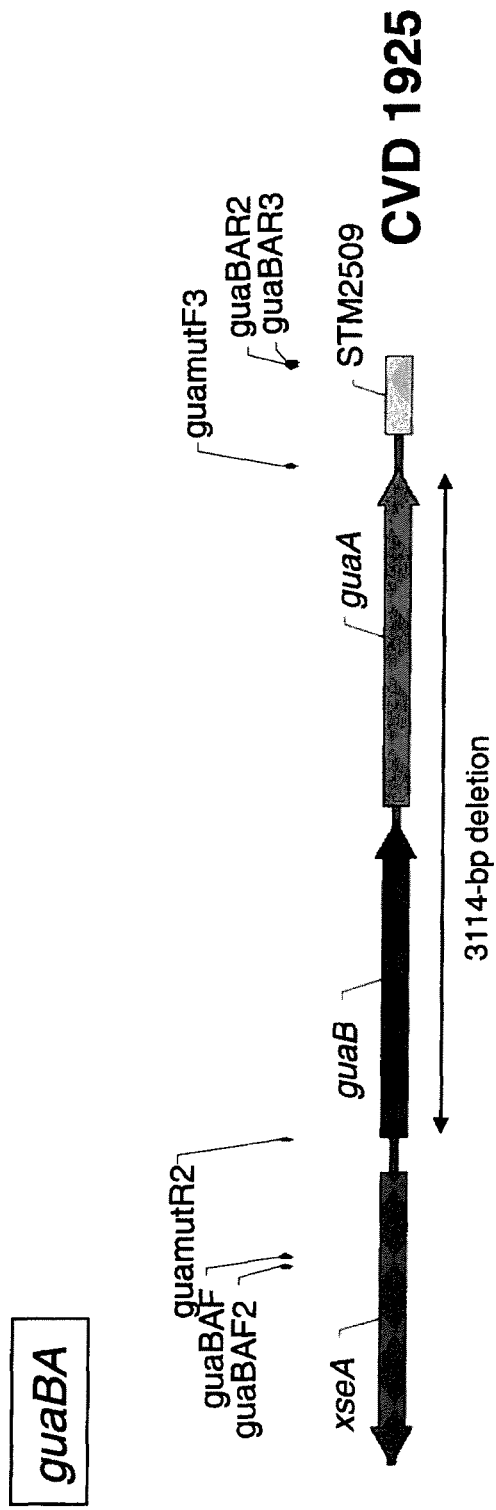
FIG. 2. Deletion of chromosomal guaBA from attenuated *Salmonella enterica* serovar Typhimurium vaccine strain CVD 1925 using lambda Red-mediated mutagenesis.

The guaBA locus was deleted from S. Typhimurium and S. Enteritidis using the lambda Red recombinase system. DNA upstream of guaB was amplified using primers guaBAF (SEQ ID NO: 11) and guamutR2 (SEQ ID NO:12) and DNA downstream of guaA was amplified using primers guamutF3 (SEQ ID NO:13) and guaBAR2 (SEQ ID NO:14) (FIG. 2). The kanamycin resistance cassette from pKD13 was amplified using primers P1 (SEQ ID NO:9) and P4 (SEQ ID NO:10). The 3 PCR products were combined and overlapping PCR was used to generate guaBA::$Km^R$ DNA. The $Km^R$ cassette was integrated into the genome by homologous recombination using lambda Red recombinase and then removed using Flp encoded by pCP20 resulting in replacement of guaBA with an ~80-bp scar sequence. The deletion was verified by amplification using primers guaBAF2 (SEQ ID NO:15) and guaBAR3 (SEQ ID NO:16) that are outside the deleted region and the PCR product from CVD 1920 was sequenced (SEQ ID NO:37).

Figure 3:
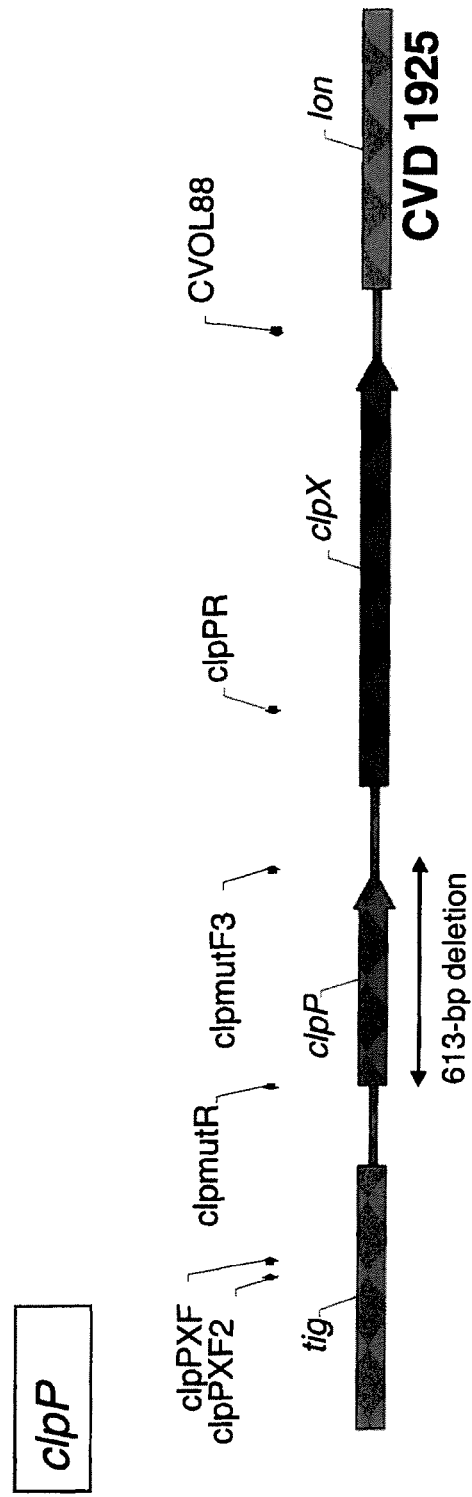
FIG. 3. Deletion of chromosomal clpP from attenuated *Salmonella enterica* serovar Typhimurium vaccine strain CVD 1925 using lambda Red-mediated mutagenesis.

For deletion of the clpP gene, DNA upstream of clpP was amplified using primers clpPXF (SEQ ID NO:17) and clpmutR (SEQ ID NO:18) and DNA downstream of clpP was amplified using primers clpmutF3 (SEQ ID NO:19) and clpPR (SEQ ID NO:20) (FIG. 3). The kanamycin resistance cassette from pKD13 was amplified using primers P1 (SEQ ID NO:9) and P4 (SEQ ID NO:10). The 3 PCR products were combined and overlapping PCR was used to generate clpP::$Km^R$ DNA. The $Km^R$ cassette was integrated into the genome by homologous recombination using lambda Red recombinase and then removed using Flp encoded by pCP20 resulting in replacement of clpP with an ~80-bp scar sequence. The resulting mutant has a clpP polar mutation (prevents translation of clpX, the second gene in the operon). The deletion was verified by amplification using primers clpPXF2 (SEQ ID NO:21) and CVOL88 (SEQ ID NO:22) that are outside the deleted region and the PCR product from CVD 1921 was sequenced (SEQ ID NO:38).

Figure 4:
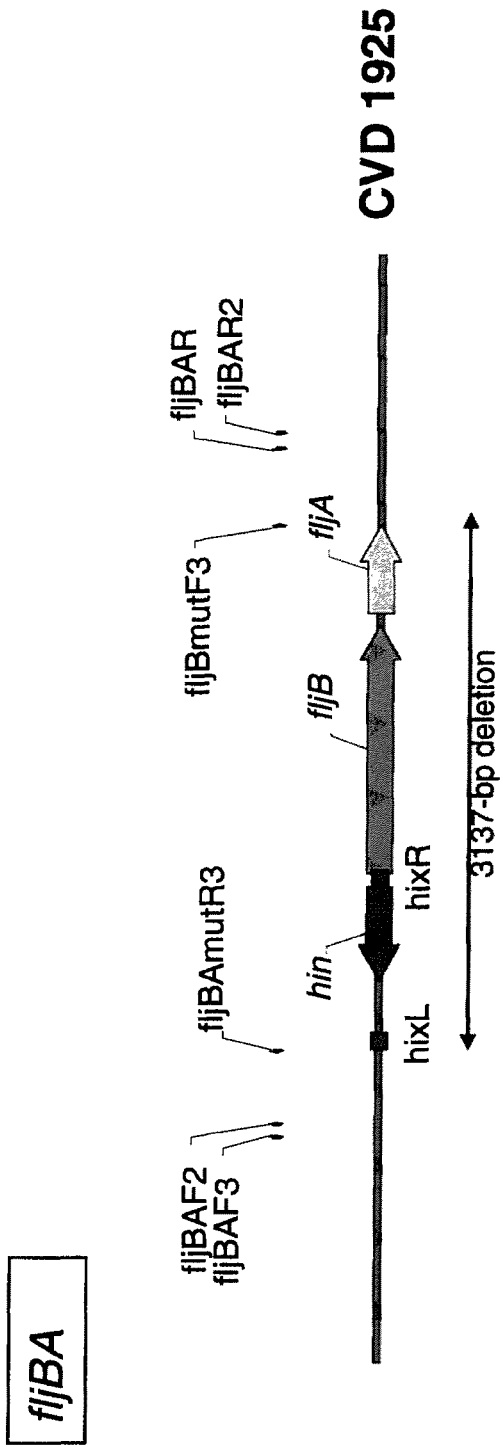
FIG. 4. Deletion of the chromosomal fliBA locus from attenuated *Salmonella enterica* serovar Typhimurium vaccine strain CVD 1925 using lambda Red-mediated mutagenesis.

The fljBA locus was deleted from S. Typhimurium by amplifying DNA upstream of hixL (the upstream site recognized by the recombinase encoded by hin) using primers fljBAF2 (SEQ ID NO:23) and fljBAmutR3 (SEQ ID NO:24) and DNA downstream of fljA was amplified using primers fljBAmutF3 (SEQ ID NO:25) and fljBAR (SEQ ID NO:26) (FIG. 4). The kanamycin resistance cassette from pKD13 was amplified using primers P1 (SEQ ID NO:9) and P4 (SEQ ID NO:10). The 3 PCR products were combined and overlapping PCR was used to generate fliBA::$Km^R$ DNA. The $Km^R$ cassette was integrated into the genome by homologous recombination using lambda Red recombinase and then removed using Flp encoded by pCP20 resulting in replacement of fljBA with an ~80-bp scar sequence. The deletion was verified by amplification using primers fljBAF3 (SEQ ID NO:27) and fljBAR2 (SEQ ID NO:28) that are outside the deleted region and the PCR products from CVD 1924 and CVD 1925 were sequenced (SEQ ID NO:39).

Figure 5:
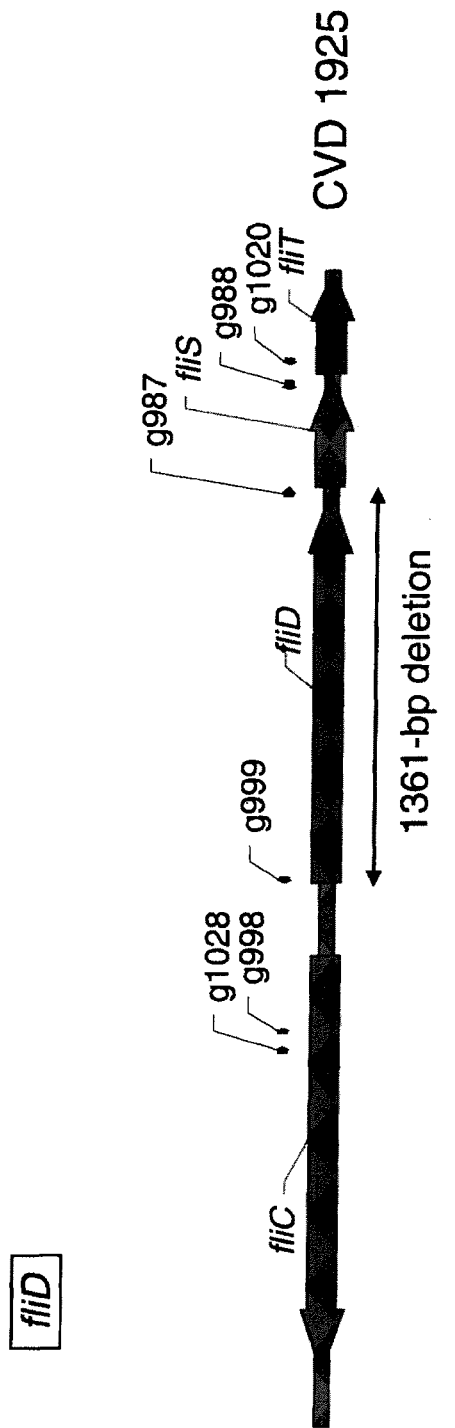
FIG. 5. Deletion of chromosomal IUD from attenuated *Salmonella enterica* serovar Typhimurium vaccine strain CVD 1925 using lambda Red-mediated mutagenesis.

For deletion of fliD a slightly different approach was taken. DNA upstream of fliD was amplified using primers g998 (SEQ ID NO:29) and g999 (SEQ ID NO:30) and DNA downstream of fliD was amplified using primers g987 (SEQ ID NO:33) and g988 (SEQ ID NO:34) (FIG. 5). The kanamycin resistance cassette from pKD13 was amplified using primers g1000 (SEQ ID NO:31) and g986 (SEQ ID NO:32), and the complete ΔfliD-aph cassette was assembled using unique restriction enzyme sites engineered within the individual cassettes. As with the previous mutations of CVD 1925, this ΔfliD-aph $Km^R$ cassette was integrated into the genome by homologous recombination using lambda Red recombinase and then removed using Flp encoded by pCP20 resulting in replacement of fliD with an ~80-bp scar sequence. The deletion was verified by amplification using primers outside the deleted region using primers g1020 (SEQ ID NO:35) and g1028 (SEQ ID NO:36) and the PCR products from CVD 1922 and CVD 1923 were sequenced (SEQ ID NO:40).

Figure 6:
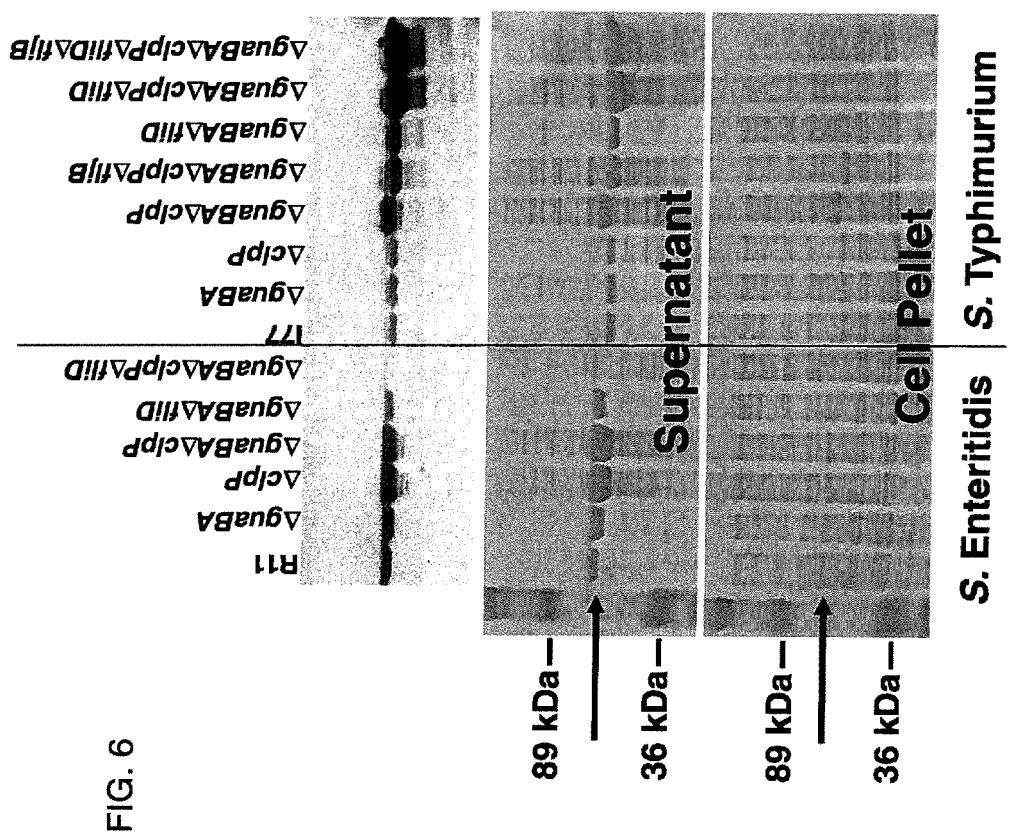
FIG. 6. Expression of flagella in the supernatants and cell pellets of attenuated NTS strains derived from *Salmonella enterica* serovar Typhimurium 177 and *Salmonella enterica* serovar Enteritidis R11. Top panel shows western blot analysis of secreted proteins using anti-flagellin antibody. Middle and lower panels show analysis of Coomassie-stained gels of supernatant and cell pellets respectively.

To ascertain which of these strains might be most useful for purification of FliC, we examined production of flagellin in supernatants using SDS-PAGE gels stained with Coomassie brilliant blue. As shown in FIG. 6, introduction of ΔclpP significantly improved production of flagella (red arrow; 51.6 kDa) in both S. Enteritidis and S. Typhimurium. Further introduction of ΔfliD into S. Enteritidis ΔguaBAΔclpP strains seemed to reduce secreted FliC production. Since this was not the expected phenotype, the S. Enteritidis R11 ΔguaBAΔclpPΔfliD strain was re-engineered as described in Example 5. The highest levels of secreted FliC production in attenuated strains of S. Typhimurium strains were observed in ΔguaBAΔclpPΔfliDΔfljBA strain CVD 1925. As expected, when examined for motility, ΔguaBAΔclpP strains appeared to be hypermotile and ΔguaBAΔclpPΔfliD strains hyper-expressing FliC monomers were non-motile. For our first attempt at synthesis of an OPS-FliC conjugate vaccine, we chose to focus on the attenuated S. Enteritidis candidate vaccine strain CVD 1941 (ΔguaBAΔclpP).

EXAMPLE 2

Synthesis of an COPS—FliC Conjugate Vaccine Against S. Enteritidis

Purification of Flagella from CVD 1941

Figure 7:
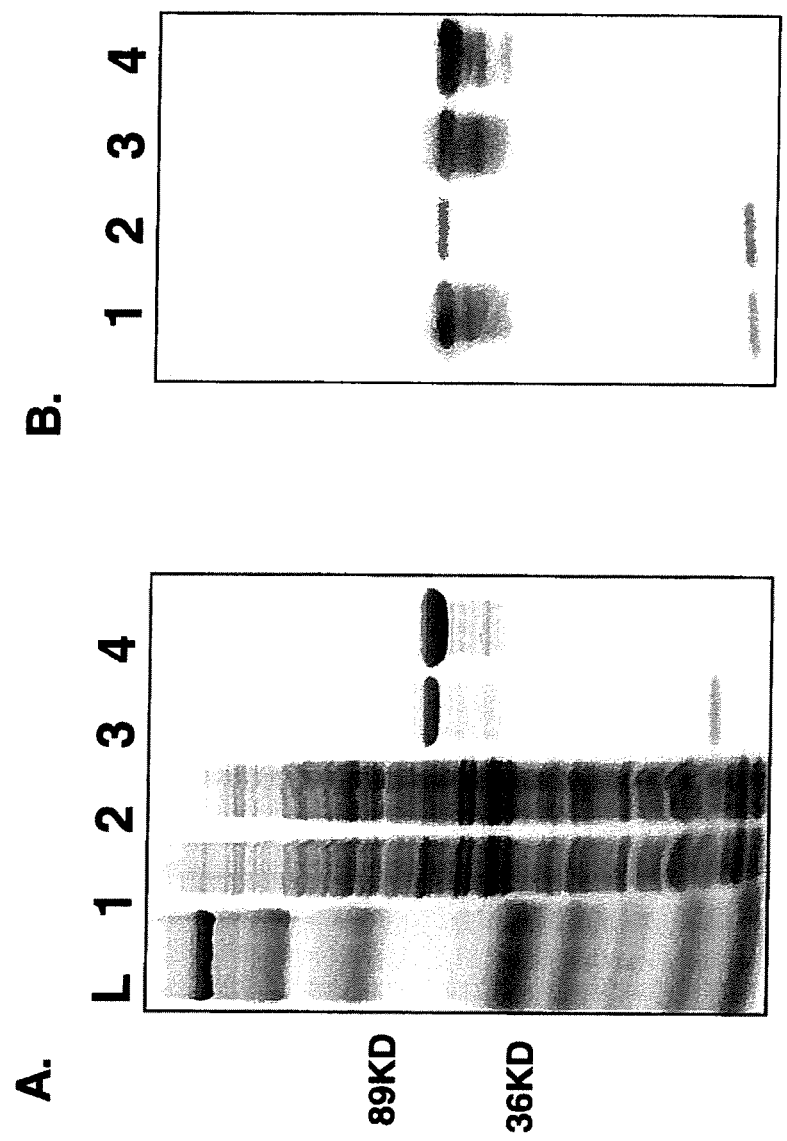
FIG. 7. Purification of *Salmonella Enteritidis* flagella. *Salmonella* flagella were isolated as described utilizing mechanical shearing followed by differential centrifugation. Protein samples were analyzed by SDS-PAGE followed by staining with Coomassie dye (A), or by transfer to a PVDF membrane followed by western blot analysis with a monoclonal antibody specific for bacterial flagellin (B). Lane 1: *Salmonella* cells; lane 2: 10 K×g centrifugation resuspended *Salmonella* cell pellet following mechanical shearing; lane 3: 10 K×g centrifugation sheared cell supernatant; lane 4: 100,000 K×g precipitated flagella material.

Several methods were tested for flagellin purification including: 1] an acidic pH2 method used to disaggregate flagella from intact cells at low pH, 2] a mechanical shearing method used to remove whole flagella from intact cells, 3] a heating method used to disaggregate flagella from intact cells, and 4] purification of passively shed flagella from bacterial supernatant. Each method was assessed for purity of the final flagellin prep, yield of protein, and ease of use. Of these, utilization of the commonly used shear method for flagellin production was found to provide the highest yield and purity with the greatest ease of use. Briefly the shear method utilizes a mechanical disruption of flagella on the surface of cells through processing in a Waring blender. Sheared flagella are then separated from large cellular debris particles through centrifugation at 10,000×g that will separate debris from intact flagella filaments. The 10,000×g supernatant is then subjected to 100,000×g centrifugation to pellet high molecular weight large flagella structures, leaving free low-molecular weight proteins and complexes in the supernatant. The whole flagella obtained from the 100,000×g centrifugation are further depleted of contaminating LPS by heating to disaggregate the flagellar filaments into individual proteins, followed by filtration through a 100 kDa molecular weight cutoff (MWCO) Amicon ultrafiltration device. Protein purity and integrity were assessed using SDS-PAGE gels stained with Coomassie brilliant blue. LPS contamination was assessed by the *Limulus Amebocyte* Lysate Assay with chromogenic endpoint analysis. As shown in FIG. 7, the resulting preparation was highly enriched for flagellin protein (lane 4). The enriched flagellin polymer preparation was disaggregated into monomers by heat dispersion at 70 degrees C. for 15 minutes and passed through a 100 KD Molecular Weight Cutoff Amicon Ultrafiltration unit. The resulting flagellin monomer sample (FIG. 7A, lane 3) contained very low levels of LPS, and was judged suitable for conjugation to polysaccharide.

Purification of LPS, and Generation of COPS from CVD 1941.

For purification of LPS, a method was developed in which a suspension of *Salmonella* was lysed in the presence of nuclease (to degrade bacterial DNA and RNA) by mechanical pressure using a French Press. Lysed cells were further treated with protease to degrade bacterial proteins. LPS was then separated from degraded cellular debris by ethanol precipitation in the presence of excess magnesium. Preparations were further purified from contaminating protein by phenol extraction. The resulting LPS was analyzed on SDS-PAGE gels and visualized by silver stain analysis. As shown in FIG. 8A, LPS preparations were determined to be of high purity. Final preparation of core-COPS polysaccharide for use in conjugation reactions involved removal of Lipid A by mild acid treatment at 100° C. for 1.5 hours in the presence of 1% acetic acid. Free Lipid A was removed by centrifugation at 100,000×g for 5 hours to pellet insoluble Lipid A complexes. The supernatant from the 100,000×g centrifugation was assessed by *Limulus Amebocyte* Lysate assay to be depleted of Lipid A. High molecular weight OPS suitable for conjugation was obtained by size exclusion chromatography (FIG. 8B). Polysaccharide concentration in elution fractions was monitored by assay with resorcinol with LPS as a standard. High molecular weight fractions were selected for use in conjugation.

Synthesis of an *S. Enteritidis* COPS-FliC Conjugate Vaccine.

Isolated monomeric flagellin was concentrated using a 10 kDa MWCO Amicon Ultrafiltration device, and then directly conjugated in approximately equivalent amounts (gram: gram) with core-COPS polysaccharide that had been derivatized and activated beforehand with CDAP chemistry. 3 mg of High Molecular weight OPS (HMW-OPS) in 10 mM Borate buffer and 150 mM NaCl at pH8.6 was added to 5 mg of 100 mg/ml CDAP in Acetonitrile. The pH was adjusted to 9.9 with TEA. At 2.5 minutes, 3 mg of flagellin monomer protein was added. The reaction was incubated at 25 degrees C. for 1.5 hours, 18 hours at 4 degrees C., and then −20 degrees C. for 4 days. The reaction was then quenched with 2M glycine. Initial assessment of conjugation was accomplished by analytical SEC-HPLC and monitoring for protein elution by UV spectroscopy absorbance at 280 nm. Evidence of conjugation was seen by broadening and flattening of the defined peaks in the elution profile, with broad peaks between 6 and 9 minutes which were not observed in the retention peaks from the unconjugated material (data not shown). The resulting conjugate was also analyzed by SDS-PAGE gels stained with Coomassie brilliant blue for protein (FIG. 9A), Emerald Green staining for polysaccharide (FIG. 9B), as well as transferred to PVDF membranes and analyzed by Western blot with a monoclonal antibody (15D8, Bioveris) for flagellin (FIG. 9C). As shown in FIGS. 9A and B, lane 4, evidence of conjugation between OPS and FliC is clearly seen in the high molecular weight species observed above the protein band corresponding to unreacted FliC, that double stains positive for both protein and polysaccharide; further evidence of successful conjugation is indicated by the fact that these higher molecular weight species are recognized by an antibody specific for flagellin, FIG. 9C, lane 2. As controls, purified LPS samples separated in FIG. 9A, lane 1 did not stain with the Coomassie protein stain, and strongly stained for polysaccharide by Emerald Green stain (FIG. 9B, lane 1) with the expected banding pattern characteristic of LPS. Purified flagellin samples separated in FIG. 9A, lane 3 strongly stained with Coomasie dye, but not with Emerald Green. The flagellin protein was also strongly recognized by anti-flagellin antibody (FIG. 9C, lane 1). Flagellin-High Molecular Weight COPS conjugates were purified from un-reacted Flagellin and COPS components by size fractionation with the use of size exclusion chromatography (FIG. 10A). High molecular weight fractions that eluted prior to unreacted flagellin (FIG. 10A, lanes 8-11) were pooled and deemed suitable for use in vaccination against the homologous NTS strains that they were derived from.

EXAMPLE 3

Purification of FliC Monomers from *Salmonella* Mutants Lacking fliD

Initial purification efforts focused on the removal of contaminating LPS from flagellin preparations recovered from the bacterial supernatants, utilizing sequential ion-exchange column chromatography steps. For the ion exchange purifications, the sample was held at a pH below the isoelectric point of flagellin, but above that of LPS, thus causing the two molecules to have overall net opposite charges since flagellin will have converted to a net positive charge under these conditions, while LPS will maintain a net negative charge. Endotoxin content of the purified material was assayed using a *Limulus Amebocyte* lysate (LAL) assay. SDS-PAGE analysis indicated that the supernatant was effectively concentrated, and flagellin was bound/eluted as expected through the ion-exchange material. Using this method, endotoxin contamination was reduced by ~90%.

EXAMPLE 4

Engineering and Pre-Clinical Evaluation of Attenuated Non-Typhoidal *Salmonella* Strains Serving as Live Oral Vaccines and as Reagent Strains This example demonstrates construction of attenuated *Salmonella enterica* serovar Typhimurium and Enteritidis strains that can serve as live oral vaccines and/or as "reagent strains" for conjugate vaccine production in a safe and economical manner. Prototype attenuated vaccine strains CVD 1921 and CVD 1941, derived from invasive wild-type strains *S. Typhimurium* 177 and *S. Enteritidis* R11, respectively, were constructed by deleting guaBA, encoding for guanine biosynthesis, and clpP, encoding for a master protease regulator. The clpP mutation resulted in a hyperflagellation phenotype. An additional deletion in fliD yielded reagent strains CVD 1923 and CVD 1943, respectively, that exports flagellin monomers. Oral $LD_{50}$ analyses showed that the NTS vaccine strains were all highly attenuated in mice. Oral immunization with CVD 1921 or CVD 1923 protected mice against lethal challenge with wild-type *S. Typhimurium* 177. Immunization with CVD 1941, but not CVD 1943, protected mice against lethal infection with *S. Enteritidis* R11. Immune responses induced by these strains included high levels of serum IgG anti-LPS and anti-flagella antibodies, with titers increasing progressively during the immunization schedule.

Materials and Methods

Bacterial Strains, Plasmids and Culture Conditions.

The bacterial strains used in this study are shown in Table 3.

0.1 M thiamine hydrochloride, 25 ml 20% glycerol, 5 ml trace salts solution (0.2 g d-Biotin dissolved in 1 ml of 2 N $NH_4OH$, 2.00 g $CuSO_4.5H_2O$, 0.08 g sodium iodide, 3.00 g $MnSO_4.H_2O$, 0.20 g $Na_2MoO_4.2H_2O$, 0.02 g boric acid, 0.50 g $CoCl_2.6H_2O$, 0.50 g $CaSO_4.2H_2O$, 7.00 g $ZnCl_2$, 22.0 g $FeSO_4.7H_2O$ per liter) to 1 L base solution (13.3 g $KH_2PO_4$, 4 g $[NH_4]_2HPO_4$, 1.7 g citric acid).

TABLE 3

Bacterial strains used in this study

| Serovar | Strain | Source/characteristics | Reference |
|---|---|---|---|
| *Salmonella Typhimurium* | I77 | Clinical isolate from blood culture, Mali; antibiotic-sensitive[a], virulence plasmid-positive[b] | c |
| | S52 | Clinical isolate from blood culture, Mali | c |
| | D65 | Clinical isolate from blood culture, Mali | c |
| | S11 | Clinical isolate from blood culture, Mali | c |
| | CVD 1920 | *S. Typhimurium* I77 ΔguaBA | NA |
| | I77 ΔclpP | *S. Typhimurium* I77 ΔclpP | NA |
| | CVD 1921 | *S. Typhimurium* I77 ΔguaBA ΔclpP | NA |
| | CVD 1921 $Km^R$ | *S. Typhimurium* I77 ΔguaBA ΔclpP::$Km^R$ | NA |
| | CVD 1922 | *S. Typhimurium* I77 ΔguaBA ΔfliD | NA |
| | CVD 1923 | *S. Typhimurium* I77 ΔguaBA ΔclpP ΔfliD | NA |
| | CVD 1924 | *S. Typhimurium* I77 ΔguaBA ΔclpP ΔfljB | NA |
| | CVD 1925 | *S. Typhimurium* I77 ΔguaBA ΔclpP ΔfliD ΔfljB | NA |
| *Salmonella Dublin* | R17 | Clinical isolate from blood culture, Mali | c |
| | P10 | Clinical isolate from blood culture, Mali | c |
| *Salmonella Enteritidis* | R11 | Clinical isolate from blood culture, Mali; antibiotic-sensitive[a], virulence plasmid-positive[b] | c |
| | P149 | Clinical isolate from blood culture, Mali | c |
| | D51 | Clinical isolate from blood culture, Mali | c |
| | J34 | Clinical isolate from blood culture, Mali | c |
| | CVD 1940 | *S. Enteritidis* R11 ΔguaBA | NA |
| | R11 ΔclpP | *S. Enteritidis* R11 ΔclpP | NA |
| | CVD 1941 | *S. Enteritidis* R11 ΔguaBA ΔclpP | NA |
| | CVD 1941 $Km^R$ | *S. Enteritidis* R11 ΔguaBA ΔclpP::$Km^R$ | NA |
| | CVD 1942 | *S. Enteritidis* R11 ΔguaBA ΔfliD | NA |
| | CVD 1943 | *S. Enteritidis* R11 ΔguaBA ΔclpP ΔfliD | NA |
| | CVD 1944 | *S. Enteritidis* R11 ΔguaBA ΔclpX | NA |
| *Salmonella* I 4,[5],12:i:- | D74 | Clinical isolate from blood culture, Mali | c |
| *Salmonella Stanleyville* | J65 | Clinical isolate from blood culture, Mali | c |

[a]Sensitive to ampicillin, ceftriaxone, chloramphenicol, gentamicin, ciprofloxacin, trimethoprim-sulfamethoxazole.
[b]As verified using primers (shown in Table 4) to amplify the spvC gene.
c Levy et al. *J. Clin. Microbiol.* 46: 1861-1866 (2008).

Plasmids pKD46, pKDl3 and pCP20 were used for chromosomal deletions (Datsenko et al. *Proc. Natl. Acad. Sci. U.S.A* 97:6640-6645 (2000)). Plasmid pCR-Blunt II-TOPO (Invitrogen, Carlsbad, Calif.) was used to clone blunt-ended polymerase chain reaction (PCR) products. *Salmonella* strains were maintained on animal product-free Lennox media (Athena Environmental Sciences, Baltimore, Md., USA) at 37° C. NTS serovars were verified by agglutination of bacteria with 0 grouping and H typing antisera (Denka Seiken Co. LTD, Japan). Phase switching was performed by preparing swarm agar (Nutrient Broth containing 0.5% agar) and dropping H:i or H:2 antiserum on the surface and then inoculating by stabbing the center of the medium. Following incubation at 37° C. for 20 h, the bacteria were agglutinated with H typing antiserum. All guaBA mutants were grown on media containing 0.005% (w/v) guanine. When required, antibiotics were used at a final concentration of 50 μg/ml carbenicillin, 50 μg/ml kanamycin or 20 μg/ml chloramphenicol. For motility tests, medium containing 1% Tryptone, 0.5% NaCl and 0.4% agar (Gillen et al. *J. Bacteriol.* 173:6453-6459 (1991)) was used. Chemically defined medium (Rondini et al. *Clin. Vaccine Immunol.* 18:460-468 (2011)) was prepared by combining 5 ml 1 M $MgSO_4$, 130 μl DNA Methods.

Plasmid extraction and gel purification of DNA fragments was performed using Wizard (Promega, Madison, Wis., USA) and QIAquick Gel Extraction (QIAGEN, Valencia, Calif., USA) kits, respectively, as directed by the manufacturer. All restriction enzymes were purchased from New England Biolabs (Ipswich, Mass., USA).

PCR amplifications were routinely performed with 1-2.5 U Taq DNA polymerase (Denville Scientific, Metuchen, N.J., USA, or Genscript, Piscataway, N.J., USA), 1×PCR Buffer containing 1.5 mM $MgCl_2$, 200 μM each dNTP and 1 μM of each primer in a reaction volume of 20 to 50 μl in an Eppendorf Mastercycler. For PCRs using long primers (>25 bp) the amount of $MgCl_2$ was increased as necessary. When error-free and/or blunt end PCR products were required, Vent$_R$® DNA polymerase (New England Biolabs) was used according to the manufacturer's instructions.

Construction of Mutants and Confirmation of Phenotypes. (i) Mutagenesis.

Deletion of guaBA, clpP or clpX and fljB was achieved by Lambda Red-mediated mutagenesis and was performed as described by Datsenko et al. (*Proc. Natl. Acad. Sci. U. S. A* 97:6640-6645 (2000)), with modifications. Linear guaBA:: $Km^R$ arid clpPX::$Km^R$ chromosomal deletion cassettes with target open reading frames replaced with a $Km^R$ gene (aphA)

were constructed using an overlapping PCR method based on that described by Chalker et at (*J. Bacteriol.* 183:1259-1268 (2001)). The DNA upstream and downstream of guaBA were amplified using primers guaBAF (SEQ ID NO: 11) and guamutR2 (SEQ ID NO: 12) and guamutF3 (SEQ ID NO: 13) and guaBAR2 (SEQ ID NO:14), respectively, using crude DNA (boiled cells) of the respective NTS strain as template. Primers guamutR2 and guamutF3 possess 5' overhangs that are homologous to a FRT-aph-FRT cassette. This latter cassette was amplified from pKDI3 using primers P1 (SEQ ID NO:9) and P4 (SEQ ID NO:10). The three PCR products were gel-purified and combined in a fill-in reaction using VentR® polymerase (New England Biolabs), 1× ThermoPol reaction buffer, 200 µM of each dNTP, 100 ng of the upstream and downstream fragments of guaBA and 40 ng of the amplified $Km^R$ gene combined in a 25 µl reaction volume. The fragments were extended using the following cycling conditions: 95° C. for 2 min, followed by 5 cycles of 95° C. for 1 min, 50° C. for 1 min and 72° C. for 2 min, and a final extension of 72° C. for 5 min. The guaBA::KmR construct was amplified by VentR® polymerase using primers guaBAF and guaBAR2 and cloned into pCR-Blunt I1-TOPO (Invitrogen). Large quantities of the fragment (approx 500 µl PCR product) were produced by amplification from the recombinant plasmid followed by gel-purification. The DNA was ethanol precipitated, suspended in 5 µl TE and used to electroporate *Salmonella* expressing lambda red recombinase. These cells were prepared by diluting an overnight culture of *Salmonella* containing the plasmid pKD46 1 in 100 in Lennox media containing 1 mM arabinose and 50 ng/ml carbenicillin and incubating at 30° C. until the $OD_{600}$ reached 0.6-0.8. The cells were washed three times with decreasing volumes (1, 0.5 and 0.25 volumes) of cold 10% glycerol. After the last wash, as much supernatant was removed as possible and the bacteria was resuspended in the remaining liquid. The linear DNA was electroporated into 50 µl of Lamda Red-expressing *Salmonella* using a 0.1-cm gap electroporation cuvette (BioRad Laboratories). Following electroporation, bacteria were repaired using Lennox medium with or without guanine for 2 hours at 30° C. Integration of the $Km^R$ gene cassette was confirmed by PCR using primers external to the disrupted gene. Loss of pKD46 was verified by testing for carbenicillin sensitivity. Removal of the $Km^{R'}$ gene resistance cassette was performed using pCP2O as described by Datsenko et al. (*Proc. Natl. Acad. Sci. U. S. A* 97:6640-6645 (2000)). The other genes, except for fliD, were deleted in the same manner using the primers shown in Table 4.

To delete fliD, primers g998 (SEQ ID NO:50) and g999 (SEQ ID NO:51) were used with appropriate chromosomal template DNA (from *S. Typhimurium* 177 or *S. Enteritidis* R11) in PCRs to generate a 573-bp EcoRI-NheI PCR product (cassette 1), upstream of fliD. Primers g987 (SEQ ID NO:52) and g988 (SEQ ID NO:53) were used in turn with chromosomal DNA to generate a 452-bp BamHI-XhoI PCR product (cassette 2), encompassing fliS and DNA downstream of fliD. An additional set of primers, g1000 (SEQ ID NO:54) and g986 (SEQ ID NO:55) were used with template pKD13 to generate a 1315-bp FRT-aph-FRT selectable cassette 3 containing 5'-terminal EcoRI-NheI sites and 3'-terminal BamHI-XhoI sites. The final cassette targeting fliD was generated by inserting cassettes 1 and 2 into appropriately digested cassette 3, creating a final mutagenesis cassette of 2307 bp. X Red-mediated mutagenesis and subsequent excision of the antibiotic cassette were performed as above. For deletion of fliD, it was imperative to preserve transcription and translation of the fliS gene, the second gene in the fliDST operon, which encodes a chaperone critical for blocking premature polymerization of FliC prior to export out of the cytoplasm (Auvray et al. *Mol. Biol.* 308:221-229 (2001); Yokoseki et al. *Microbiology* 141 (Pt 7):1715-1722 (1995)). Therefore, ΔfliD was engineered to encode a truncated non-functional protein comprised of 38 amino acids and a molecular weight of 4.0 kDa. The deletions were verified genotypically by PCR using primers (Table 4) external to the deletion and by sequencing at least 500 bp both upstream and downstream of the deletion. The mutants were tested phenotypically by performing motility tests and assessing flagellin production by SDS-PAGE and western immunoblotting.

TABLE 4

Primers used in this study.

| Purpose | Primer name | Sequence (5' to 3') |
|---|---|---|
| To amplify aphA | P1 | GTGTAGGCTGGAGCTGCTTC (SEQ ID NO: 9) |
|  | P4 | ATTCCGGGGATCCGTCGACC (SEQ ID NO: 10) |
| To detect virulence plasmid | spvCF | ACTCCTTGCACAACCAAATGCGGA (SEQ ID NO: 41) |
|  | spvCR | TGTCTTCTGCATTTCGCCACCATCA (SEQ ID NO: 42) |
| To delete guaBA | guaBAF | TGTTTATGCTGCTGATCGAAC (SEQ ID NO: 11) |
|  | guamutR2 | GAAGCAGCTCCAGCCTACACGGGCAATATCTCACCTGG (SEQ ID NO: 12) |
|  | guamutF3 | GGTCGACGGATCCCCGGAATGCCGATAATCCTTCCTGTG (SEQ ID NO: 13) |
|  | guaBAR2 | ATAACCTGGACACTTCTGAG (SEQ ID NO: 14) |
| To verify ΔguaBA | guaBAF2 | TTCGAAGTGATCACCCCAAC (SEQ ID NO: 15) |
|  | guaBAR3 | TATTTGGGCTGAATCGCCAC (SEQ ID NO: 16) |
| To delete clpP | clpPXF | TAAGCGTCGTGTAGTGTCG (SEQ ID NO: 17) |
|  | clpmutR | GAAGCAGCTCCAGCCTACACATTACATTTCCGTCTCCTGG (SEQ ID NO: 18) |
|  | clpmutF3 | GGTCGACGGATCCCCGGAATTGATGCCCTGGACGCAAGTG (SEQ ID NO: 19) |
|  | clpPR | TAACGTAATCGTCCAGGTGG (SEQ ID NO: 20) |

TABLE 4-continued

Primers used in this study.

| Purpose | Primer name | Sequence (5' to 3') |
|---|---|---|
| To verify ΔclpP | clpPXF2 | AGAAACAGGCTCTGGAGCTG (SEQ ID NO: 21) |
| | CVOL88 | ACGGCGTGTTTACAGGAAAAACGAAAGGGG (SEQ ID NO: 22) |
| To delete clpX | clpPXF6 | AACGTTTCTGCTTGCCGAAC (SEQ ID NO: 43) |
| | clpmutR2 | GAAGCAGCTCCAGCCTACACGAGTCAAAACCTC TTCTTTG (SEQ ID NO: 44) |
| | clpmutF4 | GGTCGACGGATCCCCGGAATTTAAACATTCATA CAATCAGTTAG (SEQ ID NO: 45) |
| | clpPXR | AATGTTCGCCGTTGTTCAGAC (SEQ ID NO: 46) |
| To verify ΔclpX | clpPXF7 | ATTAAGCCAGACGTCAGCAC (SEQ ID NO: 47) |
| | clpPXR7 | AGCACTTCTTGTTCACGCTC (SEQ ID NO: 48) |
| To delete fljB | fljBAmutR3 | GAAGCAGCTCCAGCCTACACCCAATAAATCGTG TGGCTG (SEQ ID NO: 24) |
| | fljBAmutF3 | GGTCGACGGATCCCCGGAATCGCCTACGGTAAT AAAAAATTC (SEQ ID NO: 25) |
| | fljBAF2 | TATGACACTTGATCATGTGATG (SEQ ID NO: 49) |
| | fljBAR | TGAGAACTTCAGCAAATCGAC (SEQ ID NO: 26) |
| To verify ΔfljB | fljBAF3 | ACGTCATAAATCGAACAAGTCG (SEQ ID NO: 27) |
| | fljBAR2 | AGCTTCAGCATTGCATCAGC (SEQ ID NO: 28) |
| To delete fliD | g998 | GAATTCTCACGCACACGCTGCAGG (SEQ ID NO: 50) |
| | g999 | GCTAGCACCTAATGATGAAATTGAAGCCATGC (SEQ ID NO: 51) |
| | g987 | GGATCCGCTATGAACAAGTCCTGATAACAGAG GT (SEQ ID NO: 52) |
| | g988 | CTCGAGTTAACGAGACTCCTGGAAAGATGCTTT CGGTGAAATCTGC (SEQ ID NO: 53) |
| | g1000 | GAATTCGCTAGCGCTGGAGCTGCTTCGAAGTTC (SEQ ID NO: 54) |
| | g986 | CTCGAGTTCCGGGGATCCGTCGACCTGCAGTTC (SEQ ID NO: 55) |
| To verify ΔfliD (S. Enteriditis) | g1021 | CTGAACAGACAACTCACGCACACGCTGC (SEQ ID NO: 56) |
| | g1022 | TGACTGAGCAGCGCAATACGCTGC (SEQ ID NO: 57) |
| To verify ΔfliD (S. Typhimurium) | g1028 | GGTGATTTCAGCCTGGATGGTGTCGA (SEQ ID NO: 36) |
| | g1020 | GATTGACTGAGCAGCGCAATACGCTG (SEQ ID NO: 35) |

(ii) Protein Methods.

Samples were prepared from cultures grown in Lennox media without shaking at 37° C. overnight. After overnight growth, the $OD_{600}$ of each culture was determined. Bacteria were pelleted by centrifugation and the supernatant was transferred to a fresh tube. The bacterial pellet was resuspended in 40-50 µl of $dH_2O$ and mixed with an equal volume of 4× Laemmli sample buffer (3.05% [w/v] SDS, 0.02% [w/v] Bromophenol Blue, 0.1 M Tris pH 6.8, 50% [v/v] glycerol, 5% [v/v] 2-mercaptoethanol) and three volumes of supernatant were mixed with 1 volume of 4× Laemmli Buffer and the samples were boiled for 5 min. Equivalent amounts of bacteria were loaded in each lane. Proteins were resolved using 4-20% Novex Tris-Glycine gels (Invitrogen) and visualized by staining with coomassie using GelCode Blue Stain Reagent (Thermo Scientific [PIERCE, Rockford, Ill., USA]). For western blots, proteins were electroblotted onto a polyvinyl difluoride membrane (Bio-Rad, Hercules, Calif.). The detection o flagellin was carried out using the mouse monoclonal antibody 15D8 at a dilution of 1:1,000 (Bioveris, Gaithersburg, Md., USA) and a peroxidase-labeled affinity-purified goat anti-mouse secondary antibody at a dilution of 1:10,000 (Kirkegaard & Perry Laboratories, Inc., Gaithersburg, Md.). Immunoblots were developed using an ECL plus detection system (GE Healthcare, Piscataway, N.J.), and blots were exposed to Kodak X-OMAT XAR-2 film.

(iii) Motility Assays.

Bacteria were stab-inoculated onto motility plates using a sterile pipette tip. The plates were incubated for 17-20 h at 37° C. and the zone of motility (diameter in mm) was measured. The ΔguaBA mutants (CVD 1920 and CVD 1940) were tested on every plate and the motility of each strain was expressed as a ratio relative to the ΔguaBA mutant.

(iv) Agglutination Tests.

NTS serovars were verified by agglutination of bacteria with O grouping and H typing antisera (Denka Seiken Co. LTD, Japan). Phase switching was performed by preparing swarm agar (Nutrient Broth containing 0.5% agar) and dropping H:i or H:2 antiserum on the surface and then inoculating by stabbing the center of the medium. Following incubation at 37° C. for 20 h, the bacteria were agglutinated with H typing antiserum.

50% Lethal Dose ($LD_{50}$) Analysis.

Mice were acclimated for seven days after arrival before starting the experiments. Ten-fold dilutions of wild-type and attenuated NTS strains were administered orally to five seven-week-old female BALB/c mice (Charles River Laboratories, Wilmington, Mass., USA). Both attenuated and wild-type *Salmonella* strains were grown by incubating at 37° C. in Lennox medium for 20 hours without shaking Bacteria were pelleted by centrifugation and resuspended in PBS at the appropriate concentration. Mice were infected with 200 μl of bacterial suspension using a 1.5" curved gavage needle with a 2.25 mm ball (Braintree Scientific, Braintree, Mass., USA). The exact number of bacteria used to infect mice was determined by viable counts. Mice were weighed and monitored daily for 28 days. Any mouse that lost >20% of its body weight (compared to weight at t=0) or that showed signs of extreme morbidity (e.g., shallow breathing, hunched posture) was euthanized and scored as a death. The 50% lethal dose of each strain was calculated by linear regression analysis.

Shedding of Vaccine Strains in Feces.

Three 12- to 16-week-old female BALB/c mice (Charles River Laboratories) were infected by gavage with $10^9$ CFU of the kanamycin-resistant precursors of CVD 1921 or CVD 1941 (i.e., ΔguaBA□ΔclpP::$Km^R$) suspended in 200 μl PBS. Bacteria were grown as for the $LD_{50}$ and immunization experiments, except that kanamycin was included in the media. Three to five fecal pellets were collected from each mouse and suspended in PBS at 100 mg/ml. Fecal samples were recovered for up to 28 days after inoculation, and the number of viable *Salmonella* per gram of stool was determined by plating onto media containing kanamycin. The limit of detection was 100 CFU/g feces.

Immunization and Challenge of Mice.

Fifteen seven-week-old female BALB/c mice (Charles River Laboratories) were immunized by gavage with $10^9$ CFU of CVD 1921, CVD 1923, CVD 1941 or CVD 1943, or PBS (30 mice) on days 0, 28 and 56. Bacteria were prepared and mice inoculated as per the $LD_{50}$ analysis. Blood samples from mice to obtain serum were collected on days −1, 27, 55, 70 and 83. Mice were challenged orally on day 84 with $2\times10^6$ CFU (100 $LD_{50}$) of the parental, virulent, wild-type strain (*S. Typhimurium* 177 or *S. Enteritidis* R11). Mice were weighed and monitored daily for 33 days and euthanized identically as in the $LD_{50}$ experiments.

Measurement of Anti-Flagellin and Anti-LPS Antibodies.

Mice were bled before the first immunization (day ~1) and then on days 27, 55, 70 and 83 and sera were stored at −20° C. until tested. Serum IgG antibodies against flagella and LPS were determined by ELISA. *Salmonella* cell-associated phase 1 flagella were isolated from CVD 1924 or CVD 1941 as previously described (Simon et al. *Biochem. Biophys. Res. Commun.* 355:280-285 (2007)). *Salmonella* LPS was isolated from CVD 1921 or CVD 1941 using the Darveau and Hancock method (Darveau et al. *J. Bacteriol.* 155:831-838 (1983)) 96-well ELISA plates were coated with 100 μl of *S. Typhimurium* or *S. Enteritidis* flagella or LPS (5 in carbonate buffer [pH 9.6]) for 3 h at 37° C. and blocked overnight with 10% dried milk in PBS. The plates were washed with PBS containing 0.05% Tween. 20 (PBST) (Sigma). Sera were tested in serial dilutions (in 10% milk in PBST). Antibodies bound to the immobilized antigens were detected using peroxidase-labeled goat anti-mouse IgG (KPL, Inc. Gaithersburg, Md.) diluted 1:1,000 in 10% dried milk in PBST, followed by TMB substrate solution (KPL). Test and control sera were run in duplicate. Titers were calculated by interpolation in a standard curve as the inverse of the dilution that produces an absorbance value of 0.2 above the blank (ELISA units). Seroconversion was defined as a four-fold increase in the antibody titer after immunization.

Serum Bactericidal Activity.

Overnight cultures of bacteria were diluted 1:1,000 in fresh Lennox medium and incubated with shaking at 37° C. until the $OD_{600}$ reached 0.2. The cultures were then diluted 1:400 in PBS to a concentration of $1\times10^5$ CFU/ml. Mouse sera (day 70) was diluted 1:10 in PBS. The antigen mixture was then prepared by combining 1.5 μl of diluted bacteria, 3 μl of guinea pig complement (CEDARLANE Laboratories Ltd, Burlington, N.C., USA) and 25.5 μl of PBS. The entire antigen mixture was incubated with 30 μl diluted mouse sera at 37° C. for 1 h. Viable counts were performed both prior to and after exposure to complement. Results were expressed as the percentage of the starting inoculum that survived exposure to mouse serum and complement. Pooled sera were tested for bactericidal activity against each strain on at least three separate occasions.

Opsonophagocytic Uptake by Macrophages.

Mouse macrophage J774 cells were maintained using DMEM containing 4.5 g/l D glucose, L-glutamine and 110 mg/l Sodium Pyruvate (GIBCO [Invitrogen]) supplemented with 10% [v/v] fetal bovine serum (FBS). 24-well plates were either seeded with $1\times10^5$ J774 cells/well and incubated for two days or seeded with $4\times10^5$ cells/well and incubated for 1 day. Semi-confluent J774 cell monolayers were washed once with sterile PBS which was replaced with fresh tissue culture medium. Bacteria were prepared by performing a 1:1,000 dilution of an overnight culture in fresh Lennox media and incubating at 37° C. until the $OD_{600}$ reached 0.2. The culture was diluted 1:20 in PBS. 90 μl of this bacterial suspension was then added to 10 μl sera (that had been heat-inactivated at 56° C. for 20 min) and incubated at room temperature for 20 min while rotating. A 10 μl aliquot of the cell suspension ($2$-$5\times10^4$ CFU) was added to a semi-confluent layer of J774 cells. The tray was then incubated at 37° C. in a 5% $CO_2$ incubator for 45 min. The cells were washed once with PBS, replaced with fresh medium containing 100 μg/ml gentamicin (which kills extracellular bacteria only), and the cells incubated for 1 hour at 37° C. in humidified atmospheric air containing 5% $CO_2$.

The medium was then removed and the cells were washed three times with PBS. Finally, the J774 cells were lysed with 500 μl of 0.5% (w/v) Triton X-100 (t-Octylphenoxypolyethoxyethanol) and vigorous pipetting to disrupt the cells. Intracellular bacteria were enumerated by performing viable counts. Each strain was tested for opsonophagocytic uptake in duplicate wells and on at least three separate occasions. The percentage of cells taken up by J774 cells (i.e. Percent opsonization) was calculated by dividing the number of bacteria that survive the gentamicin treatment by the inoculum size and multiplying by 100. For the experiments showing uptake across serovars, the results are expressed as fold uptake (the number of NTS coated with sera from immune mice which are taken up by J774 cells divided by the number of NTS coated with PBS-sera which are taken up by J774 cells) to account for differences in basal uptake.

Statistical Methods.

Data were analyzed using Student's t-test (two-tailed) or Fisher's exact test (two-tailed).

Results

Construction of Attenuated Non-Typhoidal *Salmonella* and their Phenotypes.

We chose two invasive NTS isolated from the blood of toddlers in Mali to use as the basis of live attenuated vaccine strains. Both *S. Typhimurium* 177 and *S. Enteritidis* R11 are antibiotic-susceptible and possess the *Salmonella* virulence plasmid (Table 3).

The guaBA loci of S. Typhimurium 177 and S. Enteritidis R11 were deleted using the lambda red recombinase technique. The mutants were tested phenotypically by streaking them onto chemically defined medium with or without guanine. While the respective wild-type strains, S. Typhimurium 177 and S. Enteritidis R11, grew on both media, as expected, the guaBA mutants, CVD 1920 (S. Typhimurium 177 ΔguaBA) and CVD 1940 (S. Enteritidis R11 ΔguaBA), could not grow on media lacking guanine (data not shown).

Figure 11:
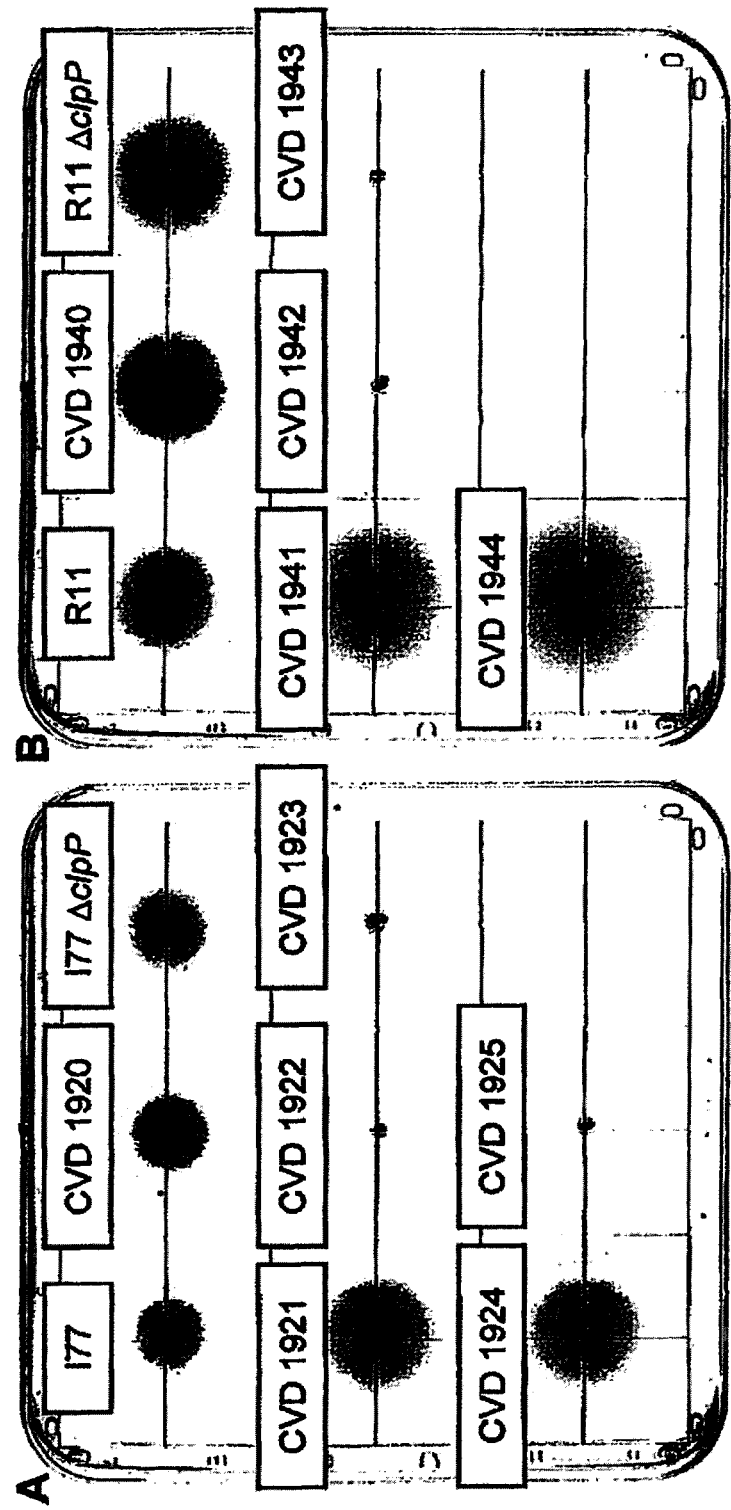
FIG. 11. Motility of attenuated NTS strains on medium containing 1% Tryptone, 0.5% NaCl, 0.005% guanine and 0.4% agar. A) *S. Typhimurium* 177, CVD 1920 (ΔguaBA), 177 ΔclpP, CVD 1921 (ΔguaBA ΔclpP), CVD 1922 (ΔguaBA ΔfliD), CVD 1923 (ΔguaBA ΔclpP ΔfliD), CVD 1924 (ΔguaBA ΔclpP ΔfljB) and, CVD 1925 (ΔguaBA ΔclpP ΔfliD ΔfljB); and B) *S. Enteritidis* R11, CVD 1940 (ΔguaBA), R11 ΔclpP, CVD 1941 (ΔguaBA ΔclpP), CVD 1942 (ΔguaBA ΔfliD), CVD 1943 (ΔguaBA ΔclpP ΔfliD), and CVD 1944 (ΔguaBA ΔclpX).
Figure 12:
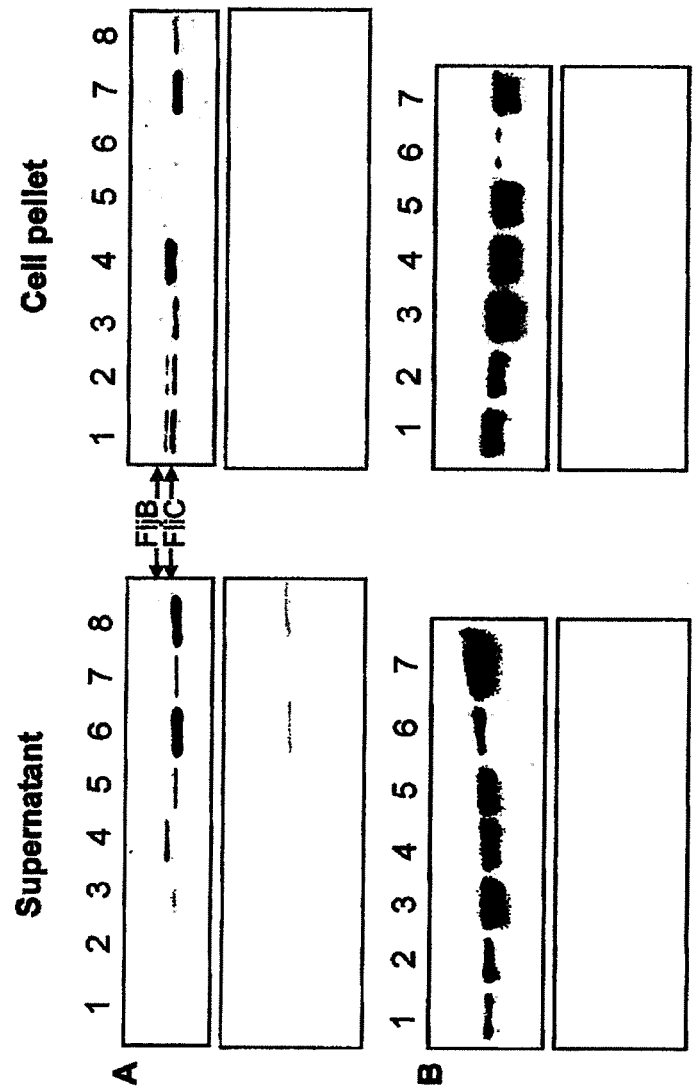
FIG. 12. Western blot (top) probed with anti-flagella 15D8 antibody and Coomassie-stain (bottom) of supernatant (left panel) and cell-associated proteins (right panel) from attenuated NTS strains. Samples were prepared from cultures grown in Lennox media without shaking at 37° C. overnight. Equivalent amounts of bacteria were loaded in each lane. A) *S. Typhimurium* 177 and mutants. Lanes 1, *S. Typhimurium* 177; 2, CVD 1920 (ΔguaBA); 3, 177 ΔclpP; 4, CVD 1921 (ΔguaBA ΔclpP); 5, CVD 1922 (ΔguaBA ΔfliD); 6, CVD 1923 (ΔguaBA ΔclpP ΔfliD); 7, CVD 1924 (ΔguaBA ΔclpP ΔfljB) and 8, CVD 1925 (ΔguaBA ΔclpP ΔfliD ΔfljB); and B) *S. Enteritidis* R11 and mutants. Lanes 1, *S. Enteritidis* R11; 2, CVD 1940 (ΔguaBA); 3, R11 ΔclpP; 4, CVD 1941 (ΔguaBA ΔclpP); 5, CVD 1944 (ΔguaBA ΔclpX); 6, CVD 1942 (ΔguaBA ΔfliD) and 7, CVD 1943 (ΔguaBA ΔclpP ΔfliD).
Figure 19:
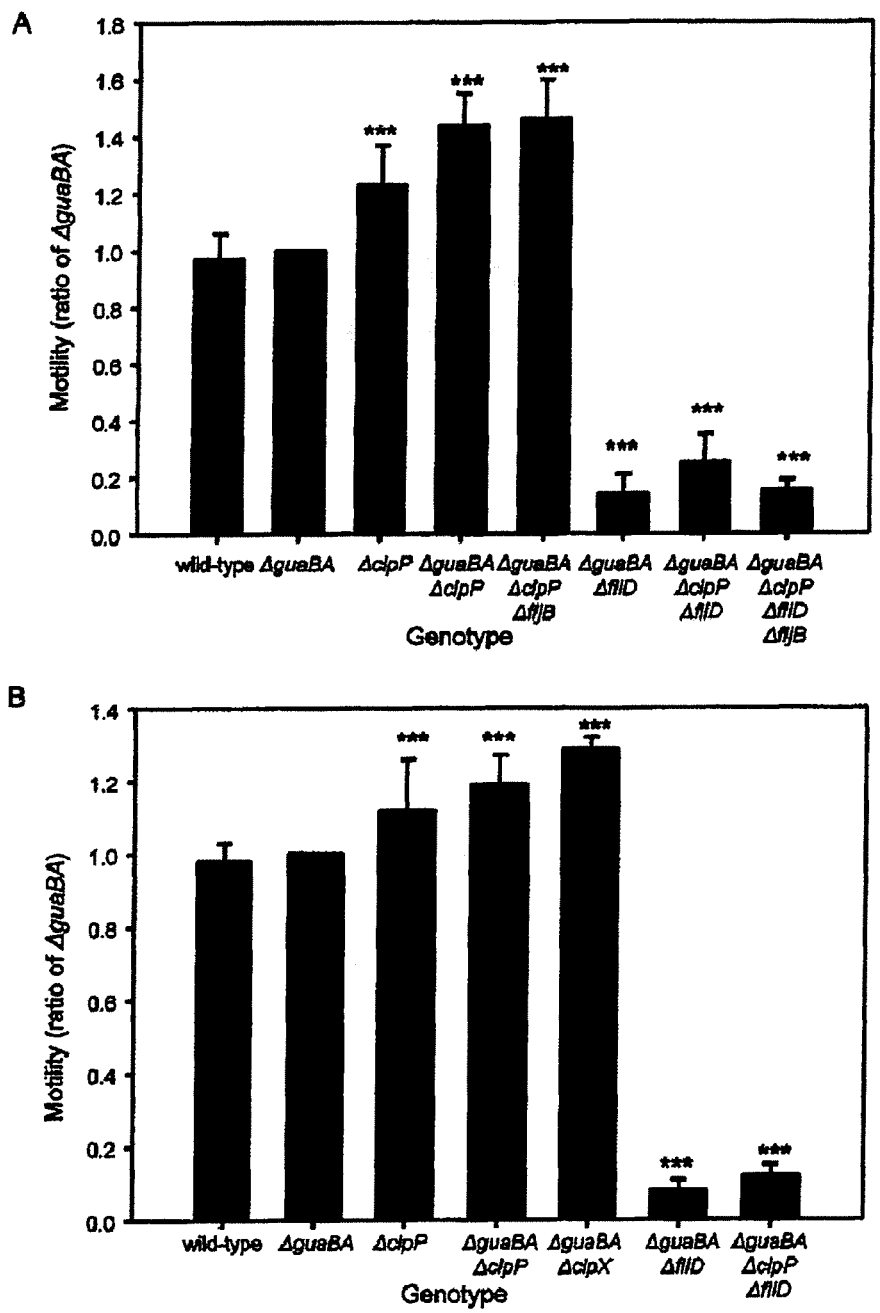
FIG. 19 Motility of attenuated NTS strains. (A) *S. Typhimurium* 177 and attenuated strains; and (B) *S. Enteritidis* R11 and attenuated strains. ***P≤0.001 vs ΔguaBA, Students t-test, two-tailed.
Figure 20:
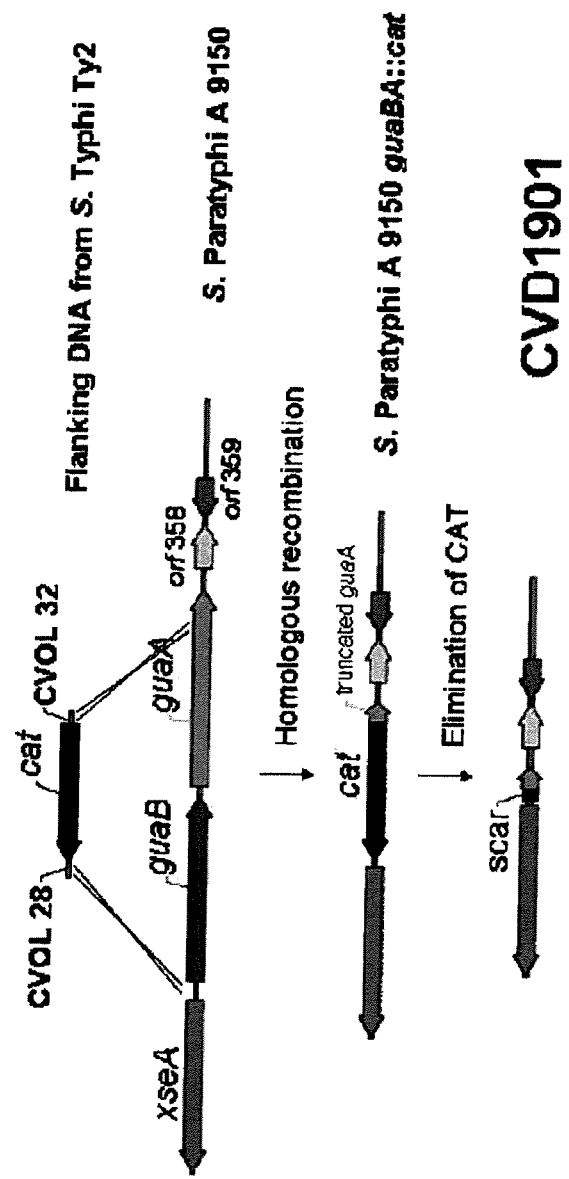
FIG. 20. Chromosomal deletion of guaBA from *S. Paratyphi* A strain 9150.
Figure 21:
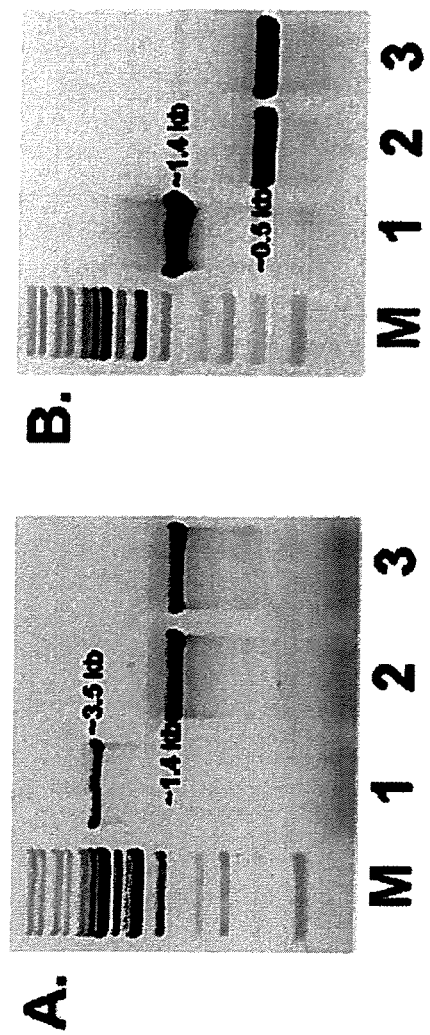
FIGS. 21 (A) and (B). Characterization of guaBA deletion mutants by PCR analysis.
Figure 22:
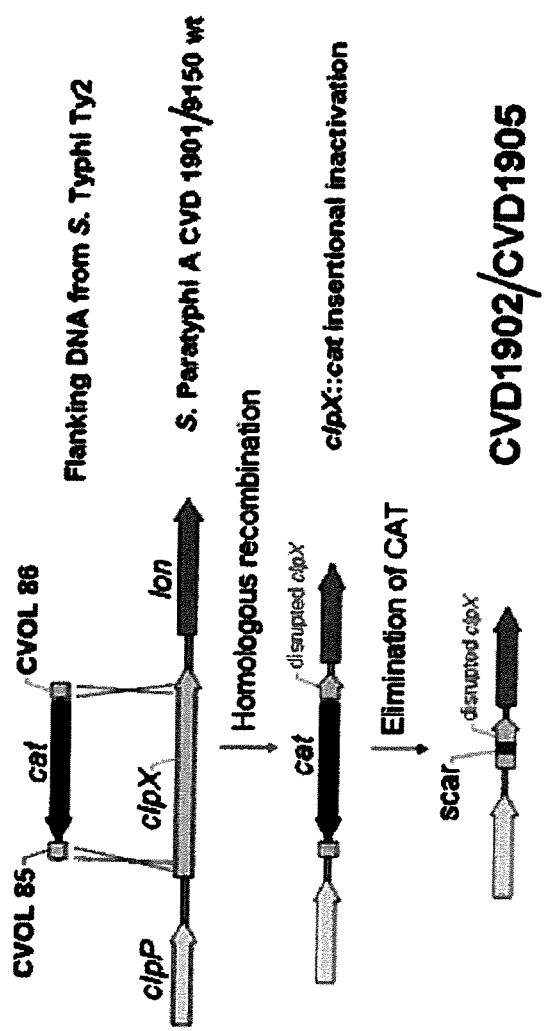
FIG. 22. Chromosomal deletion of clpX from CVD 1901.

A ΔclpP polar mutation was then introduced into the S. Typhimurium 177, S. Enteritidis R11, CVD 1920 (S. Typhimurium 177 ΔguaBA) and CVD 1940 (S. Enteritidis R11 ΔguaBA) backgrounds, to result in 177 ΔclpP, R11 ΔclpP, CVD 1921 (S. Typhimurium 177 ΔguaBA ΔclpP) and CVD 1941 (S. Enteritidis R11 ΔguaBA ΔclpP), respectively. Motility tests showed that, as expected, the ΔclpP mutants were 1.1- to 1.4-fold more motile than both the wild-type strains and the ΔguaBA mutants (FIGS. 11 and 19). SDS-PAGE and western blot analyses showed that CVD 1921 (S. Typhimurium 177 ΔguaBA ΔclpP), CVD 1941 (S. Enteritidis R11 ΔguaBA ΔclpP) and the S. Enteritidis R11 ΔclpP mutant produce more cell-associated flagella than the parental strains (FIG. 12). Although the S. Typhimurium 177 ΔclpP mutant did not appear to hyperexpress flagella, we found that hyperflagellation could be induced by subculturing at 30° C. (results not shown). Also, the SDS-PAGE and western analyses suggested that CVD 1921 (S. Typhimurium 177 ΔguaBA ΔclpP) only produces FljB. Moreover, using serotyping we found that the bacteria were able to switch phases and could be agglutinated with both H-i (Phase 1) and H-2 (Phase 2) antisera. We also deleted the clpX gene from CVD 1940 (S. Enteritidis R11 ΔguaBA) to produce mutant CVD 1944 (S. Enteritidis R11 ΔguaBA ΔclpX) and showed the same increased motility and flagellin production as CVD 1941, which possesses a ΔclpP polar mutation in the CVD 1940 background.

We deleted one more locus of CVD 1921 (S. Typhimurium 177 ΔguaBA ΔclpP) and CVD 1941 (S. Enteritidis R11 ΔguaBA ΔclpP) to determine its effect on immunogenicity and to produce safe S. Typhimurium and S. Enteritidis reagent strains for subunit vaccine production (conjugate vaccines using flagellin monomers as the carrier protein). The fliD gene was deleted from the CVD 1920 (S. Typhimurium 177 ΔguaBA), CVD 1921 (S. Typhimurium 177 ΔguaBA ΔclpP), CVD 1940 (S. Enteritidis R11 ΔguaBA) and CVD 1941 (S. Enteritidis R11 ΔguaBA ΔclpP) backgrounds, resulting in strains CVD 1922 (S. Typhimurium 177 ΔguaBA ΔfliD), CVD 1923 (S. Typhimurium 177 ΔguaBA ΔclpP ΔfliD), CVD 1942 (S. Enteritidis R11 ΔguaBA ΔfliD) and CVD 1943 (S. Enteritidis R11 ΔguaBA ΔclpP ΔfliD), respectively. The resulting mutants were no longer motile (FIGS. 11 and 19). Furthermore, SDS-PAGE and western blot analyses show that all resulting ΔfliD mutants mainly export flagellin into the supernatant (it is no longer cell-associated) and moreover, CVD 1923 (S. Typhimurium 177 ΔguaBA ΔclpP ΔfliD) and CVD 1943 (S. Enteritidis R11 ΔguaBA ΔclpP ΔfliD) export large amounts of flagellin into the supernatant (FIG. 12). Since S. Typhimurium produces both phase 1 (encoded by fliC) and phase 2 (encoded by fljB) flagella, we also deleted fljB to produce strains that hyperexpress only phase 1 cell-associated flagella or secreted flagellin only. The fljB gene was deleted from CVD 1921 (S. Typhimurium 177 ΔguaBA ΔclpP) and CVD 1923 (S. Typhimurium 177 ΔguaBA ΔclpP ΔfliD) to produce CVD 1924 (S. Typhimurium 177 ΔguaBA ΔclpP ΔfljB) and CVD 1925 (S. Typhimurium 177 ΔguaBA ΔclpP ΔfliD ΔfljB), respectively. As shown in FIG. 12, the fljB mutants only produce FliC.

Safety of Attenuated NTS Strains.

To determine whether ΔguaBA and ΔclpP can function as independently attenuating mutations, we determined the oral 50% lethal dose ($LD_{50}$) of our vaccine strains in BALB/c mice. The oral $LD_{50}$ of the wild-type strains S. Typhimurium 177 and S. Enteritidis R11 was determined to be $2 \times 10^4$ CFU for both strains. First, we determined that the oral $LD_{50}$ for S. Typhimurium 177 ΔclpP was $>4.7 \times 10^8$ CFU. Thus we confirmed the previous findings of Matsui et al. (Infect. Immun. 71:30-39 (2003)) in showing that a ΔclpP mutation greatly attenuates S. Typhimurium. Similarly, S. Enteritidis R11 ΔclpP is also highly attenuated and the $LD_{50}$ was $>1.6 \times 10^9$ CFU. Finally, CVD 1920 (S. Typhimurium 177 ΔguaBA), CVD 1921 (S. Typhimurium 177 ΔguaBA ΔclpP), CVD 1923 (S. Typhimurium 177 ΔguaBA ΔclpP ΔfliD), CVD 1940 (S. Enteritidis R11 ΔguaBA), CVD 1941 (S. Enteritidis R11 ΔguaBA ΔclpP) and CVD 1943 (S. Enteritidis R11 ΔguaBA ΔclpP ΔfliD) possess $LD_{50}$s greater than $7.8 \times 10^8$ CFU when given orally to BALB/c mice (Table 5).

TABLE 5

Oral $LD_{50}$ analysis of attenuated NTS strains

| Strains | Genotype | $LD_{50}$ |
|---|---|---|
| S. Typhimurium 177* | | |
| CVD 1920 | ΔguaBA | $>7.8 \times 10^8$ CFU |
| CVD 1921 | ΔguaBA ΔclpP | $>8.0 \times 10^9$ CFU |
| CVD 1923 | ΔguaBA ΔclpP ΔfliD | $>7.0 \times 10^9$ CFU |
| S. Enteritidis R11* | | |
| CVD 1940 | ΔguaBA | $>1.1 \times 10^9$ CFU |
| CVD 1941 | ΔguaBA ΔclpP | $>1.3 \times 10^{10}$ CFU |
| CVD 1943 | ΔguaBA ΔclpP ΔfliD | $>9.8 \times 10^9$ CFU |

*Oral $LD_{50}$ of wild-type strains is $2 \times 10^4$ CFU.

These results indicate that the ΔguaBA and ΔclpP mutations are independently attenuating and that the vaccine strains CVD 1921 (S. Typhimurium 177 ΔguaBA ΔclpP), CVD 1923 (S. Typhimurium 177 ΔguaBA ΔclpP ΔfliD), CVD 1941 (S. Enteritidis R11 ΔguaBA ΔclpP) and CVD 1943 (S. Enteritidis R11 ΔguaBA ΔclpP ΔfliD) each have an oral $LD_{50}$ greater than 4 log 10 above that of the wild-type parental strains.

Shedding of the Attenuated NTS Strains in Mouse Feces.

Figure 13:
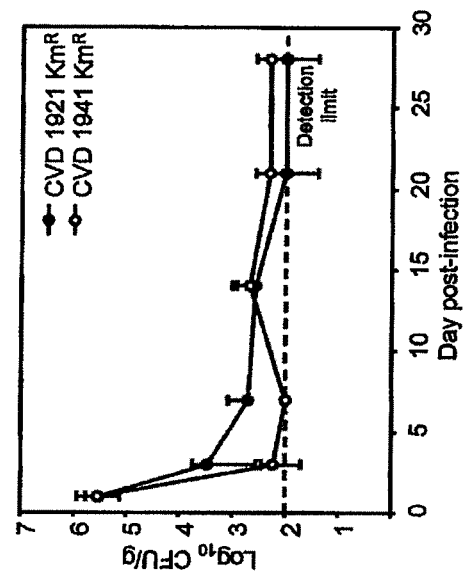
FIG. 13. Shedding of the attenuated NTS strains in mouse feces. Three BALB/c mice were gavaged with $10^9$ CFU of CVD 1921 Km$^R$ (*S. Typhimurium* 177 ΔguaBA ΔclpP::Km$^R$) or CVD 1941 Km$^R$ (*S. Enteritidis* R11 ΔguaBA ΔclpP::Km$^R$) and fecal counts (expressed as mean±standard deviation CFU/g feces) were determined for 28 days. Samples for which no bacteria were detected were assigned a count of 99 CFU/g (1 CFU/g below the detection limit of 100 CFU/g).

Since our attenuated vaccine strains do not possess any antibiotic-selection markers, we used antibiotic-resistant precursors to the final CVD 1921 and CVD 1941 strains (i.e., ΔguaBA☐ΔclpP::$Km^R$) to monitor shedding in feces. We inoculated BALB/c mice via oral gavage with $10^9$ CFU of CVD 1921 $Km^R$ (S. Typhimurium 177 ΔguaBA ΔclpP::$Km^R$) or CVD 1941 $Km^R$ (S. Enteritidis R11 ΔguaBA ΔclpP::$Km^R$) and monitored excretion of the strains for 28 days. The number of CFU/g rapidly decreased within the first week of dosing and CVD 1921 $Km^R$ (S. Typhimurium 177 ΔguaBA ΔclpP::$Km^R$) was not detected in any of the mice at days 21 and 28 (FIG. 13). At the same time-points, CVD 1941 $Km^R$ (S. Enteritidis R11 ΔguaBA ΔclpP::$Km^R$) was detected in one out of three mice.

Immune Responses Generated by the Live Attenuated NTS Vaccines.

Figure 16:
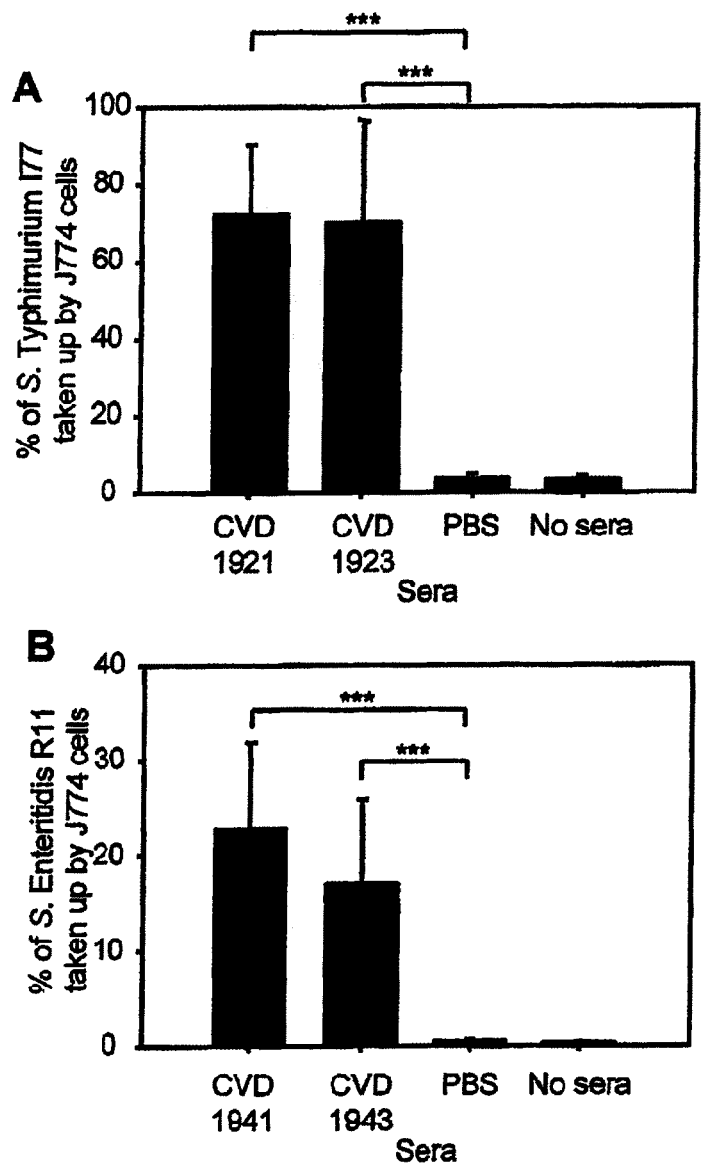
FIG. 16. Ability of individual sera from NTS-immunized mice to opsonize NTS and enable uptake by J774 cells. A) Uptake of *S. Typhimurium* 177 and B) uptake of *S. Enteritidis* R11 by J774 cells. Sera taken two weeks after the third immunization (day 70) were tested. Each serum sample was tested in duplicate wells once. Results are shown as the mean±standard deviation. ***, P≤0.001, Student's t-test, two-tailed.

Mice were immunized orally with CVD 1921 (S. Typhimurium 177 ΔguaBA ΔclpP), CVD 1923 (S. Typhimurium 177 ΔguaBA ΔclpP ΔfliD), CVD 1941 (S. Enteritidis R11 ΔguaBA ΔclpP) or CVD 1943 (S. Enteritidis R11 ΔguaBA ΔclpP ΔfliD) three times, one month apart. One mouse from each of the CVD 1921 (S. Typhimurium 177 ΔguaBA ΔclpP) and CVD 1941 (S. Enteritidis R11 ΔguaBA ΔclpP) groups died following the third immunization, possibly due to the gavage procedure. Anti-LPS and anti-FliC IgG titers increased progressively during the immunization schedule (Table 6).

higher uptake of *S. Typhimurium* 177 by J774 cells than sera from unvaccinated mice (PBS control, FIG. 16). Likewise, individual sera from mice immunized with CVD 1941 (*S. Enteritidis* R11 ΔguaBA ΔclpP) or CVD 1943 (*S. Enteritidis*

TABLE 6

Seroconversion and anti-LPS and anti-FliC IgG geometric mean titers (GMTs)[a]

| Vaccine | Day | Anti-LPS | | | Anti-FliC | | |
|---|---|---|---|---|---|---|---|
| | | Sero-conversion[b] | GMT[c] | (range) | Sero-conversion | GMT | (range) |
| CVD 1921 | 26 | 4/15 | 31 | (13-551) | 14/15 | 2,082 | (64-168,872) |
| | 55 | 14/15 | 1,100 | (25-27,483) | 15/15 | 73,618 | (15,889-299,262) |
| | 83 | 14/14[d] | 8,363 | (182-91,306) | 14/14 | 154,373 | (55,123-877,205) |
| CVD 1923 | 26 | 3/15 | 29 | (13-544) | 15/15 | 1,643 | (396-5359) |
| | 55 | 15/15 | 1,181 | (91-105,118) | 15/15 | 51,714 | (5953-264,148) |
| | 83 | 15/15 | 6,122 | (202-420,972) | 15/15 | 164,415 | (17,372-1,655,822) |
| CVD 1941 | 26 | 8/15[e] | 66 | (13-903) | 15/15[e] | 6,648 | (500-385,095) |
| | 55 | 13/15 | 967 | (13-20,730) | 15/15 | 9,198 | (276-443,634) |
| | 83 | 13/14[d] | 6,912 | (25-140,784) | 14/14 | 19,657 | (364-1,062,833) |
| CVD 1943 | 26 | 4/15[e] | 23 | (13-210) | 6/15[e] | 95 | (13-19,276) |
| | 55 | 11/15 | 268 | (25-43,706) | 11/15 | 599 | (13-156,216) |
| | 83 | 15/15 | 1,426 | (70-74,091) | 13/15 | 5,786 | (13-816,942) |

[a]Mice were immunized orally with $10^9$ CFU in a 200 μl volume, three times, one month between each immunization (on days 0, 28 and 56). Sera were collected 1-2 days prior to each immunization (on days −1, 26 and 55) as well as one month after the last immunization (day 83).
[b]Number of seroconverting mice/number of immunized mice.
[c]From two-fold serial dilutions starting at 1:50.
[d]One mouse each from the CVD 1921- and CVD 1941-vaccinated groups died following the third immunization.
[e]Anti-LPS, CVD 1941 vs CVD 1943 (P = 0.264, Fisher's exact test, two-tailed) and anti-FliC, CVD 1941 vs CVD 1943 (P < 0.001, Fisher's exact test, two-tailed).

Figure 14:
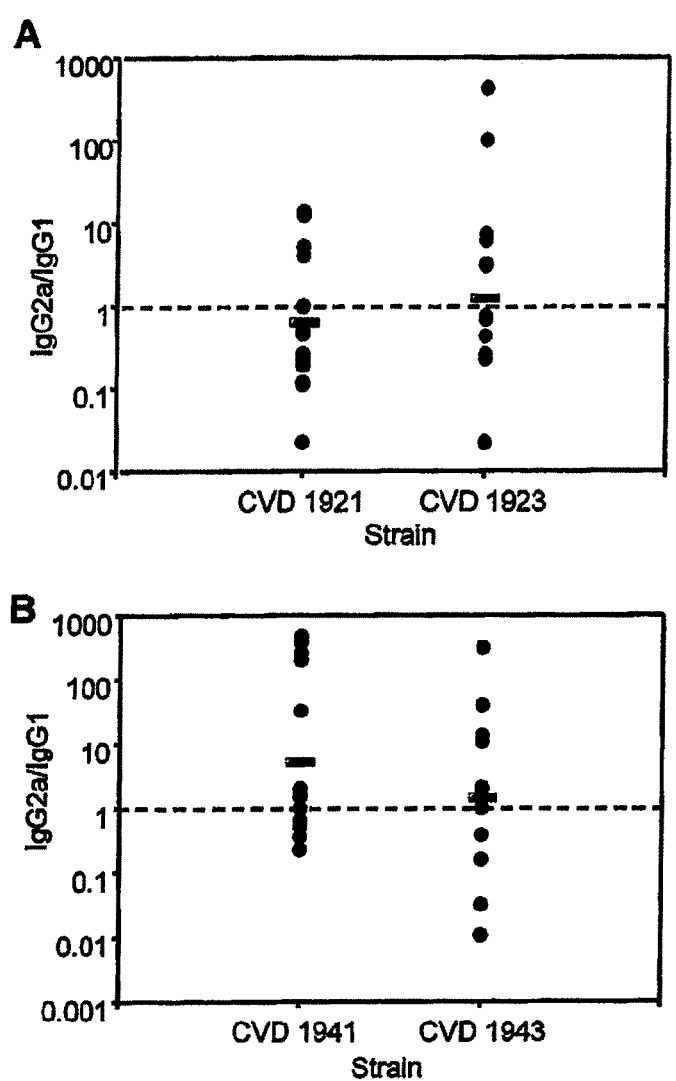
FIG. 14. IgG isotype analysis on sera from A) *S. Typhimurium*- and B) *S. Enteritidis*-immunized mice at day 83. Mice were immunized orally with $10^9$ CFU of CVD 1921 (*S. Typhimurium* 177 ΔguaBA ΔclpP), or CVD 1921 (*S. Typhimurium* 177 ΔguaBA ΔclpP ΔfliD), CVD 1941 (*S. Enteritidis* R11 ΔguaBA ΔclpP) or CVD 1943 (*S. Enteritidis* R11 ΔguaBA ΔclpP ΔfliD), three times, one month between each immunization and sera collected one month after the last immunization. IgG1 and IgG2a subclasses against *S. Typhimurium* or *S. Enteritidis* flagella were determined by ELISA.

Mice immunized with attenuated *S. Typhimurium* constructs CVD 1921 (*S. Typhimurium* 177 ΔguaBA ΔclpP) and CVD 1923 (*S. Typhimurium* 177 ΔguaBA ΔclpP ΔfliD) had excellent seroconversion rates after the second immunization (CVD 1921: 14/15 mice for anti-LPS, 15/15 mice for anti-FliC; CVD 1923: 15/15 mice for both anti-LPS and anti-FliC), and mounted robust antibody responses against both target antigens. For mice immunized with attenuated *S. Enteritidis* vaccine candidates, there was a trend of higher seroconversion rates after the first dose in mice that received CVD 1941 (*S. Enteritidis* R11 ΔguaBA ΔclpP) compared with those immunized with CVD 1943 (*S. Enteritidis* R11 ΔguaBA ΔclpP ΔfliD), which was statistically significant for anti-FliC (15/15 vs 6/15, P<0.001, Fisher's exact test). Just prior to challenge, 15/15 mice immunized with attenuated *S. Enteritidis* CVD 1943 (*S. Enteritidis* R11 ΔguaBA ΔclpP ΔfliD) showed seroconversion for anti-LPS and 13/15 mice showed seroconversion for anti-FliC. IgG isotype analysis was performed on sera from day 83 and the ratio of IgG2a/IgG1 titers was determined (FIG. 14). The mean IgG2a/IgG1 ratios were 0.64 and 1.23 for CVD 1921- and CVD 1923-immunized mice respectively (P=0.28, Student's t-test, two-tailed) and 5.17 and 1.45 for CVD 1941- and CVD 1943-immunized mice respectively (P=0.14, Student's t-test, two-tailed).

Figure 15:
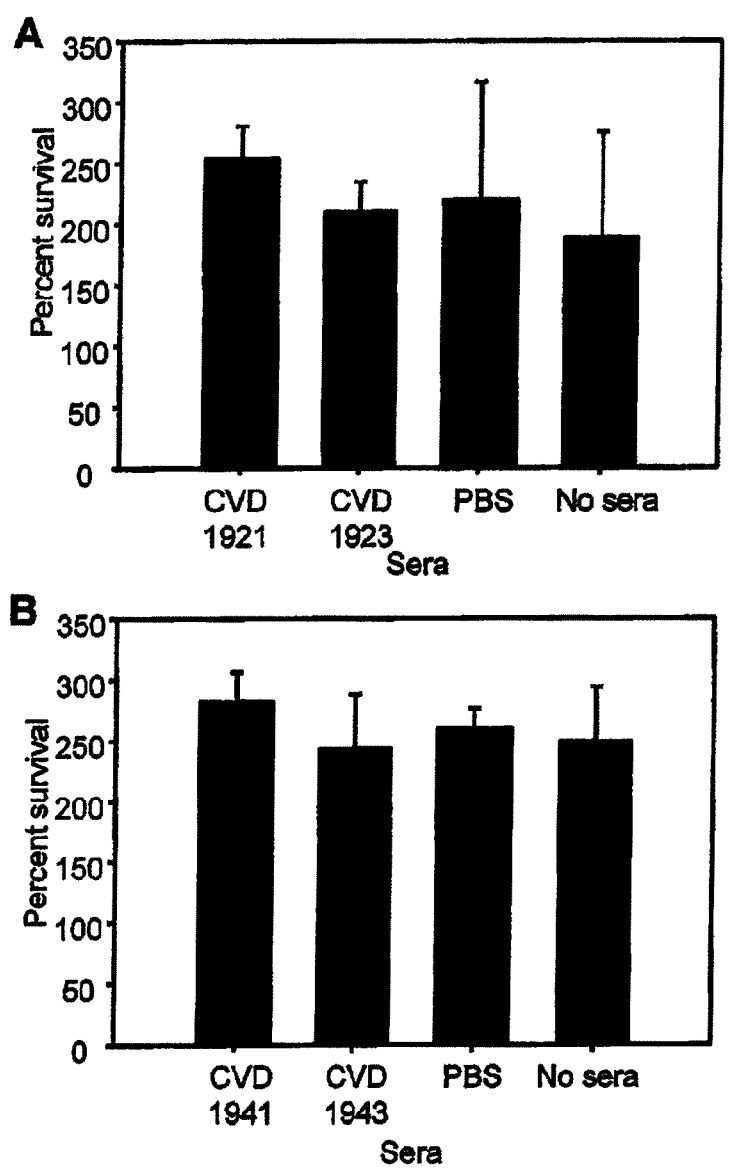
FIG. 15. Serum bactericidal activity of pooled sera (day 70) from A) CVD 1921- and PBS-immunized mice against *S. Typhimurium* 177, and B) CVD 1941- and PBS-immunized mice against *S. Enteritidis* R11. Results were expressed as the percentage of the starting inoculum that survived exposure to mouse serum and complement. Pooled sera were tested for bactericidal activity against each strain on at least three separate occasions. Results are shown as the mean±standard deviation.

Sera from the immunized mice were also examined for their ability to directly kill NTS and to mediate opsonophagocytic uptake. Pooled sera from CVD 1921- or CVD 1923-immunized mice obtained two weeks after the last immunization were unable to kill *S. Typhimurium* 177 (FIG. 15). Sera from CVD 1941- and CVD 1943-immunized mice also showed no bactericidal activity against *S. Enteritidis* R11.

Figure 17:
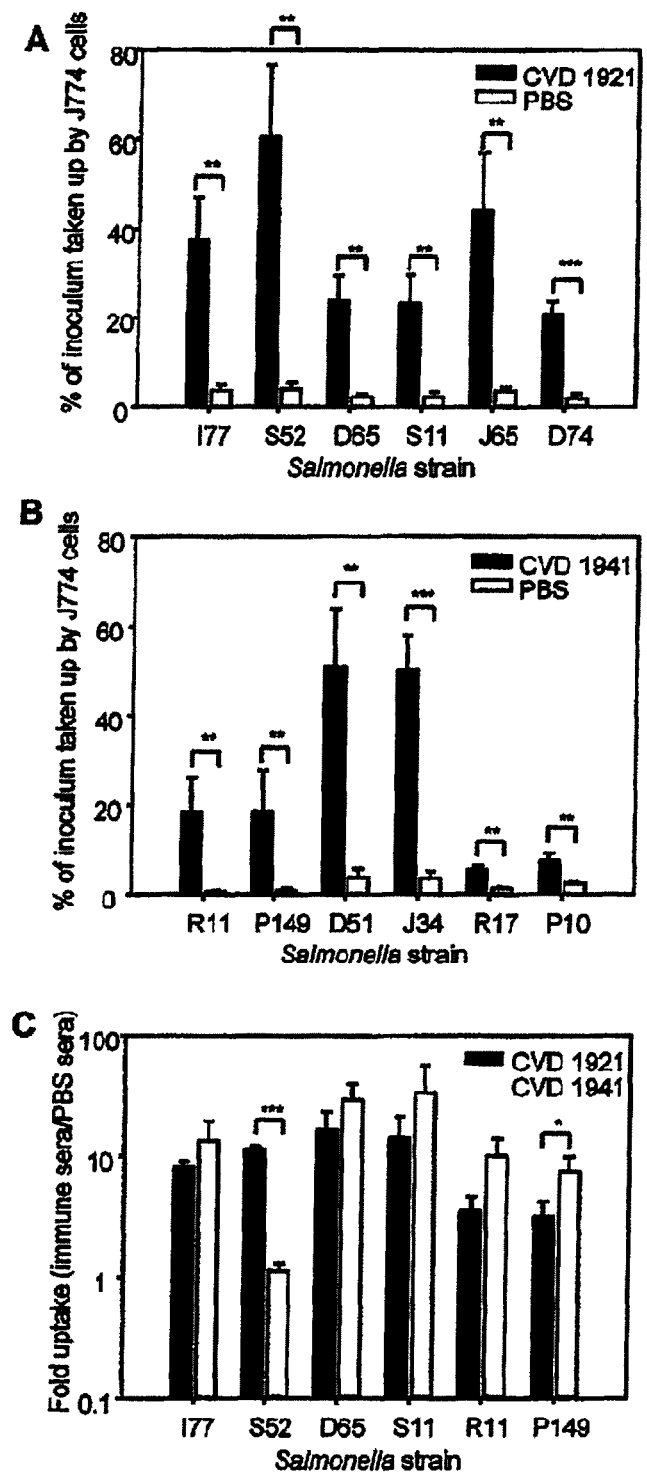
FIG. 17. Ability of pooled sera from NTS-immunized mice to opsonize NTS and enable uptake by J774 cells. A) Uptake of Group B serovars (*S. Typhimurium* strains 177, S52, D65 and S11; *S.* Stanleyville J65 and *Salmonella* I 4,[5],12:i:-D74), B) Uptake of Group D serovars (*S. Enteritidis* strains R11, P149, D51 and J34; and S. Dublin strains R17 and P10), and C) Fold uptake of *S. Typhimurium* (177, S52, D65 and S11) and *S. Enteritidis* (R11 and P149). Results were expressed as fold uptake to account for differences in basal uptake of individual *S. Typhimurium* and *S. Enteritidis* isolates. Fold uptake is defined as the number of bacteria coated with sera from mice vaccinated with CVD 1921 (*S. Typhimurium* 177 ΔguaBA ΔclpP) or CVD 1941 (*S. Enteritidis* R11 ΔguaBA ΔclpP) that are taken up by J774 cells divided by the number of bacteria coated with sera from PBS-immunized mice that are taken up by J774 cells. Sera taken two weeks after the third immunization (day 70) were tested. Each NTS strain was tested in duplicate wells and on at least three separate occasions. Results are shown as the mean±standard deviation. *, P≤0.05; , P≤0.01; *, P≤0.001, Student's t-test, two-tailed.

In contrast to the lack of bactericidal activity, the immune sera exhibited excellent opsonophagocytic activity. Individual sera from mice immunized with CVD 1921 (*S. Typhimurium* 177 ΔguaBA ΔclpP) or CVD 1923 (*S. Typhimurium* 177 ΔguaBA ΔclpP ΔfliD) were able to promote significantly higher uptake of *S. Typhimurium* 177 by J774 cells than sera from unvaccinated mice. R11 ΔguaBA ΔclpP ΔfliD) were able to promote significantly higher uptake of *S. Enteritidis* R11 by J774 cells than sera from PBS control mice. In fact, the pooled immune sera generated by the CVD 1921 (*S. Typhimurium* 177 ΔguaBA ΔclpP) vaccine enabled uptake of other strains of *S. Typhimurium* and also two other Group B serovars, S. Stanleyville and S. I 4,[5],12:i:—(FIG. 17). Higher uptake of other invasive *S. Enteritidis* isolates and two S. Dublin, a Group D serovar, strains was also observed following opsonization with pooled sera from CVD 1941-immunized mice compared to sera from PBS-inoculated mice. Interestingly, the pooled sera from mice immunized with a Group B *Salmonella* vaccine were generally able to mediate uptake of Group D *Salmonella* and vice versa (FIG. 17C). Sera from CVD 1921-immunized mice were able to opsonize and enable ~10-fold higher uptake of the *S. Typhimurium* strain S52 than sera from PBS-treated mice, whereas opsonization of this strain with sera from CVD 1941-immunized mice led to no uptake. Sera from CVD 1941-immunized mice were able to opsonize and enable uptake of the *S. Enteritidis* strains R11 and P149 more efficiently than sera from CVD 1921-immunized mice, though the difference was only significant for strain P149 (R11, P=0.057; P149, P=0.038; Student's t-test, two-tailed).

Ability of Attenuated NTS to Immunize and Protect BALB/c Mice Against a Lethal Challenge.

Figure 18:
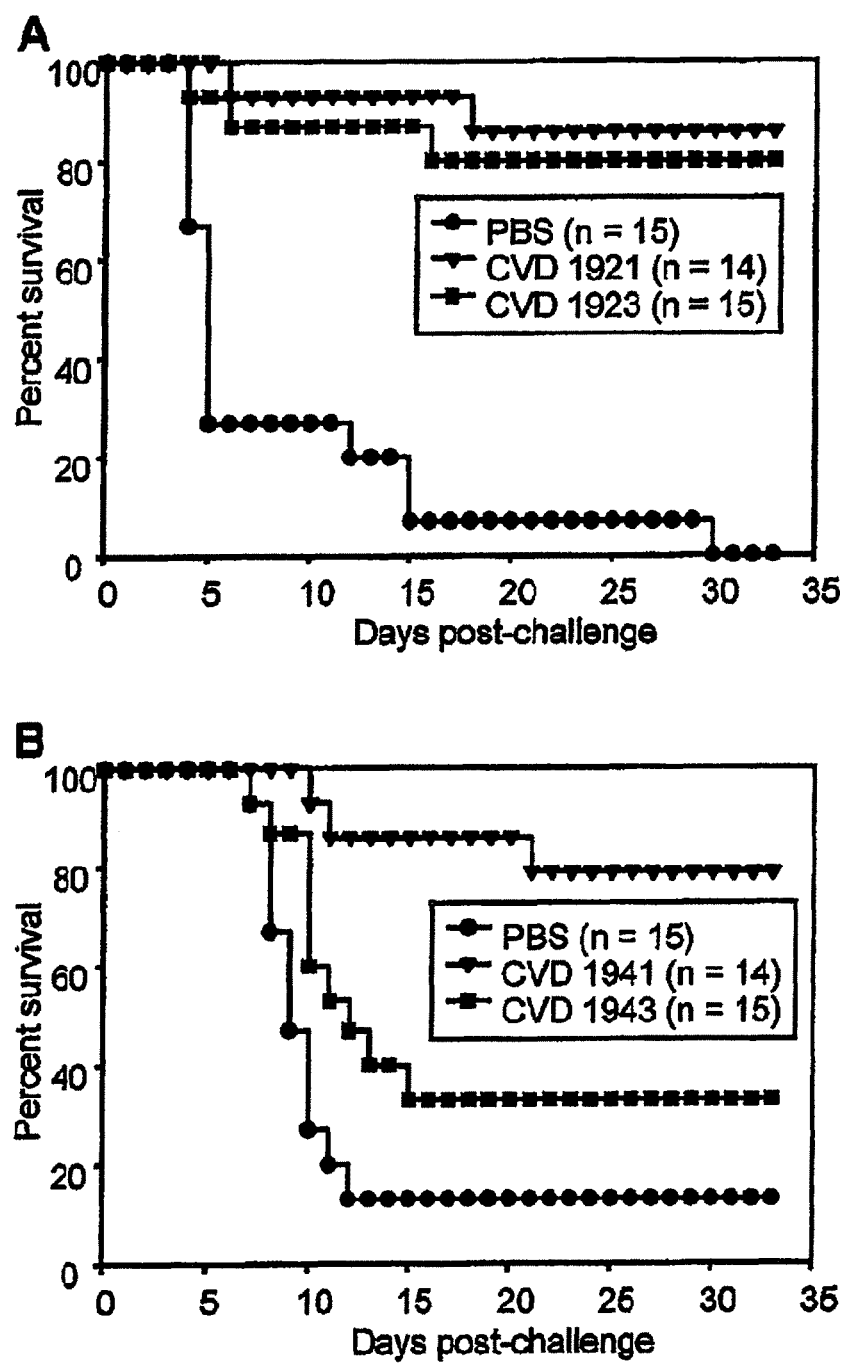
FIG. 18. Percent survival of mice immunized with live attenuated NTS strains. Mice were immunized orally with $10^9$ CFU of CVD 1921 (A) (*S. Typhimurium* 177 ΔguaBA ΔclpP), CVD 1923 (A) (*S. Typhimurium* 177 ΔguaBA ΔclpP ΔfliD), CVD 1941 (B) (*S. Enteritidis* R11 ΔguaBA ΔclpP), CVD 1943 (B) (*S. Enteritidis* R11 ΔguaBA ΔclpP ΔfliD) or PBS, three times, one month between each immunization and orally challenged one month after the last immunization with 100 LD$_{50}$s of *S. Typhimurium* 177 or *S. Enteritidis* R11.

Immunized mice were challenged with 100 $LD_{50}$s ($2 \times 10^6$ CFU) of *S. Typhimurium* 177 or *S. Enteritidis* R11. As shown in FIG. 18, none of the control mice receiving PBS and challenged with virulent *S. Typhimurium* survived at day 33, whereas 86% of the CVD 1921-immunized mice and 80% of the CVD 1923-immunized mice survived challenge out to day 33. For vaccinated mice challenged with *S. Enteritidis*, 13% receiving PBS survived challenge by day 33, whereas 79% vaccinated with CVD 1941 (*S. Enteritidis* R11 ΔguaBA ΔclpP) and 33% vaccinated with CVD 1943 (*S. Enteritidis* R11 ΔguaBA ΔclpP AlliD) survived out to day 33. These data clearly show that while both *S. Typhimurium* vaccine strains, CVD 1921 (*S. Typhimurium* 177 ΔguaBA ΔclpP) and CVD 1923 (*S. Typhimurium* 177 ΔguaBA ΔclpP ΔfliD), carrying attached and non-attached flagella respectively, are highly protective, in *S. Enteritidis*, only the flagella-carrying strain, CVD 1941 (*S. Enteritidis* R11 ΔguaBA ΔclpP), elicited high levels of homologous protection, while CVD 1943 (*S. Enteritidis* R11 ΔguaBA ΔclpP ΔfliD), which exports flagellin monomers, was much less effective (Table 7).

TABLE 7

Vaccine efficacy of live attenuated *S. Typhimurium* CVD 1921 (*S. Typhimurium* I77 ΔguaBA ΔclpP) and CVD 1923 (*S. Typhimurium* I77 ΔguaBA ΔclpP ΔfliD) and *S. Enteritidis* vaccines CVD 1941 (*S. Enteritidis* R11 ΔguaBA ΔclpP) and CVD 1943 (*S. Enteritidis* R11 ΔguaBA ΔclpP ΔfliD)[a]

| Immunized with | Challenged with | Mortality rate | Vaccine efficacy | P value[b] |
|---|---|---|---|---|
| PBS | *S. Typhimurium* I77 | 15/15 | | |
| CVD 1921 | | 2/14 | 86% | P < 0.001 |
| CVD 1923 | | 3/15 | 80% | P < 0.001 |
| PBS | *S. Enteritidis* R11 | 13/15 | | |
| CVD 1941 | | 3/14 | 76% | P < 0.001 |
| CVD 1943 | | 10/15 | 23% | P = 0.390 |

[a]Mice were immunized orally with $10^9$ CFU, three times, one month between each immunization and orally-challenged one month later with $2 \times 10^6$ CFU (100 LD$_{50}$s). The mice were monitored daily for 33 days.
[b]Fisher's exact test (two-tailed).

EXAMPLE 5

Preparation of Attenuated *S. Paratyphi* A

In this example we present details of the construction and quality control to certify the intended genetic fidelity of an attenuated *S. Paratyphi* A biological drug product, strain CVD 1902, to be tested in Phase 1 clinical trials. The parent strain of CVD 1902 is *Salmonella enterica* serovar Paratyphi A ATCC 9150, lot #11848, which was purchased from the American Type Culture Collection (Manassas, Va.).

The vaccine is prepared from a vial of frozen Working Cell Bank (WCB). The WCB is plated onto Animal-Product-Free (APF) LB (Lennox) solid medium supplemented with 0.005% guanine After incubation, single, isolated colonies that exhibit characteristic *Salmonella* morphology are confirmed using Gram stain and agglutination with typing sera directed against *Salmonella* O2 somatic antigen (Denka Seiken Co.) and *Salmonella* Ha phase 1 flagella (Remel Europe). Several well-isolated colonies are suspended in sterile saline and used to inoculate (APF) LB (Lennox) solid medium supplemented with 0.005% guanine for heavy growth. Overnight growth is harvested in sterile phosphate-buffered saline (PBS), pH 7.4, and washed three times. The heavy bacterial suspension is diluted to produce a suspension with an optical density (at 660 nm) corresponding to the desired bacterial count per ml (as specified in the clinical protocol, e.g., 107, 108 or 109 colony forming units [CFU]). The vaccine suspension is delivered to the study site on wet ice in a screw-cap tube placed inside a temperature control vaccine transport canister and used within 4 hours of preparation. The tube containing the inoculum will be labeled with the strain, concentration, date and time prepared, and the cautionary statement, "Limited by federal law to investigational use."

Differences Between Clinical Material and Material Used in Pre-Clinical Animal Studies.

Biological drug product for the proposed clinical studies will be prepared from CVD 1902 WCB lot 090904, derived from MCB lot 090902. Initial studies that involved intraperitoneal challenge of mice with bacteria suspended in hog gastric mucin carried out to document the attenuated nature of the vaccine strain were conducted using CVD 1902 inocula prepared from laboratory stocks. Having identified an acceptably attenuated candidate vaccine strain, additional immunogenicity and challenge studies in mice were conducted using CVD 1902 inocula prepared from WCB lot 090904. Biological drug product for the proposed clinical studies (a freshly harvested organism formulation) will also be prepared from WCB lot 090904.

Biological Drug Substance (Vaccine).
Strain History and Animal Product-Free Growth Media.

*Salmonella* enteric serovar Paratyphi A 9150, lot #11848, was obtained from the American Type Culture Collection (Manassas, Va.). Propagation of this strain, and subsequent genetic deletions of chromosomal gene sequences required for the construction of CVD 1901 (deleted for the guaBA locus) and CVD 1902 (derived from CVD 1901 and further deleted of the clpX locus) were carried out using a special medium free of animal products called 2× Hy-soy medium. This medium was composed of 20 g Hy-soy peptone (Quest International), 10 g Hy-Yeast 444 (Quest International), 3 g NaCl (Sigma), and 15 g of granulated agar (Difco) per liter. Since both attenuated vaccine strains CVD 1901 and 1902 possess the guaBA deletion and are therefore unable to grow in medium in the absence of guanine, vaccine strains were therefore grown on Hy-soy medium supplemented with guanine (0.005% v/v).

Although 2× Hy-soy was the first medium free of animal products that we determined would support acceptable growth of *S. Paratyphi* A strains, we noted that the generation time for these strains was long. We therefore tested a richer commercially available medium derived solely from plant and yeast products called APF (Animal-Product Free) Lennox LB medium (Athena Enzyme Systems™), comprised of 15 g of an animal-product free substitute of casein hydrolysate called Atholate, 5 g of Hy-Yeast 444, and 5 g NaCl, plus 15 g of granulated agar (Merck) per liter. This medium supported excellent growth of all *S. Paratyphi* A wild type and vaccine strains (with added guanine) and was used for all subsequent pre-clinical testing of CVD 1901 and CVD 1902.

Construction of CVD 1901 and CVD 1902.

Primers needed for the construction of all chromosomal deletions reported here are listed in Table 8.

TABLE 8

Primers used in this study.

| Name | Sequence | Target |
|---|---|---|
| CVOL 13 | 5'-ATTCCCACTCAATGGTAGC-3' (SEQ ID NO: 58) | Ty2 |
| CVOL 15 | 5'-ATTCCCACTCAATGGTAGC-3' (SEQ ID NO: 59) | Ty2 |
| CVOL 26 | 5'-ATATATATGCGGCCGCTGTAGGCTGG AGCTGCTTC-3' (SEQ ID NO: 60) | pKD3 |
| CVOL 27 | 5'-ATAGGCGCGCCATATGAATATCCTCC TTAGT-3' (SEQ ID NO: 61) | pKD3 |

TABLE 8 -continued

Primers used in this study.

| Name | Sequence | Target |
|---|---|---|
| CVOL 28 | 5'-CGAACCGTCTGGTTAAGGCGGCTTAC GGTAAAAATTGAGGAAGTTTGAGAGGATA ACATGTGAGCGGGATCAAATTCTAAATCA GCAGGTTATTCAATCGTGTAGGCTGGAGC TGCTTC-3' (SEQ ID NO: 62) | pKD3 |
| CVOL 32 | 5'-TTCATTGATGATGCGGTTGGAAACAC GACCCAGGAAGTCATACGGCAGGTGCGCC CAGTGCGCGGTCATAAAGTCGATGGTTTC GACAGCACGCAGAGAGCATATGAATATCC TCCTTAG-3' (SEQ ID NO: 63) | pKD3 |
| CVOL 64 | 5'-CATATGAAGGAGTATTGCCCATGCTA CGTATCGCTAAAGAAG-3' (SEQ ID NO: 64) | Ty2 |
| CVOL 65 | 5'-ATGCATCTGCAGTCATTCCCACTCAA TGGTAGCCGG-3' (SEQ ID NO: 65) | Ty2 |
| CVOL 85 | 5'-ACAGATAAACGCAAAGATGGCTCGGG CAAA-3' (SEQ ID NO: 66) | Ty2 |
| CVOL 86 | 5'-TTATTCGCCAGAAGCCTGCGCTTCCG GTTT-3' (SEQ ID NO: 67) | Ty2 |
| CVOL 87 | 5'-CCTGAGAATGGCATTTGCGTCGTCGT GTGC-3' (SEQ ID NO: 68) | Ty2 |
| CVOL 88 | 5'-ACGGCGTGTTTACAGGAAAAACGAAA GGGG-3' (SEQ ID NO: 69) | Ty2 |
| CVOL 124 | 5'-GCGGCCGCGAAGGAGTTTGACTCATG ACAGATAAACGCAAAGATG-3' (SEQ ID NO: 70) | Ty2 |
| CVOL 125 | 5'-CATATGTTATTCGCCAGAAGCCTGCG CTTCCGGTTT-3' (SEQ ID NO: 71) | Ty2 |

Deletions were carried out using a modified Lambda Red-mediated site-directed mutagenesis procedure. Briefly, 10 colonies of bacteria carrying Red helper plasmid pKD46 were added to 20 ml of 2× soy media supplemented with carbenicillin and L-arabinose (0.2%) and grown at 30° C., 250 rpm for 3 hrs ($OD_{600}$ nm of ~0.6). Bacteria were made electrocompetent by washing 3 times with cold sterile water and concentrating 100 fold. Competent cells were electroporated with 100 ng-1 μg of gel-purified PCR product. Following electroporation, bacteria were repaired using 2× soy medium with or without guanine Cells were incubated in 2× soy media at 37° C. for 3 hrs prior to plating on 2× soy agar containing guanine and chloramphenicol (cml) overnight. Antibiotic resistant colonies were selected and screened via PCR for alterations in the chromosomal regions of interest. Positive colonies were restreaked onto 2× soy media containing chloramphenicol, but lacking carbenicillin, to ensure loss of pKD46. Removal of the cml resistance cassette was then carried out using pCP20 encoding FLP recombinase. Colonies exhibiting the desired genotype were re-streaked on 2× soy media lacking antibiotics to ensure the loss of the antibiotic resistance phenotype.

Those selected for storage were re-screened via PCR prior to freezing at −70° C. in 2× soy media containing 20% (v/v) glycerol.

Chromosomal Deletion of guaBA from *S. Paratyphi* A 9150 to create CVD 1901.

The complete genome sequence of *S. Paratyphi* A strain 9150 was not available at the commencement of this project. Since it was critical to have a completely characterized genetic sequence for precise construction of the deletions required for strain constructions, we chose to design all oligonucleotides primers and subsequent DNA templates for chromosomal mutagenesis based on the annotated *S. Typhi* Ty2 genome sequence (Genbank accession number NC_004631). Subsequent to the construction of CVD 1901 and 1902, the complete annotated sequence of *S. Paratyphi* A strain 9150 was reported (Genbank accession number NC_006511) and was used to confirm the intended genomic sequence of the completed deletions of guaBA in CVD 1901 and 1902, and clpX in CVD 1902.

The genes which encode inosine-5'-monophosphate dehydrogenase (guaB) and guanosine monophosphate synthetase (guaA) form an operon in the chromosome of *S. Paratyphi* 9150. The strategy employed for deletion of the guaBA operon is shown in FIG. 20. Primers CVOL 28 and CVOL 32 were used for PCR using pKD3 as a template DNA to generate a cassette encoding resistance to chloramphenicol, flanked by ~100 bp of chromosomal DNA needed to replace the guaBA genes by homologous crossing over. These chromosomal crossovers were catalyzed by the lambda Red recombination system encoded on the temperature-sensitive plasmid pKD46.

*S. Paratyphi* A 9150 was made electrocompetent and transformed with pKD46 and the cat PCR cassette. Transformants were plated at 37° C., and those exhibiting resistance to chloramphenicol were screened by PCR using CVOL 13 and CVOL 15 which hybridize outside of the guaBA region. Unmodified guaBA amplified from *S. Paratyphi* A 9150 was found to be ~3.5 kb (FIG. 21A, lane 1), whereas a ~1.4 kb fragment was found in two clones carrying the desired replacement of guaBA with cat (FIG. 21A, lanes 2 and 3). This cat gene used to replace guaBA was also flanked by a set of direct repeats of a special FLP recombination sequence specifically recognized by an Flp recombinase from *Saccharomyces cerevisiae*. Since vaccine strains intended for oral vaccination of humans cannot encode resistance to antibiotics, removal of the cat resistance cassette was accomplished by introduction of the plasmid pCP20, encoding Flp recombinase, into the guaBA mutants by electroporation. Four deletants were analyzed by PCR with primers CVOL 13 and CVOL 15 and found to yield the desired ~0.5 kb amplicon (FIG. 21B, lanes 2 and 3) in comparison with the guaBA::cat progenitor (lane 1). One of these guaBA deletants of *S. Paratyphi* A 9150 was designated CVD 1901, which was used for all subsequent studies.

Chromosomal Deletion of clpX from CVD 1901 to Create CVD 1902.

Although extremely unlikely, it is theoretically possible that the engineered auxotrophy in CVD 1901, requiring supplementation with guanine for growth to occur, could be restored by a illegitimate recombination event of unknown mechanism with a guaBA genetic sequence of unknown origin. In order to reduce to an infinitesimally minute probability the chance of reversion of guaBA-deleted CVD 1901 to a wild type (wt) genotype, one additional gene, clpX, was targeted for deletion as a secondary independent attenuating mutation, thereby creating CVD 1902. clpX encodes a chaperone ATPase which works together with a serine protease encoded by clpP. Disruption of either ClpX and/or ClpP has been shown to significantly reduce the colonization potential of *Salmonella enterica* serovar Typhimurium in mice. In order to demonstrate the independent attenuating capacity of this deletion, clpX was deleted from wild type *S. Paratyphi* A 9150 to create CVD 1905. The strategy employed for deletion of the guaBA operon is shown in FIG. 22.

Figure 23:
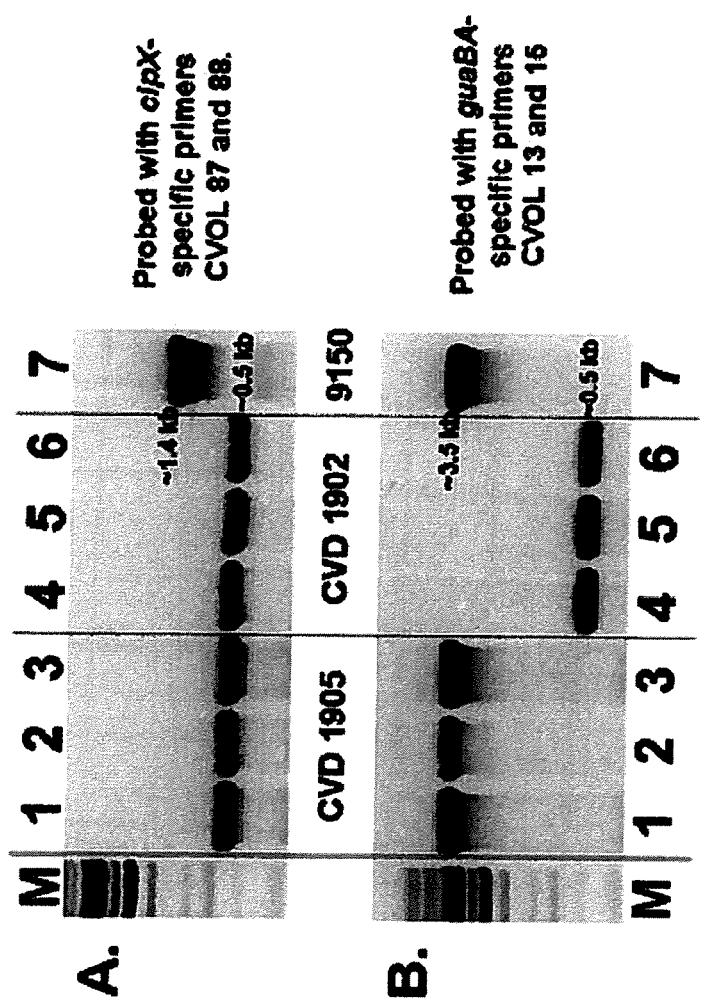
FIGS. 23 (A) and (B). Characterization of clpX deletion mutants by PCR analysis.
Figure 24:
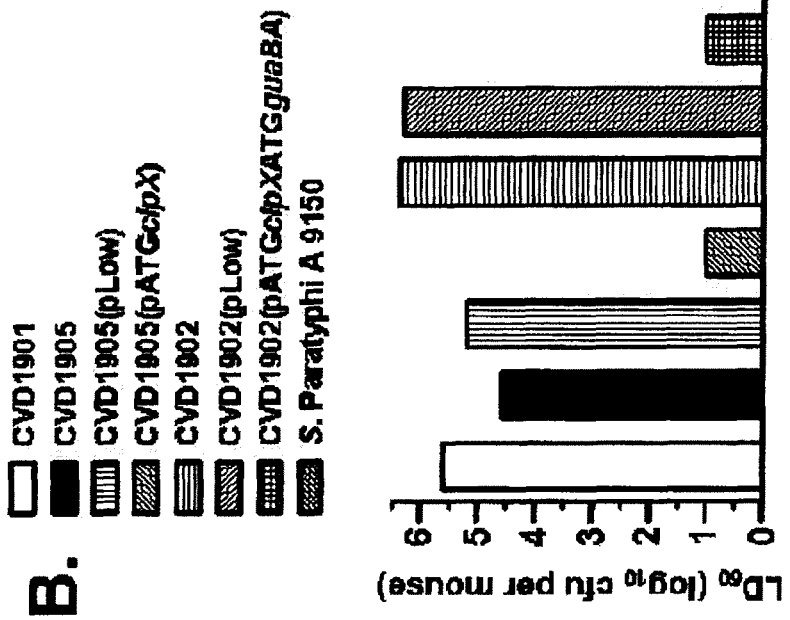
FIGS. 24 (A) and (B). LD$_{50}$ determination for CVD 1901, CVD 1902, CVD 1905, and complemented strains.
Figure 24:
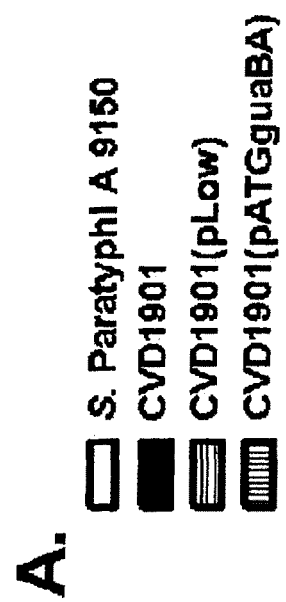

To delete clpX, primers CVOL 85 and 86 were designed to amplify a ~1.3 kb fragment encoding clpX lacking a start codon from S. Typhi Ty2 vaccine strain CVD 908-htrA. This fragment was recovered in the plasmid pGEM®-T and subsequently digested with NruI and EcoRI to remove an internal ~0.9 kb fragment; the digested termini were treated with T4 DNA polymerase to create blunt ends, and a cat cassette encoding resistance to chloramphenicol was inserted. The resulting ~1.4 kb clpX::cat cassette was re-amplified using primers CVOL 85 and 86 and electroporated into either S. Paratyphi A 9150 or CVD 1901 containing pKD46. As described above with the construction of CVD 1901, transformants were plated at 37° C., and those exhibiting resistance to chloramphenicol were screened by PCR using primers CVOL 87 and CVOL 88, which hybridize outside of the clpX deletion region. Mutants carrying the desired clpX::cat insertion were then selected for treatment with pCP20 to remove the cat cassette. FIG. 23 shows that mutants constructed from either wild type S. Paratyphi A (lanes 1-3) or CVD 1901 (lanes 4-6) contained an altered clpX gene that produced a smaller ~0.5 kb amplicon from PCR reactions using primers CVOL 87 and CVOL 88 (FIG. 23, Panel A, lanes 1-6) compared to ~1.4 kb amplicons observed for unaltered *S. Paratyphi* A 9150 (lane 7). PCR analysis of the same strains with CVOL 13 and 15 confirmed that guaBA was absent only from clpX-deleted strains derived from CVD 1901 to produce CVD 1902 (FIG. 23, Panel B, lanes 4-6) and not from clpX-deleted strains derived from *S. Paratyphi* A 9150 which produced CVD 1905 (FIG. 23, Panel B, lanes 1-3).

Identifying an Attenuated Candidate CVD 1902 Vaccine Strain.

Prior to establishing master cell bank (MCB) and working cell bank (WCB) of CVD 1902, the relative degree of attenuation of CVD 1902 was assessed by intraperitoneal (i.p) challenge of mice with organisms suspended in hog gastric mucin, a well documented method for assessing decreased virulence in candidate vaccine strains derived from human-restricted pathogens such as *S. Typhi* and Paratyphi A (Hone et al. *Vaccine.* 9:810-816 (1991); Wang et al. *Infect Immun.* 4647-52 (2000); Wang et al. *Infect Immun.* 69:4734-41 (2001); Powell et al. *J Biol Stand.* 8:79-85 (1980)). In addition to demonstrating attenuation, it was also critical to rule out any cryptic mutations that could have unintentionally arisen during the manipulation of strains for vaccine construction, which could unexpectedly affect virulence or make a strain unpredictable in its biochemical behavior. Wild type *S. Paratyphi* A 9150 contains a heretofore undefined auxotrophy, making it incapable of growth on minimal medium without the addition of casamino acids. Other clinical isolates of *S. Paratyphi* A are also unable to grow on minimal medium, suggesting that serovar *Paratyphi* A has an as yet undefined natural mutation in one or more metabolic pathways that must be complemented by addition of casamino acids. Taking this unknown defect into account, we tested the hypothesis that genetic complementation of both the guaBA and clpX chromosomal lesions by providing these wild type genes on a single multicopy plasmid would restore the virulence of CVD 1902 to wild type levels observed using the intraperitoneal hog gastric mucin assay.

Construction of Low Copy Plasmids for Complementation Analysis.

To carry out the plasmid-based complementation of virulence, plasmids were constructed containing minimal fragments encoding either clpX, guaBA, or both genes inserted in tandem to form an operon. Constitutive expression of the genes in these plasmids was controlled by the lacZ promoter PlacZ. Primers CVOL 64 and CVOL 65 were used to PCR amplify guaBA from CVD 908-htrA, containing an enhanced ribosome binding site with Nde I and Nsi I restriction sites at the 5' and 3' ends, respectively. This ~3.5 kb Nde I-Nsi I cassette was inserted into the low copy number plasmid pLowBlul 84 (referred to in FIG. 24 as pLow), creating the complementing plasmid pATGguaBA. To create a low copy plasmid encoding clpX, primers CVOL 124 and CVOL 125 were used to amplify clpX from CVD 908-htrA, containing an enhanced ribosome binding site and Not I and Nde I sites at the 5' and 3' ends respectively. This ~1.3 kb product was inserted into either the low copy number plasmid pLowBlul 84, or the complementing plasmid pATGguaBA, creating either pATGclpX or pATGclpXATGguaBA respectively. All strains carrying complementing plasmids were grown in the presence of chloramphenicol to maintain complementation, concentrated by centrifugation, and then resuspended in sterile PBS prior to assessment of virulence in mice.

Assessment of Virulence by Intraperitoneal Challenge of Mice with Hog Gastric Mucin.

Female BALB/c mice (Charles River Breeding Laboratories, Inc., Wilmington, Mass.) aged 6 to 8 weeks (three mice per group, three groups per vaccine strain) were injected i.p with various 10-fold dilutions of the bacteria grown in the presence of guanine and antibiotics (to maintain plasmid complementation) where necessary and resuspended in phosphate-buffered saline PBS. Bacterial suspensions were mixed with 10% (wt/vol) hog gastric mucin (Difco, lot #4092018) in a final volume of 0.5 ml. Mice were monitored for extreme moribundity (close to death) or death every 24 h for 72 h after inoculation. Severely moribund mice, in which loss of 20% body weight and/or dehydration could be documented, were immediately euthanized and recorded as “dead” for purposes of data analysis. The 50% lethal dose (LD50) for each group of mice was calculated by linear regression analysis. All experiments were carried out in accordance with the guidance and approval of Institutional Animal Care and Use Committee (IACUC) of the University of Maryland Baltimore. During a three-decade period, this assay has become our most helpful quantitative tool for assessing the relative attenuation of candidate attenuated *S. Typhi* live strains intended for uses as live oral vaccines in humans and has been the best predictor of how such candidate vaccine strains will behave in clinical trials. For this reason, the assay based on mouse intraperitoneal challenge with *Salmonella* suspended in hog gastric mucin was used to assess the degree of attenuation of the guaBA and clpX deletion mutations, independently and in combination, in the *S. Paratyphi* A background. To reiterate, *S. Paratyphi* A is a serovar that, like *S. Typhi*, is human host restricted and has a similar pathogenesis and causes an identical clinical syndrome (enteric fever) in humans as *S. Typhi*.

FIG. 24A shows the LD50 data obtained from the injection of mice with wild type *S. Paratyphi* A 9150 or guaBA-deleted CVD 1901. Wild type *S. Paratyphi* A 9150 was observed to have an LD50 value of <10 bacteria per mouse. In contrast, the LD50 of guaBA-deleted CVD 1901 increased ~4.5 logs in value. Complementation of the guaBA mutant with the empty cloning plasmid pLow did not alter the LD50 value, whereas the introduction of the complementing plasmid pATGguaBA restored the virulence of CVD 1901 to wild type levels. These data indicate that deletion of the guaBA is directly and solely responsible for the level of attenuation observed in CVD 1901. FIG. 24B shows the LD50 data obtained with the injection of mice with wild type 9150, clpX-deleted CVD1905, or ΔguaBAΔclpX CVD1902. The LD50 values of *S. Paratyphi* A 9150 and CVD 1901 were in excellent agreement with those of the experiment reported in FIG. 24A. In addition, the LD50 of clpX-deleted CVD 1905 increased ~3.5 logs when compared with wild type 9150, demonstrating the independent attenuating capacity of a deletion in chromosomal clpX. Deletion of both guaBA and clpX in candidate vaccine strain CVD 1902 appeared to act synergistically, increasing the LD50 value to over 6 logs. Plasmid-mediated genetic complementation of the clpX and clpX-guaBA chromosomal deletions with pATGclpX and pATGclpXATGguaBA, respectively, restored the virulence of CVD 1905 and CVD 1902 to wild type levels, while complementation with the empty cloning plasmid pLow had no effect, as expected.

Non-Clinical Studies

Invasion Assays to Determine the Fitness of CVD 1902.

Phenotypic analysis of the CVD 1902 WCB included assessment of invasion and intracellular replication within a Henle 407 human intestinal epithelial cell line (ATCC #CCL-6). In brief, Henle 407 monolayers were incubated with S. Paratyphi A strains at a multiplicity of infection (MOI) of 100:1 for 90 minutes. Cells were then washed with media containing gentamicin (100 µg/ml) to kill extracellular bacteria. After washing, cells were lysed with triton x-100 (1% in PBS) at O and 4 hours post infection, and intracellular bacteria enumerated. Two independent experiments were carried out. In Experiment 1, attenuated strains were compared with wild type S. Paratyphi A ATCC 9150 and a non-invasive S. flexneri 2a negative control strain, M4243A (Table 9); in Experiment 2 (Table 10), attenuated strains were compared with wild type S. Paratyphi A ATCC 9150 and a non-invasive Escherichia coli negative control strain, HS. In both experiments, viable counts for ATCC 9150 were observed to increase slightly over a 4-hour period after cell invasion, while viable counts for attenuated CVD 1901 and 1902 strains were reduced in a manner similar to both the licensed attenuated typhoid oral vaccine strain Ty21a and non-invasive E. coli strain HS. These experiments clearly show that CVD 1902 (as well as its less attenuated immediate precursor strain CVD 1901) is incapable of sustained intracellular replication due to its strict requirement for guanine for growth, as expected.

TABLE 9

Invasion and intracellular replication assay with CVD 1902: EXPERIMENT 1.

| Strain | Genotype | Initial Dose (cfu) | 0 hours | 4 hours |
|---|---|---|---|---|
| ATCC 9150 | S. Paratyphi A wild type | $2.5 \times 10^7$ | $5.8 \times 10^4$ | $6.1 \times 10^4$ |
| CVD 1901 | ΔguaBA S. Paratyphi A | $2.0 \times 10^7$ | $6.3 \times 10^2$ | $3.9 \times 10^2$ |
| CVD 1902 | ΔguaBA, clpX S. Paratyphi A | $1.5 \times 10^7$ | $1.6 \times 10^3$ | $1.4 \times 10^3$ |
| M4243A | non-invasive Shigella flexneri 2a | $1.2 \times 10^7$ | $5.0 \times 10^0$ | $5.8 \times 10^0$ |

TABLE 10

Invasion and intracellular replication assay with CVD 1902: EXPERIMENT 2.

| Strain | Genotype | Initial Dose (cfu) | 0 hours | 4 hours |
|---|---|---|---|---|
| ATCC 9150 | S. Paratyphi A wild type | $1.6 \times 10^7$ | $9.2 \times 10^4$ | $1.2 \times 10^5$ |
| CVD 1901 | ΔguaBA S. Paratyphi A | $1.5 \times 10^7$ | $1.4 \times 10^3$ | $7.7 \times 10^2$ |
| CVD 1902 | ΔguaBA, clpX S. Paratyphi A | $1.5 \times 10^7$ | $1.9 \times 10^3$ | $1.2 \times 10^3$ |
| Ty21a | Licensed attenuated S. Typhi oral vaccine | $5.3 \times 10^6$ | $1.9 \times 10^3$ | $1.5 \times 10^3$ |
| HS | Non-invasive normal flora Escherichia coli strain | $1.5 \times 10^7$ | $6.5 \times 10^2$ | $4.5 \times 10^2$ |

Murine Mucosal Immunization and Immune Responses

MUCOSAL (Intranasal) Immunization of Mice by an Accelerated Schedule.

S. Paratyphi A resembles S. Typhi in being a highly human host restricted bacterial pathogen. Consequently, oral administration of wild type organisms of these serovars to mice does not result in a productive infection, nor can one successfully immunize mice with attenuated strains administered orally. However, almost 20 years ago CVD investigators discovered that attenuated S. Typhi live oral vaccine strains can successfully immunize mice if they are administered mucosally by the intranasal route (Galen et al. Vaccine. 15:700-708 (1997); Barry et al. Infect Immun. 64:4172-81 (1996)). The nasal associated lymphoid tissue (so-called NALT) of mice can serve as a successful inductive site for productive immune responses leading to serum and mucosal antibody responses and cell mediated immune responses (Pickett et al. Infect Immun. 68:205-13 (2000); Pasetti et al. Vaccine. 18:3208-13 (2000); Pasetti et al. Vaccine. 21:401-18 (2003)). Therefore IN immunization of mice was used to assess the immunogenicity of CVD 1902.

In an initial immunogenicity study, a total of 25 BALB/c mice (6-8 weeks of age) were randomly allocated into three groups to be immunized intranasally according to an accelerated immunization regimen with doses administered on days 0, 7, and 15 and with post-immunization sera collected on day 20, a mere 5 days after the 3rd IN immunization. One group (N=10 mice) was given ~1×10⁹ CFU of ΔguaBA strain CVD 1901, a second group (N=10 mice) received ~1×10⁹ CFU of ΔguaBA,clpX vaccine CVD 1902, while the third group was given PBS.

Mice were bled on day 0 (preimmunization) and day 20 (5 days after the 3rd IN dose) to obtain serum samples for measurement of antibody titers to S. Paratyphi A antigens. Specific anti-Salmonella serum IgG titers were measured as described by Pasetti et al (Clin Immunol. 92:76-89 (1999)). Briefly, Immulon II plates were coated with 5-10 µg/ml of S. Paratyphi O polysaccharide-core polysaccharide antigen (OPS-core PS) or S. Paratyphi A flagella in carbonate buffer for 3 h at 37° C. and blocked overnight with 10% dry milk in PBS. The purified S. Paratyphi A flagella (referred as "Ha" antigen). Wells of the microtiter plates were then washed with PBS containing 0.05% Tween 20 (PBST) and serum samples (diluted in PBST-milk) were added for 1 h at 37° C. HRP-labeled anti-mouse IgG (KPL) was used as conjugate and TMB Peroxidase (KPL) as substrate. After 15 min of incubation, the reaction was stopped by the addition of 1 M $H_3PO_4$ and Absorbance at 450 nm was measured. Sera were run in duplicate, along with negative and positive calibrated controls. Titers were calculated from regression curves as the inverse of the dilution that produces an Absorbance value of 0.2 above the blanks Serological results are reported as ELISA Units/ml.

Figure 25:
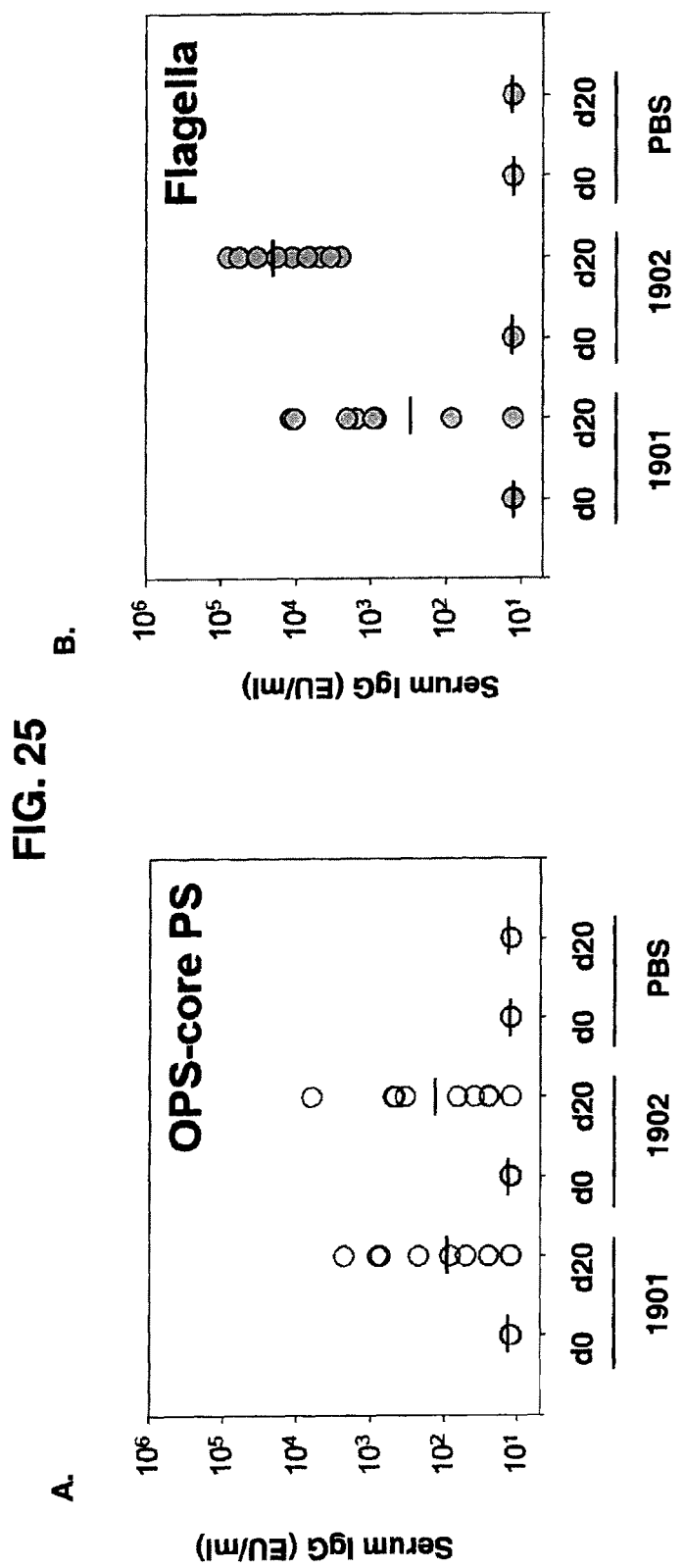
FIG. 25. Comparison of responses to *S. Paratyphi* OPS-core PS (A) and flagella (B) following intranasal immunization of mice with CVD 1901 and CVD 1902.

The serum IgG responses to S. Paratyphi A O polysaccharide-core polysaccharide antigen and Ha flagella in mice immunized with either CVD 1901 or CVD 1902 are shown in FIG. 25. Data represent individual titers from 10 mice per group, measured on day 0, prior to vaccination and on day 20; lines indicate geometric mean titers (GMT). Titers of serum antibody to OPS-core polysaccharide of S. Paratyphi A rose 2 logs over baseline after this accelerated immunization schedule of 3 mucosal immunizations over 15 days, comparing pre-immunization sera with sera from day 20. The day 20 GMT in mice immunized with CVD 1901 (GMT=102 EU/ml) and CVD 1902 (GMT=110 EU/ml) were almost identical.

The serum antibody responses of the mice to S. Paratyphi A flagella were stronger. In particular, the anti-flagella antibody titers of mice immunized with the hyperflagellated ΔguaBA,clpX vaccine strain CVD 1902 (GMT=11,980 EU/ml) were significantly higher than the titers recorded in mice immunized with isogenic strain CVD 1901 (GMT=569 EU/ml) (p<0.004, Mann-Whitney test). As expected, no significant responses were detected in the PBS control group when tested against either O polysaccharide-core polysaccharide or flagella antigens.

Mucosal (Intranasal) Immunization of Mice by a More Extended Immunization Schedule.

A total of 40 BALB/c mice (6-8 weeks of age) were randomly allocated into two groups, and immunized intranasally on days 0, 21, and 28 with either PBS (N=20 mice) or ~1×10$^9$ CFU of CVD 1902 (N=20 mice).

polysaccharide-core polysaccharide of S. Enteritidis, LPS from S. Typhi and purified flagella from these two serovars, each ELISA assay was optimized for coating concentrations, reagents and conditions that allow for maximum antibody binding.

Figure 26:
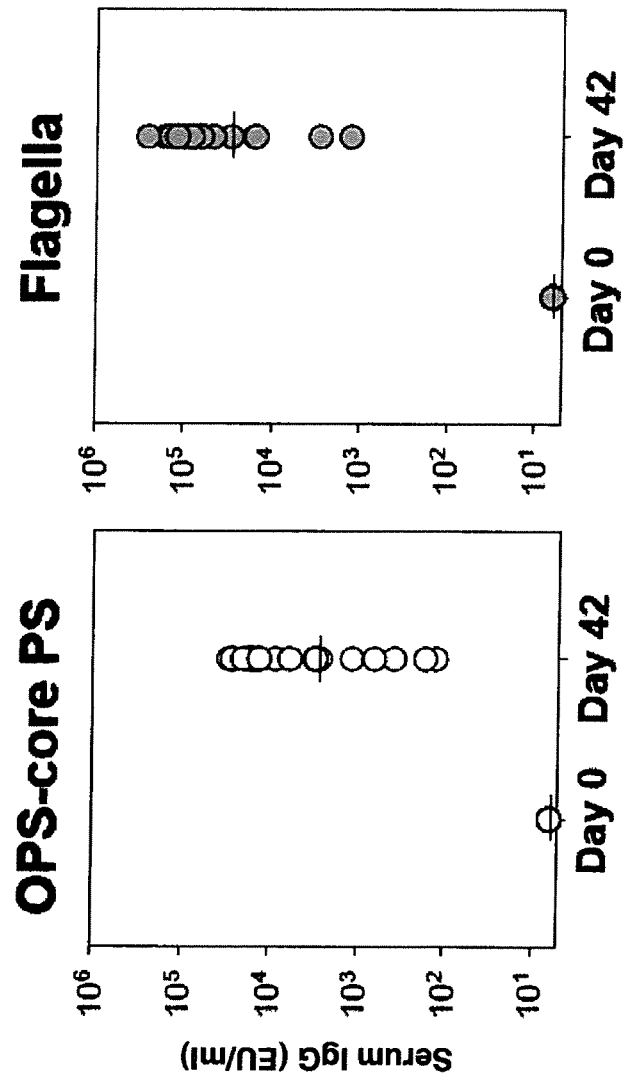
FIG. 26. Antibody responses to purified *S. Paratyphi* A OPS-core PS and flagella following intranasal immunization of mice with CVD 1902.

The serum IgG responses against S. Paratyphi A O polysaccharide-core polysaccharide and flagella are shown in FIG. 26 for mice immunized intranasally with CVD 1902 on days 0, 21 and 28. Data represent individual titers measured on day 42 (2 weeks after the 3rd IN dose and 2 weeks prior to challenge); lines indicate geometric mean titers (GMT). Serum IgG antibody titers to O polysaccharide-core polysaccharide rose 3 logs after this immunization schedule to reach a GMT of 4,783 EU/ml. Serum IgG titers against flagella rose almost 4 logs to achieve a GMT of 50,860 EU/ml. No responses were detected in the PBS control group (GMT of 6.3 EU/ml at both baseline and on day 42).

We also examined the cross-reactivity of antibodies elicited by mucosal immunization of mice with attenuated S. Paratyphi A biological drug product CVD 1902 against purified LPS and flagella antigens from S. Typhi and S. Enteritidis. For these assays, pooled sera from day 42 were tested. The results are shown in Table 11. The cross-reacting titers of antibody observed against S. Typhi LPS (GMT=1,118 EU/ml) and S. Enteritidis O polysaccharide-core polysaccharide (GMT=438 EU/ml) were fairly modest. In contrast, the cross-reacting antibody responses observed against heterologous flagella were much more prominent. Antigen-specific titers against S. Typhi flagella rose 300-fold over baseline to reach a GMT of 19,296 EU/ml, while responses against S. Enteritidis flagella rose almost 100-fold to attain a GMT of 576 EU/ml.

TABLE 11

Cross-reactivity of antibodies against O polysaccharide-core polysaccharide antigen and flagella of Salmonella Paratyphi with LPS and flagella.

| | Serum IgG titers against serovar specific LPS and flagella (EU/ml)* | | | | | | | |
|---|---|---|---|---|---|---|---|---|
| | S. Typhi LPS | | S. Enteritidis OPS-core PS | | S. Typhi flagella | | S. Enteritidis flagella | |
| Group | Pre | Post | Pre | Post | Pre | Post | Pre | Post |
| CVD 1902 | 89.5 | 1,118 | 6.3 | 438 | 64.2 | 19,296 | 6.3 | 576 |
| PBS | 102.5 | 119 | 6.3 | 6.3 | 82.1 | 108 | 6.3 | 6.3 |

*Data represent GMT for pooled samples from each cage (4 pools per group).

Measurement of Antibody Responses.

Mice were bled on days −1, 20, 27, 42, and 55 to obtain serum for measurement of antibodies. Serum IgG responses were measured as previously described by Pasetti et al. (Clin Immunol. 92:76-89 (1999)). Briefly, Immulon II plates were coated with 5-10 µg/ml of S. Paratyphi, S. Enteritidis or S. Typhi LPS, or flagella, in carbonate buffer for 3 h at 37° C. and blocked overnight with 10% dry milk in PBS. The wells were then washed with PBS containing 0.05% Tween 20 (PBST) and serum samples (diluted in PBST-milk) added for 1 h at 37° C. HRP-labeled anti-mouse IgG (KPL) was used as conjugate and TMB Peroxidase (KPL) as substrate. After 15 min of incubation, the reaction was stopped by the addition of 1 M H$_3$PO$_4$ and Absorbance at 450 nm was measured. Sera were run in duplicate, along with negative and positive calibrated controls. Titers were calculated from regression curves as the inverse of the dilution that produces an Absorbance value of 0.2 above the blanks Serological results were reported as ELISA Units/ml. For analyzing crossreactivity against O The serum antibodies induced by intranasal immunization of mice with S. Paratyphi A biological drug product CVD 1902 that cross-react with S. Typhi LPS (Group D) and to S. Enteritidis OPS-core PS (also Group D) are likely to be antibodies directed against the mannosyl-rhamnosyl-galactose trisaccharide repeat that forms the 0 polysaccharide backbone common to Salmonella Groups A and D (Verma et al. J. Bacteriol. 1989; 171:5694-701 (1989)). In S. Paratyphi A and other Group A Salmonella, a paratose residue is linked alpha 1,3 to the mannose residue of the backbone (Verma et al. J. Bacteriol. 1989; 171:5694-701 (1989)), resulting in the immunodominant antigen "2" that serologically designates Group A Salmonella. In Group D Salmonella, a tyvelose residue is linked alpha 1,3 to the mannose residue of the backbone (Verma et al. J. Bacteriol. 1989; 171:5694-701 (1989)), thereby creating immunodominant antigen "9" that serologically designates Group D Salmonella. The mannosyl-rhamnosyl-galactose trisaccharide repeat constitutes minor antigen "12" of Salmonella (Blixt et al. Glycoconj J.

25:27-36 (2008)). It is likely that the cross-reacting antibodies in part are directed against this epitope "12" that is shared by *Salmonella* serovars of Group A (like *S. Paratyphi* A) and Group D (like *S. Typhi* and *S. Enteritidis*). It is also possible that some crossreacting antibodies are directed against antigens of the conserved core polysaccharide. However, because these core antigens are often not very exposed in smooth lipopolysaccharide, they tend to be only minimally immunogenic.

Because many antigens located in the conserved regions of flagellin are shared, cross-reactivities are expected. These are distinct from the serovar-specific flagella responses that are directed against the specific serovar antigens of the flagella (e.g., antigen "Ha" found on *S. Paratyphi* A flagella). It is not clear why the cross-reacting antibody response was so much stronger to the *S. Typhi* flagella than to the *S. Enteritidis* flagella.

Challenge of Mice After Mucosal (Intranasal) Immunization to Assess Vaccine Efficacy Intraperitoneal Challenge of Vaccinated and Control Mice with Wild Type *S. Paratyphi* A Suspended in Hog Gastric Mucin to Assess the Ability of the Biological Drug Product CVD 1902 to Protect against Severe and Lethal Disease.

Twenty mice vaccinated intranasally with doses of CVD 1902 administered on days 0, 21 and 28 and a parallel group of 20 mice given PBS intranasally were challenged on day 56 by the IP route with wild type bacteria suspended in hog gastric mucin. The method of challenge was similar to the method used to ascertain the LD50 of the wild type strain ATCC 9150 and various vaccine strains except that the vaccinated cohorts of mice were older and heavier than the mice used in the LD50 tests. One mouse in the vaccine group died during the IP injection procedure, leaving 19 for follow-up and analysis. An additional control group of somewhat younger and lighter mice was challenged IP with hog gastric mucin only (i.e., without wild type bacteria suspended in the mucin).

Mice were challenged on day 56 with wild type strain *Salmonella Paratyphi* A ATCC 9150 from working seed vial #98 (prepared Sep. 11, 2009). The wild type bacterial challenge suspension was diluted 10-fold in 10% hog gastric mucin (Difco, Mucin Bacteriological, REF 21211, LOT 4092018, manufactured 2005-09-11). The final suspension of bacteria contained 200 CFU/ml. Mice were injected IP with 0.5 ml (100 CFU) using a 21 gauge needle. As an additional control group, a separate group of 7-week-old negative control mice were injected IP with 0.5 ml 10% mucin. Mice were observed twice daily for 5 days for mortality and the number that died was recorded. In addition, mice were observed daily for signs of significant morbidity (ruffled fur, weight loss versus pre-challenge weight, collapse, difficulty breathing or severe dehydration) and these signs were recorded. Mice that showed the above signs of severe morbidity were euthanized according to IACUC directives.

By day 3 of follow-up post-challenge, 4 of 20 PBS control mice and O of 19 vaccinated mice were dead ($p=0.059$, Fisher's exact test, single tail) (Table 12), indicating a protective trend. Three of the mice died on day 1 and one died on day 2; no other mice died by day 5. The mortality rate in the PBS control group was lower than expected, presumably because these cohorts of mice were approximately two months older and heavier than the cohorts of mice used in the earlier challenges used to compare the LD50 of the wild type parent versus the vaccine strains.

On the day of challenge, there was no significant difference in the weight of the mice in the vaccinated group versus mice in the control group (Table 12) ($p=0.73$, 2-tailed Mann Whitney test); indeed they were almost identical. However, on day 3, 4 and 5 the control mice had lost weight compared to their baseline weight. This was true when the baseline weights of the 16 surviving mice were compared by 2-tailed paired t-test to their weights on day 3 ($p<0.0001$), day 4 ($p<0.0001$) and day 5 ($p<0.0001$). There was no significant weight loss among the 19 vaccinated mice when baseline weights were compared to weights on day 3 ($p=0.12$), day 4 ($p=0.99$) and day 5 ($p=0.99$), independently, by 2-tailed paired t-test. When the weights of the 19 vaccinated mice were compared to weights of the 16 surviving control mice, the latter were significantly lighter on day 3 ($p=0.0061$), day 4 ($p=0.0002$) and day 5 ($p=0.0006$) (2-tailed Mann-Whitney test), as summarized in Table 12.

Vaccinated and control mice were also compared on 3 combined endpoints, defined as time to death (in days) for mice that died and change in weight at day 3, day 4, or day 5, respectively, for surviving mice. Ranks were calculated for these endpoints, with mice that died given the lowest ranks, surviving mice with the greatest loss in weight the next lowest ranks, etc. Vaccinated mice had better outcomes than unvaccinated mice on all of these endpoints ($p<0.0001$ by 2-tailed Mann-Whitney test for all 3 endpoints).

None of the 5 mice in the mucin control group that were inoculated with only hog gastric mucin intraperitoneally died, nor did they suffer significant weight loss on day 3 ($p=>0.99$), day 4 ($p=0.17$) or day 5 ($p=0.17$), by 2-tailed paired t-tests (Table 12).

TABLE 12

Efficacy of CVD 1902 in preventing severe and fatal disease in mucosally immunized mice versus controls following intraperitoneal challenge with wild type *Salmonella Paratyphi* A suspended in hog gastric mucin

| Group | No. Challenged | No. fatalities by day 3 | Baseline body weight | Weight on day 3 post-challenge | Weight on day 4 post-challenge | Weight on day 5 post-challenge |
|---|---|---|---|---|---|---|
| PBS | 20 | 4 p = 0.059 2-tailed Mann-Whitney test | 20.5 g ± 1.4 g p = 0.79 2-tailed Mann-Whitney test | 18.0 g ± 1.5 g p = 0.0061 2-tailed Mann-Whitney test | 17.9 g ± 1.5 g p = 0.0002 2-tailed Mann-Whitney test | 18.1 g ± 1.4 g p = 0.0006 2-tailed Mann-Whitney test |
| CVD 1902 | 19 | 0 | 20.2 g ± 1.4 g | 19.7 g ± 1.6 g | 20.2 g ± 1.5 g | 20.2 g ± 1.8 g |
| Mucin controls | 5 | 0 | 16.6 g ± 0.5 g | 16.4 g ± 0.4 g | 16.8 g ±0.4 g | 16.8 g ± 0.4 g |

EXAMPLE 6

This example describes preparation and testing of *Salmonella Enteritidis* Core-O Polysaccharide (COPS) conjugated to H:g,m flagellin for protection against invasive infection with *Salmonella Enteritidis*

Materials and Methods

Bacterial Strains:

*S. Enteritidis* R11 was isolated from the blood of a toddler in Mali (Levy et al. *J Clin Microbiol* 46:1861-1866 (2008)) and its serotype confirmed by the Clinical Microbiology Unit of the Center for Vaccine Development (CVD). CVD 1941 (R11 ΔguaBA ΔclpP) is an attenuated derivative of *S. Enteritidis* R11 that hyperexpresses flagella and was used as a "reagent strain" for safe and efficient bulk purification of LPS and flagellin proteins. Mutant derivatives of R11 deficient in the invA, fliC, and rfaL genes were constructed by lambda red mutagenesis (Datsenko et al. *Proc Natl Acad Sci USA* 97:6640-6645 (2000)). *S. Enteritidis* was grown in or on animal product-free LB Lennox medium (Athena E S, Baltimore, Md.) supplemented with 0.005% guanine (w/v) as necessary (for growth of CVD 1941) at 37° C. *Salmonella* cells used for in vitro analyses and in vivo challenge experiments were grown to mid-log phase on solid medium, harvested and suspended in sterile PBS.

Cell Culture:

J774 murine macrophage cells and human epithelial kidney cells stably expressing the firefly luciferase reporter under control of an NF-κB dependent promoter (HEK293-Luc, generously provided by S. Ghosh; Yale University, New Haven, Conn.) (Zhang et al. Science 303:1522-1526 (2004)), were maintained in) DMEM (Invitrogen, Carlsbad, Calif.) supplemented with 10% (v/v) fetal bovine serum, 1mM sodium pyruvate and 100 μg/ml penicillin/streptomycin. Cells were incubated at 37° C. in 5% $CO_2$ atmosphere.

Polysaccharide and Protein Analyses:

Polysaccharide concentration was assessed using the resorcinol sulfuric acid assay (Monsigny et al. *Anal Biochem* 175:525-530 (1988)). Protein concentration was determined by absorbance at 280 nm using the calculated extinction coefficients of *S. Enteritidis* flagellin or $CRM_{197}$ determined by the Expasy Protparam tool with protein sequences obtained from the NCBI database. For SDS-polyacrylamide gel electrophoresis (SDS-PAGE) analysis, samples were fractionated by 4-20% Tris-Glycine acrylamide gels (Invitrogen) and stained with Coomassie Gel-code Blue (ThermoFisher). For polysaccharide staining, gels were stained using the Pro-Q staining system (Invitrogen) as per the manufacturer's instructions.

Purification of Flagellin Polymers:

*Salmonella* cell-associated flagella were isolated as described (Simon et al. *Biochem Biophys Res Commun* 355: 280-285 (2007)). Flagella protein was assessed for identity by western blot with flagellin specific monoclonal antibody 15D8 (Bioveris) (see FIG. 27).

Preparation of Flagellin Polymers and Monomers for Conjugation:

Generation of monomers for construction of O:H 1:1 lot 1 was as described by heating of flagella filaments at 70° C. for 15 minutes (Smith et al. *Nat Immunol* 4:1247-1253 (2003)). For preparation of polymers and monomers for conjugation in all other flagellin based conjugates, a modified method of Ibrahim et al. *J Clin Microbiol* 22:1040-1044 (1985)) was utilized. Dispersion of purified flagella filaments into monomers was accomplished by lowering the pH to 2 for 30 min with stirring. For flagella purification, flagellin in solution at pH 2 was subjected to 100,000×g centrifugation for 3 h at 4° C. in order to pellet LPS vesicles. The supernatant was then adjusted to 2.67 M ammonium sulfate, and incubated overnight at 4° C. with stirring. The precipitate was recovered by 10,000×g centrifugation, resuspended in water, and dialyzed against saline in 10 kDa molecular weight cutoff (MWCO) dialysis cassettes (Thermo). Depolymerized flagellin monomers prepared by either method were filtered through a 100 kDa MWCO ultrafiltration (UF) centrifugal device (Amicon) to remove any remaining high molecular weight flagella polymers and LPS vesicles, followed by concentration with 30 kDa MWCO UF and adjustment to pH 7.2 with 10×PBS. The residual endotoxin level was measured with the chromogenic endpoint *Limulus Amebocyte* Lysate Assay (Lonza). These purification methods effectively removed >99% of contaminating LPS, leaving <50 endotoxin units per μg of protein. Flagellin monomers were assessed for size as compared to flagella polymers (See FIG. 27).

Preparation of *Salmonella* LPS:

CVD 1941 was grown in medium supplemented with 0.005% guanine (w/v) and 1 mM $MgCl_2$ to supplement the gua deficiency and enhance production of long-chain LPS (Ernst R. K. and Miller S. I., unpublished data) respectively, overnight in flasks at 37° C./250 rpm. Cells were harvested by centrifugation at 7,000×g for 20 min at 4° C. and LPS was isolated by the method of Darveau and Hancock essentially as described with the addition of a final phenol purification step (Darveau et al. *J Bacteriol* 155:831-838 (1983); Hirschfeld et al. *J Immunol* 165:618-622 (2000)). Purified LPS was resuspended in pyrogen free water (PFW) to 20 mg/ml for subsequent manipulation.

Isolation of *Salmonella* Core/Outer-Membrane Polysaccharide (COPS):

*Salmonella* COPS was isolated from purified LPS as described previously (Watson et al. *Infect Immun* 60:4679-4686 (1992)). Briefly, LPS was brought to 10 mg/ml in 1% acetic acid, and incubated for 1.5 h at 100° C. Insoluble lipid A was removed by ultracentrifugation for 5 h at 100,000×g and discarded in the pelleted fraction. The supernatant fraction was concentrated by lyophilization and re-suspended in PFW. High molecular weight COPS was fractionated by size exclusion chromatography on a Superdex 75 10/300 GL column (GE/Amersham) with an AKTA Explorer (GE/Amersham) run at 0.5 ml/min in saline solution with 1 ml fractions taken. Fractions were monitored for polysaccharide using the resorcinol sulfuric acid assay. High molecular weight fractions used for conjugation were pooled, concentrated by lyophilization, and resuspended in PFW. The final COPS concentration was determined with the resorcinol sulfuric acid assay using purified CVD 1941 LPS as standards. The endotoxin level was assessed by LAL to be <1 endotoxin unit per μg of polysaccharide.

Synthesis of COPS Conjugates:

i. Conjugation by CDAP:

Direct conjugation between COPS at random points along the polysaccharide chain with either flagellin monomers, flagella polymers, or $CRM_{197}$ (a generous gift from L. Martin, Novartis Vaccine Institute for Global Health, Sienna, Italy) was accomplished using 1-cyano-4-dimethylaminopyridinium tetrafluoroborate (CDAP, Research Organics) (Lees et al. *Vaccine* 14:190-198 (1996); Shafer et al. *Vaccine* 18:1273-1281 (2000)). Briefly, random activation of hydroxyl groups on COPS was accomplished by addition of 100 mg/ml CDAP in acetonitrile to an equivalent amount (wt/wt) of either 4 mg/ml (for O:H 1:1 lot 1 conjugate) or 10 mg/ml (for all other CDAP linked conjugates) COPS in 10 mM sodium borate buffer pH 9 (pH goes to 8-8.5). After 30 seconds, 1/100$^{th}$ volume of triethylamine (Sigma) was added to bring the pH to 9-10. After 2 min, protein (3 mg/ml flagellin monomers, 12 mg/ml flagella polymers, 13 mg/ml $CRM_{197}$) was added at predefined ratios of polysaccharide to protein (1:1 or 10:1, wt/wt). The conjugation reaction was incubated at room temperature for 2 h with tumbling rotation, and then 4° C. for 3 days with tumbling rotation, at which point the reaction was quenched by bringing the solution to 10 mM glycine and assayed for conjugation.

ii. Conjugation at KDO Terminus by Aminooxyoxime Thioether Chemistry:

Conjugation at the carboxyl group present at the KDO terminus on COPS with flagellin monomers was accomplished with aminooxy chemistry (Lees et al. *Vaccine* 24:716-729 (2006)). COPS was suspended to 10 mg/ml in 100 mM MES pH 5/28 mg/ml EDC (Sigma)/11 mg/ml diaminooxy cysteamine (33) (custom synthesis from Solulink, CA) and incubated for 3 h at room temp and then overnight at 4° C. on a rotating mixer. The derivatized COPS was brought to 250 mM DTT the next day, and dialyzed in 3 kDa MWCO dialysis cassettes (Thermo) against 10 mM sodium acetate/10 mM EDTA pH 6 overnight at 4° C. Activated flagellin monomers (3 mg/ml) were prepared by incubation with 1.5 mg/ml sulfo-GMBS (Molecular BioSciences) in 25 mM HEPES pH 7.5 for 3 h at room temperature. The reaction was then brought to 100 mM sodium acetate pH 5 and incubated overnight at 4° C. The derivatized protein was dialyzed the next day in 3 kDa MWCO dialysis cassettes (Thermo) against 10 mM sodium acetate/10 mM EDTA pH 6 overnight at 4° C. The thiol labeled COPS polysaccharide was added to sulfo-GMBS derivatized flagellin monomer protein at a ratio of 3:1 (wt/wt) and the pH was incrementally raised to 6.8 with 10×PBS pH 7.4. Conjugation was allowed to proceed for three days at 4° C. with tumbling before the reaction was assayed for conjugation.

Purification and characterization of COPS conjugates i. Purification by Size-Exclusion Chromatography (SEC):

The conjugation reaction was concentrated with 30 kDa UF and then fractionated on a Superdex 200 10/300 GL column (GE/Amersham) with an AKTA Explorer (GE/Amersham) run at 0.5 ml/min in 10 mM Tris pH 7.5 with monitoring at 280 nm. High molecular weight conjugate eluted fractions were assessed by the OD 280 nm trace, and SDS-PAGE with Coomassie blue staining for fractions. Conjugate containing fractions were pooled and concentrated by 30 kDa UF.

ii. Purification by Anion-Exchange Chromatography (IEX):

Some conjugates were further purified by membrane-anion exchange chromatography. Briefly, flagellin monomer and $CRM_{197}$ conjugates purified by SEC, or unpurified flagella polymer conjugates, in 10 mM Tris pH 7.5, were applied to a 3 ml Sartobind Nano-Q anion exchange membrane (Sartorius) with an AKTA Explorer (GE/Amersham) at 1 ml/min with monitoring at 280 nm. The membrane was washed first with 15 ml of 10 mM Tris pH 7.5 and then with 30 ml of either 10 mM Tris/80 mM NaCl pH 7.5 for flagellin containing conjugates or 10 mM Tris/50 mM NaCl pH 7.5 for $CRM_{197}$ conjugates. The membranes were eluted with a gradient in 24 ml of the indicated wash buffer to 10 mM Tris/1 M NaCl pH 7.5. The eluate fraction was pooled and concentrated by 30 kDa MWCO UF, and used for immunogenicity experiments in mice.

iii. Characterization of Purified Conjugates:

Polysaccharide concentration in conjugate constructs was assessed with the resorcinol sulfuric acid assay with CVD 1941 LPS as standards. Protein concentration in conjugates synthesized with CDAP was assessed by BCA assay (Thermo) with unconjugated protein as standards. Conjugates prepared by thioether chemistry were assessed for protein concentration by measurement of absorbance at 280 nm using the calculated extinction coefficient of *S. Enteritidis* flagellin.

Flagellin Stimulation of Epithelial Cells:

Monolayers of HEK293-Luc cells seeded at $1.7 \times 10^4$ cells/well in 96-well plates for NF-κB activation analyses, were treated for 4 h with purified flagellin protein, conjugate, or LPS. Extracts were prepared and luciferase activity assessed by the Luciferase Assay System (Promega) according to the manufacturer's instructions using a Versamax II plate luminometer. Normalization to the total protein level was determined by Bradford reagent (BioRad).

Mice:

Female outbred CD-1 and inbred BALB/c mice (8-10 week old) were purchased from Charles River Laboratories (Wilmington, Mass.) and maintained in the University of Maryland School of Medicine animal facility.

Immunizations:

Mice were injected intramuscularly (IM) in the right hind limb with antigen suspended in 50 μl of sterile PBS. For immunizations with conjugate vaccines mice were immunized at 0, 28 and 56 days and serum samples were obtained 21-22 days following each immunization and stored at −20° C. until use. For immunization with purified flagellin monomers or flagella polymers, mice were immunized at O and 10 days.

Challenge:

CD-1 mice immunized with conjugate vaccines were challenged by the intraperitoneal (IP) route 28 days after the third immunization (on day 84), with either $5 \times 10^5$, $1 \times 10^6$, or $5 \times 10^6$ CFU of virulent wild type *S. Enteritidis* strain R11. Mice immunized with purified flagellin were challenged 14 days following the second dose (on day 24) with $5 \times 10^5$ CFU of virulent wild-type *S. Enteritidis* strain R11. The IP $LD_{50}$ of *S. Enteritidis* R11 in CD-1 mice was determined to be $2.2 \times 10^5$ CFU. Mice were monitored for 21 days post challenge, recording overall health, weight loss and mortality. As alternative endpoints, moribund mice exhibiting symptoms including lethargy, non-responsiveness and >20% weight loss were euthanized and recorded as dead.

Serum Antibody Analysis:

i. ELISA:

Serum IgG levels against LPS, flagellin protein or $CRM_{197}$ protein were measured by ELISA. Briefly, 96-well plates were coated with *S. Enteritidis* LPS (5 μg/ml), "H" polymer (2 μg/ml) in 0.05 M sodium carbonate pH 9.6 and $CRM_{197}$ (5 μg/ml) in PBS pH 7.4 for 3 h at 37° C., and blocked overnight with 10% dried milk in PBS. After each incubation, the plates were washed with PBS containing 0.05% Tween 20 (PBST) (Sigma). Sera were tested in serial dilutions in 10% milk PBST. Specific antibodies were detected using peroxidase-labeled anti-mouse IgG (KPL) diluted 1:1,000 in 10% dried milk in PBST. TMB was used as substrate (KPL). Test and control sera were run in duplicate. Titers were calculated by interpolation of Absorbance values of test samples into the linear regression curve of a calibrated control (reference serum). The end-point titers reported as ELISA units (EU) represent the inverse of the serum dilution that produces an Absorbance value of 0.2 above the blank. Seroconversion in vaccinated mice was defined as a four-fold increase in the antibody titer after immunization as compared to control mice immunized with PBS.

ii. Opsonophagocytic Uptake:

Analysis of functional antibody was by opsonophagocytic assay measuring serum mediated uptake into phagocytes. Briefly, logarithmic growth cultures of wild-type *S. Enteritidis* R11 cells were adjusted to $3 \times 10^6$ CFU/ml and incubated in 10% heat-inactivated serum for 20 min at room temperature. Opsonized R11 cells were added to monolayers of J774 cells in 24-well plates ($1 \times 10^5$ cells/well), in antibiotic-free media at a ratio of 1:1 (cell/cell) and centrifuged for 10 min at 1000×g at room temperature. At 1 h post addition, the growth media was replaced with media containing 100 µg/ml gentamicin (Gibco). At the 2 h time-point, cell monolayers were washed three times with sterile PBS, lysed with PBS containing 0.5% Triton-X 100 (Sigma), and assessed for viable CFU. Results are expressed as the percentage of phagocytosis as defined by the number of recovered CFU/number of CFU added to the J774 cells. For experiments involving uptake by immune sera of different *Salmonella Enteritidis* mutants, the fold uptake relative to control sera is shown to account for variations in the basal level of uptake between different mutants.

Statistical Analysis:

Statistical significance between geometric mean IgG titers from different experimental groups and comparative protection from mortality by different conjugate vaccines was assessed by Mann-Whitney rank-sum analysis, t-test, and Fisher's exact test (FET) respectively using the Sigma-Stat software package.

Results

Characterization of *S. Enteritidis* COPS

Figure 28:
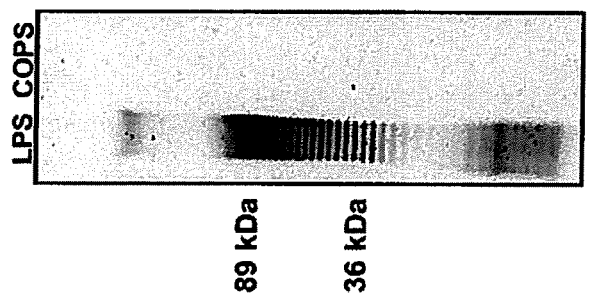
FIG. 28. Gel filtration profile of S. Enteritidis LPS and COPS. (A) SDS-PAGE analysis with Pro-Q staining for lanes 1, 10 μg S. Enteritidis LPS; and 2, 10 μg S. Enteritidis COPS. (B) Size exclusion gel filtration profile of S. Enteritidis COPS through Superdex 75 assessed by resorcinol assay for polysaccharide.
Figure 28:
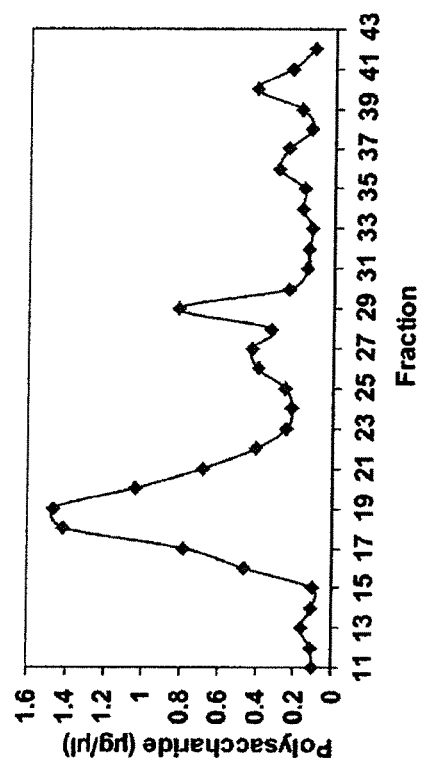

The LPS of *S. Enteritidis* was fractionated by SDS-PAGE into several isoforms, ranging from high molecular weight very-long species to low molecular weight short species (FIG. 28A). Following removal of lipid A, COPS similarly separated into high and low molecular weight species by size exclusion chromatography (FIG. 28B). COPS with lipid A removed did not enter an SDS-PAGE gel, indicating removal of the negatively charged phosphate groups present in and around lipid A (FIG. 28A). Removal of lipid A in COPS preparations was further confirmed by *Limulus Amebocyte* Lysate (LAL) assay which showed <1 endotoxin unit per µg of COPS polysaccharide. For conjugation, pooled high molecular weight COPS species from SEC were used, since conjugates with long chain OPS were previously shown to be more immunogenic than conjugates made with short chain OPS (Jorbeck et al. *Infect Immun* 32:497-502 (1981)).

Synthesis, Purification and Characterization of COPS:Protein Carrier Conjugates

To test the ability of COPS to conjugate with flagellin, a COPS:flagellin conjugate was constructed by CDAP chemistry. This conjugate construct, designated "O:H 1:1 lot 1", was used in immunogenicity experiments in BALB/c and CD-1 mice. Additional conjugates were subsequently prepared to test the contribution of various parameters known to influence the immunogenicity of polysaccharide:protein glycoconjugates (Table 13). The experimental parameters tested include various carrier proteins (flagellin monomer, flagella polymer, $CRM_{197}$), conjugation chemistries (CDAP or aminooxy thioether), and polysaccharide:protein ratios (1:1 or 10:1). These constructs were tested in CD-1 mice.

Conjugation of COPS with protein by CDAP chemistry generates a heterogeneous glycoconjugate population due to the generation of reactive cyano-

TABLE 13

Preparation and characterization of *S. Enteritidis* COPS-Conjugates used for immunization experiments in mice

| Conjugate lot designation | Carrier protein | Polysaccharide: Protein conjugation ratio (wt/wt)[a] | Conjugation chemistry | Purification scheme | Final Polysaccharide/ Protein ratio (wt/wt)[b] | Mouse Studies |
| --- | --- | --- | --- | --- | --- | --- |
| O:H 1:1 lot 1 | Flagellin monomer | 1:1 | CDAP | SEC | 0.78 | BALB/c & CD-1 |
| O:H 1:1 lot 2 | Flagellin monomer | 1:1 | CDAP | SEC-IEX | 0.26 | CD-1 |
| O:H polymer | Flagella polymer | 1:1 | CDAP | IEX | 0.56 | CD-1 |
| O:H 10:1 | Flagellin monomer | 10:1 | CDAP | SEC-IEX | 0.97 | CD-1 |
| O:H Amox. | Flagellin monomer | 3:1 | Aminooxy | SEC-IEX | 0.45 | CD-1 |
| O:$CRM_{197}$ | $CRM_{197}$ | 1:1 | CDAP | SEC-IEX | 0.55 | CD-1 |

Figure 29:
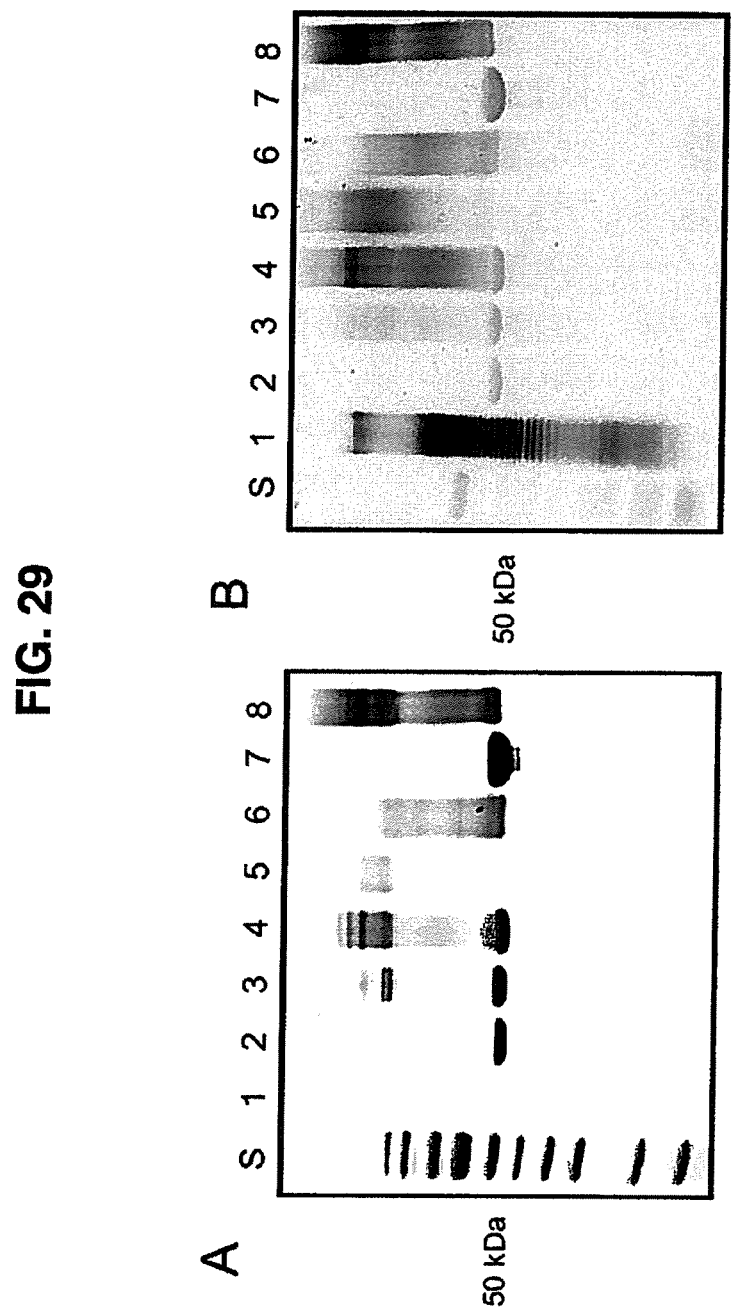
FIG. 29. Conjugation of S. Enteritidis COPS Conjugates. 4-20% SDS-PAGE showing Coomassie (A) or Pro-Q (B) staining of COPS conjugates. Lanes S, protein standards; 1, 10 μg S. Enteritidis LPS; 2, 10 μg S. Enteritidis flagella; 3, 10 μg O:H polymer; 4, 10 μg O:H 1:1 lot 2; 5, 10 μg O:H 10:1; 6, 10 μg O:H Amox.; 7, 10 μg $CRM_{197}$; 8, 10 μg $O:CRM_{197}$.

[a]Ratio of polysaccharide to protein used in the conjugation reaction.
[b]Final ratio of polysaccharide to protein in the purified conjugate.

esters on carbohydrate hydroxyl groups throughout the polysaccharide which can conjugate to several available lysine residues on the protein. This results in covalent links being formed at multiple potential points. Coupling by this method can produce conjugates consisting of a single protein molecule linked to one or more COPS molecules, as well as a lattice that can be formed by inter-molecular linkage by a single COPS molecule with multiple protein subunits. We observed that conjugation of protein with COPS produced a spectrum of high molecular weight species that migrated above the molecular weight of unconjugated protein by SDS-PAGE and were readily visualized in conjugates constructed with a 1:1 equivalent polysaccharide:protein coupling ratio (FIGS. 29A and B, lane 3, 4, 8). By comparison, the single weakly staining band observed by SDS-PAGE with the COPS-flagellin constructed at a 10:1 polysaccharide to protein coupling ratio (FIGS. 29A and B, lane 5) suggests that all of the protein was conjugated, and that the majority of conjugates were likely linked in a lattice type structure that was too large to enter the 4-20% SDS-PAGE gel. These high molecular weight COPS conjugates also stained positive for both protein (FIG. 29A) and polysaccharide (FIG. 29B), indicating the presence of both components in the conjugate.

Conjugation of COPS by aminooxy thio-ether chemistry limits coupling to a single point at the terminal KDO region by activation of the KDO carboxyl, and should result in conjugates consisting of COPS molecules conjugated at the polysaccharide terminus to one or more available lysine residues on the protein. Since coupling by this method precludes the formation of a lattice, it resulted in a comparatively less heterogenous lower molecular weight conjugate population as compared to conjugates prepared by CDAP (FIGS. 29A and B, lane 6).

Figure 30:
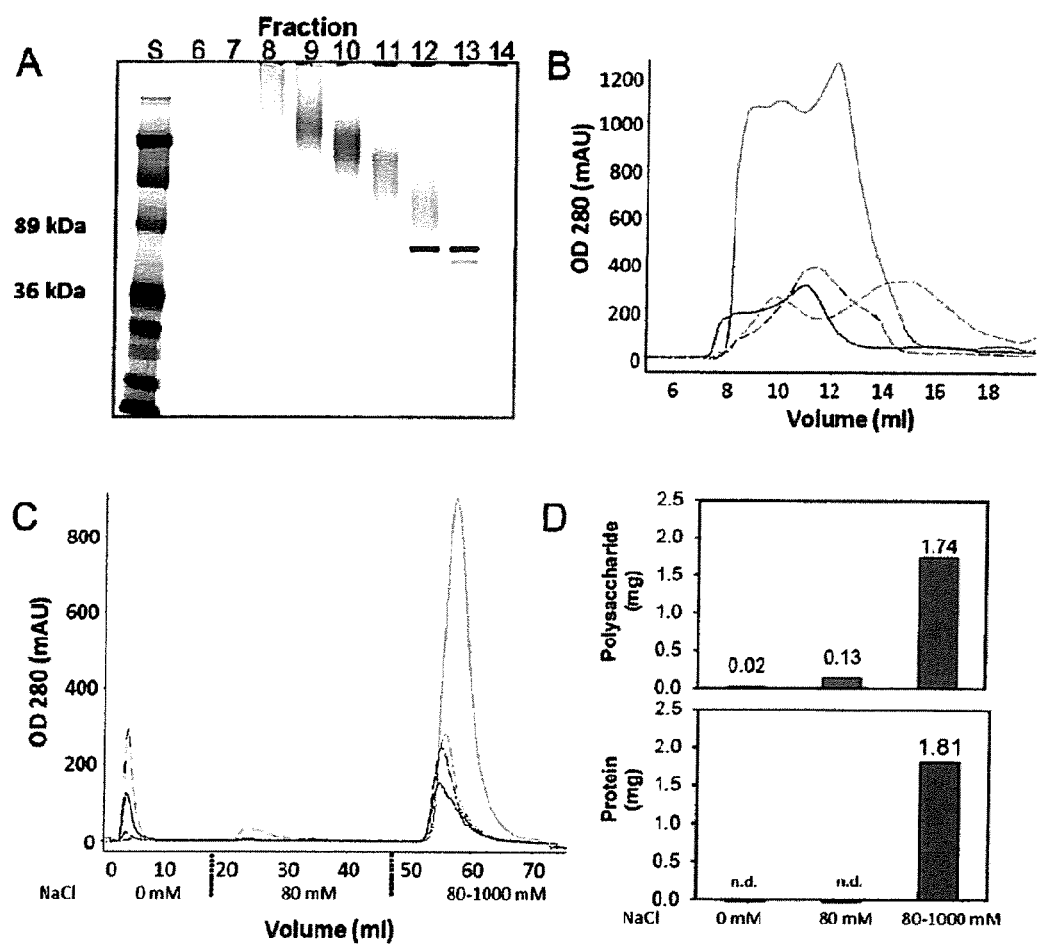
FIG. 30. Purification of S. Enteritidis COPS Conjugates. (A) 4-20% SDS-PAGE with Coomassie staining of O;H 1:1 lot 1 fractions from Superdex 200 SEC. (B) OD 280 nm trace of SEC filtration pattern through Superdex 200 and (C) OD 280 nm trace of IEX purification pattern from Sartobind Nano Q membranes at indicated NaCl concentrations of O;H 1:1 lot 2 (-), O:H 10:1 (- - -) O:H Amox. (---), $O:CRM_{197}$ (——). (D) Total polysaccharide and protein detected in indicated fractions from anion exchange membrane purification of the O:H 10:1 conjugate as assessed by resorcinol and BCA assay respectively (n.d.: not detected, below the limit of detection.

Unconjugated free polysaccharide is recognized as being deleterious to the efficacy of polysaccharide-protein conjugate vaccines and can impair anti-polysaccharide immune responses (Pollard et al. *Nat Rev Immunol* 9:213-220 (2009)). Unreacted polysaccharide and protein were removed by size-exclusion chromatography (FIGS. 30A and B). Fractionation of conjugates by SEC resulted in a clear separation of high molecular weight conjugated species (>75 kDa) from low molecular weight unreacted proteins (<75 kDa), with very high molecular weight fractions eluting in the column void volume (FIGS. 30A and B).

As COPS is neutral or weakly negatively charged as compared to the protein carrier (FIG. 28A), separation by ion exchange is possible as well. To remove residual unconjugated high molecular weight COPS that may remain following SEC purification, a second purification step utilizing separation by charge was accomplished by anion exchange (FIG. 30C). A novel membrane chromatography method was used to remove residual unconjugated carbohydrate. High molecular weight conjugates usually do not bind well to conventional chromatography resins due to limited accessibility to narrow pores within the resin beads (Lees, unpublished observations). Macroporous sorbents that utilize large channels such as monoliths and membranes can be used to purify conjugate vaccines (Lees, PCT Application Publication WO2011/017101). For the O:H flagella polymer conjugate, membrane anion exchange chromatography alone was used for removal of unreacted polysaccharide. Since CDAP reagent absorbs strongly at OD 280, unreacted CDAP-labeled polysaccharide intermediates also absorb strongly at OD 280. Following application of the SEC-purified conjugates to the anion exchange membrane, unreacted CDAP labeled polysaccharide was evident in the flow-through and low-salt wash step, as indicated by both OD 280 and the resorcinol assay (FIGS. 30C and D). Negligible protein was detected by BCA assay in these fractions (FIG. 30D). High levels of both protein and polysaccharide were detected in the high-salt elution step, indicating successful elution of the conjugate and efficient removal of unreacted polysaccharide.

The final assessed polysaccharide:protein ratio varied between conjugate preparations as a function of the ratio of individual antigens used in the conjugation reaction (Table 13). Notably, conjugates constructed at a 10:1 polysaccharide to protein ratio maintained a higher final polysaccharide level as compared to conjugates constructed with lower coupling ratios.

Figure 27:
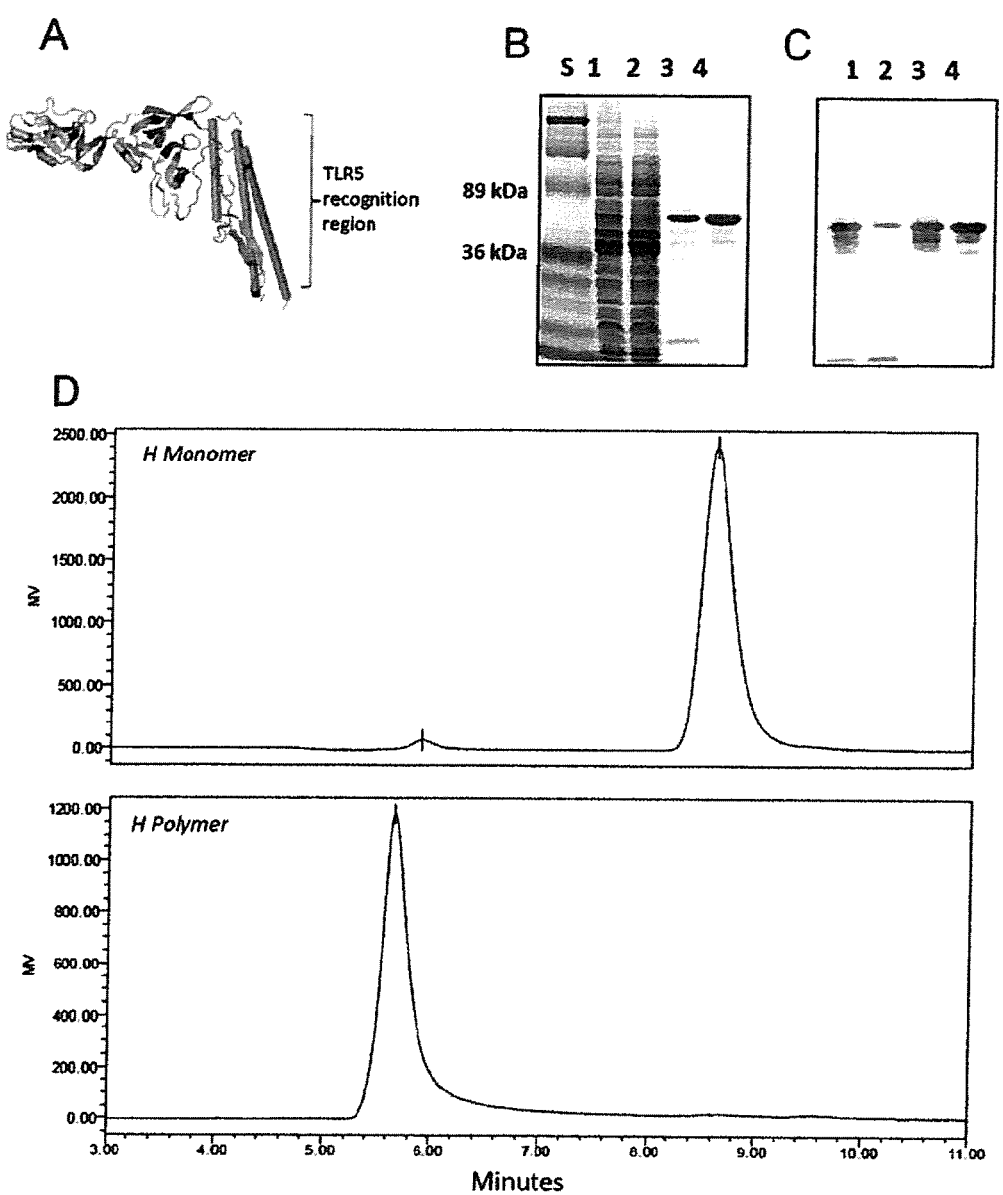
FIG. 27. Purification of *S. Enteriditis* flagella. (A) F41 Truncated Flagellin Crystal Structure with lysine residues highlighted (from Samatey et al. 2001 Nature 410:331-7; deposited in the Protein Data Base #1io1. Protein samples purified by mechanical shearing followed by differential centrifugation were analyzed by SDS-PAGE with staining by Coomassie dye (B) or by transfer to a PVDF membrane followed by western blot analysis with monoclonal antibody 15D8 specific for bacterial flagellin (C). Lanes S, protein standards; 1, *S. Enteritidis* cells [B, 4 µg protein; C, 1 g protein]; 2, cell pellet following mechanical shearing [B, 1.5 µg protein; C, 1 µg protein]; 3, sheared cell supernatant [B, 1.5 μg protein; C, 0.35 μg protein]; 4, 100,000×g pelleted flagella [B, 1.5 μg protein; C, 0.35 μg protein]. (D) Depolymerized flagellin monomers flagella polymers were assessed for relative size by SEC-HPLC separation with monitoring by refractive index.
Figure 31:
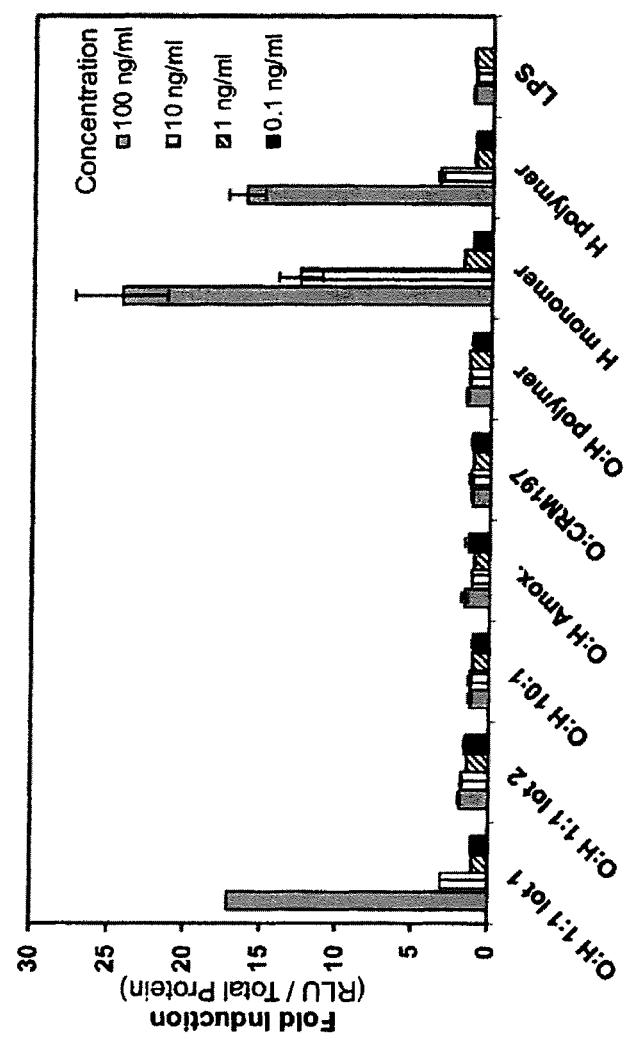
FIG. 31. NF-κB activation in epithelial cells by flagellin and COPS conjugates. HEK293 cells stably transformed with a firefly luciferase reporter gene under control of an NF-κB-dependent promoter were treated in triplicate with increasing concentrations of COPS based conjugate vaccines, S. Enteritidis flagellin monomer, S. Enteritidis flagella polymer or S. Enteritidis LPS. The cells were harvested at 4 h after treatment and luciferase activity (RLU) determined. Luciferase activity was normalized to HEK293 extract protein. Average and standard error are from three independent experiments, with the exception of O:H 1:1 lot 1 that is representative of two independent experiments.

When assessed for activation of the transcription factor NF-κB in an epithelial cell line that is responsive to flagellin (Simon et al. *Biochem Biophys Res Commun* 355:280-285 (2007)), the initial O:H 1:1 lot 1 conjugate retained significant bioactivity in vitro. In contrast, the subsequent conjugate constructs were virtually devoid of NF-κB stimulatory activity (FIG. 31). Conjugation by either of the chemistries utilized occurs at random lysine residues on flagellin, several of which appear in or near the TLR5 stimulatory region (FIG. 27A). Thus, the modified scale-up methods used in preparing the later lots of conjugates, which resulted in loss of NF-κB stimulatory activity, may be a result of conjugation at or near these residues, resulting in steric hindrance for receptor binding (Andersen-Nissen et al. *J Exp Med* 204:393-403 (2007); Smith et al. *Nat Immunol* 4:1247-1253 (2003)).

Parenteral Immunization with Flagellin Monomers or Flagella Polymers Protects CD-1 Mice Against Challenge with Wild-Type *S. Enteritidis*

Outbred CD-1 mice were immunized IM on days 0 and 10 with either PBS, 2.5 μg of flagellin monomer, or 2.5 μg of flagella polymer to assess the capacity of flagellin alone to serve as a protective vaccine antigen against fatal infection with wild type *S. Enteritidis*. The use of CD-1 mice (instead of inbred mice) enables the assessment of candidate vaccines in a genetically heterogeneous model system that better resembles the genetic diversity of humans. CD-1 mice are also a better animal model for testing the protective efficacy of non-living *Salmonella* vaccines as compared to BALB/c mice, due to their innate resistance to *Salmonella* infection (Simon et al. *Vaccine* doi: 10.1016/j.vaccine.2011.05.022.). At 14 days following the second immunization (day 24), mice were challenged IP with a lethal dose ($5 \times 10^5$ CFU) of wild-type *S. Enteritidis* R11. Whereas high mortality (19/20) was seen in PBS control mice, strikingly, no mortality (0/20) was seen in mice immunized with either flagellin monomers or flagella polymers (Table 14).

TABLE 14

Efficacy of *Salmonella Enteritidis* FliC monomers or polymers in protecting CD-1 mice from lethal challenge[a] with wild-type *S. Enteritidis* R11

| Vaccine | Mortality (dead/total) | p value[b] | Vaccine Efficacy |
|---|---|---|---|
| PBS | 19/20 | — | — |
| Flagellin monomer | 0/20 | <0.0001 | 100% |
| Flagella polymer | 0/20 | <0.0001 | 100% |

[a]Mice were challenged with $5 \times 10^5$ CFU *S. Enteritidis* R11 (IP LD$_{50}$ = $2.2 \times 10^5$ CFU).
[b]Mortality rate of vaccine group compared to PBS control animals by two-tailed Fisher's exact test.

Immunogenicity of COPS, Flagellin and O:H 1:1 Lot 1 in BALB/c Mice

Figure 32:
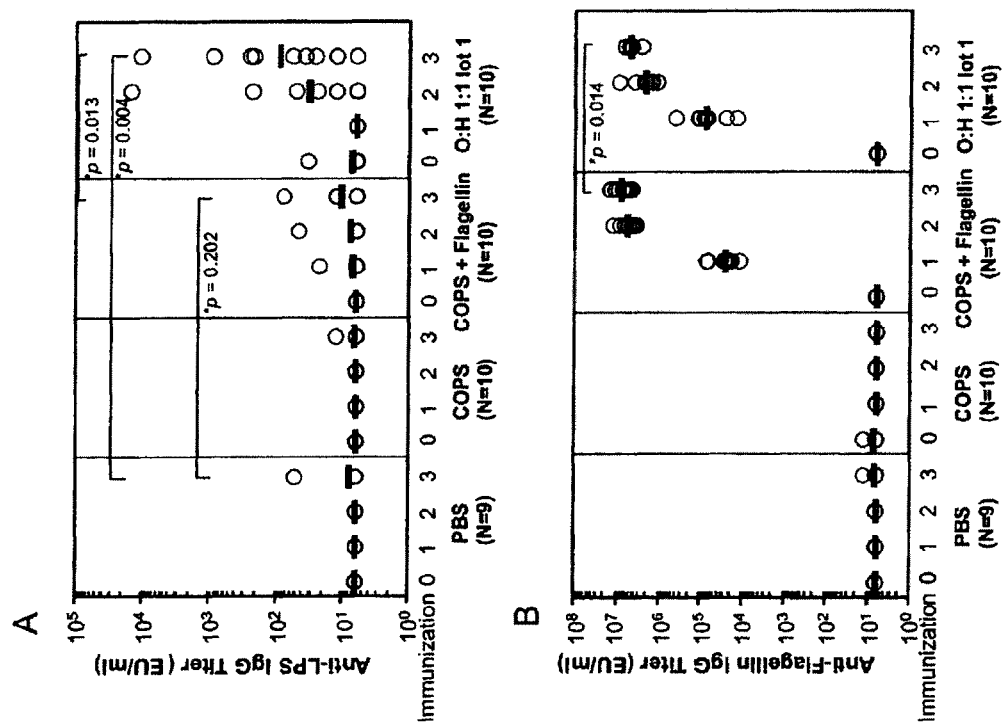
FIG. 32. Humoral immune responses in BALB/c mice following immunization with PBS sham, S. Enteritidis COPS, COPS admixed with flagellin monomers, or O:H 1:1 lot 1 conjugate. Serum anti-LPS IgG (A) and anti-flagellin IgG (B) levels in individual mice (○) and geometric means (-) before immunization (time 0) and at 21 days following the $1^{st}$ (1), $2^{nd}$ (2), or $3^{rd}$ (3) immunization. * compared to PBS by Mann-Whitney Rank-Sum test.

To assess the ability of COPS conjugated to flagellin to stimulate anti-LPS and anti-flagellar immune responses, inbred BALB/c mice were immunized intramuscularly at 0, 28 and 56 days with PBS or with 2.5 μg of COPS alone or admixed with purified flagellin monomers, or with the O:H 1:1 lot 1 conjugate. BALB/c mice were used in these experiments because this strain is genetically homogenous and animal-to-animal variability in antibody levels may be diminished. As shown in FIG. 32A, immunization with COPS alone or COPS admixed with flagellin failed to stimulate a significant increase in serum anti-LPS IgG titer. In contrast, anti-LPS was detected by 14 days following the second immunization in mice that received the conjugate vaccine, with higher levels achieved after the third immunization. LPS seroconversion (≥4 fold increase over baseline of 6 EU) was observed in 70% of mice that received the conjugate, and anti-LPS levels were significantly elevated relative to mice receiving PBS (p<0.05).

The serum anti-flagellin monomer IgG levels elicited in mice immunized with either purified flagellin admixed with COPS, or with O:H 1:1 lot 1 were observed as early as 14 days after the first immunization (FIG. 32B). Anti-flagellin antibodies reached the highest levels (>$10^6$ EU/ml) after only two doses of vaccine and the individual responses within the groups were similar. Mice immunized with O:H 1:1 lot 1 conjugate exhibited anti-flagellin IgG levels that were similar to those of mice immunized with COPS admixed with flagellin, suggesting that conjugation does not interfere with the ability to mount an anti-flagellin immune response.

Figure 33:
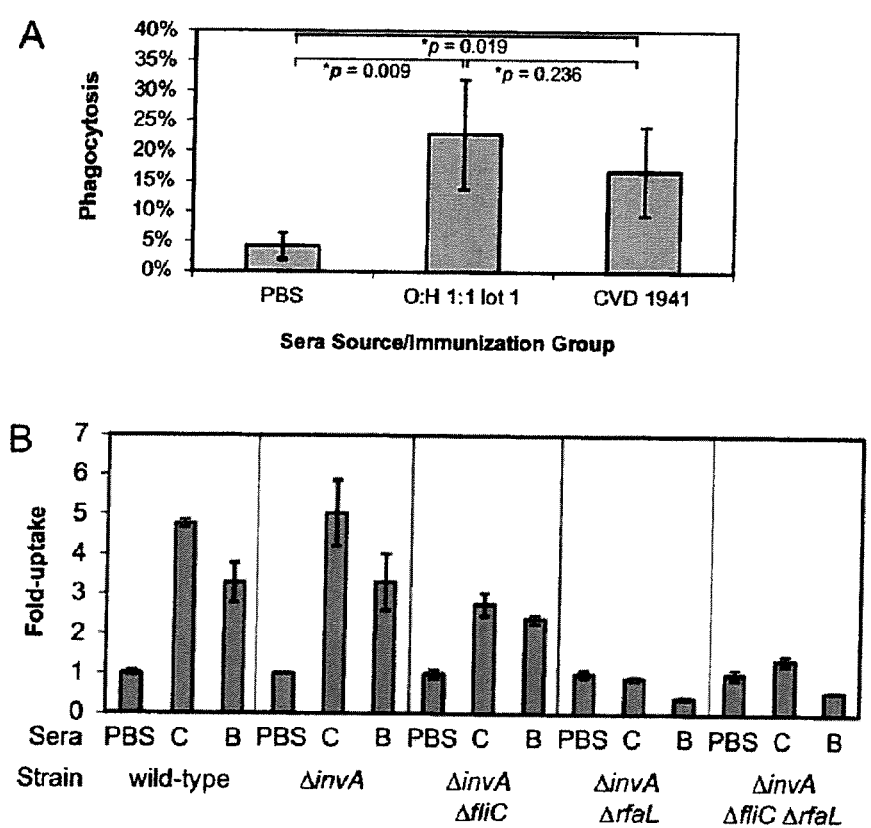
FIG. 33. Opsonophagocytic uptake of wild-type S. Enteritidis R11 by J774 mouse macrophages following treatment with sera from BALB/c mice immunized with O:H 1:1 lot 1 conjugate (A) Bacterial uptake in the presence of individual PBS control (N=3), or immune sera (N=6) displaying high anti-LPS and anti-flagellin IgG levels (average±standard deviation; *, statistical significance assessed by t-test). (B) Uptake by pooled sera from mice immunized with O:H 1:1 lot 1 [C] relative to PBS, of wild-type S. Enteritidis R11 and derivatives mutated in invA, fliC and rfaL as indicated. Average and standard error from duplicate wells and representative of two independent experiments are shown.

Serum opsonophagocytic assays were performed to confirm the presence of functional antibody in BALB/c mice immunized with COPS:flagellin conjugate. Individual serum samples from high responder animals immunized with O:H 1:1 lot 1 significantly increased the opsonophagocytic uptake of wild-type S. Enteritidis R11 by J774 mouse macrophages compared to negative control sera from unvaccinated mice (FIG. 33A).

Engineered defined mutants of S. Enteritidis were used in the opsonophagocytic assay to assess the role of antibodies to COPS and flagellin in mediating opsonophagocytosis. S. Enteritidis R11 cells lacking fliC (in a AinvA background) were taken up at a slightly reduced level by pooled sera from mice immunized with O:H 1:1 lot 1 as compared to wild-type bacteria (FIG. 33B). S. Enteritidis R11 cells that possess a deletion in rfaL, which is required for synthesis of long-chain OPS, showed no increased level of opsonophagocytosis by immune sera as compared to uptake by sera from PBS control mice.

Figure 34:
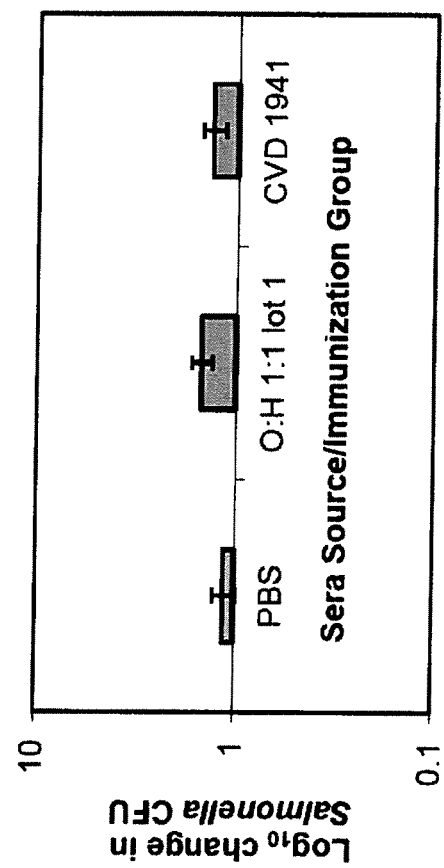
FIG. 34. Serum and complement mediated bactericidal activity against S. Enteritidis R11 from mice immunized with O:H 1:1 lot 1 and live attenuated CVD 1941 ΔguaBAΔclpP vaccines.

In contrast to the enhanced opsonophagocytic uptake mediated by sera from conjugate immunized mice, the same sera did not exhibit evidence of complement mediated serum bactericidal activity (SBA) against wild-type S. Enteritidis R11 (FIG. 34). Similar SBA resistance was found against several other S. Enteritidis clinical isolates from Mali (data not shown).

Immunogenicity of Definitive Conjugates in CD-1 Mice

Figure 35:
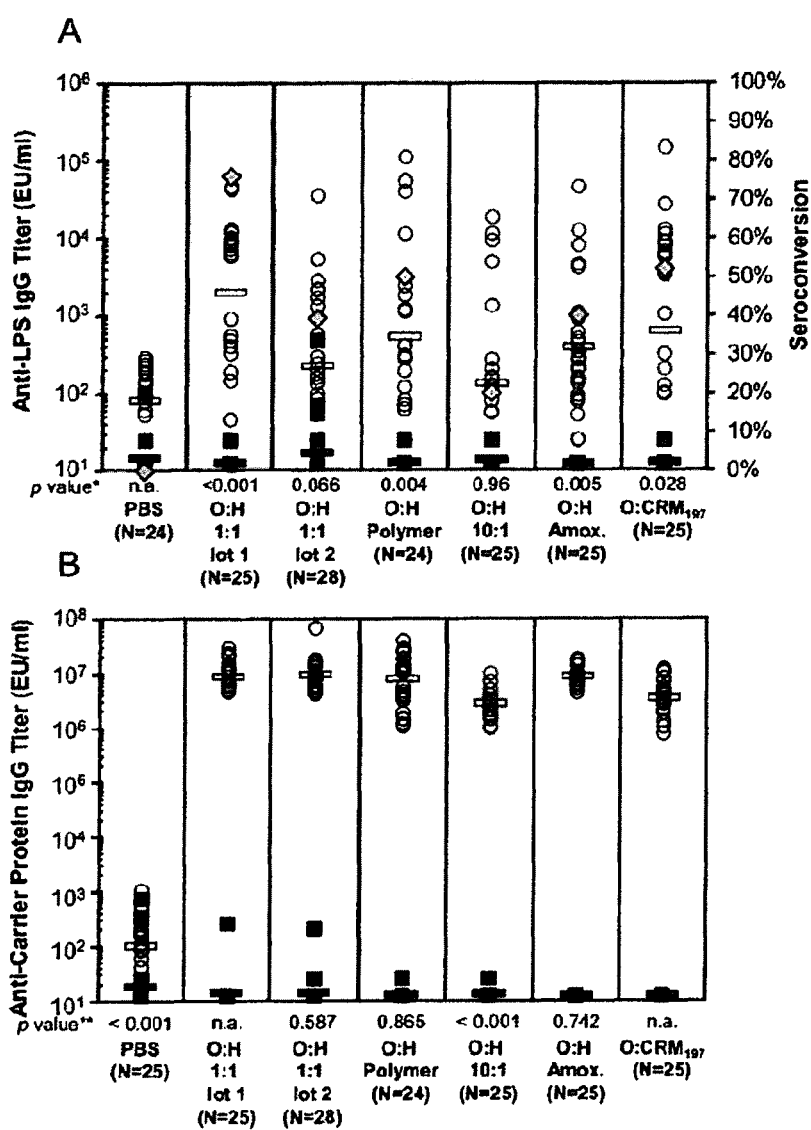
FIG. 35. Humoral immune response in CD-1 mice immunized with COPS conjugates. Anti-LPS IgG (A) and anti-carrier protein (flagella or $CRM_{197}$) IgG (B) levels in pre-immune sera (individual mice [black squares] and geometric mean [closed bars]) and 21 days after the third immunization (individual mice [open circles] and geometric mean [open bars]) with the indicated S. Enteritidis COPS conjugate. Percent seroconversion to anti-LPS IgG is indicated by grey diamonds (≥4-fold increase over basal level of 100 EU). *statistical significance for anti-LPS IgG as compared to PBS, and **anti-flagella IgG as compared to O:H 1:1 lot 1, between groups by Mann-Whitney Rank-Sum test (n.a.=not applicable).
Figure 36:
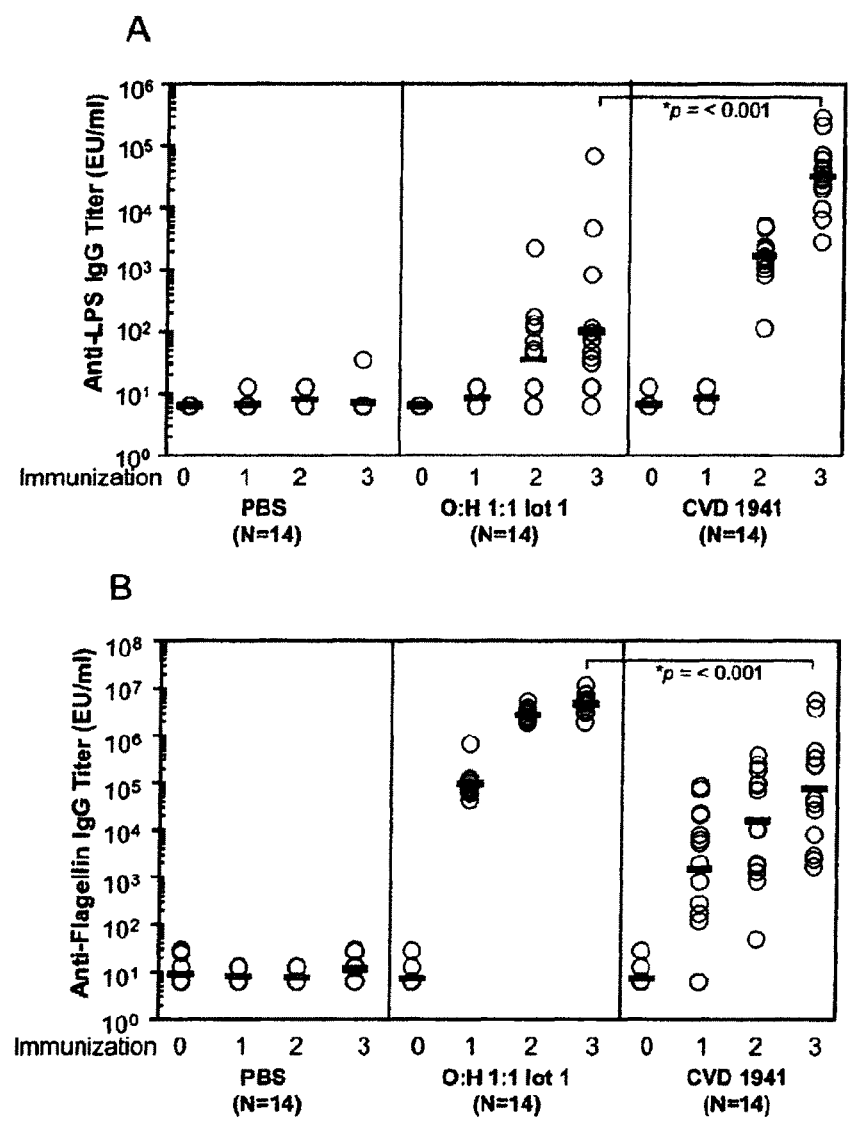
FIG. 36 Humoral immune responses in BALB/c mice following immunization with PBS sham, O:H 1:1 lot 1 conjugate or live attenuated S. Enteritidis CVD 1941 ΔguaBA ΔclpP. Serum anti-LPS IgG (A) and anti-flagellin IgG (B) titers in individual mice (○) and geometric means (-) at time 0 and at 21 days following the $1^{st}$ (1), $2^{nd}$ (2), or $3^{rd}$ (3) immunization. * Statistical significance for group comparison by Mann-Whitney Rank-Sum test.
Figure 37:
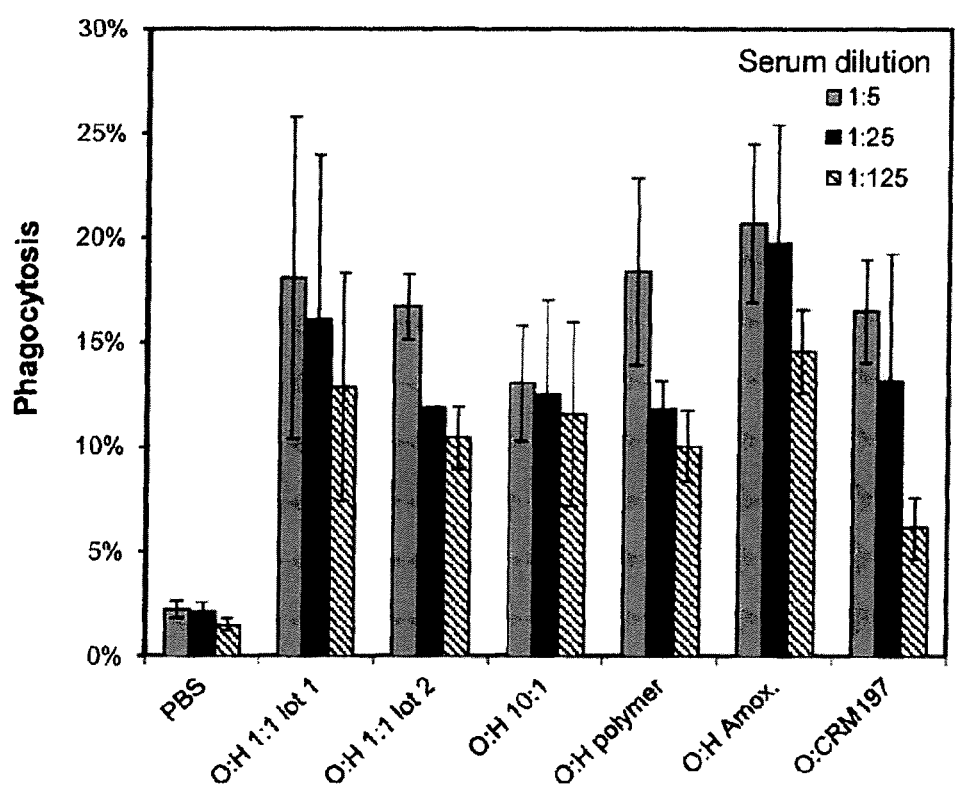
FIG. 37 Opsonophagocytic uptake of wild-type S. Enteritidis R11 by J774 mouse macrophages using pooled sera from CD-1 mice immunized three times with COPS conjugates. Sera from mice immunized with the indicated COPS conjugates were diluted in PBS at the indicated concentration and measured for opsonophagocytic activity. Average and standard error are from duplicate samples in two independent experiments.

Based on the encouraging results seen in inbred BALB/c mice with O:H 1:1 lot 1, outbred CD1 mice were immunized to compare the immunogenicity of the conjugates that varied in carrier protein, polysaccharide:protein ratio, and conjugation chemistry, along with preliminary O:H 1:1 lot 1 conjugate serving as a bridge to the study in BALB/c mice. Immunization was performed as described above; 2.5 µg of conjugate was administered at 0, 28 and 56 days. Consistent with results seen in BALB/c mice, anti-LPS IgG levels exhibited significant animal-to-animal variability within individual experimental conjugate groups (FIG. 35A). The geometric mean titers and seroconversion rates differed between conjugate preparations. The highest overall anti-LPS levels were seen in mice immunized with O:H 1:1 lot 1 (76% seroconversion, GMT=2,042 EU/ml), the lowest levels were seen in O:H 10:1 immunized mice (20% seroconversion, GMT=134 EU/ml). Intermediate, and comparably elevated levels were seen between the other conjugates tested (39-52% seroconversion, GMT 227-640 EU/ml). All except one of the conjugates constructed with flagellin as the carrier protein stimulated comparably high anti-flagella IgG levels following immunization with three doses of conjugate (FIG. 35B); the exception was O:H 10:1, which elicited an elevated but significantly lower titer of anti-flagellin IgG (p=<0.001) as compared to O:H 1:1 lot 1. High anti-CRM$_{197}$ IgG levels were seen in mice immunized with the COPS:CRM$_{197}$ conjugate. Sera from CD-1 mice immunized with the various conjugate preparations exhibited increased opsonophagocytic activity compared to sera from negative control mice inoculated with PBS, with little difference noted in sera from groups of mice given the different conjugates (data not shown).

COPS:Flagellin Conjugates are Protective in CD-1 Mice Against Lethal Wild-Type S. Enteritidis Challenge CD-1 mice immunized with any of the COPS based conjugate vaccines were significantly protected against IP challenge with 5×10$^5$ CFU S. Enteritidis R11, with low mortality observed in the vaccine groups as compared to 100% mortality in the PBS group (Table 15). Somewhat higher mortality was seen in all conjugate vaccine groups following challenge with 1×10$^6$ CFU S. Enteritidis R11 IP; however, significant protection was still observed for all the conjugates, with the exception of the COPS:flagellin monomer 10:1 CDAP linked conjugate. A small group of mice immunized with O:H 1:1 lot 2 conjugate were challenged IP with a higher inoculum (5×10$^6$ CFU) and were also protected.

TABLE 15

Efficacy of COPS:Protein conjugate vaccines in protecting CD-1 mice from lethal challenge with wild-type S. Enteritidis R11

| Vaccine | Intraperitoneal challenge dose (CFU)$^a$ | Mortality (dead/total) | p value$^b$ | Vaccine Efficacy |
|---|---|---|---|---|
| PBS | 5 × 10$^5$ | 12/12 | — | — |
| O:H 1:1 lot 1 | 5 × 10$^5$ | 0/12 | <0.001 | 100.0% |
| O:H 1:1 lot 2 | 5 × 10$^5$ | 1/12 | <0.001 | 91.7% |
| O:H polymer | 5 × 10$^5$ | 2/12 | <0.001 | 83.3% |
| O:H 10:1 | 5 × 10$^5$ | 2/12 | <0.001 | 83.3% |
| O:H Amox. | 5 × 10$^5$ | 1/12 | <0.001 | 91.7% |
| O:CRM$_{197}$ | 5 × 10$^5$ | 3/12 | <0.001 | 75.0% |
| PBS | 1 × 10$^6$ | 12/13 | — | — |
| O:H 1:1 lot 1 | 1 × 10$^6$ | 1/13 | <0.001 | 91.7% |
| O:H 1:1 lot 2 | 1 × 10$^6$ | 3/13 | <0.01 | 75.0% |
| O:H polymer | 1 × 10$^6$ | 2/12 | <0.001 | 81.9% |
| O:H 10:1 | 1 × 10$^6$ | 8/13 | 0.16 | 33.3% |
| O:H Amox. | 1 × 10$^6$ | 2/13 | <0.001 | 83.3% |
| O:CRM$_{197}$ | 1 × 10$^6$ | 3/13 | <0.01 | 75.0% |
| O:H 1:1 lot 2 | 5 × 10$^6$ | 0/3 | — | — |

$^a$IP LD$_{50}$ = 2.2 × 10$^5$ CFU.
$^b$Mortality rate of conjugate vaccine group compared to PBS control animals by two-tailed Fisher's exact test.

EXAMPLE 7

Live Attenuated S. Choleraesuis and S. Paratyphi B Vaccines and Reagent Strains for Purification of Conjugate Vaccine Components Either the guaB or the guaA (or both if possible) loci of S. Choleraesuis and S. Paratyphi B will be deleted using the lambda red recombinase technique. At the time of this submission, genome data for the sequence of guaB is unknown for S. Choleraesuis and only provisionally identified for *S. Paratyphi* B. Mutants will then be tested phenotypically by streaking them onto chemically defined medium with or without guanine. While the wild-type strains are expected to grow on both media, the guaBA mutants should not grow on media lacking guanine. This will be the primary attenuating mutation.

A ΔclpP polar mutation or a clpX mutation (clpX is the second gene in the bicistronic clpPX operon) will then be introduced into the ΔguaBA backgrounds. In a preferred embodiment, we will delete only clpX for two reasons: ] It is easier to complement and therefore advantageous for regulatory purposes; and 2] clpP has only been provisionally identified in the only currently available genome sequence for *S. Paratyphi* B strain SPB7. The resulting strains are designated in this example as S. Choleraesuis ΔguaBA ΔclpX and *S. Paratyphi* B ΔguaBA ΔclpX. Motility tests, SDS-PAGE and western blot analyses will be performed to show that the ΔclpX mutants are more motile than both the wild-type strains and the Δgua mutants and produce more cell-associated flagella than the parental strains. The ΔclpX mutation is the secondary attenuating mutation which independently attenuates the *Salmonella*. Bacteria that possess two independently attenuating mutations are unlikely to revert back to wild-type.

Flagellin, a powerful stimulator of the innate immune system via activation of TLR5 (and perhaps other mechanisms), serves as an adjuvant to enhance immune responses to coupled haptens or antigens, leading some to question whether flagellin in vaccines may cause systemic (malaise and fever) or local (erythema and induration) adverse reactions from over-stimulation of the innate immune system. *Salmonella* strains that express Phase 1 flagellin with markedly reduced TLR5 stimulating activity will therefore be constructed. As the size of FliC can vary depending on the serovar, we will incorporate the point mutation corresponding to our previously defined isoleucine residue 411 of FliC to be mutated to an alanine (designated I411A), which has been reported to prevent both filament formation of flagellin as well as removing TLR5-stimulating activity (Andersen-Nissen et al. *J. Exp. Med. Vol.* 204, No. 2, 393-403 (2007)).

For the reagent strains intended to be used to safely and economically purify large quantities of components for subunit vaccine production (conjugate vaccines using flagellin monomers as the carrier protein), we will introduce further mutations. In some embodiments, if a strain of S. Choleraesuis is chosen which expresses both Phase 1 and Phase 2 H (flagella) antigens, the fljB gene (which encodes Phase 2 flagella) will be deleted from S. Choleraesuis such that it only produces Phase 1 H antigen. *S. Paratyphi* B only has Phase 1 flagella. FliD is a capping protein on the tip of the flagella filament and in the absence of FliD, flagellin monomers are exported into the supernatant. The IUD gene will be deleted from the S. Choleraesuis and *S. Paratyphi* B reagent strains. The resulting mutants are expected to be non-motile. Furthermore, SDS-PAGE and western blot analyses are expected to show that the ΔfliD mutants export flagellin into the supernatant (no longer cell-associated).

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein. All patents and publications mentioned and/or cited herein are incorporated by reference to the same extent as if each individual publication was specifically and individually indicated as having been incorporated by reference in its entirety.

What is claimed is:

1. A method of inducing an immune response, comprising administering to a subject in need thereof an immunologically-effective amount of a composition comprising
   1) a conjugate comprising a phase 1 flagella protein from the *Salmonella enterica* serovar *S*. Typhimurium wherein the phase 1 flagella protein is FliC or FliC$^{J411\Delta}$ and a core-O polysaccharide, wherein the core-O polysaccharide is from a *Salmonella enterica* serovar selected from the group consisting of *S*. Typhimurium, S. Enteritidis, S. Choleraesuis, S. Typhi and *S*. Paratyphi A and combinations thereof;
   2) a conjugate comprising a phase 1 flagella protein from the *Salmonella enterica serovar S. Enteritidis* wherein the phase 1 flagella protein is FliC or FliC$^{J411\Delta}$ and a core-O polysaccharide, wherein the core-O polysaccharide is from a *Salmonella enterica* serovar selected from the group consisting of *S*. Typhimurium, *S*. Enteritidis, *S*. Choleraesuis, *S*. Typhi and *S*. Paratyphi A and combinations thereof;
   3) a conjugate comprising a phase 1 flagella protein from the *Salmonella enterica* serovar *S. Choleraesuis* wherein the phase 1 flagella protein is FliC or FliC$^{J411\Delta}$ and a core-O polysaccharide, wherein the core-O polysaccharide is from a *Salmonella enterica* serovar selected from the group consisting of *S*. Typhimurium, *S*. Enteritidis, *S*. Choleraesuis, S. Typhi and *S*. Paratyphi A and combinations thereof;
   4) a conjugate comprising a phase 1 flagella protein from the *Salmonella enterica* serovar *S. Typhi* wherein the phase 1 flagella protein is FliC or FliC$^{J411\Delta}$ and a core-O polysaccharide, wherein the core-O polysaccharide is from a *Salmonella enterica* serovar selected from the group consisting of *S*. Typhimurium, *S*. Enteritidis, *S*. Choleraesuis, *S*. Typhi and *S*. Paratyphi A and combinations thereof; and
   5) a conjugate comprising a phase 1 flagella protein from the *Salmonella enterica* serovar *S*. Paratyphi A wherein the phase 1 flagella protein is FliC or FliC$^{J411\Delta}$ and a core-O polysaccharide, wherein the core-O polysaccharide is from a *Salmonella enterica* serovar selected from the group consisting of *S*. Typhimurium, *S*. Enteritidis, *S*. Choleraesuis, *S*. Typhi and *S*. Paratyphi A and combinations thereof.

2. The method of claim 1, wherein the composition further comprises a *S*. Paratyphi B conjugate comprising core-O polysaccharide (COPS) linked to a phase 1 flagella protein (FliC).

3. A composition comprising
   1) a conjugate comprising a phase 1 flagella protein from the *Salmonella enterica* serovar *S*. Typhimurium wherein the phase 1 flagella protein is FliC or FliC$^{J411\Delta}$ and a core-O polysaccharide, wherein the core-O polysaccharide is from a *Salmonella enterica* serovar selected from the group consisting of *S*. Typhimurium, *S*. Enteritidis, *S*. Choleraesuis, *S*. Typhi and *S*. Paratyphi A and combinations thereof;
   2) a conjugate comprising a phase 1 flagella protein from the *Salmonella enterica* serovar *S. Enteritidis* wherein the phase 1 flagella protein is FliC or FliC$^{J411\Delta}$ and a core-O polysaccharide, wherein the core-O polysaccharide is from a *Salmonella enterica* serovar selected from the group consisting of *S*. Typhimurium, *S*. Enteritidis, *S*. Choleraesuis, *S*. Typhi and *S*. Paratyphi A and combinations thereof;
   3) a conjugate comprising a phase 1 flagella protein from the *Salmonella enterica* serovar *S*. Choleraesuis wherein the phase 1 flagella protein is FliC or FliC$^{J411\Delta}$ and a core-O polysaccharide, wherein the core-O polysaccharide is from a *Salmonella enterica* serovar selected from the group consisting of *S*. Typhimurium, *S*. Enteritidis, *S*. Choleraesuis, *S*. Typhi and *S*. Paratyphi A and combinations thereof;
   4) a conjugate comprising a phase 1 flagella protein from the *Salmonella enterica* serovar *S*. Typhi wherein the phase 1 flagella protein is FliC or FliC$^{J411\Delta}$ and a core-O polysaccharide, wherein the core-O polysaccharide is from a *Salmonella enterica* serovar selected from the group consisting of *S*. Typhimurium, *S*. Enteritidis, *S*. Choleraesuis, *S*. Typhi and *S*. Paratyphi A and combinations thereof; and
   5) a conjugate comprising a phase 1 flagella protein from the *Salmonella enterica* serovar *S*. Paratyphi A wherein the phase 1 flagella protein is FliC or FliC$^{J411\Delta}$ and a core-O polysaccharide, wherein the core-O polysaccharide is from a *Salmonella enterica* serovar selected from the group consisting of *S*. Typhimurium, *S*. Enteritidis, *S*. Choleraesuis, *S*. Typhi and *S*. Paratyphi A and combinations thereof.

4. The composition of claim 3, further comprising a *S*. Paratyphi B conjugate comprising core-O polysaccharide (OPS) linked to a phase 1 flagella protein.

5. The composition of claim 3, wherein the phase 1 flagella protein of parts 1-5) is FliC.

6. The composition of claim 3, wherein the conjugate of part 1) comprises a phase 1 flagella protein from the *Salmonella enterica* serovar *S*. Typhimurium wherein the phase 1 flagella protein is FliC or FliC$^{T4114}$ and a core-O polysaccharide, wherein the core-O polysaccharide is from *S.* Typhimurium.

7. The composition of claim 3, wherein the conjugate of part 2) comprises a phase 1 flagella protein from the *Salmonella enterica* serovar *S.* Enteritidis wherein the phase 1 flagella protein is FliC or FliC$^{T4114}$ and a core-O polysaccharide, wherein the core-O polysaccharide is from *S.* Enteritidis.

8. The composition of claim 3, wherein the conjugate of part 3) comprises a phase 1 flagella protein from the *Salmonella enterica* serovar *S.* Choleraesuis wherein the phase 1 flagella protein is FliC or FliC$^{T4114}$ and a core-O polysaccharide, wherein the core-O polysaccharide is from *S.* Choleraesuis.

9. The composition of claim 3, wherein the conjugate of part 4) comprises a phase 1 flagella protein from the *Salmonella enterica* serovar *S.* Typhi wherein the phase 1 flagella protein is FliC or FliC$^{T4114}$ and a core-O polysaccharide, wherein the core-O polysaccharide is from *S.* Typhi.

10. The composition of claim 3, wherein the conjugate of part 5) comprises a phase 1 flagella protein from the *Salmonella enterica* serovar *S.* Paratyphi A wherein the phase 1 flagella protein is FliC or FliC$^{FT4114}$ and a core-O polysaccharide, wherein the core-O polysaccharide is from *S.* Paratyphi A.

11. The composition of claim 3,
wherein the conjugate of part 1) comprises a phase 1 flagella protein from the *Salmonella enterica* serovar *S.* Typhimurium wherein the phase 1 flagella protein is FliC or FliC$^{T4114}$ and a core-O polysaccharide, wherein the core-O polysaccharide is from S. Typhimurium, wherein the conjugate of part 2) comprises a phase 1 flagella protein from the *Salmonella enterica* serovar *S.* Enteritidis wherein the phase 1 flagella protein is FliC or FliC$^{T4114}$ and a core-O polysaccharide, wherein the core-O polysaccharide is from *S.* Enteritidis, wherein the conjugate of part 3) comprises a phase 1 flagella protein from the *Salmonella enterica* serovar *S.* Choleraesuis wherein the phase 1 flagella protein is FliC or FliC$^{T4114}$ and a core-O polysaccharide, wherein the core-O polysaccharide is from *S.* Choleraesuis, wherein the conjugate of part 4) comprises a phase 1 flagella protein from the *Salmonella enterica* serovar *S.* Typhi wherein the phase 1 flagella protein is FliC or FliC$^{T4114}$ and a core-O polysaccharide, wherein the core-O polysaccharide is from *S.* Typhi, wherein the conjugate of part 5) comprises a phase 1 flagella protein from the *Salmonella enterica* serovar *S.* Paratyphi A wherein the phase 1 flagella protein is FliC or FliC$^{T4114}$ and a core-O polysaccharide, wherein the core-O polysaccharide is from *S.* Paratyphi A.

12. The composition of claim 11, wherein the phase 1 flagella protein of parts 1-5) is FliC.

13. The composition of claim 11, wherein the phase 1 flagella protein of parts 1-5) is FliC$^{T4114}$.

* * * * *

SEQUENCE LISTING

```
<160> NUMBER OF SEQ ID NOS: 104

<210> SEQ ID NO 1
<211> LENGTH: 1578
<212> TYPE: DNA
<213> ORGANISM: Salmonella enterica

<400> SEQUENCE: 1
atgacggaaa acattcataa gcatcgcatc ctcattctgg acttcggttc tcagtacact      60
caactggttg cgcgccgcgt gcgtgagctg ggtgtttact gtgaactgtg ggcgtgggat     120
gtgacagaag cacaaattcg tgacttcaac ccaagcggca ttattctttc cggcggcccg     180
gaaagcacca ccgaagaaaa cagcccgcgc gcgccgcagt atgtctttga agcaggcgtg     240
ccggtatttg gcgtttgcta tggtatgcag accatggcga tgcagcttgg cggtcatgta     300
gaaggttcta atgagcgtga atttggttat gcgcaggtcg aagtgttgac cgacagcgcg     360
ctggttcgcg gtattgaaga ttccctgacc gcagacggca aaccgctgct ggacgtgtgg     420
atgagccacg gcgataaagt gacggcgatt ccgtccgact tcgtgaccgt cgccagcacc     480
gagagctgcc cgttcgccat tatggccaac gaagaaaaac gcttctacgg cgtacagttc     540
cacccggaag tgactcacac ccgccagggt atgcgcatgc tggagcgttt tgtacgcgat     600
atctgccagt gtgaagcgtt gtggacgccg gcgaagatca tcgatgacgc cgtggcgcgc     660
attcgcgagc aggtaggcga cgataaagtg atcctcggtc tctccggcgg cgtggattct     720
tccgtcaccg ccatgctgct gcaccgcgcg atcggtaaaa atctgacctg tgttttcgtc     780
gacaacggcc tgttgcgcct gaacgaagcc gagcaggtga tggacatgtt tggcgaccat     840
tttggtctga acattgttca cgtaccggca gaagatcgct tcctgtccgc gctggctggt     900
gagaacgatc cggaagccaa gcgtaagatc atcggccgcg ttttcgttga agtgttcgac     960
gaagaagcgc tgaaactgga agacgtgaaa tggctggcgc agggcaccat ctaccctgac    1020
gttatcgaat ctgcggcgtc tgcaaccggt aaagcgcacg tcatcaaatc tcaccacaat    1080
gtcggcggcc tgccgaaaga gatgaagatg gggctggttg aaccgctgaa agagctgttc    1140
aaagacgaag tgcgtaagat tggtctggag ctggcctgc cgtacgacat gctgtatcgc    1200
catccgttcc cgggggccggg cctcggcgtg cgcgtactgg gcgaagtgaa gaaagagtac    1260
```

```
tgcgacctgc tgcgtcgcgc ggacgctatc ttcattgaag agctgcgcaa agcggatctg    1320
tacgacaaag tcagtcaggc gtttaccgtc ttcctgccgg tccgttccgt aggcgtgatg    1380
ggcgatggtc gtaagtacga ttggggttgtc tctctgcgtg ctgtcgaaac catcgacttt   1440
atgaccgcac actgggcaca tctgccgtat gatttcctgg tcgtgtttc caaccgcatc     1500 atcaatgaag tcaacgggat tcccgtgtg gtgtatgaca tcagcggtaa accaccagct     1560
accattgagt gggaataa                                                  1578

<210> SEQ ID NO 2
<211> LENGTH: 1578
<212> TYPE: DNA
<213> ORGANISM: Salmonella enterica

<400> SEQUENCE: 2
atgacggaaa acattcataa gcatcgcatc ctcattctgg acttcggttc tcagtacact     60
caactggttg cgcgccgcgt gcgtgagctg ggtgtttact gtgaactgtg ggcgtgggat    120
gtgacagaag cacaaattcg tgacttcaac ccaagcggca ttattctttc cggcggcccg    180
gaaagcacca ccgaagaaaa cagcccgcgc gcgctgcagt atgtctttga agcaggcgtg    240
ccggtatttg gcgtttgcta tggtatgcag accatggcga tgcagcttgg cggtcatgta    300
gaaggttcta atgagcgtga atttggttat gcgcaggtcg aagtgttgac cgacagcgcg    360
ctggttcgcg gtattgaaga ttccctgacc gcagacggca aaccgctgct ggacgtgtgg    420
atgagccacg gcgataaagt gacggcgatt ccgtccgact cgtgaccgt cgccagcacc     480 gagagctgcc cgttcgccat tatggccaac gaagaaaaac gcttctacgg tgtacagttc    540
cacccggaag tgactcacac ccgccagggt atgcgcatgc tggagcgttt tgtacgcgat    600
atctgccagt gtgaagcgtt gtggacgccg gcgaagatca tcgacgacgc cgtggcgcgc    660
attcgcgagc aggtgggcga cgacaaagtg atcctcggcc tctctggtgg cgtggattct    720
tccgtcaccg caatgctgct gcaccgcgcg atcggtaaaa atctgacctg tgtattcgtc    780
gacaacggcc tgctgcgtct caacgaagcc gagcaggtga tggacatgtt tggcgaccat    840
tttggcctga atatcgttca cgtaccggca gaagagcgct tcctgtccgc gctggctggc    900
gagaacgatc cggaagccaa gcgtaagatc atcggtcgtg tttttgtaga agtgttcgac    960
gaagaagcgc tcaaactgga agacgtgaag tggctggcgc aaggcaccat ttaccctgac   1020
gttatcgaat ctgcggcgtc tgcaaccggt aaagcgcacg tcatcaaatc tcaccacaat   1080
gtcggcggct tgccgaaaga gatgaagatg gggctggttg aaccgctgaa agagctgttc   1140
aaagacgaag tgcgtaagat tggtctggag ctgggcctgc cgtatgacat gctgtatcgc   1200
catccgttcc cggggccggg cctcggccgtt cgtgttctgg gtgaagtgaa gaagagtac    1260 tgcgacctgc tgcgccgtgc tgacgctatc ttcattgaag agctgcgcaa agcggatctg   1320
tacgacaaag tcagtcaggc gtttaccgtc ttcctgccgg ttcgttccgt tggcgttatg   1380
ggcgatggtc gtaagtatga ctgggttgtc tctctgcgtg ccgtcgaaac catcgacttt   1440
atgaccgcac actgggcgca cctgccgtat gacttcctcg gtcgcgtttc caaccgcatc   1500
atcaatgaag tcaacgggat tcccgtgtg gtgtatgaca tcagcggtaa accgccggct    1560
accattgagt gggaataa                                                 1578

<210> SEQ ID NO 3
<211> LENGTH: 1467
<212> TYPE: DNA
```

<213> ORGANISM: Salmonella enterica

<400> SEQUENCE: 3

| | | | | | |
|---|---|---|---|---|---|
| atgctacgta | tcgctaaaga | agctctgacg | tttgacgacg | tcctccttgt | tcccgctcac | 60 |
| tccaccgttt | tgccgaatac | tgccgatctc | agcacgcagt | tgacgaaaac | tattcgtctg | 120 |
| aatattccta | tgctttctgc | ggcgatggac | accgtgacgg | aagcgcgcct | ggcaattgcc | 180 |
| ctggcccagg | aaggcggcat | tggttttatc | cacaaaaaca | tgtctattga | gcgccaggcg | 240 |
| gaagaagttc | gccgcgtgaa | gaaacacgag | tccggcgtag | tgaccgaccc | gcagaccgtc | 300 |
| ctgccaacca | ccacgttgca | tgaagtgaaa | gccctgaccg | agcgtaacgg | ttttgcgggc | 360 |
| tatccggtgg | tgactgaaga | taacgagctg | gtgggtatca | tcaccggtcg | tgacgtgcgt | 420 |
| tttgtgactg | acctgaacca | gccggtgagt | gtctacatga | caccgaaaga | gcgtctggtg | 480 |
| accgttcgtg | aaggcgaagc | ccgtgaagtc | gtgctggcaa | aaatgcacga | aaaacgcgta | 540 |
| gaaaaagcgc | tggtcgttga | tgataacttc | catctgcttg | gcatgattac | cgtaaaagat | 600 |
| ttccagaaag | cggaacgtaa | accaaactcc | tgtaaagatg | agcagggccg | tttacgtgtc | 660 |
| ggcgcggcgg | tcggcgcagg | cgcgggcaac | gaagagcgcg | ttgacgcgct | ggtggcggca | 720 |
| ggcgttgacg | tactgctgat | cgactcctct | cacggtcact | ctgaaggcgt | gttgcaacgt | 780 |
| atccgtgaga | cgcgtgctaa | atatcctgac | ctgcaaatca | tcggcggcaa | cgttgcgacg | 840 |
| ggcgcaggcg | ctcgcgcact | ggcggaagcc | ggttgcagcg | cggtgaaagt | gggtatcggc | 900 |
| ccgggttcca | tctgtacgac | tcgtatcgtg | actggtgtgg | gcgttccgca | gatcaccgct | 960 |
| gtttctgacg | cggtggaagc | gctggaaggc | accgggattc | cggttatcgc | tgacggcggt | 1020 |
| atccgttttct | ccggcgacat | cgccaaagcc | atcgccgcag | gcgcgagcgc | ggtaatggtg | 1080 |
| ggttctatgc | tggccggtac | cgaagaatcc | ccgggcgaaa | tcgaactcta | ccagggccgt | 1140 |
| tcttacaaat | cttatcgcgg | tatgggttct | ctgggcgcga | tgtccaaagg | ttcctccgac | 1200 |
| cgttacttcc | agagcgacaa | cgccgccgac | aaactggtgc | cggaaggtat | cgaaggccgc | 1260 |
| gtagcctata | aaggtcgcct | gaaagagatc | attcaccagc | agatgggcgg | cctgcgctcc | 1320 |
| tgtatggggc | tgaccggttg | tgctaccatc | gacgaactgc | gtactaaagc | ggagtttgtg | 1380 |
| cgtatcagcg | gtgcgggtat | ccaggaaagc | cacgttcacg | acgtgaccat | caccaaagag | 1440 |
| tccccgaact | accgtctggg | ctcctga | | | | 1467 |

<210> SEQ ID NO 4
<211> LENGTH: 1467
<212> TYPE: DNA
<213> ORGANISM: Salmonella enterica

<400> SEQUENCE: 4

| | | | | | |
|---|---|---|---|---|---|
| atgctacgta | tcgctaaaga | agccctgacg | tttgacgacg | tcctccttgt | tcccgctcac | 60 |
| tccaccgttt | tgccgaatac | tgccgatctc | agcacgcagt | tgacgaaaac | tattcgtctg | 120 |
| aatattccta | tgctttctgc | ggcgatggac | accgtgacgg | aagcgcgcct | ggcaattgcc | 180 |
| ctggcccagg | aaggcggcat | tggttttatc | cacaaaaaca | tgtccattga | gcgccaggcg | 240 |
| gaagaagttc | gccgcgtgaa | gaaacacgag | tccggcgtag | tgaccgaccc | gcagaccgtc | 300 |
| ctgccaacca | ccacgttgca | tgaagtgaaa | gccctgaccg | agcgtaacgg | ttttgcgggc | 360 |
| tatccggtgg | tgactgaaga | taacgagctg | gtgggtatca | tcaccggtcg | tgacgtgcgt | 420 |
| tttgtgactg | acctgaacca | gccggttagc | gtttacatga | cgccgaaaga | gcgtctggtg | 480 |
| accgttcgtg | aaggcgaagc | ccgtgaagtc | gtgctggcaa | aaatgcacga | aaaacgcgta | 540 |

-continued

```
gaaaaagcgc tggtcgttga tgataacttc catctgcttg gcatgattac cgtaaaagat    600
ttccagaaag cggaacgtaa accaaactcc tgcaaagatg agcagggccg tttacgtgtc    660
ggcgcggcgg tcggcgcagg cgcgggcaac gaagagcgcg ttgacgcgct ggtggcggca    720
ggcgttgacg tactgctgat cgactcctct cacggtcatt cagaaggcgt gttgcaacgt    780
atccgtgaaa cccgtgctaa atatcctgac ctgcaaatca tcggcggcaa cgtcgcgaca    840
ggcgcaggcg ctcgcgcact ggcggaagcc ggttgcagcg cggtgaaagt cggtattggc    900
ccgggttcca tctgtaccac tcgtatcgtg actggcgtgg gcgttccgca gatcaccgct    960
gtttctgacg cagttgaagc gctggaaggt accggtattc cggttatcgc tgacggcggt   1020 atccgttttct ccggcgacat agccaaagcg attgccgcag gtgcaagcgc ggtaatggtg   1080
ggttccatgc tggcgggtac ggaagaatcc ccgggcgaaa tcgaactcta ccagggccgt   1140
tcttacaaat cttaccgcgg catgggctcg ctgggtgcga tgtccaaagg ttcctccgac   1200
cgttacttcc agagcgacaa cgccgctgac aaactggtgc cggaaggtat cgaaggtcgc   1260
gtagcctata aaggtcgcct gaaagagatc attcaccagc agatgggcgg cctgcgctcc   1320
tgtatggggc tgaccggttg tgctaccatc gacgaactgc gtactaaagc ggagtttgtg   1380
cgtatcagcg gtgcgggcat tcaggaaagc cacgttcacg acgtgaccat caccaaagag   1440
tccccgaact accgtctggg ctcctga                                       1467
```

<210> SEQ ID NO 5
<211> LENGTH: 624
<212> TYPE: DNA
<213> ORGANISM: Salmonella enterica

<400> SEQUENCE: 5

```
atgtcataca gcggagaacg agataatttg gcccctcata tggcgctggt gccgatggtc     60
attgaacaga cctcacgcgg tgagcgctct tttgatatct attctcgtct acttaaggaa    120
cgcgtcatat ttctgaccgg ccaggtcgaa gaccatatgg ctaacctgat cgtggcgcag    180
atgctgttcc tggaagcgga aaacccggaa aaagatatct atctgtacat taattctcct    240
ggcggcgtaa ttactgcggg gatgtccatc tatgacacca tgcagtttat taagccagac    300
gtcagcacca tttgtatggg acaggcggcc tctatggggg cgtttctgct gactgccggg    360
gcgaaaggca aacgtttctg cttgccgaac tctcgcgtca tgatccacca gccgctgggc    420
ggctaccagg ccaggcgac ggatattgaa attcacgccc gcgaaatttt gaaagtaaaa    480
gggcgcatga atgaacttat ggcgcatcat acgggtcaat ctcttgagca gattgaacgt    540
gatactgagc gcgatcgctt cctctccgcg cctgaagcgg tagagtacgg tttggttgac    600
tcaattttga cccatcgtaa ttga                                           624
```

<210> SEQ ID NO 6
<211> LENGTH: 624
<212> TYPE: DNA
<213> ORGANISM: Salmonella enterica

<400> SEQUENCE: 6

```
atgtcataca gcggagaacg agataatttg gcccctcata tggcgctggt gccgatggtc     60
attgaacaga cctcacgcgg tgagcgctct tttgatatct attctcgtct acttaaggaa    120
cgcgtcatat ttctgaccgg ccaggtcgaa gaccatatgg ctaacctgat cgtggcgcag    180
atgctgttcc tggaagcgga aaacccggaa aaagatatct atctgtacat taattctcct    240
```

```
ggcggcgtaa ttactgcggg gatgtccatc tatgacacca tgcagtttat taagccagac    300
gtcagcacca tttgtatggg acaggcggcc tctatggggg cgtttctgct gactgccggg    360
gcgaaaggca aacgtttctg cttgccgaac tctcgcgtca tgatccacca gccgctgggc    420
ggctaccagg gccaggcgac ggatattgaa attcacgccc gcgaaatttt gaaagtaaaa    480
gggcgcatga atgaacttat ggcgcatcat acgggtcaat ctcttgagca gattgaacgt    540
gatactgagc gcgatcgctt cctctccgcg cctgaagcgg tagagtacgg tttggttgac    600
tcaattttga cccatcgtaa ttga                                            624

<210> SEQ ID NO 7
<211> LENGTH: 1272
<212> TYPE: DNA
<213> ORGANISM: Salmonella enterica

<400> SEQUENCE: 7
atgacagata aacgcaaaga tggctcgggc aaattgttgt actgctcttt ttgcggcaaa     60
agccagcatg aagtgcgcaa gctgattgcc ggtccatccg tgtatatctg cgacgaatgc    120
gtcgatttat gtaacgacat tattcgcgaa gaaattaaag aagttgctcc gcaccgtgaa    180
cgtagtgcgc tgccgacgcc gcatgaaatt cgtacccacc tggacgatta cgttatcggc    240
caggagcagg cgaaaaaagt gctggcgctg gcggtctata accactacaa gcgtctgcgt    300
aacggcgata ccagcaatgg cgtcgagtta ggtaaaagca acattctgct gattggaccg    360
accggttccg gtaaaacgct gctggcggaa acgctggcgc gcttgctgga tgtgccgttc    420
actatggcgt atgcgaccac gctaaccgaa gcgggttacg ttggtgaaga cgtcgagaat    480
atcattcaga aactgttgca gaaatgcgac tacgacgtgc aaaaagcgca gcgtgggatt    540
gtctacattg atgaaatcga taagatttcg cgtaaatcag acaatccgtc cattacccgc    600
gatgtttccg gcgaaggcgt acagcaggcg ttgctgaaac tgatcgaagg caccgtcgcc    660
gcggttccac gcagggcgg tcgcaaacat ccgcagcagg agttcttaca ggtagatacc    720
tctaagattc tgtttatctg cggcggcgcg tttgccggtc tggataaagt gatcgctaac    780
cgtgttgaaa ccggctccgg cattggtttt ggcgcgacgt gaaagcgaa gtccgacaaa    840
gccagcgaag gcgagctgtt gtcgcaggtt gaaccggaag atttgatcaa atttggtctg    900
attcctgagt ttatcggtcg tctgccagtg gtagcgacgc tgaatgaact cagcgaagaa    960
gcgctgattc aaatcctgaa agagccgaaa aatgcgctga ccaagcagta tcaggcgctg   1020
tttaacctgg aaggcgtcga tctggaattc cgtgacgaag cgctggacgc tatcgccagg   1080
aaagcaatgg cgcgtaaaac cggcgcccgt ggcctgcgtt ctatcgtcga agcggcgctg   1140
ctggatacca tgtacgattt gcatctatg gaagacgtcg aaaaagtggt gatcgacgag   1200
tccgttattg ccggtcagag taagccgttg ctgatttacg gcaaaccgga agcgcaggct   1260
tctggcgaat aa                                                      1272

<210> SEQ ID NO 8
<211> LENGTH: 1272
<212> TYPE: DNA
<213> ORGANISM: Salmonella enterica

<400> SEQUENCE: 8
atgacagata aacgcaaaga tggctcgggc aaattgttgt actgctcttt ttgcggcaaa     60
agccagcatg aagtgcgcaa gctgattgcc ggtccatccg tgtatatctg cgacgaatgc    120
gtcgatttat gtaacgacat tattcgcgaa gaaattaaag aagttgctcc gcaccgtgaa    180
```

```
cgtagtgcgc tgccgacgcc gcatgaaatt cgtacccacc tggacgatta cgttatcggc    240
caggagcagg cgaaaaaagt gctggcggtg gcggtctata accactacaa gcgtctgcgt    300
aacggcgata ccagcaatgg cgtcgagtta ggtaaaagca acattctgct gattggaccg    360
accggttccg gtaaaacgct gctggcggaa acgctggcgc gcttgctgga tgtgccgttc    420
actatggcgg atgcgaccac gctaaccgaa gcgggttacg ttggtgaaga cgtcgagaat    480
atcattcaga aactgttgca gaaatgcgac tacgacgtgc aaaaagcgca gcgtgggatt    540
gtctacattg atgaaatcga taagatttcg cgtaaatcag acaatccgtc cattacccgc    600
gatgtttccg gcgaaggcgt acagcaggcg ttgctgaaac tgatcgaagg caccgtcgcc    660
gcggttccac cgcagggcgg tcgcaaacat ccgcagcagg agttcttaca ggtagatacc    720
tctaagattc tgtttatctg cggcggcgcg tttgccggtc tggataaagt gatcgctaac    780
cgtgttgaaa ccggctccgg cattggtttt ggcgcgacgg tgaaagcgaa gtccgacaaa    840
gccagcgaag gcgagctgtt gtcgcaggtt gaaccggaag atttgatcaa atttggtctg    900
attcctgagt ttatcggtcg tctgccagtg gtagcgacgc tgaatgaact cagcgaagaa    960
gcgctgattc aaatcctgaa agagccgaaa aatgcgctga ccaagcagta tcaggcgctg   1020
tttaacctgg aaggcgtcga tctggaattc cgtgacgaag cgctggacgc tatcgccagg   1080
aaagcaatgg cgcgtaaaac cggcgcccgt ggcctgcgtt ctatcgtcga agcggcgctg   1140
ctggatacca tgtacgattt gccatctatg gaagacgtcg aaaaagtggt gatcgacgag   1200
tccgttattg ccggtcagag taagccgttg ctgatttacg gcaaaccgga agcgcaggct   1260
tctggcgaat aa                                                       1272

<210> SEQ ID NO 9
<211> LENGTH: 20
<212> TYPE: DNA
<213> ORGANISM: artificial sequence
<220> FEATURE:
<223> OTHER INFORMATION: synthetic primer

<400> SEQUENCE: 9
gtgtaggctg gagctgcttc                                                20

<210> SEQ ID NO 10
<211> LENGTH: 20
<212> TYPE: DNA
<213> ORGANISM: artificial sequence
<220> FEATURE:
<223> OTHER INFORMATION: synthetic primer

<400> SEQUENCE: 10
attccgggga tccgtcgacc                                                20

<210> SEQ ID NO 11
<211> LENGTH: 21
<212> TYPE: DNA
<213> ORGANISM: artificial sequence
<220> FEATURE:
<223> OTHER INFORMATION: synthetic primer

<400> SEQUENCE: 11
tgtttatgct gctgatcgaa c                                              21

<210> SEQ ID NO 12
<211> LENGTH: 38
<212> TYPE: DNA
```

```
<213> ORGANISM: artificial sequence
<220> FEATURE:
<223> OTHER INFORMATION: synthetic primer

<400> SEQUENCE: 12
gaagcagctc cagcctacac gggcaatatc tcacctgg                              38

<210> SEQ ID NO 13
<211> LENGTH: 38
<212> TYPE: DNA
<213> ORGANISM: artificial sequence
<220> FEATURE:
<223> OTHER INFORMATION: synthetic primer

<400> SEQUENCE: 13
ggtcgacgga tccccggatg ccgataatcc ttcctgtg                              38

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
ataacctgga cacttctgag                                                  20

<210> SEQ ID NO 15
<211> LENGTH: 20
<212> TYPE: DNA
<213> ORGANISM: artificial sequence
<220> FEATURE:
<223> OTHER INFORMATION: primer

<400> SEQUENCE: 15
ttcgaagtga tcaccccaac                                                  20

<210> SEQ ID NO 16
<211> LENGTH: 20
<212> TYPE: DNA
<213> ORGANISM: artificial sequence
<220> FEATURE:
<223> OTHER INFORMATION: primer

<400> SEQUENCE: 16
tatttgggct gaatcgccac                                                  20

<210> SEQ ID NO 17
<211> LENGTH: 20
<212> TYPE: DNA
<213> ORGANISM: artificial sequence
<220> FEATURE:
<223> OTHER INFORMATION: primer

<400> SEQUENCE: 17
taagcgtcgt gtagttgtcg                                                  20

<210> SEQ ID NO 18
<211> LENGTH: 40
<212> TYPE: DNA
<213> ORGANISM: artificial sequence
<220> FEATURE:
<223> OTHER INFORMATION: primer

<400> SEQUENCE: 18
gaagcagctc cagcctacac attacatttc cgtctcctgg                            40
```

<210> SEQ ID NO 19
<211> LENGTH: 40
<212> TYPE: DNA
<213> ORGANISM: artificial sequence
<220> FEATURE:
<223> OTHER INFORMATION: primer

<400> SEQUENCE: 19
ggtcgacgga tccccggaat tgatgccctg gacgcaagtg                          40

<210> SEQ ID NO 20
<211> LENGTH: 20
<212> TYPE: DNA
<213> ORGANISM: artificial sequence
<220> FEATURE:
<223> OTHER INFORMATION: primer

<400> SEQUENCE: 20
taacgtaatc gtccaggtgg                                                20

<210> SEQ ID NO 21
<211> LENGTH: 20
<212> TYPE: DNA
<213> ORGANISM: artificial sequence
<220> FEATURE:
<223> OTHER INFORMATION: primer

<400> SEQUENCE: 21
agaaacaggc tctggagctg                                                20

<210> SEQ ID NO 22
<211> LENGTH: 30
<212> TYPE: DNA
<213> ORGANISM: artificial sequence
<220> FEATURE:
<223> OTHER INFORMATION: primer

<400> SEQUENCE: 22
acggcgtgtt tacaggaaaa acgaaagggg                                     30

<210> SEQ ID NO 23
<211> LENGTH: 22
<212> TYPE: DNA
<213> ORGANISM: artificial sequence
<220> FEATURE:
<223> OTHER INFORMATION: primer

<400> SEQUENCE: 23
tatgacactt gatcatgtga tg                                             22

<210> SEQ ID NO 24
<211> LENGTH: 39
<212> TYPE: DNA
<213> ORGANISM: artificial sequence
<220> FEATURE:
<223> OTHER INFORMATION: primer

<400> SEQUENCE: 24
gaagcagctc cagcctacac ccaataaatc gtgtggctg                           39

<210> SEQ ID NO 25
<211> LENGTH: 42
<212> TYPE: DNA
<213> ORGANISM: artificial
<220> FEATURE:

<223> OTHER INFORMATION: primer

<400> SEQUENCE: 25
ggtcgacgga tccccggaat cgcctacggt aataaaaaat tc          42

<210> SEQ ID NO 26
<211> LENGTH: 21
<212> TYPE: DNA
<213> ORGANISM: artificial
<220> FEATURE:
<223> OTHER INFORMATION: primer

<400> SEQUENCE: 26
tgagaacttc agcaaatcga c                                 21

<210> SEQ ID NO 27
<211> LENGTH: 22
<212> TYPE: DNA
<213> ORGANISM: artificial
<220> FEATURE:
<223> OTHER INFORMATION: primer

<400> SEQUENCE: 27
acgtcataaa tcgaacaagt cg                                22

<210> SEQ ID NO 28
<211> LENGTH: 20
<212> TYPE: DNA
<213> ORGANISM: artificial
<220> FEATURE:
<223> OTHER INFORMATION: primer

<400> SEQUENCE: 28
agcttcagca ttgcatcagc                                   20

<210> SEQ ID NO 29
<211> LENGTH: 24
<212> TYPE: DNA
<213> ORGANISM: artificial
<220> FEATURE:
<223> OTHER INFORMATION: primer

<400> SEQUENCE: 29
gaattctcac gcacacgctg cagg                              24

<210> SEQ ID NO 30
<211> LENGTH: 32
<212> TYPE: DNA
<213> ORGANISM: artificial
<220> FEATURE:
<223> OTHER INFORMATION: primer

<400> SEQUENCE: 30
gctagcacct aatgatgaaa ttgaagccat gc                     32

<210> SEQ ID NO 31
<211> LENGTH: 33
<212> TYPE: DNA
<213> ORGANISM: artificial
<220> FEATURE:
<223> OTHER INFORMATION: sequence

<400> SEQUENCE: 31
gaattcgcta gcgctggagc tgcttcgaag ttc                    33

```
<210> SEQ ID NO 32
<211> LENGTH: 33
<212> TYPE: DNA
<213> ORGANISM: artificial
<220> FEATURE:
<223> OTHER INFORMATION: primer

<400> SEQUENCE: 32
ctcgagttcc ggggatccgt cgacctgcag ttc                         33

<210> SEQ ID NO 33
<211> LENGTH: 34
<212> TYPE: DNA
<213> ORGANISM: artificial
<220> FEATURE:
<223> OTHER INFORMATION: primer

<400> SEQUENCE: 33
ggatccgcta tgaacaagtc ctgataacag aggt                        34

<210> SEQ ID NO 34
<211> LENGTH: 46
<212> TYPE: DNA
<213> ORGANISM: artificial
<220> FEATURE:
<223> OTHER INFORMATION: primer

<400> SEQUENCE: 34
ctcgagttaa cgagactcct ggaaagatgc tttcggtgaa atctgc           46

<210> SEQ ID NO 35
<211> LENGTH: 26
<212> TYPE: DNA
<213> ORGANISM: artificial
<220> FEATURE:
<223> OTHER INFORMATION: primer

<400> SEQUENCE: 35
gattgactga gcagcgcaat acgctg                                 26

<210> SEQ ID NO 36
<211> LENGTH: 26
<212> TYPE: DNA
<213> ORGANISM: artificial
<220> FEATURE:
<223> OTHER INFORMATION: primer

<400> SEQUENCE: 36
ggtgatttca gcctggatgg agtcga                                 26

<210> SEQ ID NO 37
<211> LENGTH: 2109
<212> TYPE: DNA
<213> ORGANISM: artificial
<220> FEATURE:
<223> OTHER INFORMATION: synthetic

<400> SEQUENCE: 37
ctcctgctgg ttacggctga caatttctgc cgctgctgat ggcgtaggcg cgcgcaggtc    60
ggcgacaaaa tcagctatcg tgacgtccgt ttcgtgaccg acggcgctga ccaccggaat   120
gcggctggca aaatcgccc gcgccacgcg ttcgtcgtta aaactccaca aatcttccag    180
cgaaccgccg ccgcgcccga cgatcagtac atcacattcg ccgcgcgcgt tcgccagttc   240
gatagcacga acgatctgcc ccggcgcgtc gtcgccctgg actgcggttg gatagataat   300
```

```
aacgggcagg gatgggtcac gacgctttag cacgtggaga atatcgtgca gcgccgcgcc    360
ggttttcgaa gtgatcaccc caacgcagtg ggccggggag ggcaacggct gtttatgctg    420
ctgatcgaac aagccttcgg cctgcagttt ggcttttagc tgctcatatt tctgctgcaa    480
caagccttcg cccgcgggct gcatactttc ggcgatgatt tgataatcgc cgcgcggctc    540
gtacagcgta atgttggcgc gtaccagcac ctgctgcccg tgctgcgggc ggaacgtcac    600
ccggcgattg ctgttacgga acatcgcaca gcgcacctga gcggtatcgt ctttgagcgt    660
aaagtaccag tggcccgacg caggctgcgt gaaattagaa atctcgccgc tgatccatac    720
ctgtcccatc tcctgttcta acagcagacg aaccgtctgg ttaaggcggc ttacggtaaa    780
aattgaggaa gtttgagagg ataacatgtg agcgggatca aattctaaat cagcaggtta    840
ttcaatcgat agtaacctgc tcacggggga tcgcaagcac tatttgcaaa aaaatgtaga    900
tgcaaccgat tacgttctgt ataatgccgc ggcaatattt attaacctcc caggtgagat    960
attgcccgtg taggctggag ctgcttcgaa gttcctatac tttctagaga ataggaactt   1020
cgaactgcag gtcgacggat ccccggaatg ccgataatcc ttcctgtgtt ttcatgaaca   1080
ggtaaaggtg aatttaaccc tctgttttta cagagggttt ttatttatgt gcattcatga   1140
attttctatg tggcgcacag ttcctgacgg caaatttgac gtaattacga acccacgaag   1200
gttggttgta tcttgccgtg gtcgttgatt tgttctcgtg caaagttatc ggttggtcaa   1260
tgcaaccacg aatgacaaaa gatattgttc tgaatgcgct tctgatggcc gtgtggcgac   1320
gtcatcccca aaaacaggtg ctggttcagt ctgatcaggg tagtcagtac acccgctatg   1380
aatggctgaa attgcacgga ctggagggca gtatgagccg ttgtggcaac tgtcatgaca   1440
atgcggttgc agaaagcttt ttccagctac tgaagcgtga acggataaag aaaaagatct   1500
accaacgact cagaagtgtc caggttatcc gtggcgattc agcccaaata gggggtattt   1560
aaaatatagt aactttattc ttcaactata taaccaacgc ccagctttag cactttcaac   1620
gagcatacca accgttagtg gcttacgcgg atcaggctct ttacttccaa agtactctgg   1680
attcagatag ttgagtatgt caaatccttc tgaatctaca ttccaacgct gaagtactt    1740 ttgtagaagt tcttcactat cttcaaaaac gagtttaaga tcatccctaa tactggtatc   1800
aagcgtgatg attcgctttg gcccacagag aaagtacttt ttagtgttat attcctgatc   1860
gataaaatcg ataatttctt tctcaatatc tctcattaga agtacgtcca cttaatgcga   1920
tctttaggaa ccgccacacg attaaatgta tctttaatat tacgctggat atcataaatc   1980
gtagtgaatg tcataaccca accgagccag ggtacattac gaccaacgaa acgacctaaa   2040
ttattcgttg agcttagctg taatgagttg atagttttgc ctgtcaacgt tggtaatctg   2100
atcccaggt                                                          2109
```

<210> SEQ ID NO 38
<211> LENGTH: 1094
<212> TYPE: DNA
<213> ORGANISM: artificial
<220> FEATURE:
<223> OTHER INFORMATION: synthetic

<400> SEQUENCE: 38

```
agcgtcgtgt agttgtcggt ctgctgctcg gcgaagtcat tcgtaccaac gagctgaaag     60
cggacgaaga acgcgttaaa ggcctgatcg aagagatggc gtctgcttac gaagatccga    120
aagaagtgat tgagttctac agcaaaaaata aagagctgat ggacaatatg cgtaacgtcg    180
ctctggaaga acaggctgtt gaagcggttc tggcaaaagc gaaagtgtct gaaaaagcca    240
```

```
cttccttcaa tgagctgatg aaccagcagg cgtaatttttt cgcgttaaaa gcacgaaatt      300
tgcacaaaaa cccgtcacct ttcagtgacg ggttttttttt gtcacgtatt ttgcatggta      360
agggtgcgaa aaccgcgttt cagtgttagc gttagagcaa aagattgtta tgcttgaatt      420
atggcgatgc cgtacccatt acagagggac tggctgataa tccgtccatc aggttacaat      480
cagtacagca gattttttca attttttatcc aggagacgga aatgtaatgt gtaggctgga      540
gctgcttcga agttcctata ctttctagag aataggaact tcgaactgca ggtcgacgga      600
tccccggaat tgatgccctg gacgcaagtg tgccgctata cacttcatcc ttcacgctac      660
ctcggtgttg gctgccagcg cgcctcccag tgacttactt atgtaagcgc ctgcagagtc      720
gacgagttgc cgccttgatg tagctcgaat gattttgtgt atatactaat gaagggcggc      780
acaacgctga ttagcggctt gcgcctgaga atggcatttg cgtcgtcgtg tgcggcacaa      840
agaacaaaga agaggttttg actcatgaca gataaacgca aagatggctc gggcaaattg      900
ttgtactgct cttttgcgg caaaagccag catgaagtgc gcaagctgat tgccggtcca      960
tccgtgtata tctgcgacga atgcgtcgat ttatgtaacg acattattcg cgaagaaatt     1020
aaagaagttg ctccgcaccg tgaacgtagt gcgctgccga cgccgcatga aattcgtacc     1080
cacctggacg atta                                                        1094

<210> SEQ ID NO 39
<211> LENGTH: 1218
<212> TYPE: DNA
<213> ORGANISM: artificial
<220> FEATURE:
<223> OTHER INFORMATION: synthetic

<400> SEQUENCE: 39
cgaacaagtc gttaatgaga atgataataa ttaccaatat catttgtaaa atgcaataac       60
taatatgaca cttgatcatg tgatgatttt ttgcgtaaaa atcgggaaag atgagagcgt      120
taagcggtga agtttggttt caggcttatt tacgcgcgta tggtcgcaca ggcaaagcgc      180
caggattggg gaactggatt cgcataccag acgcccgtgg attattaatg ataacttcgc      240
aaataaccct tcagacaatg aggtaaacgt accgacagca aggtaacggg aaacgtaggg      300
agtagtattg ataacacgtt gcggggcaat ttaatggtgt ccggcggcag atcgtgttct      360
gtgcagactt tccggcgtta aatcccgtat cacctgcgag cctggactat ctctgtggta      420
tcaactctgt aggaattttg tccccttcgt cttcattagc caatgaaacc ggctttaacg      480
tcaccgttcg aatgttgcga acgaacagct ccttatgcgg aatatcgtca ccgctctgcg      540 attttatag cgcatcagcc acacgattta ttgggtgtag gctggagctg cttcgaagtt      600
cctatacttt ctagagaata ggaacttcga actgcaggtc gacggatccc cggaatcgcc      660
tacggtaata aaaaattccg tgagaaaagt aaaacttagg gggctaccgg aggggaccta      720
atgaacggag gtcatggaag gtattcatcg tgccagactc ttgctcttgt cagaagaagg      780
taaaagtagg ttccgcgacg catttgggtt cacgggcatc ataagagaga tgaacactga      840
taaagtactt tctcctggga taccggaaca gtccaggaaa gagggcagtt acactattgt      900
cgtctggtga tgattactct tcattcatgc ttgccgaacg agttgaagcg atgtaagagg      960
ccgtagctat cgatcccaat aatcccaaaa tttaccaggc ctttattgaa ggctcaaatt     1020
tggctcaatg ggtacgccaa cgccttctgt gatactgtag gggttccaag ttttacatag     1080 tgtctaatttt aatgctattt gtgggttgat aaccccaactc acttcgaact ggtttgtcga     1140
```

```
tttgctgaag ttctcaattt gcctgaaggt taattctacg cgctggatga cagctttgct   1200
gatgcaatgc tgaagcta                                                 1218
```

<210> SEQ ID NO 40
<211> LENGTH: 983
<212> TYPE: DNA
<213> ORGANISM: artificial
<220> FEATURE:
<223> OTHER INFORMATION: synthetic

<400> SEQUENCE: 40

```
ggttgttgtt gatttcgttc agcgcgcctt cagtggtctg cgcaatggag ataccgtcgt    60
tagcgttacg ggaagcctga gtcagacctt tgatgttcgc ggtaaaacgg ttagcaatcg   120
cctgacctgc cgcatcgtct ttcgcgctgt tgatacgcag accggaagac agacgctcga   180
tagcggtgcc cagagcggac tgggatttgt tcaggttatt ctgggtcaac agcgacaggc   240
tgtttgtatt aatgacttgt gccatgatct tttccttatc aattacaact tgatgttatt   300
gggctgttgc ccacggtttc tcaccgtaac ccttgtatcg gcacctgaat tcgaactttc   360
agaaaatttt tcacttcccc cgatcttttt cttaggcggc gaaatagccg ctttatgcat   420
cattattccg cgcattattt ttgcaaaatt atcattaaac tttgcctcca gattgccgat   480
aacgcgctta actactgttt gcaatcaaaa aggaagaagg catggcttca atttcatcat   540
taggtgctag cgctggagct gcttcgaagt tcctatactt tctagagaat aggaacttcg   600
aactgcaggt cgacggatcc gctatgaaca agtcctgata acagaggtca ccatgtacac   660
cgcgagcggt atcaaagctt atgcgcaagt cagcgtggaa agcgccgtga tgagcgccag   720
cccgcatcag ttgattgaaa tgttgtttga tggcgcgaat agcgctctgg tgcgcgctcg   780
cctgttttta gaacaaggcg atgttgtcgc gaaaggtgaa gcgttaagca agccatcaa    840 tattatcgat aacgggctga agccggcct cgatcaggaa aaaggcggtg agattgcgac    900 gaatcttttcc gagctatacg actatatgat tcgccgttta ctgcaggcta atttgcgtaa   960
cgacgctcag gccatcgaag aag                                           983
```

<210> SEQ ID NO 41
<211> LENGTH: 24
<212> TYPE: DNA
<213> ORGANISM: artificial
<220> FEATURE:
<223> OTHER INFORMATION: primer

<400> SEQUENCE: 41

```
actccttgca caaccaaatg cgga                                           24
```

<210> SEQ ID NO 42
<211> LENGTH: 25
<212> TYPE: DNA
<213> ORGANISM: artificial
<220> FEATURE:
<223> OTHER INFORMATION: primer

<400> SEQUENCE: 42

```
tgtcttctgc atttcgccac catca                                          25
```

<210> SEQ ID NO 43
<211> LENGTH: 20
<212> TYPE: DNA
<213> ORGANISM: artificial
<220> FEATURE:
<223> OTHER INFORMATION: primer

<400> SEQUENCE: 43
aacgtttctg cttgccgaac                                           20

<210> SEQ ID NO 44
<211> LENGTH: 40
<212> TYPE: DNA
<213> ORGANISM: artificial
<220> FEATURE:
<223> OTHER INFORMATION: primer

<400> SEQUENCE: 44
gaagcagctc cagcctacac gagtcaaaac ctcttctttg                     40

<210> SEQ ID NO 45
<211> LENGTH: 44
<212> TYPE: DNA
<213> ORGANISM: artificial
<220> FEATURE:
<223> OTHER INFORMATION: primer

<400> SEQUENCE: 45
ggtcgacgga tccccggaat ttaaacattc atacaatcag ttag                44

<210> SEQ ID NO 46
<211> LENGTH: 21
<212> TYPE: DNA
<213> ORGANISM: artificial
<220> FEATURE:
<223> OTHER INFORMATION: primer

<400> SEQUENCE: 46
aatgttcgcc gttgttcaga c                                         21

<210> SEQ ID NO 47
<211> LENGTH: 20
<212> TYPE: DNA
<213> ORGANISM: artificial
<220> FEATURE:
<223> OTHER INFORMATION: primer

<400> SEQUENCE: 47
attaagccag acgtcagcac                                           20

<210> SEQ ID NO 48
<211> LENGTH: 20
<212> TYPE: DNA
<213> ORGANISM: artificial
<220> FEATURE:
<223> OTHER INFORMATION: primer

<400> SEQUENCE: 48
agcacttctt gttcacgctc                                           20

<210> SEQ ID NO 49
<211> LENGTH: 22
<212> TYPE: DNA
<213> ORGANISM: artificial
<220> FEATURE:
<223> OTHER INFORMATION: primer

<400> SEQUENCE: 49
tatgacactt gatcatgtga tg                                        22

<210> SEQ ID NO 50

```
<211> LENGTH: 24
<212> TYPE: DNA
<213> ORGANISM: artificial
<220> FEATURE:
<223> OTHER INFORMATION: primer

<400> SEQUENCE: 50
gaattctcac gcacacgctg cagg                                          24

<210> SEQ ID NO 51
<211> LENGTH: 32
<212> TYPE: DNA
<213> ORGANISM: artificial
<220> FEATURE:
<223> OTHER INFORMATION: primer

<400> SEQUENCE: 51
gctagcacct aatgatgaaa ttgaagccat gc                                 32

<210> SEQ ID NO 52
<211> LENGTH: 34
<212> TYPE: DNA
<213> ORGANISM: artificial
<220> FEATURE:
<223> OTHER INFORMATION: primer

<400> SEQUENCE: 52
ggatccgcta tgaacaagtc ctgataacag aggt                               34

<210> SEQ ID NO 53
<211> LENGTH: 46
<212> TYPE: DNA
<213> ORGANISM: artificial
<220> FEATURE:
<223> OTHER INFORMATION: primer

<400> SEQUENCE: 53
ctcgagttaa cgagactcct ggaaagatgc tttcggtgaa atctgc                  46

<210> SEQ ID NO 54
<211> LENGTH: 33
<212> TYPE: DNA
<213> ORGANISM: artificial
<220> FEATURE:
<223> OTHER INFORMATION: primer

<400> SEQUENCE: 54
gaattcgcta gcgctggagc tgcttcgaag ttc                                33

<210> SEQ ID NO 55
<211> LENGTH: 33
<212> TYPE: DNA
<213> ORGANISM: artificial
<220> FEATURE:
<223> OTHER INFORMATION: primer

<400> SEQUENCE: 55
ctcgagttcc ggggatccgt cgacctgcag ttc                                33

<210> SEQ ID NO 56
<211> LENGTH: 28
<212> TYPE: DNA
<213> ORGANISM: artificial
<220> FEATURE:
<223> OTHER INFORMATION: primer

<400> SEQUENCE: 56
```

-continued ctgaacagac aactcacgca cacgctgc                                                    28

<210> SEQ ID NO 57
<211> LENGTH: 24
<212> TYPE: DNA
<213> ORGANISM: artificial
<220> FEATURE:
<223> OTHER INFORMATION: primer

<400> SEQUENCE: 57
tgactgagca gcgcaatacg ctgc                                                        24

<210> SEQ ID NO 58
<211> LENGTH: 19
<212> TYPE: DNA
<213> ORGANISM: artificial
<220> FEATURE:
<223> OTHER INFORMATION: primer

<400> SEQUENCE: 58
attcccactc aatggtagc                                                              19

<210> SEQ ID NO 59
<211> LENGTH: 19
<212> TYPE: DNA
<213> ORGANISM: artificial
<220> FEATURE:
<223> OTHER INFORMATION: primer

<400> SEQUENCE: 59
attcccactc aatggtagc                                                              19

<210> SEQ ID NO 60
<211> LENGTH: 35
<212> TYPE: DNA
<213> ORGANISM: artificial
<220> FEATURE:
<223> OTHER INFORMATION: primer

<400> SEQUENCE: 60
atatatatgc ggccgctgta ggctggagct gcttc                                            35

<210> SEQ ID NO 61
<211> LENGTH: 31
<212> TYPE: DNA
<213> ORGANISM: artificial
<220> FEATURE:
<223> OTHER INFORMATION: primer

<400> SEQUENCE: 61
ataggcgcgc catatgaata tcctccttag t                                                31

<210> SEQ ID NO 62
<211> LENGTH: 119
<212> TYPE: DNA
<213> ORGANISM: artificial
<220> FEATURE:
<223> OTHER INFORMATION: primer

<400> SEQUENCE: 62
cgaaccgtct ggttaaggcg gcttacggta aaaattgagg aagtttgaga ggataacatg           60
tgagcgggat caaattctaa atcagcaggt tattcaatcg tgtaggctgg agctgcttc          119

<210> SEQ ID NO 63

```
<211> LENGTH: 120
<212> TYPE: DNA
<213> ORGANISM: artificial
<220> FEATURE:
<223> OTHER INFORMATION: primer

<400> SEQUENCE: 63
ttcattgatg atgcggttgg aaacacgacc caggaagtca tacggcaggt gcgcccagtg      60
cgcggtcata aagtcgatgg tttcgacagc acgcagagag catatgaata tcctccttag     120

<210> SEQ ID NO 64
<211> LENGTH: 42
<212> TYPE: DNA
<213> ORGANISM: artificial
<220> FEATURE:
<223> OTHER INFORMATION: primer

<400> SEQUENCE: 64
catatgaagg agtattgccc atgctacgta tcgctaaaga ag                         42

<210> SEQ ID NO 65
<211> LENGTH: 36
<212> TYPE: DNA
<213> ORGANISM: artificial
<220> FEATURE:
<223> OTHER INFORMATION: primer

<400> SEQUENCE: 65
atgcatctgc agtcattccc actcaatggt agccgg                               36

<210> SEQ ID NO 66
<211> LENGTH: 30
<212> TYPE: DNA
<213> ORGANISM: artificial
<220> FEATURE:
<223> OTHER INFORMATION: primer

<400> SEQUENCE: 66
acagataaac gcaaagatgg ctcgggcaaa                                      30

<210> SEQ ID NO 67
<211> LENGTH: 30
<212> TYPE: DNA
<213> ORGANISM: artificial
<220> FEATURE:
<223> OTHER INFORMATION: primer

<400> SEQUENCE: 67
ttattcgcca gaagcctgcg cttccggttt                                      30

<210> SEQ ID NO 68
<211> LENGTH: 30
<212> TYPE: DNA
<213> ORGANISM: artificial
<220> FEATURE:
<223> OTHER INFORMATION: primer

<400> SEQUENCE: 68
cctgagaatg gcatttgcgt cgtcgtgtgc                                      30

<210> SEQ ID NO 69
<211> LENGTH: 30
<212> TYPE: DNA
<213> ORGANISM: artificial
<220> FEATURE:
<223> OTHER INFORMATION: primer
```

<400> SEQUENCE: 69
acggcgtgtt tacaggaaaa acgaaagggg　　　　　　　　　　　　　　　　　30

<210> SEQ ID NO 70
<211> LENGTH: 45
<212> TYPE: DNA
<213> ORGANISM: artificial
<220> FEATURE:
<223> OTHER INFORMATION: primer

<400> SEQUENCE: 70
gcggccgcga aggagtttga ctcatgacag ataaacgcaa agatg　　　　　　　　45

<210> SEQ ID NO 71
<211> LENGTH: 36
<212> TYPE: DNA
<213> ORGANISM: artificial
<220> FEATURE:
<223> OTHER INFORMATION: primer

<400> SEQUENCE: 71
catatgttat tcgccagaag cctgcgcttc cggttt　　　　　　　　　　　　　36

<210> SEQ ID NO 72
<211> LENGTH: 1578
<212> TYPE: DNA
<213> ORGANISM: Salmonella enterica

<400> SEQUENCE: 72

| atgacggaaa acattcataa gcatcgcatc ctcattctgg acttcggttc tcagtacact | 60 |
| caactggttg cgcgccgcgt gcgtgagctg ggtgtttact gcgaactgtg ggcgtgggat | 120 |
| gtgacagaag cacaaattcg tgacttcaac ccaagcggca ttattctttc cggcggcccg | 180 |
| gaaagcacca ccgaagaaaa cagcccgcgc gcgccgcagt atgtctttga agcaggcgtg | 240 |
| ccggtatttg gcgtctgcta cgggatgcag accatggcga tgcagcttgg cggtcatgta | 300 |
| gaaggttcta atgagcgtga atttggttac gcgcaggtcg aagtgctgac cgacagcgcg | 360 |
| ctggttcgcg gtattgaaga ttccctgacc gccgacggca aaccgctgct ggacgtgtgg | 420 |
| atgagccacg gcgataaagt gacggcgatt ccgtccgact tcgtgaccgt agccagcacc | 480 |
| gaaagctgcc cgttcgccat catggctaac gaagaaaaac gcttctacgg cgtacagttc | 540 |
| cacccggaag tgactcacac ccgccagggt atgcgcatgc tggagcgttt tgtgcgtgat | 600 |
| atctgccagt gtgaagccct gtggacgccg gcgaagatca tcgacgacgc cgtggcgcgc | 660 |
| attcgcgagc aggtaggcga cgataaagtg atcctcggtc tctccggcgg cgtggattct | 720 |
| tccgtaaccg caatgctgct gcaccgcgcg atcggtaaaa atctgacctg tgtattcgtc | 780 |
| gacaacggcc tgctgcgtct caacgaagcc gagcaggtga tggacatgtt tggcgaccat | 840 |
| tttggtctga acatcgttca cgtaccggca gaagatcgct tcctgtccgc gttggctggc | 900 |
| gaaaacgatc cggaagcgaa gcgtaagatc attggccgtg tttttgtgga agtgttcgac | 960 |
| gaagaagcgt tgaaactgga agacgtgaaa tggctggcgc agggcaccat ctaccctgac | 1020 |
| gtcatcgaat ctgcggcgtc tgcaaccggt aaagcgcacg tcatcaaatc tcaccacaat | 1080 |
| gttggcggcc tgccgaaaga gatgaagatg gggctggttg aaccgctgaa agagctgttc | 1140 |
| aaagacgaag tgcgtaagat tggtctggag ctgggcctgc cgtacgacat gctgtaccgt | 1200 |
| catccgttcc cggggccggg cctcggcgta cgtgtactgg gtgaagtgaa gaaagagtac | 1260 |

| | |
|---|---|
| tgcgacctgc tgcgccgtgc tgatgccatc ttcattgaag agctgcgtaa ggcggatctg | 1320 |
| tacgacaaag tcagccaggc gttcaccgtc ttcctgccag tacgctccgt tggcgtaatg | 1380 |
| ggcgatggtc gtaagtacga ttgggtggtc tctctgcgtg ctgtcgaaac catcgacttt | 1440 |
| atgaccgcgc actgggcgca cctgccgtat gacttcctgg gtcgtgtttc caaccgcatc | 1500 |
| atcaatgaag tcaacgggat ttcccgtgtg gtgtatgaca tcagcggtaa accaccggct | 1560 |
| accattgagt gggaataa | 1578 |

<210> SEQ ID NO 73
<211> LENGTH: 1578
<212> TYPE: DNA
<213> ORGANISM: Salmonella enterica

<400> SEQUENCE: 73

| | |
|---|---|
| atgacggaaa acattcataa gcatcgcatc ctcattctgg acttcggttc tcagtacact | 60 |
| caactggttg cgcgccgcgt gcgtgagctg ggtgtttact gcgaactgtg ggcgtgggat | 120 |
| gtgacagaag cacaaattcg tgacttcaac ccaagcggca ttattctttc cggcggcccg | 180 |
| gaaagcacca ccgaagaaaa cagcccgcgc gcgccgcagt atgtctttga agcaggcgtg | 240 |
| ccggtatttg gcgtttgcta tggtatgcag accatggcga tgcagcttgg cggtcatgta | 300 |
| gaaggttcta atgagcgtga atttggttat gcgcaggtcg aagtgttgac cgacagcgcg | 360 |
| ctggttcgcg gtattgaaga ttccctgacc gcagacggca aaccgctgct ggacgtgtgg | 420 |
| atgagccacg gcgataaagt gacggcgatt ccgtccgact tcgtgaccgt cgccagcacc | 480 |
| gagagctgcc cgttcgccat catggctaac gaagaaaaac gcttctacgg cgtacagttc | 540 |
| cacccggaag tgacccacac ccgccagggg atgcgcatgc tggagcgttt tgtgcgtgat | 600 |
| atctgccagt gtgaagcgtt gtggacgccg gcgaagatca tcgacgacgc cgtggcgcgc | 660 |
| attcgcgagc aggtaggcga cgataaagtg atcctcggtc tctccggcgg cgtggattct | 720 |
| tccgtcaccg caatgctgct gcaccgcgcg atcggtaaaa atctgacctg tgtattcgtc | 780 |
| gacaacggcc tgctgcgtct caacgaagcc gagcaggtga tggacatgtt tggcgaccat | 840 |
| tttggcctga atatcgttca cgttccggcg gaagagcgct tcctgtccgc gttggctggc | 900 |
| gaaaacgatc cggaagcgaa gcgtaagatc attggccgtg ttttttgtgga agtgttcgac | 960 |
| gaagaagcgt tgaaactgga agacgtgaaa tggctggcgc agggcaccat ctaccctgac | 1020 |
| gtcatcgagt ctgcggcgtc tgcaaccggt aaagcgcacg tcatcaaatc tcaccacaat | 1080 |
| gttggcggcc tgccgaaaga gatgaagatg gggctggttg aaccgctgaa agagctgttc | 1140 |
| aaagacgaag tgcgtaagat tggtctggag ctgggcctgc cgtacgacat gctgtaccgt | 1200 |
| catccgttcc cggggccggg cctcggcgta cgtgtactgg gtgaagtgaa gaaagagtac | 1260 |
| tgcgacctgt tgcgccgtgc tgacgccatc ttcattgaag agctgcgtaa ggcggatctg | 1320 |
| tacgacaaag tcagccaggc gttcaccgtc ttcctgccag tacgctccgt tggcgtaatg | 1380 |
| ggcgatggtc gtaagtacga ttgggtggtc tccctgcgtg ctgtcgaaac catcgacttt | 1440 |
| atgactgcgc actgggcgca tctgccgtat gacttcctgg gtcgtgtttc caaccgcatc | 1500 |
| atcaatgaag tcaacgggat ttcccgtgtg gtgtatgaca tcagcggtaa accaccggct | 1560 |
| accattgagt gggaataa | 1578 |

<210> SEQ ID NO 74
<211> LENGTH: 1578
<212> TYPE: DNA
<213> ORGANISM: Salmonella enterica

<400> SEQUENCE: 74

| | | | | | |
|---|---|---|---|---|---|
| atgacggaaa | acattcataa | gcatcgcatc | ctcattctgg | acttcggttc | tcagtacact | 60
| caactggttg | cgcgccgcgt | gcgtgagctg | ggtgtttact | gcgaactgtg | ggcgtgggat | 120
| gtgacagaag | cacaaattcg | tgacttcaac | ccaagcggca | ttattctttc | cggcggcccg | 180
| gaaagcacca | ccgaagaaaa | cagcccgcgc | gcgccgcagt | atgtctttga | agcaggcgtg | 240
| ccggtatttg | cgtttgcta | tggtatgcag | accatggcga | tgcagcttgg | cggtcatgta | 300
| gaaggttcta | atgagcgtga | atttggttat | gcgcaggtcg | aagtgttgac | cgacagcgcg | 360
| ctggttcgcg | gtattgaaga | ttccctgact | gcagacggca | aaccgctgct | ggacgtgtgg | 420
| atgagccacg | gcgataaagt | gacggcgatt | ccgtccgact | tcgtgaccgt | cgccagcacc | 480
| gagagctgcc | cgttcgccat | tatggccaac | gaagaaaaac | gcttctacgg | tgtacagttc | 540
| cacccggaag | tgactcacac | ccgccagggt | atgcgcatgc | tggagcgttt | tgtacgcgat | 600
| atctgccagt | gtgaagccct | gtggacgccg | gcgaagatca | tcgacgacgc | cgtggcgcgc | 660
| attcgcgagc | aggtgggcga | cgacaaagtg | atcctcggtc | tctccggcgg | cgtggattct | 720
| tccgtcaccg | cgatgctgct | gcaccgcgcc | atcggtaaaa | atctgacctg | tgttttcgtc | 780
| gacaacggcc | tgttgcgcct | gaacgaagcc | gagcaggtga | tggacatgtt | tggcgaccat | 840
| tttggcctga | atatcgttca | cgtaccggca | gaagagcgct | tcctgtccgc | gctggctggc | 900
| gagaacgatc | cggaagccaa | gcgtaagatc | atcggtcgtg | tttttgtaga | agtgttcgac | 960
| gaagaagcgc | tcaaactgga | agacgtgaag | tggctggcgc | aaggcaccat | ttaccctgac | 1020
| gttatcgaat | ctgcggcgtc | tgcaaccggt | aaagcgcacg | tcatcaaatc | tcaccacaat | 1080
| gtcggcggct | tgccgaaaga | gatgaagatg | gggctggttg | aaccgctgaa | agagctgttc | 1140
| aaagacgaag | tgcgtaagat | tggtctggag | ctgggcctgc | cgtatgacat | gctgtatcgc | 1200
| catccgttcc | cgggggccggg | cctcggcgtt | cgtgttctgg | gtgaagtgaa | gaaagagtac | 1260
| tgcgacctgc | tgcgccgtgc | tgacgctatc | ttcattgaag | agctgcgcaa | agcggatctg | 1320
| tacgacaaag | tcagtcaggc | gtttaccgtc | ttcctgccgg | ttcgttccgt | tggcgttatg | 1380
| ggcgatggtc | gtaagtatga | ctgggttgtc | tctctgcgtg | ccgtcgaaac | catcgacttt | 1440
| atgaccgcac | actgggcgca | cctgccgtat | gacttcctcg | gtcgcgtttc | caaccgcatc | 1500
| atcaatgaag | tcaacgggat | tccccgtgtg | gtgtatgaca | tcagcggtaa | accgccggct | 1560
| accattgagt | gggaataa | | | | | 1578

<210> SEQ ID NO 75
<211> LENGTH: 1578
<212> TYPE: DNA
<213> ORGANISM: Salmonella enterica

<400> SEQUENCE: 75

| | | | | | |
|---|---|---|---|---|---|
| atgacggaaa | acattcataa | gcatcgcatc | ctcattctgg | acttcggttc | tcagtacact | 60
| caactggttg | cgcgccgcgt | gcgtgagctg | ggtgtttact | gcgaactgtg | ggcgtgggat | 120
| gtgacagaag | cacaaattcg | tgacttcaac | ccaagcggca | ttattctttc | cggcggcccg | 180
| gaaagcacca | ccgaagaaaa | cagcccgcgc | gcgccgcagt | atgtctttga | agcaggcgtg | 240
| ccggtatttg | cgtttgcta | tgggatgcag | accatggcga | tgcagcttgg | cggtcatgta | 300
| gaaggttcta | atgagcgtga | atttggttat | gcgcaggttg | aagtgttgac | cgacagcgcg | 360
| ctggttcgcg | gtattgaaga | ttccctgacc | gcagacggca | aaccgctgct | ggacgtgtgg | 420

```
atgagccacg gcgataaagt gacggcgatt ccgtccgact tcgtgaccgt cgccagcacc      480
gagagctgcc cgttcgccat tatgccaac gaagaaaaac gcttctacgg tgtacagttc       540 caccggaag tgacccacac ccgccagggt atgcgcatgc tggagcgttt tgtgcgtgat       600
atctgccagt gtgaagcgct gtggacgccg gcgaagatca tcgacgacgc cgtggcgcgc      660
attcgcgagc aggtaggcga cgataaagtg atcctcggtc tctccggcgg cgtggattct      720
tccgtcaccg cgatgctgct gcaccgcgcg atcggtaaaa atctgacctg tgtattcgtc      780
gacaacggcc tgctgcgtct caacgaagcc gagcaggtga tggacatgtt tggcgaccat      840
tttggcctga atatcgttca cgttccggcg gaagagcgct tcctgtccgc gttggctggc      900
gaaaacgatc cagaagccaa gcgtaagatc attggccgtg tttttgtgga agtgttcgac      960
gaagaagcgc tgaaactgga agacgtgaaa tggctggcgc agggcaccat ctaccctgac     1020
gttatcgaat ctgcggcgtc tgcaaccggt aaagcgcacg tcatcaaatc tcaccacaat     1080
gtcggcggcc tgccgaaaga gatgaagatg ggtctggttg aaccgctgaa agagctgttc     1140
aaagacgaag tgcgtaagat tggtctggag ctggccctgc cgtacgacat gctgtatcgc     1200
catccgttcc cggggccggg cctcggcgtg cgcgtactgg gcgaagtgaa gaaagagtac     1260
tgcgacctgc tgcgtcgcgc ggacgctatc ttcattgaag agctgcgcaa gcggatctg      1320 tacgacaaag tcagtcaggc gtttactgtc ttcctgccgg tccgttccgt tggcgtcatg     1380
ggcgatggtc gtaagtatga ctgggttgtc tctctgcgtg ccgtcgaaac catcgacttt     1440
atgaccgcac actgggcgca cctgccgtat gacttcctcg gtcgtgttc caaccgcatc      1500 atcaatgaag tcaacgggat ttcccgtgtg gtgtatgaca tcagcggtaa accaccggct     1560
accattgagt gggaatga                                                   1578

<210> SEQ ID NO 76
<211> LENGTH: 1473
<212> TYPE: DNA
<213> ORGANISM: Salmonella enterica

<400> SEQUENCE: 76
ttgcccatgc tacgtatcgc taaagaagcc ctgacgtttg acgacgtcct ccttgttccc       60
gctcactcca ccgttttgcc gaatactgct gatctcagca cgcagttgac gaaaactatt      120
cgtctgaata ttcctatgct ttctgcggcg atggacaccg tgacggaagc gcgcctggca      180
attgccctgg cccaggaagg cggcatcggt tttatccaca aaaacatgtc tattgagcgc      240
caggcggaag aagttcgccg cgtgaagaaa cacgagtccg cgtagtgac cgacccgcag       300 accgtcctgc caaccaccac gttgcatgaa gtgaaagccc tgaccgagcg taacggtttt      360
gcgggctatc cggtggtgac tgaagataac gagctggtgg gtatcatcac cggtcgtgac      420
gtgcgttttg tgactgacct gaaccagccg gtgagtgttt acatgacgcc gaaagagcgt      480
ctggtgaccg ttcgtgaagg cgaagcccgt gaagtcgtgc tggcaaaaat gcacgaaaaa      540
cgcgtagaaa aagcgctggt cgttgatgat aacttccatc tgcttggcat gattaccgta      600
aaagatttcc agaaagcgga acgtaaacca aactcctgta agatgagca gggccgttta      660 cgtgtcggcg cggcggtcgg cgcaggcgcg ggcaacgaag agcgcgttga cgcgctggtg      720
gcggcaggcg ttgacgtcct gctgatcgac tcttctcacg gtcactctga aggcgtgttg      780
caacgtatcc gtgaaacccg tgctaaatat cctgacctgc aaatcatcgg cggcaacgtc      840
gcgacgggcg caggcgctcg cgcactggcg gaagccggtt gcagcgcggt gaaagtcggt      900
atcggcccgg gttccatctg taccactcgt atcgtgactg gcgtgggcgt tccgcagatt      960
```

```
accgctgttt ctgacgcagt tgaagcgctg gaaggcaccg ggattccggt tatcgctgac    1020
ggcggtatcc gtttctccgg cgacatcgcc aaagccatcg ccgcaggcgc gagcgctgtc    1080
atggtcggtt ctatgctggc gggtaccgaa gaatccccgg gcgaaatcga actctaccag    1140
ggccgttctt acaaatctta ccgcggcatg ggctcgctgg gcgcgatgtc caaaggttcc    1200
tctgaccgtt acttccagag cgacaacgcc gccgacaaac tggtgccgga aggtatcgaa    1260
ggccgcgtag cctataaagg tcgcctgaaa gagatcattc accagcagat gggcggcctg    1320
cgctcctgta tggggctgac cggttgtgct accatcgacg aactgcgtac taaagcggag    1380
tttgtgcgta tcagcggtgc gggtatccag gaaagccacg ttcacgacgt gaccatcacc    1440
aaagagtccc cgaactaccg tctgggctcc tga                                 1473
```

<210> SEQ ID NO 77
<211> LENGTH: 1467
<212> TYPE: DNA
<213> ORGANISM: Salmonella enterica

<400> SEQUENCE: 77

```
atgctacgta tcgctaaaga agccctgacg tttgacgacg tcctccttgt tcccgctcac      60
tccaccgttt tgccgaatac tgccgatctc agcacgcagt tgacgaaaac tattcgtctg     120
aatattccta tgctttctgc ggcgatggac accgtgacgg aagcgcgcct ggcaattgcc     180
ctggcccagg aaggcggcat tggttttatc acaaaaaaca tgtccattga cgccaggcg      240 gaagaagttc gccgcgtgaa gaaacacgag tccggcgtag tgaccgaccc gcagaccgtc     300
ctgccaacca ccacgttgca tgaagtgaaa gccctgaccg agcgtaacgg ttttgcgggc     360
tatccggtgg tgactgaaga taacgagctg gtggggatca tcaccggtcg tgacgtgcgt     420
tttgtgactg acctgaacca gccggtaagt gtctacatga cgccgaaaga gcgtctggtg     480
accgttcgtg aaggcgaagc ccgtgaagtc gtgctggcaa aaatgcacga aaaacgcgta     540
gaaaaagcgc tggtcgttga tgataacttc catctgcttg gcatgattac cgtaaaagat     600
ttccagaaag cggaacgtaa accaaactcc tgtaaagatg agcagggccg tttacgtgtc     660
ggcgcggcgg tcggcgcagg cgcgggcaac gaagagcgcg ttgacgcgct ggtggcggca     720
ggcgttgacg tactgctgat cgactcctct cacggtcact ctgaaggcgt gttgcaacgt     780
atccgtgaga cgcgtgctaa atatcctgac ctgcaaatca tcggcggcaa cgttgcgacg     840
ggcgcaggcg ctcgcgcact ggcggaagcc ggttgcagcg cggtgaaagt gggtatcggc     900
ccgggctcca tctgtaccac tcgtatcgtg actggtgtgg cgttccgca gatcaccgct     960 gtttccgacg cggtagaagc gctggaaggc accggaattc cggttatcgc tgacggcggt    1020
atccgtttct ccggcgacat cgccaaagcc atcgccgcag cgcgagcgc cgtgatggtg    1080 ggctctatgc tggccggtac cgaagaatcc ccgggcgaaa tcgaactcta ccagggccgt    1140
tcgtacaaat cttaccgcgg catgggctcg ctgggcgcga tgtccaaagg ttcctccgac    1200
cgttacttcc agagcgacaa cgccgctgac aaactggtgc cggaaggtat cgaaggccgc    1260
gtagcctata aggtcgcct gaaagagatc attcaccagc agatgggcgg cctgcgctcc    1320
tgtatggggc tgaccggttg tgctaccatc gacgaactgc gtactaaagc ggagtttgtg    1380
cgtatcagcg gtgcgggtat ccaggaaagc cacgttcacg acgtgaccat caccaaagag    1440
tccccgaact accgtctggg ctcctga                                        1467
```

<210> SEQ ID NO 78

<211> LENGTH: 1551
<212> TYPE: DNA
<213> ORGANISM: Salmonella enterica

<400> SEQUENCE: 78

```
ttgcaaaaaa atgtagatgc aaccgattac gttctgtata atgccgcggc aatatttatt      60
aacctcccag gtgagatatt gcccatgcta cgtatcgcta agaagccct gacgtttgac      120
gacgtcctcc ttgttcccgc tcactccacc gttttgccga atactgccga tctcagcacg     180
cagttgacga aaactattcg tctgaatatt cctatgcttt ctgcggcgat ggacaccgtg     240
acggaagcgc gcctggcaat tgccctggcc caggaaggcg gcattggttt tatccacaaa     300
aacatgtcca ttgagcgcca ggcggaagaa gttcgccgcg tgaagaaaca cgagtccggc     360
gtagtgaccg acccgcagac cgtcctgcca accaccacgt tgcatgaagt gaaagccctg     420
accgagcgta acggttttgc gggctatccg gtggtgactg aagataacga gctggtgggt     480
atcatcaccg tcgtgacgt gcgttttgtg actgacctga accagccggt gagtgtctac     540
atgacgccga aagagcgtct ggtgaccgtt cgtgaaggcg aagcccgtga agtcgtgctg     600
gcaaaaatgc acgaaaaacg cgtagaaaaa gcgctggtcg ttgatgataa cttccatctg     660
cttggcatga ttaccgtaaa agatttccag aaagcggaac gtaaaccaaa ctcctgcaaa     720
gatgagcagg gccgtttacg tgtcggcgcg gcggtcggcg caggcgcggg caacgaagag     780
cgcgttgacg cgctggtggc ggcaggcgtt gacgtactgc tgatcgactc ctctcacggt     840
cactctgaag gcgtgttgca acgtatccgt gagacgcgtg ctaaatatcc tgacctgcaa     900
atcatcggcg gcaacgttgc gacgggcgca ggcgctcgcg cactggcgga agccggttgc     960
agcgcggtga agtgggtat cggcccgggc tccatctgta ccactcgtat cgtgactggt     1020
gtgggcgttc cgcagatcac cgctgtttcc gacgcggtag aagcgctgga aggcaccgga     1080
attccggtta tcgctgacgg cggtatccgt ttctccggcg acatcgccaa agccatcgcc     1140
gcaggcgcga cgccgtgat ggtgggctct atgctggccg gtaccgaaga atccccgggc     1200
gaaatcgaac tctaccaggg ccgttcgtac aaatcttacc gcggcatggg ctcgctgggc     1260
gcgatgtcca aaggttcctc cgaccgttac ttccagagcg acaacgccgc tgacaaactg     1320
gtgccggaag gtatcgaagg ccgcgtagcc tataaaggtc gcctgaaaga gatcattcac     1380
cagcagatgg gcgcctgcg ctcctgtatg gggctgaccg gttgtgctac catcgacgaa     1440
ctgcgtacta agcggagtt tgtgcgtatc agcggtgcgg gtatccagga aagccacgtt     1500
cacgacgtga ccatcaccaa agagtccccg aactaccgtc tgggctcctg a            1551
```

<210> SEQ ID NO 79
<211> LENGTH: 624
<212> TYPE: DNA
<213> ORGANISM: Salmonella enterica

<400> SEQUENCE: 79

```
atgtcataca gcggagaacg agataatttg gccctcata tggcgctggt gccgatggtc       60
attgaacaga cctcacgcgg tgagcgctct tttgatatct attctcgtct acttaaggaa     120
cgcgtcatat ttctgaccgg ccaggtcgaa gaccatatgg ctaacctgat cgtggcgcag     180
atgctgttcc tggaagcgga aaacccggaa aaagatatct atctgtacat taattctcct     240
ggcggcgtaa ttactgcggg gatgtccatc tatgacacca tgcagtttat taagccagac     300
gtcagcacca tttgtatggg acaggcggcc tctatgggg cgtttctgct gactgccggg     360
gcgaaaggca aacgtttctg cttgccgaac tctcgcgtca tgatccacca gccgctgggc     420
```

```
ggctatcagg gccaggcgac ggatattgaa attcacgccc gcgaaatttt gaaagtaaaa    480
gggcgcatga atgaacttat ggcgcatcat acgggtcaat ctcttgagca gattgaacgt    540
gatactgagc gcgatcgctt cctctccgcg cctgaagcgg tagagtacgg tttggttgac    600 tcaatttttga cccatcgtaa ttga                                           624
```

<210> SEQ ID NO 80
<211> LENGTH: 624
<212> TYPE: DNA
<213> ORGANISM: Salmonella enterica

<400> SEQUENCE: 80

```
atgtcataca gcggagaacg agataatttg gcccctcata tggcgctggt gccgatggtc     60
attgaacaga cctcacgcgg tgagcgctct tttgatatct attctcgtct acttaaggaa    120
cgcgtcatat ttctgaccgg ccaggtcgaa gaccatatgg ctaacctgat cgtggcgcag    180
atgctgttcc tggaagcgga aaacccggaa aagatatct atctgtacat taattctcct     240
ggcggcgtaa ttactgcggg gatctccatc tatgacacca tgcagtttat taagccagac    300
gtcagcacca tttgtatggg acaggcggcc tctatggggg cgtttctgct gactgccggg    360
gcgaaaggca aacgtttctg cttgccgaac tctcgcgtca tgatccacca gccgctgggc    420
ggctaccagg gccaggcgac ggatattgaa attcacgccc gcgaaatttt gaaagtaaaa    480
gggcgcatga atgaacttat ggcgcatcat acgggtcaat ctcttgagca gattgaacgt    540
gatactgagc gcgatcgctt cctctccgcg cctgaagcgg tagagtacgg tttggttgac    600 tcaatttttga cccatcgtaa ttga                                           624
```

<210> SEQ ID NO 81
<211> LENGTH: 732
<212> TYPE: DNA
<213> ORGANISM: Salmonella enterica

<400> SEQUENCE: 81

```
ttgaattatg gcgatgccgt acccattaca gagggactgg ctgataatcc gtccatcagg     60
ttacaatcag tacagcaggt tttttcaatt tttatccagg agacggaaat gtcatacagc    120
ggagaacgag ataatttggc ccctcatatg gcgctggtgc cgatggtcat tgaacagacc    180
tcacgcggtg agcgctcttt tgatatctat tctcgtctac ttaaggaacg cgtcatattt    240
ctgaccggcc aggtcgaaga ccatatggct aacctgatcg tggcgcagat gctgttcctg    300
gaagcggaaa acccggaaaa agatatctat ctgtacatta attctcctgg cggcgtaatt    360
actgcgggga tgtccatcta tgacaccatg cagtttatta gccagacgt cagcaccatt     420 tgtatgggac aggcggcctc tatggggcg tttctgctga ctgccgggc gaaaggcaaa     480 cgtttctgct tgccgaactc tcgcgtcatg atccaccagc cgctgggcgg ctaccagggc    540
caggcgacgg atattgaaat tcacgcccgc gaaattttga agtaaaagg gcgcatgaat    600 gaacttatgg cgcatcatac gggtcaatct cttgagcaga ttgaacgtga tactgagcgc    660
gatcgcttcc tctccgcgcc tgaagcggta gagtacggtt tggttgactc aatttttgacc   720 catcgtaatt ga                                                         732
```

<210> SEQ ID NO 82
<211> LENGTH: 624
<212> TYPE: DNA
<213> ORGANISM: Salmonella enterica

<400> SEQUENCE: 82

```
atgtcataca gcggagaacg agataatttg gcccctcata tggcgctggt gccgatggtc        60
attgaacaga cctcacgcgg tgagcgctct tttgatatct attctcgtct acttaaggaa       120
cgcgtcatat ttctgaccgg ccaggtcgaa gaccatatgg ctaacctaat cgtggcgcag       180
atgctgttcc tggaagcgga aaacccggaa aaagatatct atctgtacat taattctcct       240
ggcggcgtaa ttactgcggg gatgtccatc tatgacacca tgcagtttat taagccagac       300
gttagcacca tttgtatggg acaggcggcc tctatggggg cgtttctgct gactgccggg       360
gcgaaaggca aacgtttctg cttgccgaac tctcgcgtca tgatccacca gccgctgggc       420
ggctaccagg gccaggcgac ggatattgaa attcacgccc gcgaaatttt gaaagtaaaa       480
gggcgcatga atgaacttat ggcgcatcat acgggtcaat ctcttgagca gattgaacgt       540
gatactgagc gcgatcgctt cctctccgcg cctgaagcgg tagagtacgg tttggttgac       600
tcaatttga cccatcgtaa ttga                                               624
```

<210> SEQ ID NO 83
<211> LENGTH: 1272
<212> TYPE: DNA
<213> ORGANISM: Salmonella enterica

<400> SEQUENCE: 83

```
atgacagata aacgcaaaga tggctcgggc aaattgttgt actgctcttt ttgcggcaaa        60
agccagcatg aagtgcgcaa gctgattgcc ggtccatccg tgtatatctg cgacgaatgc       120
gtcgatttat gtaacgacat tattcgcgaa gaaattaaag aagttgctcc gcaccgtgaa       180
cgtagtgcgc tgccgacgcc gcatgaaatt cgtactcacc tggacgatta cgttatcggc       240
caggagcagg cgaaaaaagt gctggcggtg gcggtctata accactacaa gcgtctgcgt       300
aacggcgata ccagcaatgg cgtcgagtta ggcaaaagca acattctgct gactggaccg       360
accggttccg gtaaaacgct gctggcggaa acgctggcgc gcttgctgga tgtgccgttc       420
actatggcgg atgcgaccac gctgaccgaa gcgggttacg tgggggaaga cgtcgagaat       480
atcattcaga aactgttgca gaaatgcgac tacgacgtgc aaaaagcgca gcgtgggatt       540
gtctacattg atgaaatcga taagatttcg cgtaaatcag acaatccgtc cattacccgc       600
gatgtttccg gcgaaggcgt acagcaggcg ttgctgaaac tgatcgaagg caccgtcgcc       660
gcggttccac cgcagggcgg tcgcaaacat ccgcagcagg agttcttaca ggtagatacc       720
tctaagattc tgtttatctg cggcggcgcg tttgccggtc tggataaagt gatcgctaac       780
cgtgttgaaa ccggctccgg cattggtttt ggcgcgacgt gaaagcgaa gtccgacaaa       840
gccagtgaag gcgagctgtt gtcgcaggtt gaaccggaag attgatcaa atttggtctg       900
attcctgagt ttatcggtcg tctgccagtg gtggcgacgc tgaacgaact cagcgaagaa       960
gcgctggttc aaatcctgaa agagccgaaa aatgcgctga ccaagcagta tcaggcgctg      1020
tttaacctgg aaggcgtcga tctggaattc cgtgacgaag cgctgaacgc tatcgccagg      1080
aaagcgatgg cgcgtaaaac tggtgcccgt ggcctgcgtt ctatcgtcga agcggcgctg      1140
ctggatacca tgtacgattt gccatctatg gaagacgtcg aaaaagtggt gattgacgag      1200
tccgttattg ccggtcagag taagccgttg ctgatttacg gcaaaccgga agcgcaggct      1260
tctggcgaat aa                                                         1272
```

<210> SEQ ID NO 84
<211> LENGTH: 1272

```
<212> TYPE: DNA
<213> ORGANISM: Salmonella enterica

<400> SEQUENCE: 84
atgacagata acgcaaaga tggctcgggc aaattgttgt actgctcttt ttgcggcaaa      60
agccagcatg aagtgcgcaa gctgattgcc ggtccatccg tgtatatctg cgacgaatgc    120
gtcgatttat gtaacgacat tattcgcgaa gaaattaaag aagttgctcc gcaccgtgaa    180
cgtagtgcgc tgccgacgcc gcatgaaatt cgtacccacc tggacgatta cgttatcggc    240
caggagcagg cgaaaaaagt gctggcggtg gcggtctata accactacaa gcgtctgcgt    300
aacggtgata ccagcaatgg cgtcgagtta ggcaaaagca acattctgct gattggaccg    360
accggttccg gtaaaacgct gctggcggaa acgctggcgc gcttgctgga tgtgccgttc    420
actatggcgg atgcgaccac gctgaccgaa gcgggttacg tgggtgaaga cgtcgagaat    480
atcattcaga actgttgcga gaaatgcgac tacgacgtgc aaaaagcgca gcgtgggatt    540
gtctacattg atgaaatcga taagatttcg cgtaaatcag acaatccgtc cattacccgc    600
gatgtttccg gcgaaggcgt acagcaggcg ttgctgaaac tgatcgaagg caccgtcgcc    660
gcggttccac cgcagggcgg tcgcaaacat ccgcagcagg agttcttaca ggtagatacc    720
tctaagattc tgtttatctg cggcggcgcg tttgctggtc tggataaagt gatcgctaac    780
cgtgttgaaa ccggctccgg cattggtttt ggcgcgacgg tgaaagcgaa gtccgacaaa    840
gccagcgaag gcgagctgtt gtcgcaggtt gaaccggaag atttgatcaa atttggtctg    900
attcctgagt ttatcggtcg tctgccagtg gtggcgacgc tgaacgaact cagcgaagaa    960
gcgctgattc aaatcctgaa agagccgaaa aatgcgctga ccaagcagta tcaggcgctg   1020
tttaacctgg aaggcgtcga tctggaattc cgtgacgaag cgctggacgc tatcgccagg   1080
aaagcaatgg cgcgtaaaac cggtgcccgt ggtctgcgtt ctatcgtcga agcggcgctg   1140
ctggatacca tgtacgattt gccatctatg gaagacgtcg aaaaagtggt gatcgacgag   1200
tccgttattg ccggtcagag taagccgttg ctgatttacg gcaaaccgga agcgcaggct   1260
tctggcgaat aa                                                      1272

<210> SEQ ID NO 85
<211> LENGTH: 1272
<212> TYPE: DNA
<213> ORGANISM: Salmonella enterica

<400> SEQUENCE: 85
atgacagata acgcaaaga tggctcgggc aaattgttgt actgctcttt ttgcggcaaa      60
agccagcatg aagtgcgcaa gctgattgcc ggtccatccg tgtatatctg cgacgaatgc    120
gtcgatttat gtaacgacat tattcgcgaa gaaattaaag aagttgctcc gcaccgtgaa    180
cgtagtgcgc tgccgacgcc gcatgaaatt cgtacccacc tggacgatta cgttatcggc    240
caggagcagg cgaaaaaagt gctggcggtg gcggtctata accactacaa gcgtctgcgt    300
aacggcgata ccagcaatgg cgtcgagtta ggcaaaagca acattctgct gattggaccg    360
accggttccg gtaaaacgct gctggcggaa acgctggcgc gcttgctgga tgtgccgttc    420
actatggcgg atgcgaccac gctaaccgaa gcgggttacg ttggtgaaga cgtcgagaat    480
atcattcaga actgttgcga gaaatgcgac tacgacgtgc aaaaagcgca gcgtgggatt    540
gtctacattg atgaaatcga taagatttcg cgtaaatcag acaatccgtc cattacccgc    600
gatgtttccg gcgaaggcgt acagcaggcg ttgctgaaac tgatcgaagg caccgtcgcc    660
```

```
gcggttccac cgcagggcgg tcgcaaacat ccgcagcagg agttcttaca ggtagatacc    720
tctaagattc tgtttatctg cggcggcgcg tttgccggtc tggataaagt gatcgctaac    780
cgtgttgaaa ccggctccgg cattggtttt ggcgcgacgg tgaaagcgaa gtccgacaaa    840
gccagcgaag gcgagctgtt gtcgcaggtt gaaccggaag atttgatcaa atttggtctg    900
attcctgagt ttatcggtcg tctgccagtg gtagcgacgc tgaatgaact cagcgaagaa    960
gcgctgattc aaatcctgaa agagccgaaa aatgcgctga ccaagcagta tcaggcgctg   1020
tttaacctgg aaggcgtcga tctggaattc cgtgacgaag cgctggacgc tatcgccagg   1080
aaagcaatgg cgcgtaaaac cggcgcccgt ggcctgcgtt ctatcgtcga agcggcgctg   1140
ctggatacca tgtacgattt gccatctatg gaagacgtcg aaaaagtggt gatcgacgag   1200
tccgttattg ccggtcagag taagccgttg ctgatttacg gcaaaccgga agcgcaggct   1260
tctggcgaat aa                                                       1272
```

<210> SEQ ID NO 86
<211> LENGTH: 1272
<212> TYPE: DNA
<213> ORGANISM: Salmonella enterica

<400> SEQUENCE: 86

```
atgacagata aacgcaaaga tggctcgggc aaattgttgt actgctcttt ttgcggcaaa     60
agccagcatg aagtgcgcaa gctgattgcc ggtccatccg tgtatatctg cgacgaatgc    120
gtcgatttat gtaacgacat tattcgcgaa gaaattaaag aagttgctcc gcaccgtgaa    180
cgtagtgcgc tgccgacgcc gcatgaaatt cgtacccacc tggacgatta cgttatcggc    240
caggagcagg cgaaaaaagt gctggcggtg gcggtctata ccactacaa gcgtctgcgt    300 aacggcgata ccagcaatgg cgtcgagtta ggcaaaagca acattctgct gattggaccg    360
accggttccg gtaaaacgct gctggcggaa acgctggcgc gcttgctgga tgtgccgttc    420 actatgcgg atgcgaccac gctaactgaa gcgggttacg ttggtgaaga cgtcgagaat    480
atcattcaga aactgttgca gaaatgcgac tacgacgtgc aaaaagcgca gcgtgggatt    540
gtctacattg atgaaatcga taagatttcg cgtaaatcag acaatccgtc cattacccgc    600
gatgtttccg gcgaaggcgt acagcaggcg ttgctgaaac tgatcgaagg caccgtcgcc    660
gcggttccac cgcagggcgg tcgcaaacat ccgcagcagg agttcttaca ggtagatacc    720
tctaagattc tgtttatctg cggcggcgcg tttgccggtc tggataaagt gatcgctaac    780
cgtgttgaaa ccggctccgg cattggtttt ggcgcgacgg tgaaagcgaa gtccgacaaa    840
gccagcgaag gcgagctgtt gtcgcaggtt gaaccggaag atttgatcaa atttggtctg    900
attcctgagt ttatcggtcg tctgccagtg gtagcgacgc tgaatgaact cagcgaagaa    960
gcgctgattc aaatcctgaa agagccgaaa aatgcgctga ccaagcagta tcaggcgctg   1020
tttaacctgg aaggcgtcga tctggaattc cgtgacgaag cgctggacgc tatcgccagg   1080
aaagcaatgg cgcgtaaaac cggtgcccgt ggtctgcgtt ctatcgtcga agcggcgctg   1140
ctggatacca tgtacgattt gccatctatg gaagacgtcg aaaaagtggt gatcgacgag   1200
tccgttattg ccggtcagag taagccgttg ctgatttacg gcaaaccgga agcgcaggct   1260
tctggcgaat aa                                                       1272
```

<210> SEQ ID NO 87
<211> LENGTH: 1086
<212> TYPE: DNA
<213> ORGANISM: Salmonella enterica

<400> SEQUENCE: 87

```
atggcaggaa acacaattgg acaactcttt cgcgtaacca ctttcggcga atcacacggg    60
ctggcgcttg ggggtatcgt cgatggcgtg ccgcccggca tcccgttgac ggaggccgat   120
ctgcagcacg atctcgacag acgccgccct ggcacctcgc gctatactac tcagcgccgc   180
gaaccggacc aggtaaaaat tctctccggc gtgtttgatg gcgtgacgac cggcaccagt   240
attggcctgc tgattgaaaa caccgatcag cgctcgcagg actacagcgc gattaaagat   300
gttttcgcc cggacacgc ggattacacc tatgagcaga atacggcct gcgcgattac    360
cgcggcggtg gacgttcttc cgcgcgtgaa accgcgatgc cgtagcggc aggggcgatc   420
gccaagaaat acttggcgga aaagttcggc atcgaaatcc gcggctgcct gacccagatg   480
ggcgacattc cgctggagat taaagactgg cgtcaggttg agcttaatcc gttcttttgc   540
cccgatgcgg acaaacttga cgcgctggac gaactgatgc gcgcgctgaa aaagagggt   600
gactccatcg gcgcgaaagt gacggtgatg gcgagcggcg tgccggcagg gcttggcgaa   660
ccggtatttg accgactgga tgcggacatc gcccatgcgc tgatgagcat caatgcggtg   720
aaaggcgtgg agatcggcga aggatttaac gtggtggcgc tgcgcggcag ccagaatcgc   780
gatgaaatca cggcgcaggg ttttcagagc aaccacgctg gcggcatcct cggtggcatc   840
agtagtgggc aacacattgt ggcgcatatg gcgctgaaaac ctacctccag cattaccgtg   900
ccgggacgta cgatcaaccg gatgggtgaa gaggtcgaga tgatcaccaa agggcgccac   960
gatccgtgtg tggggattcg cgcagtgccg atcgcagaag ccatgctggc gatcgtactg  1020
atggatcacc tgctgcgcca tcgggcacag aatgcggatg taaagacaga gattccacgc  1080
tggtaa                                                             1086
```

<210> SEQ ID NO 88
<211> LENGTH: 759
<212> TYPE: DNA
<213> ORGANISM: Salmonella enterica

<400> SEQUENCE: 88

```
atgaaaaccg tcaccgtaaa aaatcttatc attggcgaag ggatgcccaa aattatcgtg    60
tcgttgatgg aaagagacat caatagcgtg aaagcggagg cgctggccta ccgcgaagct   120
acattcgata ttctggagtg gcgcgtggat cactttatgg atatcgcatc gactcaatcc   180
gttcttaccg ctgcgcgtgt tatccgcgat gcgatgcctg acattccgtt actgttttact   240
ttccgcagcg ccaaagaagg cggcgagcag acaataacca ctcagcatta tctcacgctt   300
aatcgtgccg caatcgacag cggcctggtc gatatgatcg atcttgagct atttaccggt   360
gatgctgacg ttaaagccac tgtcgattat gcccatgcgc ataatgttta tgtcgtgatg   420
tctaaccacg attttcacca gacgccgtcc gcagaggaaa tggttctgcg gctacgtaaa   480
atgcaagcac tcggcgcgga tattcccaag attgccgtta tgccgcaaag caagcatgat   540
gtattaacgt tactcactgc cacgctggag atgcagcaac attacgccga ccgtccggta   600
attactatgt caatggcgaa agagggtgtc atttcacgtc tggcagggga agtgtttggc   660
tctgccgcca cgtttggcgc ggtgaagcag gcttcagcgc cggggcaaat cgccgtaaat   720
gatctacgca gtgtattaat gattctgcac aacgcctga                         759
```

<210> SEQ ID NO 89
<211> LENGTH: 1428
<212> TYPE: DNA

<213> ORGANISM: Salmonella enterica

<400> SEQUENCE: 89

| | |
|---|---|
| atgaaaaaaa ccacattagc aatgagtgca ctggctctga gtttaggttt ggcattgtcg | 60 |
| cctctgtctg ccacggcggc tgaaacgtcc tcttcagcaa tgactgccca gcagatgcca | 120 |
| agcctggcac cgatgctcga aaaagtgatg ccatcggtgg tcagtattaa tgtagaaggt | 180 |
| agcaccacgg tgaatacgcc gcgtatgccg cgtaatttcc agcaattctt tggcgatgac | 240 |
| tccccgttct gccaggacgg ttctccgttc cagaattctc cgttctgcca gggcggcggt | 300 |
| aacggcggca acggcggtca acaacagaaa ttcatggcgc tgggctccgg cgtaattatt | 360 |
| gacgccgcga agggctacgt cgtcaccaac aaccacgtgg ttgataacgc cagcgtgatt | 420 |
| aaagtacagc ttagcgatgg cgtaaattc gatgctaaag tggtgggcaa agatccgcgt | 480 |
| tctgatatcg cgctgattca aattcagaat ccgaagaacc tgacggcgat taagctggcg | 540 |
| gactccgacg cgctgcgcgt gggggattat accgtcgcta ttggtaaccc gtttggtctg | 600 |
| ggcgaaacgg tgacgtcagg tatcgtttcg gcgctgggc gtagcggcct gaacgtagaa | 660 |
| aattacgaga ctttattca gaccgacgcc gcgattaacc gcggtaactc cggcggcgcg | 720 |
| ctggtgaacc tgaacggtga gctgatcggt attaacaccg cgattctggc gccggacggc | 780 |
| ggcaacatcg gtatcggctt cgctatcccc agtaacatgg tgaaaaacct gacgtcgcag | 840 |
| atggtggaat acgccaggt gaaacgcggc gaactgggga tcatggggac tgagctgagc | 900 |
| tctgagctgg cgaaagcgat gaaagtcgac gcccagcgtg gcgcgttcgt cagccaggtg | 960 |
| atgccgaatt cgtccgcagc gaaagcgggt atcaaagccg gggatgtcat acctcgctg | 1020 |
| aacggtaaac cgatcagcag cttttgcggcg ctgcgcgctc aggtcggcac tatgccggtc | 1080 |
| ggcagcaaaa tcagcctcgg tctgctgcgt gaaggtaaag cgattacggt taatctggaa | 1140 |
| ctgcagcaga gcagccagag tcaggttgat tccagcacca tcttcagcgg gattgagggc | 1200 |
| gctgaaatga gtaataaagg ccaggataaa ggcgttgtgg tgagcagcgt gaaagcgaac | 1260 |
| tcacccgccg cgcaaattgg cctcaaaaaa ggcgatgtga ttatcggcgc taaccagcag | 1320 |
| ccggtgaaaa atatcgccga gctgcgtaag attctcgaca gcaagccgtc ggtgctggcg | 1380 |
| ctgaatattc agcgtggtga tagttctatt tatttgctga tgcagtaa | 1428 |

<210> SEQ ID NO 90
<211> LENGTH: 1518
<212> TYPE: DNA
<213> ORGANISM: Salmonella enterica

<400> SEQUENCE: 90

| | |
|---|---|
| atggcacaag tcattaatac aaacagcctg tcgctgttga cccagaataa cctgaacaaa | 60 |
| tctcagtcct cactgagttc cgctattgag cgtctgtcct ctggtctgcg tatcaacagc | 120 |
| gcgaaagacg atgcggcagg ccaggcgatt gctaaccgct tcacttctaa tatcaaaggt | 180 |
| ctgactcagg cttcccgtaa cgctaacgac ggcatttcta ttgcgcagac cactgaaggt | 240 |
| gcgctgaatg aaatcaacaa caacctgcag cgtgtgcgtg agttgtctgt tcaggccact | 300 |
| aacgggacta ctctgattcc cgatctgaaa tctatccagg atgaaattca gcaacgtctg | 360 |
| gaagaaatcg atcgcgtttc taatcagact caatttaacg gtgttaaagt cctgtctcag | 420 |
| gacaaccaga tgaaaatcca ggttggtgct aacgatggtg aaaccattac catcgatctg | 480 |
| caaaaaattg atgtgaaaag ccttggcctt gatgggttca atgttaatgg ccaaaagaa | 540 |
| gcgacagtgg gtgatctgaa atccagcttc aagaatgtta cggggttacga cacctatgca | 600 |

```
gcgggtgccg ataaatatcg tgtagatatt aattccggtg ctgtagtgac tgatgcagca    660
gcaccggata aagtatatgt aaatgcagca aacggtcagt taacaactga cgatgcggaa    720
aataacactg cggttgatct ctttaagacc actaaatcta ctgctggtac cgctgaagcc    780
aaagcgatag ctggtgccat aaaggtggt aaggaaggag atacctttga ttataaaggc     840 gtgacttta  ctattgatac aaaaactggt gatgacggta atggtaaggt ttctactacc    900
atcaatggtg aaaagttac  gttaactgtc gctgatattg ccactggcgc gacggatgtt    960
aatgctgcta ccttacaatc aagcaaaaat gtttatacat ctgtagtgaa cggtcagttt   1020 actttgatg  ataaaaccaa aaacgagagt gcgaaacttt ctgatttgga agcaaacaat   1080
gctgttaagg gcgaaagtaa aattacagta aatggggctg aatatactgc taacgccacg   1140
ggtgataaga tcaccttagc tggcaaaacc atgtttatt  ataaaacagc ttctggcgta   1200
agtacattaa tcaatgaaga cgctgccgca gccaagaaaa gtaccgctaa cccactggct   1260
tcaattgatt ctgcattgtc aaagtggac  gcagttcgtt cttctctggg ggcaattcaa   1320
aaccgttttg attcagccat taccaacctt ggcaatacgg taaccaatct gaactccgcg   1380
cgtagccgta tcgaagatgc tgactatgca acggaagttt ctaatatgtc taaagcgcag   1440
attctgcagc aggctggtac ttccgttctg gcgcaggcta accaggttcc gcaaaacgtc   1500
ctctctttac tgcgttaa                                                 1518

<210> SEQ ID NO 91
<211> LENGTH: 1488
<212> TYPE: DNA
<213> ORGANISM: Salmonella enterica

<400> SEQUENCE: 91
atggcacaag tcattaatac aaacagcctg tcgctgttga cccagaataa cctgaacaaa     60
tcccagtccg ctctgggcac cgctatcgag cgtctgtctt ccggtctgcg tatcaacagc    120
gcgaaagacg atgcggcagg tcaggcgatt gctaaccgtt ttaccgcgaa catcaaaggt    180
ctgactcagg cttcccgtaa cgctaacgac ggtatctcca ttgcgcagac cactgaaggc    240
gcgctgaacg aaatcaacaa caacctgcag cgtgtgcgtg aactggcggt tcagtctgct    300
aacagcacca actcccagtc tgacctcgac tccatccagg ctgaaatcac ccagcgcctg    360
aacgaaatcg accgtgtatc cggccagact cagttcaacg gcgtgaaagt cctggcgcag    420
gacaacaccc tgaccatcca ggttggtgcc aacgacggtg aaactatcga tatcgatctg    480
aagcagatca actctcagac cctgggtctg gatacgctga atgtgcaaca aaaatataag    540
gtcagcgata cggctgcaac tgttacagga tatgccgata ctacgattgc tttagacaat    600
agtactttta aagcctcggc tactggtctt ggtggtactg accagaaaat tgatggcgat    660
ttaaaatttg atgatacgac tggaaaatat tacgccaaag ttaccgttac gggggggaact   720 ggtaaagatg gctattatga gtttccgtt  gataagacga acggtgaggt gactcttgct   780
ggcggtgcga cttccccgct tacaggtgga ctacctgcga cagcaactga ggatgtgaaa    840
aatgtacaag ttgcaaatgc tgatttgaca gaggctaaag ccgcattgac agcagcaggt    900
gttaccggca cagcatctgt tgttaagatg tcttatactg ataataacgg taaaactatt    960
gatggtggtt tagcagttaa ggtaggcgat gattactatt ctgcaactca aaataaagat   1020
ggttccataa gtattaatac tacgaaatac actgcagatg acggtacatc caaaactgca   1080
ctaaacaaac tgggtggcgc agacggcaaa accgaagttg tttctattgg tggtaaaact   1140
```

```
tacgctgcaa gtaaagccga aggtcacaac tttaaagcac agcctgatct ggcggaagcg    1200
gctgctacaa ccaccgaaaa cccgctgcag aaaattgatg ctgctttggc acaggttgac    1260
acgttacgtt ctgacctggg tgcggtacag aaccgtttca actccgctat taccaacctg    1320
ggcaacaccg taaacaacct gacttctgcc cgtagccgta tcgaagattc cgactacgcg    1380
accgaagttt ccaacatgtc tcgcgcgcag attctgcagc aggccggtac ctccgttctg    1440
gcgcaggcga accaggttcc gcaaaacgtc ctctctttac tgcgttaa                 1488
```

<210> SEQ ID NO 92
<211> LENGTH: 1521
<212> TYPE: DNA
<213> ORGANISM: Salmonella enterica

<400> SEQUENCE: 92

```
atggcacaag tcattaatac aaacagcctg tcgctgttga cccagaataa cctgaacaaa      60
tcccagtccg cactgggcac tgctatcgag cgtttgtctt ccggtctgcg tatcaacagc     120
gcgaaagacg atgcggcagg acaggcgatt gctaaccgtt ttaccgcgaa catcaaaggt     180
ctgactcagg cttcccgtaa cgctaacgac ggtatctcca ttgcgcagac cactgaaggc     240
gcgctgaacg aaatcaacaa caacctgcag cgtgtgcgtg aactggcggt tcagtctgcg     300
aatggtacta actcccagtc tgacctcgac tccatccagg ctgaaatcac ccagcgcctg     360
aacgaaatcg accgtgtatc cggccagact cagttcaacg gcgtgaaagt cctggcgcag     420
gacaacaccc tgaccatcca ggttggtgcc aacgacggtg aaactatcga tattgattta     480
aaagaaatca gctctaaaac actgggactt gataagctta atgtccaaga tgcctacacc     540
ccgaaagaaa ctgctgtaac cgttgataaa actacctata aaatggtac  agatcctatt    600 acagcccaga gcaatactga tatccaaact gcaattggcg gtggtgcaac gggggttact     660
ggggctgata tcaaatttaa agatggtcaa tactatttag atgttaaagg cggtgcttct     720
gctggtgttt ataagccac ttatgatgaa actacaaaga aagttaatat tgatacgact      780
gataaaactc cgttggcaac tgcggaagct acagctattc ggggaacggc cactataacc     840
cacaaccaaa ttgctgaagt aacaaaagag ggtgttgata cgaccacagt tgcggctcaa     900
cttgctgcag caggggttac tggcgccgat aaggacaata ctagccttgt aaaactatcg     960
tttgaggata aaaacggtaa ggttattgat ggtggctatg cagtgaaaat gggcgacgat    1020
ttctatgccg ctacatatga tgagaaaaca ggtgcaatta ctgctaaaac cactacttat    1080
acagatggta ctggcgttgc tcaaactgga gctgtgaaat tggtggcgc aaatggtaaa    1140 tctgaagttg ttactgctac cgatggtaag acttacttag caagcgacct tgacaaacat    1200
aacttcagaa caggcggtga gcttaaagag gttaatacag ataagactga aaacccactg    1260
cagaaaattg atgctgcctt ggcacaggtt gatacacttc gttctgacct gggtgcggtt    1320
cagaaccgtt tcaactccgc tatcaccaac ctgggcaata ccgtaaataa cctgtcttct    1380
gcccgtagcc gtatcgaaga ttccgactac gcaaccgaag tctccaacat gtctcgcgcg    1440
cagattctgc agcaggccgg tacctccgtt ctggcgcagg cgaaccaggt tccgcaaaac    1500
gtcctctctt tactgcgtta a                                             1521
```

<210> SEQ ID NO 93
<211> LENGTH: 1488
<212> TYPE: DNA
<213> ORGANISM: Salmonella enterica

<400> SEQUENCE: 93

```
atggcacaag tcattaatac aaacagcctg tcgctgttga cccagaataa cctgaacaaa        60
tcccagtccg ctctgggcac cgctatcgag cgtctgtctt ccggtctgcg tatcaacagc       120
gcgaaagacg atgcggcagg tcaggcaatt gctaaccgtt tcaccgcgaa catcaaaggt       180
ctgactcagg cttcccgtaa cgctaacgac ggtatctcca ttgcgcagac cactgaaggc       240
gcgctgaacg aaatcaacaa caacctgcag cgtgtgcgtg aactggcggt tcagtctgct       300
aacagcacca actcccagtc tgacctcgac tccatccagg ctgaaatcac ccagcgcctg       360
aacgaaatcg accgtgtatc cggtcagact cagttcaacg gcgtgaaagt cctggcgcag       420
gacaacaccc tgaccatcca ggttggtgcc aacaacggtg aaaccattga tatcgatctg       480
aaacagatca actctcagac cctgggtctg gatacgctga atgtgcagaa aaaatatgat       540
gtgaagagcg aagcggtcac gccttcggct acattaagca ctactgcact tgatggtgct       600
ggcctcaaaa ccggaaccgg ttctacaact gatactggtt caattaagga tggtaaggtt       660
tactataaca gcacctctaa aaattattat gttgaagtag aatttaccga tgcgaccgat       720
caaaccaaca aaggcggatt ctataaagtt aatgttgctg atgatggtgc agtcacaatg       780
actgcggcta ccaccaaaga ggctacaact cctacaggta ttactgaagt tactcaagtc       840
caaaaacctg tggctgctcc agctgctatc caggctcagt tgactgctgc ccatgtgacc       900
ggcgctgata ctgctgaaat ggttaagatg tcttatacgg ataaaaacgg taagactatt       960
gatggcggtt tcggtgttaa agttggggct gatatttatg ctgcaacaaa aaataaagat      1020
ggatcgttca gcattaacac cactgaatat accgataaag acggcaacac taaaactgca      1080
ctaaaccaac tgggtggcgc agacggtaaa actgaagttg tttctatcga cggtaaaacc      1140
tacaatgcca gcaaagccgc tggtcacaac tttaaagcac agccagagct ggctgaagcg      1200
gctgctgcaa ccaccgaaaa cccgctggct aaaattgatg ccgcgctggc gcaggttgat      1260
gcgctgcgtt ctgacttggg tgcggttcag aaccgtttca actccgctat caccaacctg      1320
ggcaataccg taaataacct gtcttctgcc cgtagccgta tcgaagattc cgactacgcg      1380
accgaagttt ccaacatgtc tcgcgcgcag atcctgcagc aggccggtac ctccgttctg      1440
gcgcaggcga accaggttcc gcaaaacgtc ctctctttac tgcgttaa                   1488
```

<210> SEQ ID NO 94
<211> LENGTH: 1488
<212> TYPE: DNA
<213> ORGANISM: Salmonella enterica

<400> SEQUENCE: 94

```
atggcacaag tcattaatac aaacagcctg tcgctgttga cccagaataa cctgaacaaa        60
tcccagtccg ctctgggcac cgctatcgag cgtctgtctt ctggtctgcg tatcaacagc       120
gcgaaagacg atgcggcagg tcaggcgatt gctaaccgtt ttaccgcgaa catcaaaggt       180
ctgactcagg cttcccgtaa cgctaacgac ggtatctcca ttgcgcagac cactgaaggc       240
gcgctgaacg aaatcaacaa caacctgcag cgtgtgcgtg aactggcggt tcagtctgct       300
aacagcacca actcccagtc tgacctcgac tccatccagg ctgaaatcac ccagcgcctg       360
aacgaaatcg accgtgtatc cggccagact cagttcaacg gcgtgaaagt cctggcgcag       420
gacaacaccc tgaccatcca ggttggcgcg aacgacggtg aaactatcga tatcgatctg       480
aagcagatca actctcagac cctgggtctg gatactttaa gtgtacagga tgcctatacg       540
ccaaaaggta ccgctgttac cagagatgtt accacctata aaaatggtgg tactactctt       600
```

| | |
|---|---:|
| acagcaccta acgcagcagc aattgatacc gctttaggta cgactggtgc ggcgggtact | 660 |
| gcggctgtga aatttaaaga cggtaactac ttcgttgagg tgaccggtac aactaaagat | 720 |
| ggtctgtatg aagcgacagt tgatgcagct ggcgcggtga caatgaccgc aaataaagca | 780 |
| acagtaactg gggctagtac agttactgaa aaccaaattg tagacgctgt tacaccgacg | 840 |
| ccagttgata cagtcgcagc agctactgca ttgaccaatg caggtgtgac aggtgcgaca | 900 |
| ggtaatacca gcttggttaa aatgtcattt gaagataaaa atggcaaagt tactgatgcg | 960 |
| ggttacgcgc ttaaagttgg aaatgattat tatgccgctg attacgatga aaaaactggt | 1020 |
| gagataaaag ctaaaactgt aaattatact gacgctactg gtgcgacaaa accggtgct | 1080 |
| gtgaaatttg gcggtgcgaa tggtaaaact gaagttgtga ccaccgttga tggtaatact | 1140 |
| tatcaggcta gtgatgtaaa agggcataat ttccagagtg gtggcgcttt aagcgaggct | 1200 |
| gtaaccacta aaactgaaaa cccgctggct aaaattgatg ccgcgctggc gcaagttgat | 1260 |
| gcgctgcgtt ctgacttggg tgcggttcag aaccgtttca actccgctat caccaacctg | 1320 |
| ggcaataccg taaacaacct gtctgaagcc cgtagccgta tcgaagattc cgactacgcg | 1380 |
| accgaagtct ccaacatgtc ccgcgcgcag attctgcagc aggccggtac ctccgttctg | 1440 |
| gcgcaggcga accaggttcc gcaaaacgtc ctctctttac tgcgttaa | 1488 |

<210> SEQ ID NO 95
<211> LENGTH: 1506
<212> TYPE: DNA
<213> ORGANISM: Salmonella enterica

<400> SEQUENCE: 95

| | |
|---|---:|
| atggcacaag tcattaatac aaacagcctg tcgctgttga cccagaataa cctgaacaaa | 60 |
| tcccagtctg ctctgggtac cgctatcgag cgtctgtctt ccggtctgcg tatcaacagc | 120 |
| gcgaaagacg atgcggcagg tcaggcgatt gctaaccgtt tcaccgcgaa catcaaaggt | 180 |
| ctgactcagg cttcccgtaa cgctaacgac ggtatttcta ttgcgcagac cactgaaggc | 240 |
| gcgctgaacg aaatcaacaa caacctgcag cgtgtgcgtg aactggcggt tcagtctgct | 300 |
| aacagcacca actcccagtc tgacctcgac tccatccagg ctgaaatcac ccagcgtctg | 360 |
| aacgaaatcg accgtgtatc cggtcagact cagttcaacg gcgtgaaagt cctggcgcag | 420 |
| gacaacactc tgaccatcca ggttggtgcc aacgacggtg aaactatcga tatcgatctg | 480 |
| aagcagatca actctcagac cctgggccta gatacgctga atgtgcagaa aaatatgat | 540 |
| gtgagcgata ctgctgtagc tgcttcctat tccgactcga acagaatat tgctgttcct | 600 |
| gataaaacag ctattactgc aaaaattggt gcagcaacca gtggtggtgc tggtataaaa | 660 |
| gcagatatta gctttaaaga tggcaagtat tacgcgactg tcagtggata cgatgatgcc | 720 |
| gcagatacag ataaaaatgg aacctatgaa gtcactgttg ccgcagatac aggagcagtt | 780 |
| acttttgcga ctacaccaac agtggttgac ttaccaactg atgcaaaagc agtttcaaaa | 840 |
| gttcaacaga atgatactga aatagcagca acaaatgcga aagctgcatt aaaagctgca | 900 |
| ggagttgcag atgcagaagc tgatacagct actttagtga aatgtcttta cagataat | 960 |
| aatggcaaag ttattgatgg tgggttcgca tttaagacct ccggtggtta ttatgcagca | 1020 |
| tctgttgata aatctggcgc agctagcttg aaagttacta gctacgttga cgctaccact | 1080 |
| ggtaccgaaa aaactgctgc gaataaatta ggtggcgcag acggtaaaac cgaagttgtt | 1140 |
| actatcgacg gtaaaaccta caatgccagc aaagccgctg gcacaacttt caaagcacag | 1200 |
| ccagagctgg cggaagcggc tgctacaacc actgaaaacc cgctgcagaa aattgatgct | 1260 |

```
gctttggcgc aggtggatgc gctgcgttct gacctgggtg cggttcagaa ccgtttcaac      1320
tccgctatca ccaacctggg caataccgta ataaccctgt cttctgcccg tagccgtatc      1380
gaagattccg actacgcgac cgaagtttcc aacatgtctc gcgcgcagat tctgcagcag      1440
gccggtacct ccgttctggc gcaggcgaac caggttccgc aaaacgtcct ctctttactg      1500
cgttaa                                                                 1506
```

<210> SEQ ID NO 96
<211> LENGTH: 1407
<212> TYPE: DNA
<213> ORGANISM: Salmonella enterica

<400> SEQUENCE: 96

```
atggcttcaa tttcatcatt aggtgtaggg tcaaacttac ctctggattc actgctgact        60
aaactgacca acgctgaaaa aggacgctta acgccgatca cacagcagca gagtgctaat       120
acggcccgtc taacggcata cggtacttta aaaagtgcac tggagaagtt tcaaacagca       180
aacacggcgt taaataaagc cgatctgttt aaaagtacga atgtcaccag cagtacagaa       240
gacctgaaag tctcgacgga agctggggcc gcacctggaa cttatgtggt tagcgtaact       300
cagttagcac aagcacaatc tttgagtaca gcaaccaaaa ttacatctac caaagaagtg       360
ctgggagata ccacatctga cagccgtacc ataaaaattg aacagaaagg ccgtaaagaa       420
ccacttgaaa tcaagctcac taaagatcaa acctctttag agggtatccg tgacgccatt       480
aatgatgctg acagtggtat ttccgccagt atcgttaaag ttaaagaagg cgattatcag       540
cttgtactga ccgcagatag tggcacggat aatcaaatga ctatctctgt ggaaggcgat       600
agcaaactca gcgatctgtt gtcctatgat agtagtactg gcacgggcaa atgaagcaa        660 ctggttgctg cagataatgc tttgttaacc gttaacggca ttgatattga gcgaccgagt       720
aataaaatca ctgacgctcc acaaggcgtg acgcttgaac taaccaaaga agtaaaagat       780
gcccgtatta ccgtcacaaa agataatgaa aaggcgaccg aagccgtcaa aggttgggtt       840
gatgcctaca actcactgct tgatacctt agttcattaa caaatatac agaggttgat         900 ccaggggctg aagaacagga caaaaacaac ggtgcactac ttggagatac cgtggtgcga       960
acgattcaaa ctggaatccg cgctcagttc gctaatggtg caagtacagg tacatttaag      1020
accctgaatg aaattggtat tacttctgat ggtaccaccg aaaactaaa attgatgat        1080 accaagctta aaaagcgct ggatgaaaat accgcttctg tacgtgagct gctggtaggt      1140
gatggtaaag aaacgcgggat caccaccaaa attgccaccg aagtgaaag ttatctggcc     1200 gatgacggca ttattgacag cgcccaggac agtattaacg ccacgctgaa aaagctgact      1260
aagcaatatc tgaccgtcag cagtagcatt gacgacaccg ttgcccgtta caaggcccag      1320
tttacccaac tggataccat gatgagtaag ctgaataaca ccagtactta tttgacccag      1380
caatttaatg ctatgaacaa gtcctga                                         1407
```

<210> SEQ ID NO 97
<211> LENGTH: 1404
<212> TYPE: DNA
<213> ORGANISM: Salmonella enterica

<400> SEQUENCE: 97

```
atggcttcaa tttcatcatt aggtgtggga tcaaacttac cgttagacca gttgttgaca        60
gacctgacaa agaacgaaaa aggacgctta acgccaatta ccaaacagca gagcgcgaat       120
```

```
tcggcaaagc taaccgccta tggcacattg aaaagcgcat tagaaaaatt ccagacggca    180
aataccgcgt taaataaagc ggatttattt aagtctaccg tggcgtccag caccactgaa    240
gatctcaaag tcagtactac cgctggcgct gccgcaggga cttataagat taacgtaacc    300
cagcttgccg ccgcacagtc gctggcgaca aaaaccacct tcgcgaccac caaagagcag    360
ttgggcgata cgtcggtcac gtcccggaca attaaaattg aacagccggg acgtaaagag    420
ccgctggaaa ttaagctgga taaaggcgac acctccatgg aggcgatccg tgacgccatc    480
aatgacgccg acagcggtat cgccgccagt atcgttaagg tcaaagagaa cgaattccag    540
ttggtgctta ccgccaatag cggtaccgac aatacgatga agatcacggt ggaaggcgat    600
acaaaactta acgatctact cgcttatgac agcaccacca ataccggcaa tatgcaagag    660
ctggtgaaag cagaaaacgc gaagctgaac gtaaacggca tcgacattga gcgtcagagc    720
aataccgtaa ccgacgcccc tcagggaatt acgctcaccc tgaccaagaa agtgaccgac    780
gcgaccgtga cggtaacgaa agatgatacc aaggcgaaag aggcgattaa atcctgggtg    840
gatgcctata actcgctggt ggataccttt agctcgttaa ccaaatatac cgccgttgag    900
ccgggcgaag aagccagcga taaaaacggc gcgctgttag gcgatagtgt ggttcgtact    960
atccagaccg ggattcgggc acaatttgcc aatagcggga gtaattctgc gttcaaaaca   1020
atggcggaaa ttggcatcac ccaggatggg acttccggca aactgaagat tgatgatgat   1080
aagctgacca agtactgaa agataacaca gccgcagcgc gtgagctgct ggtaggcgat   1140
ggtaaagaaa cgggtatcac caccaaaatt gccaccgaag tgaaaagtta tctggcggat   1200
gacggcatta ttgataatgc gcaggacaac gttaacgcca cgctgaaaag cctgacaaaa   1260
cagtacctgt ccgttagcaa cagcatcgat gaaaccgttg cccgttacaa ggcccagttt   1320
acccaactgg ataccatgat gagtaagctg aataacacca gtagttattt gacccagcaa   1380
tttacagcta tgaacaagtc ctga                                          1404

<210> SEQ ID NO 98
<211> LENGTH: 1404
<212> TYPE: DNA
<213> ORGANISM: Salmonella enterica

<400> SEQUENCE: 98
atggcttcaa tttcatcatt aggtgtggga tcaaacttac cgttagacca gttgttgaca     60
gacctgacaa agaacgaaaa aggacgctta acgccaatta ccaaacagca gagcgcgaat    120
tcggcaaagc taaccgccta tggcacattg aaaagcgcat tagaaaaatt ccagacggca    180
aataccgcgt taaataaagc ggatttattt aagtctaccg tggcgtccag cacgacagag    240
gacctcaaag tcagtactac cgcaggcgct gccgcaggga cttataagat tagcgtaacc    300
cagcttgccg ccgcgcagtc gctggcgaca aaaaccacct tcgcaaccac caaagagcag    360
ttgggcgata cgtcggtcac atcccggaca attaaaattg aacagccggg acgtaaagag    420
ccgctggaaa ttaagctgga taaggcgac acctccatgg aggcgatccg tgacgccatt    480
aatgacgccg acagcggtat cgccgccagt atcgttaagg tcaaagagaa cgaattccag    540
ttggtgctta ccgccaatag cggtaccgac aatacgatga agatcacggt ggaaggcgat    600
acaaaactta acgatctact cgcttatgac agcaccacca ataccggcaa tatgcaagag    660
ctggtgaaag cagaaaacgc gaagctgaac gtaaacggca tcgacattga gcgtcagagc    720
aataccgtaa ccgacgcccc tcagggaatt acactcaccc tgaccaagaa agtgaccgac    780
gcgaccgtga cggtgacgaa agatgatacc aaggcgaaag aggcgattaa atcctgggtg    840
```

```
gatgcctata actcgctggt ggatacttt  agctcattaa ctaaatatac cgccgttgag      900
ccgggcgaag aagccagcga taaaaacggc gcgctgttag gcgatagtgt ggttcgtgct      960
atccagaccg ggattcgggc acaatttgcc aatagcggca gtaattctgc gttcaaaaca     1020
atggcggaaa ttggcatcac ccaggatggg acttccggca aactgaagat tgacgatgat     1080
aagctgacca aggtactgaa agataacacg gccgcagcgc gtgagctgct ggtaggcgat     1140
ggtaaagaaa cgggtatcac caccaaaatt gccaccgaag tgaaaagtta tctggcggat     1200
gacggcatta ttgataatgc gcaggacaac gttaacgcca cgctgaaaag cctgacaaaa     1260
cagtacctgt ccgttagcaa cagcatcgat gaaaccgttg cccgttacaa ggcccagttt     1320
acccaactgg ataccatgat gagtaagctg aataacacca gtagttattt gacccagcaa     1380
tttacagcta tgaacaagtc ctga                                            1404

<210> SEQ ID NO 99
<211> LENGTH: 1404
<212> TYPE: DNA
<213> ORGANISM: Salmonella enterica

<400> SEQUENCE: 99
atggcttcaa tttcatcatt aggtgtggga tcaaacttac cgttagacca gttgttgaca       60
gacctgacaa agaacgaaaa aggacgctta acgccaatta ccaaacagca gagcgcgaat      120
tcggcaaagc taaccgccta tggcacattg aaaagcgcat tagaaaaatt ccagacggca      180
aataccgcgt taaataaagc ggatttattt aagtctaccg tggcgtccag cacgacagag      240
gacctcaaag tcagtactac cgcaggcgct gccgcaggga cttataagat tagcgtaacc      300
cagcttgccg ccgcgcagtc gctggcgaca aaaaccacct tcgcaaccac caaagagcag      360
ttgggcgata cgtcggtcac gtcccggaca attaaaattg aacagccggg acgtaaagag      420
ccgctggaaa ttaagctgga taaaggcgac acctccatgg aggcgatccg tgacgccatc      480
aatgacgccg acagcggtat cgccgccagt atcgttaagg tcaaagagaa cgaattccag      540
ttggtgctta ccgccaatag cggtaccgac aatacgatga agatcacggt ggaaggcgat      600
acaaaactta acgatctact cgcttatgac agcaccacca ataccggcaa tatgcaagag      660
ctggtgaaag cagaaaacgc gaagctgaac gtaaacggca tcgacattga gcgtcagagc      720
aataccgtaa ccgacgcccc tcagggaatt acgctcaccc tgacgaagaa agtgaccgac      780
gcgaccgtga cggtaacgaa agatgatacc aaggcgaaag aggcgattaa atcctgggtg      840
gatgcctata actcgctggt ggataccttt agctcgttaa ccaaatatac cgccgttgag      900
ccgggcgaag aagccagcga taaaaacggc gcgctgttag gcgatagtgt ggttcgtact      960
atccagaccg ggattcgggc acaatttgcc aatagcggca gtaattctgc gttcaaaaca     1020
atggcggaaa ttggcatcac ccaggatggg acttccggca aactgaagat tgatgatgat     1080
aagctgacca aggtactgaa agataacaca gccgcagcgc gtgagctgct ggtaggcgat     1140
ggtaaagaaa cgggtatcac caccaaaatt gccaccgaag tgaaaagtta tctggcggat     1200
gacggcatta ttgataatgc gcaggacaac gttaacgcca cgctgaaaag cctgacaaaa     1260
cagtacctgt ccgttagcaa cagcatcgat gaaaccgttg cccgttacaa ggcccagttt     1320
acccaactgg atactatgat gagtaagctg aataacacca gtagttattt gacccagcaa     1380
tttacagcta tgaacaagtc ctga                                            1404

<210> SEQ ID NO 100
```

```
<211> LENGTH: 1404
<212> TYPE: DNA
<213> ORGANISM: Salmonella enterica

<400> SEQUENCE: 100
atggcttcaa tttcatcatt aggtgtggga tcaaacttac cgttagacca gttgttgaca      60
gacctgacaa agaacgaaaa aggacgctta acgccaatta ccaaacagca gagcgcgaat     120
tcggcaaagc taaccgccta tggcacattg aaaagcgcat tagaaaaatt ccagacggca     180
aataccgcgt taaataaagc ggacttattt aagtctaccg tggcgtccag cacgacagag     240
gacctcaaag tcagtactac cgcaggcgct gccgcaggga cttataagat tagcgtaacc     300
cagcttgccg ccgcgcagtc gctggcgaca aaaaccacct tcgcaaccac caaagagcag     360
ttgggcgata cgtcggtcac gtcccggaca attaaaattg aacagccggg acgtaaagag     420
ccgctggaaa ttaagctgga taaaggcgac acctccatgg aggcgatccg tgacgccatc     480
aatgacgccg acagcggtat cgccgccagc atcgttaagg tcaaagagaa cgaattccag     540
ttggtgctta ccgccaatag cggtaccgac aatacgatga agatcacggt ggaaggcgat     600
acaaaactta atgatctact cgcttatgac agcaccacca ataccggcaa tatgcaagag     660
ctggtgaaag cagaaaacgc gaagctgaac gtaaacggca tcgacattga gcgtcagagc     720
aataccgtaa ccgacgcccc tcagggaatt acgctcaccc tgaccaagaa agtgaccgac     780
gcgaccgtga cggtaacgaa agatgatacc aaggcgaaag aggcgattaa atcctgggtg     840
gatgcctata actcgctggt ggataccttt agctcgttaa ccaaatatac cgccgttgag     900
ccgggcgaag aagccagcga taaaaacggc gcgctgttag gcgatagtgt ggttcgtact     960
atccagaccg ggattcgggc acaatttgcc aatagcggca gtaattctgc gttcaaaaca    1020
atggcgaaaa ttggcatcac ccaggatggg acttccggca aactgaagat tgacgatgat    1080
aagctgacca aggtactgaa agataacacg gccgcagcgc gtgagctgct ggtaggcgat    1140
ggtaaagaaa cgggtatcac caccaaaatt gccaccgaag tgaaaagtta tctggcggat    1200
gacggcatta ttgataatgc gcaggacaac gttaacgcca cgctgaaaag cctgacaaaa    1260
cagtacctgt ccgttagcaa cagcatcgat gaaaccgttg cccgttacaa ggcccagttt    1320
acccaactgg ataccatgat gagtaagctg aataacacca gtagttattt gacccagcaa    1380
tttacagcta tgaacaagtc ctga                                           1404

<210> SEQ ID NO 101
<211> LENGTH: 1404
<212> TYPE: DNA
<213> ORGANISM: Salmonella enterica

<400> SEQUENCE: 101
atggcttcaa tttcatcatt aggtgtggga tcaaacttac cattagacca gttgttgaca      60
gacctgacaa agaacgaaaa aggacgctta acgccaatta ccaaacagca gagcgcgaat     120
tcggcaaagc taaccgccta tggcacattg aaaagcgcat tagaaaaatt ccagacggca     180
aataccgcgt taaataaagc ggatttattt aagtctaccg tggcgtccag cacgacagag     240
gacctcaaag tcagtactac cgctggcgct gccgcaggga cttataagat taacgtaacc     300
cagcttgccg ccgcacaatc gctggcgaca aaaaccacct tcgcgaccac caaagagcag     360
ttgggcgata cgtcggtcac gtcccggaca attaaaattg aacagccggg acgtaaagag     420
ccgctggaaa ttaagctgga taaaggcgac acctccatgg aggcgatccg taacgccatc     480
aatgacgccg acagcggtat cgccgccagt atcgttaagg tcaaagagaa cgaattccag     540
```

```
ttggtgctta ccgccaatag cggtaccgac aatacgatga agatcacggt ggaaggcgat      600
acaaaactta acgatctact cgcttatgac agcaccacca ataccggcaa tatgcaagag      660
ctggtgaaag cagaaaacgc gaagctgaac gtaaacggca tcgacattga gcgtcagagc      720
aataccgtaa ccgacgcccc tcagggaatt acgctcaccc tgacgaagaa agtgaccgac      780
gcgaccgtga cggtaacgaa agatgatacc aaggcgaaag aggcgattaa atcctgggtg      840
gatgcctata actcgctggt ggatacctt t agctcgttaa ccaaatatac cgccgttgag      900
ccgggcgaag aagccagcga taaaaacggc gcgctgttag gcgatagtgt ggttcgtact      960
atccagaccg ggattcgggc acaatttgcc aatagcggca gtaattctgc gttcaaaaca     1020
atggcggaaa ttggcatcac tcaggatggg acttccggca aactgaagat tgatgatgat     1080
aagctgacca aagtactgaa agataacaca gccgcagcgc gtgagctgct ggtgggcgat     1140
ggtaaagaaa cggggatcac caccaaaatt gccaccgaag tgaaaagtta tctggcggat     1200
gacggcatta ttgataatgc gcaggacaac gttaacgcca cgctgaaaag cctgacgaaa     1260
cagtacctgt ccgttagcaa cagcatcgat gaaaccgttg cccgttacaa ggcccagttt     1320
acccaactgg ataccatgat gagtaagctg aataacacca gtagttattt gacccagcaa     1380
tttacagcta tgaacaagtc ctga                                            1404

<210> SEQ ID NO 102
<211> LENGTH: 1521
<212> TYPE: DNA
<213> ORGANISM: Salmonella enterica

<400> SEQUENCE: 102
atggcacaag taatcaacac taacagtctg tcgctgctga cccagaataa cctgaacaaa       60
tcccagtccg cactgggcac cgctatcgag cgtctgtctt ctggtctgcg tatcaacagc      120
gcgaaagacg atgcggcagg tcaggcgatt gctaaccgtt tcaccgcgaa catcaaaggt      180
ctgactcagg cttcccgtaa cgctaacgac ggtatctcca ttgcgcagac cactgaaggc      240
gcgctgaacg aaatcaacaa caacctgcag cgtgtgcgtg aactggcggt tcagtctgct      300
aacagcacca actcccagtc tgacctcgac tccatccagg ctgaaatcac ccagcgcctg      360
aacgaaatcg accgtgtatc cggccagact cagttcaacg gcgtgaaagt cctggcgcag      420
gacaacaccc tgaccatcca ggttggcgcc aacgacggta aactatcga tatcgatctg      480 aagcagatca actctcagac cctgggtctg gactcactga acgtgcagaa agcgtatgat      540
gtgaaagata cagcagtaac aacgaaagct tatgccaata atggtactac actggatgta      600
tcgggtcttg atgatgcagc tattaaagcg ctacggg tg gtacgaatgg tacggcttct      660
gtaaccggtg gtgcggttaa atttgacgca gataataaca gtactttgt tactattggt      720 ggctttactg gtgctgatgc cgccaaaaat ggcgattatg aagttaacgt tgctactgac      780
ggtacagtaa cccttgcggc tggcgcaact aaaaccacaa tgcctgctgg tgcgacaact      840
aaaacagaag tacaggagtt aaaagataca ccggcagttg tttcagcaga tgctaaaaat      900
gccttaattg ctggcggcgt tgacgctacc gatgctaatg cgctgagtt ggtcaaaatg      960 tcttataccg ataaaaatgg taagacaatt gaaggcggtt atgcgcttaa agctggcgat     1020
aagtattacg ccgcagatta cgatgaagcg acaggagcaa ttaaagctaa aactacaagt     1080
tatactgctg ctgacggcac taccaaaaca gcggctaacc aactgggtgg cgtagacggt     1140
aaaaccgaag tcgttactat cgacggtaaa acctacaatg ccagcaaagc cgctggtcat     1200
```

| | |
|---|---|
| gatttcaaag cacaaccaga gctggcggaa gcagccgcta aaaccaccga aaacccgctg | 1260 |
| cagaaaattg atgccgcgct ggcgcaggtg gatgcgctgc gctctgatct gggtgcggta | 1320 |
| caaaaccgtt tcaactctgc tatcaccaac ctgggcaata ccgtaaacaa tctgtctgaa | 1380 |
| gcgcgtagcc gtatcgaaga ttccgactac gcgaccgaag tttccaacat gtctcgcgcg | 1440 |
| cagattctgc agcaggccgg tacttccgtt ctggcgcagg ctaaccaggt cccgcagaac | 1500 |
| gtgctgtctc tgttacgtta a | 1521 |

<210> SEQ ID NO 103
<211> LENGTH: 2859
<212> TYPE: DNA
<213> ORGANISM: Salmonella enterica

<400> SEQUENCE: 103

| | |
|---|---|
| atggcacaag taatcaacac taacagtctg tcgctgctga cccagaataa cctgaacaaa | 60 |
| tcccagtccg cactgggcac tgatgaatcc cctaatgatt ttggtaaaaa tcattaagtt | 120 |
| aaggtggata cacatcttgt catatgatca atggtttcg cgaaaaatca ataatcagac | 180 |
| aacaagatgt gcgaactcga tattttacac gactctcttt accaattctg ccccgaatta | 240 |
| cacttaaaac gactcaacag cttaacgttg gcttgccacg cattacttga ctgtaaaact | 300 |
| ctcactctta ccgaacttgg ccgtaacctg ccaaccaaag cgagaacaaa acataacatc | 360 |
| aaacgaatcg accgattgtt aggtaatcgt cacctccaca aagagcgact cgctgtatac | 420 |
| cgttggcatg ctagctttat ctgttcgggc aatacgatgc ccattgtact tgttgactgg | 480 |
| tctgatattc gtgagcaaaa acgacttatg gtattgcgag cttcagtcgc actacacggt | 540 |
| cgttctgtta ctctttatga gaaagcgttc ccgctttcag agcaatgttc aaagaaagct | 600 |
| catgaccaat ttctagccga ccttgcgagc attctaccga gtaacaccac accgctcatt | 660 |
| gtcagtgatg ctggctttaa agtgccatgg tataaatccg ttgagaagct gggttggtac | 720 |
| tggttaagtc gagtaagagg aaaagtacaa tatgcagacc taggagcgga aaactggaaa | 780 |
| cctatcagca acttacatga tatgtcatct agtcactcaa agactttagg ctataagagg | 840 |
| ctgactaaaa gcaatccaat ctcatgccaa attctattgt ataaatctcg ctctaaaggc | 900 |
| cgaaaaaatc agcgctcgac acggactcat tgtcaccacc cgtcacctaa aatctactca | 960 |
| gcgtcggcaa aggagccatg ggttctagca actaacttac ctgttgaaat tcgaacaccc | 1020 |
| aaacaacttg ttaatatcta ttcgaagcga atgcagattg aagaaacctt ccgagacttg | 1080 |
| aaaagtcctg cctacggact aggcctacgc catagccgaa cgagcagctc agagcgtttt | 1140 |
| gatatcatgc tgctaatcgc cctgatgctt caactaacat gttggcttgc gggcgttcat | 1200 |
| gctcagaaac aaggttggga caagcacttc caggctaaca cagtcagaaa tcgaaacgta | 1260 |
| ctctcaacag ttcgcttagg catggaagtt tgcggcatt ctggctacac aataacaagg | 1320 |
| gaagacttac tcgtggctgc aaccctacta gctcaaaatt tattcacaca tggttacgct | 1380 |
| ttggggaaat tatgagggga tctctcagca ctgggcaccg ctatcgagcg tctgtcttcc | 1440 |
| ggtctgcgta tcaacagcgc gaaagacgat gcggcaggtc aggcgattgc taaccgtttt | 1500 |
| accgcgaaca tcaaaggtct gactcaggct tcccgtaacg ctaacgacgg tatttctatt | 1560 |
| gcgcagacca ctgaaggcgc gctgaacgaa atcaacaaca acctgcagcg tgtgcgtgaa | 1620 |
| ctggcggttc agtctgctaa cagcaccaac tcccagtctg acctcgactc catccaggct | 1680 |
| gaaatcaccc agcgtctgaa cgaaatcgac cgtgtatccg gtcagactca gttcaacggc | 1740 |
| gtgaaagtcc tggcgcagga caacactctg accatccagg ttggtgccaa cgacggtgaa | 1800 |

```
actatcgata tcgatctgaa gcagatcaac tctcagaccc tgggtctgga ctcactgaac    1860
gtgcagaaag cgtatgatgt gaaagataca gcagtaacaa cgaaagctta tgccaataat    1920
ggtactacac tggatgtatc gggtcttgat gatacagcta tcaaagcggc tataggtggt    1980
acgactggta cggctgctgt aaccggtagt gcggttaaat ttgacgcaga taataacaag    2040
tactttgtta ctattggtgg ctttactggt gctgatgccg ccaaaaatgg cgattatgaa    2100
gttaacgttg ctactgacgg tacagtaacc cttgcggctg cgcaactaa aaccacaatg    2160 cctgctggtg cgacaactaa aacagaagta caggagttaa agatacacc ggcagttgtt    2220 tcagcagatg ctaaaaatgc cttaattgct ggcggcgttg acgctaccga tgctaatggc    2280
gctgagttgg tcaaaatgtc ttataccgat aaaaatggta agacaattga aggcggttat    2340
gcgcttaaag ctggcgataa gtattacgcc gcagattacg atgaagcgac aggagcaatt    2400
aaagctaaaa ccacaagtta tactgctgct gacggcacta ccaaaacagc agctaaccaa    2460
ctgggtggcg tagacggtaa aaccgaagtc gttactatcg acggtaaaac ctacaatgcc    2520
agcaaagccg ctggtcatga tttcaaagca caaccagagc tggcggaagc agccgctaaa    2580
accaccgaaa acccgctgca gaaaattgat gccgcgctgg cgcaggtgga tgcgctgcgc    2640
tctgatctgg gtgcggtaca aaaccgtttc aactccgcta tcaccaacct gggcaatacc    2700
gtaaacaacc tgtctgaagc gcgtagccgt atcgaagatt ccgactacgc gaccgaagtt    2760
tccaacatgt ctcgcgcgca gattctgcag caggccggta cttccgttct ggcgcaggct    2820
aaccaggtcc gcagaacgt gctgtctctg ttacgttaa                           2859
```

<210> SEQ ID NO 104
<211> LENGTH: 1467
<212> TYPE: DNA
<213> ORGANISM: Salmonella enterica

<400> SEQUENCE: 104

```
atgctacgta tcgctaaaga agccctgacg tttgacgacg tcctccttgt tcccgctcac      60
tccaccgttt tgccgaatac tgccgatctc agcacgcagt tgacgaaaac tattcgtctg     120
aatattccta tgctttctgc ggcgatggac accgtgacgg aagcgcgcct ggcaattgcc     180
ctggcccagg aaggcggcat tggttttatc cacaaaaata tgtccattga gcgccaggcg     240
gaagaagttc gccgcgtgaa gaaacacgag tccggcgtag tgaccgaccc gcagaccgtc     300
ctgccaacca ccacgttgca tgaagtgaaa gccctgaccg agcgtaacgg ttttgcgggc     360
tatccggtgg tgactgaaga taacgagctg gtgggtatca tcaccggtcg tgacgtgcgt     420
tttgtgactg acctgaacca gccggtgagt gtctacatga cgccgaaaga gcgtctggtg     480
accgttcgtg aaggcgaagc ccgtgaagtg gtgctggcaa aaatgcacga aaaacgcgta     540
gaaaaagcgc tggtcgttga tgataacttc catctgcttg gcatgattac cgtaaaagat     600
ttccagaaag cggaacgtaa accaaactcc tgtaaagatg agcagggccg tttacgtgtc     660
ggcgcggcgg tcggcgcagg cgcgggcaac gaagagcgcg ttgacgcgct ggtggcggca     720
ggcgttgacg tactgctgat cgactcctct cacggtcact ctgaaggcgt gttgcaacgt     780
atccgtgaga cgcgcgctaa atatcctgac ctgcaaatca tcggcggcaa cgtcgccact     840
ggcgcaggcg ctcgcgcact ggcggaagcc ggttgcagcg cggtgaaagt gggtatcggc     900
ccgggctcca tctgtaccac tcgtatcgtg actggcgtgg gcgttccgca gatcaccgct     960
gtttccgacg cggtagaagc gctggaaggc accggaattc cggttatcgc tgacggcggt    1020
```

-continued

```
atccgtttct ccggcgatat cgccaaagcc atcgccgcag gcgcgagcgc ggtaatggtt   1080
ggctctatgc tggccggtac cgaagaatcc ccgggcgaaa tcgaactcta ccagggccgt   1140
tcgtacaaat cttaccgcgg catgggttct ctgggcgcga tgtccaaagg ttcctccgac   1200
cgttacttcc agagcgataa cgccgccgac aaactggtgc cggaaggtat cgaaggccgc   1260
gtagcctata aaggtcgcct gaaagagatc attcaccagc agatgggcgg cctgcgctcc   1320 tgtatgggc tgaccggttg tgctaccatc gacgaactgc gtactaaagc ggagtttgtg   1380
cgtatcagcg gtgcgggtat ccaggaaagc cacgttcacg acgtgaccat caccaaagag   1440
tccccgaact accgtctggg ctcctga                                       1467
```